(12) United States Patent
Elbadry et al.

(10) Patent No.: US 11,865,241 B2
(45) Date of Patent: Jan. 9, 2024

(54) SENSOR MONITORING SYSTEM FOR IN-DWELLING CATHETER BASED TREATMENTS

(71) Applicant: GastroKlenz Inc., San Francisco, CA (US)

(72) Inventors: Aly R. Elbadry, San Francisco, CA (US); Eric Hsiang Yu, San Francisco, CA (US); Ahmad Naim Saleh, San Leandro, CA (US); Michael Austin Snyder, San Angelo, TX (US)

(73) Assignee: GastroKlenz Inc., Stanford, CA (US)

( * ) Notice: Subject to any disclaimer, the term of this patent is extended or adjusted under 35 U.S.C. 154(b) by 1273 days.

(21) Appl. No.: 16/221,361

(22) Filed: Dec. 14, 2018

(65) Prior Publication Data

US 2019/0358387 A1    Nov. 28, 2019

Related U.S. Application Data

(60) Provisional application No. 62/731,339, filed on Sep. 14, 2018, provisional application No. 62/599,619, filed on Dec. 15, 2017.

(51) Int. Cl.
 *A61B 5/1455*     (2006.01)
 *A61M 1/36*       (2006.01)
 (Continued)

(52) U.S. Cl.
 CPC .............. *A61M 1/361* (2014.02); *A61M 1/28* (2013.01); *A61M 1/3663* (2013.01);
 (Continued)

(58) Field of Classification Search
 CPC .................................................. A61B 5/1455
 See application file for complete search history.

(56) References Cited

U.S. PATENT DOCUMENTS 4,243,883 A   1/1981   Schwarzmann
4,725,148 A   2/1988   Endo et al.
(Continued)

FOREIGN PATENT DOCUMENTS

CN        203263900 U     11/2013
WO     WO 2010/056740 A1   5/2010
(Continued)

OTHER PUBLICATIONS

International Search Report and Written Opinion for PCT/US2018/065853 dated May 24, 2019, 23 pages.
(Continued)

*Primary Examiner* — Marjan Fardanesh
(74) *Attorney, Agent, or Firm* — Shay Glenn LLP

(57) ABSTRACT

A patient monitoring system may be used with catheters to monitor the infusion and drainage of any solution into the human body. The system may be used, for example, with in-dwelling catheters for peritoneal dialysis in end stage renal disease (ESRD) patients, urinary tract catheters, insulin pumps in diabetic patients, feeding tubes and central venous line catheters. The patient monitoring system includes one or more fluid pathways for infusing into and/or draining solutions out of the catheter, and one or more sensors to monitor the fluid. The patient monitoring system transmits the patient monitoring data to a database, allowing data storage, processing, and access through graphical user interfaces to patients and providers via device applications or browser-based web access portals.

16 Claims, 90 Drawing Sheets

(51) Int. Cl.
*A61M 1/28* (2006.01)
*A61B 5/145* (2006.01)
*A61B 5/00* (2006.01)
*A61M 25/00* (2006.01)

(52) U.S. Cl.
CPC ......... *A61B 5/1455* (2013.01); *A61B 5/14546* (2013.01); *A61B 5/6866* (2013.01); *A61B 2562/0233* (2013.01); *A61M 25/0017* (2013.01); *A61M 2205/3313* (2013.01); *A61M 2205/3584* (2013.01); *A61M 2230/20* (2013.01)

(56) References Cited

U.S. PATENT DOCUMENTS

| | | | |
|---|---|---|---|
| 4,745,279 A | 5/1988 | Karkar et al. | |
| 5,601,080 A * | 2/1997 | Oppenheimer | G01N 21/532 |
| | | | 356/39 |
| 6,228,047 B1 | 5/2001 | Dadson | |
| 6,547,766 B1 | 4/2003 | Fitz | |
| D476,730 S | 7/2003 | O'Mahony et al. | |
| 6,758,835 B2 | 7/2004 | Close et al. | |
| 6,913,590 B2 | 6/2005 | Sorenson et al. | |
| 7,033,539 B2 | 4/2006 | Krensky et al. | |
| 7,420,658 B2 | 9/2008 | Petterson et al. | |
| 7,659,980 B1 | 2/2010 | Mitchell et al. | |
| 7,666,170 B2 | 2/2010 | Guala | |
| 7,998,115 B2 | 8/2011 | Bedingfield | |
| 8,033,157 B2 | 10/2011 | Yardimci et al. | |
| 8,211,048 B2 | 7/2012 | Szamosfalvi et al. | |
| 8,216,156 B2 | 7/2012 | Dalebout et al. | |
| 8,239,010 B2 | 8/2012 | Banet et al. | |
| 8,285,487 B2 | 10/2012 | Bergstrom et al. | |
| 8,348,844 B2 | 1/2013 | Kunjan et al. | |
| 8,440,140 B2 | 5/2013 | Nagai et al. | |
| D694,396 S | 11/2013 | Belt et al. | |
| 8,628,724 B2 | 1/2014 | Kuenstner | |
| 8,708,950 B2 | 4/2014 | Scarpaci et al. | |
| 8,728,023 B2 | 5/2014 | Landherr et al. | |
| 8,747,333 B2 | 6/2014 | Burkholz | |
| 8,777,891 B2 | 7/2014 | Landherr et al. | |
| 8,801,652 B2 | 8/2014 | Landherr et al. | |
| 8,870,769 B2 | 10/2014 | Deshpande | |
| 8,886,273 B2 | 11/2014 | Li et al. | |
| 8,924,161 B2 | 12/2014 | Moerman | |
| 9,125,979 B2 | 9/2015 | Behzadi et al. | |
| 9,215,985 B2 | 12/2015 | Gross et al. | |
| D753,313 S | 4/2016 | Kim et al. | |
| D760,890 S | 7/2016 | Guala | |
| 9,381,289 B2 | 7/2016 | Hedmann et al. | |
| 9,603,622 B2 | 3/2017 | Kamen et al. | |
| 9,724,458 B2 | 8/2017 | Grant et al. | |
| 9,764,074 B1 | 9/2017 | Childers et al. | |
| D801,519 S | 10/2017 | Sabin et al. | |
| D803,387 S | 11/2017 | Bodwell et al. | |
| 9,861,733 B2 | 1/2018 | Burbank et al. | |
| 9,894,894 B2 | 2/2018 | Hassanein et al. | |
| D816,831 S | 5/2018 | Sacchetti | |
| 9,962,524 B2 | 5/2018 | Andino | |
| 9,968,725 B2 | 5/2018 | Fulkerson et al. | |
| 9,968,742 B2 | 5/2018 | Van Antwerp et al. | |
| 10,032,270 B2 | 7/2018 | Turner | |
| 10,078,438 B2 | 9/2018 | Wang et al. | |
| D830,540 S | 10/2018 | Rolfs et al. | |
| D833,030 S | 11/2018 | Sasano | |
| 10,155,081 B2 | 12/2018 | Chen et al. | |
| D842,468 S | 3/2019 | Juan | |
| D850,625 S | 6/2019 | Schmid | |
| D851,759 S | 6/2019 | Jones et al. | |
| 10,332,482 B2 | 6/2019 | Yik et al. | |
| D866,762 S | 11/2019 | Lee | |
| D868,957 S | 12/2019 | Chase et al. | |
| D877,896 S | 3/2020 | Ritter | |
| D879,290 S | 3/2020 | Harman et al. | |
| D879,952 S | 3/2020 | Schneider et al. | |
| 10,925,549 B2 | 2/2021 | Yu et al. | |
| 11,331,052 B2 | 5/2022 | Yu et al. | |
| 11,344,261 B2 | 5/2022 | Yu et al. | |
| 2003/0142291 A1 | 7/2003 | Padmanabhan et al. | |
| 2005/0256447 A1 | 11/2005 | Richardson et al. | |
| 2009/0149776 A1 | 6/2009 | Adams | |
| 2011/0196304 A1 | 8/2011 | Kramer et al. | |
| 2014/0329265 A1 | 11/2014 | Wanders et al. | |
| 2015/0005699 A1 | 1/2015 | Burbank et al. | |
| 2015/0254490 A1 | 9/2015 | Cohen et al. | |
| 2016/0139114 A1 | 5/2016 | Bollmann et al. | |
| 2016/0216150 A1 | 7/2016 | Groeber et al. | |
| 2016/0320228 A1 | 11/2016 | Hudson | |
| 2016/0370287 A1 | 12/2016 | Barnes et al. | |
| 2017/0045455 A1 | 2/2017 | Robertson et al. | |
| 2017/0128653 A1 | 5/2017 | Yuds et al. | |
| 2017/0181678 A1 | 6/2017 | Newberry | |
| 2017/0216521 A1 | 8/2017 | Kolko et al. | |
| 2017/0266031 A1 | 9/2017 | Sanchez et al. | |
| 2017/0281846 A1 | 10/2017 | Manda et al. | |
| 2018/0021560 A1 | 1/2018 | Ueda et al. | |
| 2018/0028794 A1 | 2/2018 | Browd et al. | |
| 2018/0043075 A1 | 2/2018 | Gerber et al. | |
| 2018/0043078 A1 | 2/2018 | Gerber et al. | |
| 2018/0043080 A1 | 2/2018 | Gerber et al. | |
| 2018/0070841 A1 | 3/2018 | Honore et al. | |
| 2018/0073991 A1 | 3/2018 | Lura et al. | |
| 2018/0193546 A1 | 6/2018 | Gerber et al. | |
| 2018/0353671 A1 | 12/2018 | Tessendorf | |
| 2019/0228526 A1 | 7/2019 | Wuepper et al. | |
| 2020/0405243 A1 | 12/2020 | Yu et al. | |
| 2021/0186433 A1 | 6/2021 | Yu et al. | |
| 2021/0186434 A1 | 6/2021 | Yu et al. | |
| 2021/0215666 A1 | 7/2021 | Kotanko et al. | |

FOREIGN PATENT DOCUMENTS

| | | |
|---|---|---|
| WO | WO 2014/163815 A1 | 10/2014 |
| WO | WO 2015/012990 A1 | 1/2015 |
| WO | WO 2015/164620 A1 | 10/2015 |
| WO | WO 2016/046634 A1 | 3/2016 |
| WO | WO 2016/205744 A1 | 12/2016 |
| WO | WO 2017/092871 A1 | 6/2017 |
| WO | WO 2017/132132 A1 | 8/2017 |
| WO | WO 2018/007013 A2 | 1/2018 |
| WO | WO 2018/142406 A1 | 8/2018 |
| WO | WO 2019/118929 A1 | 6/2019 |

OTHER PUBLICATIONS

International Preliminary Examination Report for Application No. PCT/US2020/039986, dated Jan. 6, 2022, 11 pages.
International Search Report and Written Opinion for PCT/US2020/039986 dated Nov. 13, 2020, 19 pages.

* cited by examiner

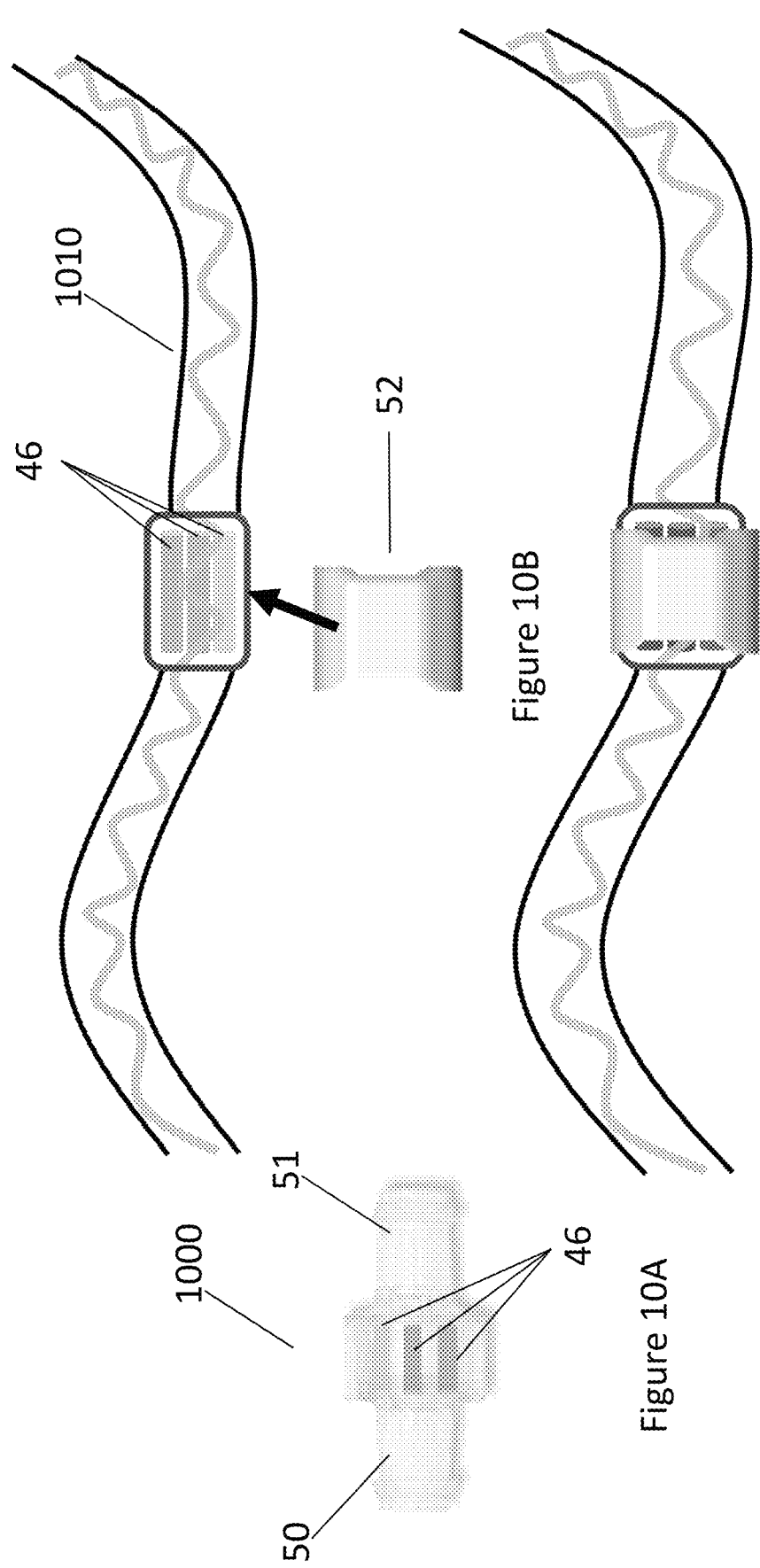

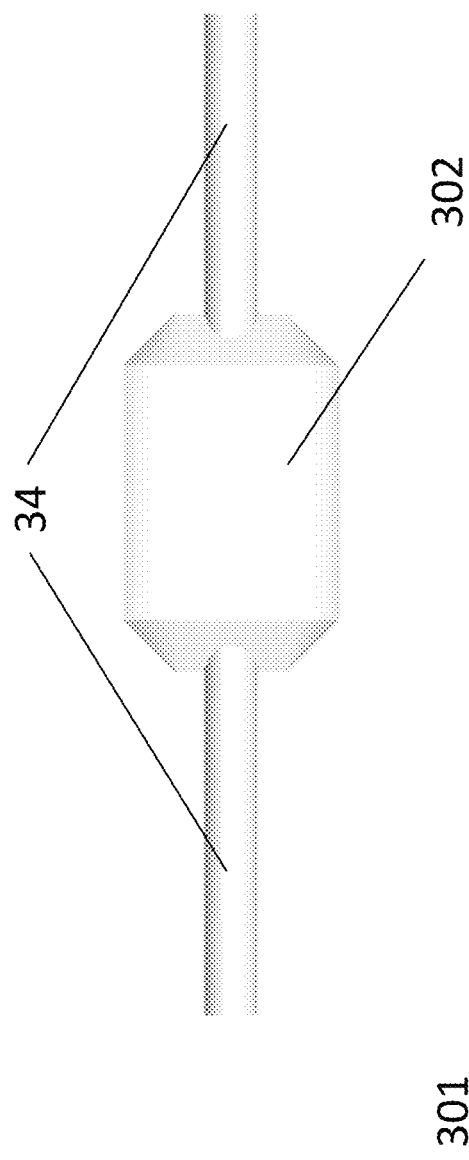
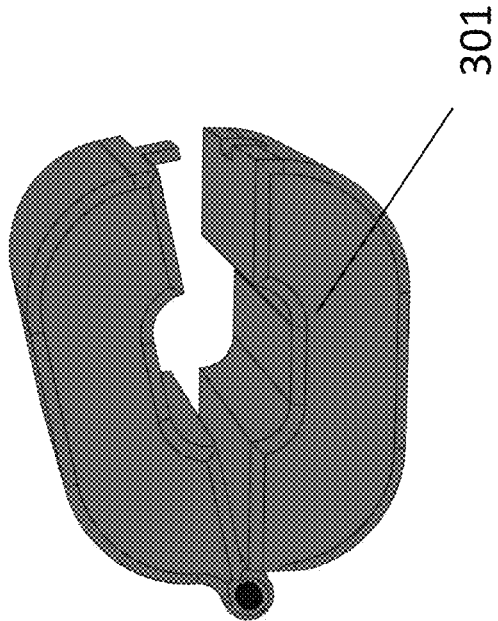
Figure 20B
Figure 20A

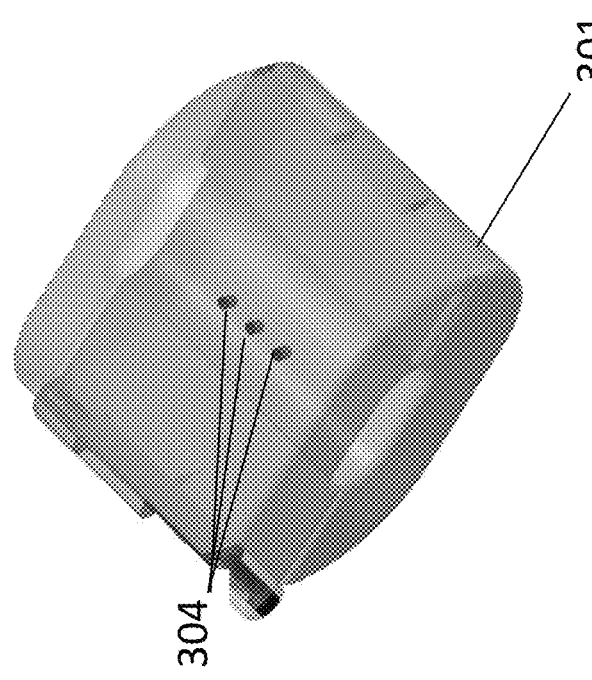
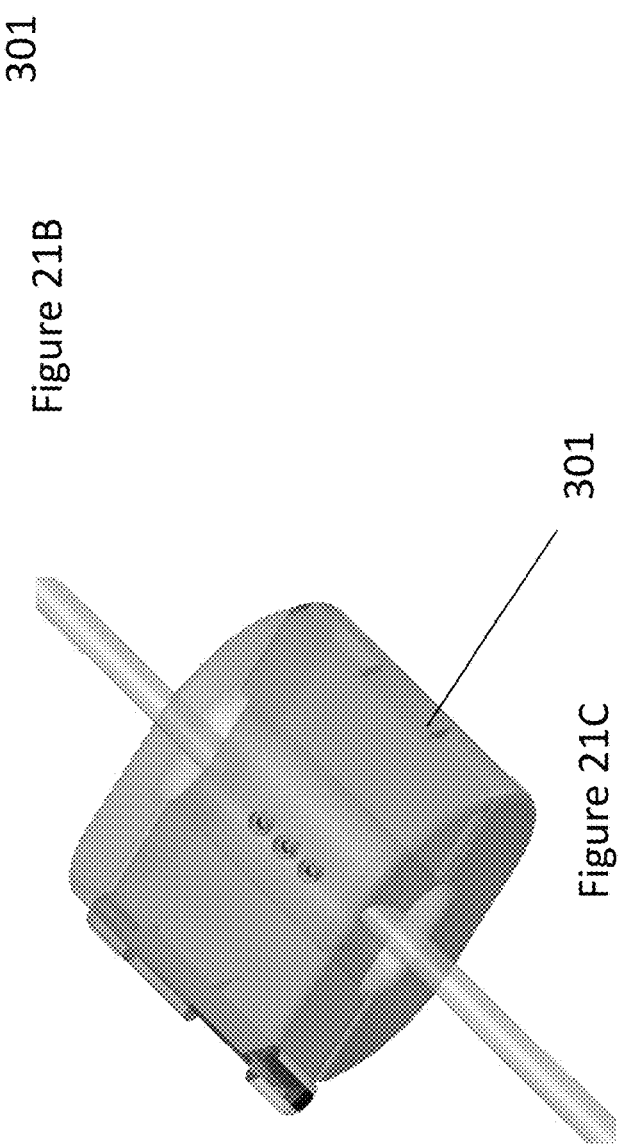
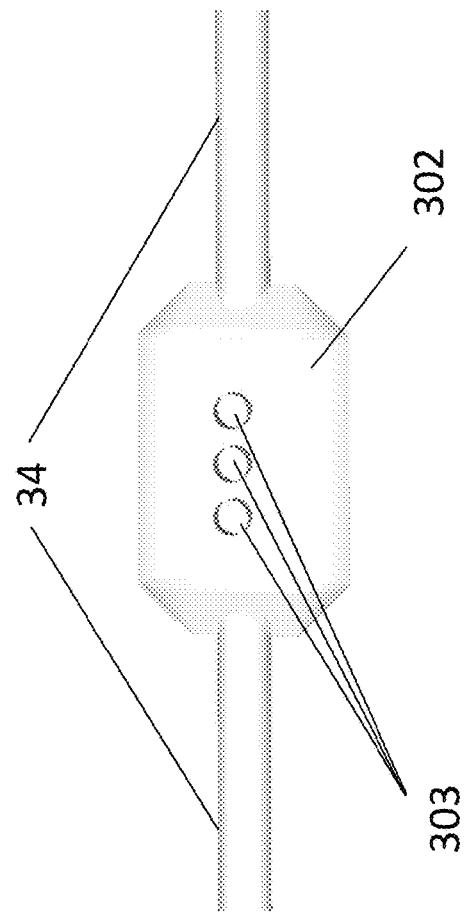
Figure 21B
Figure 21C
Figure 21A

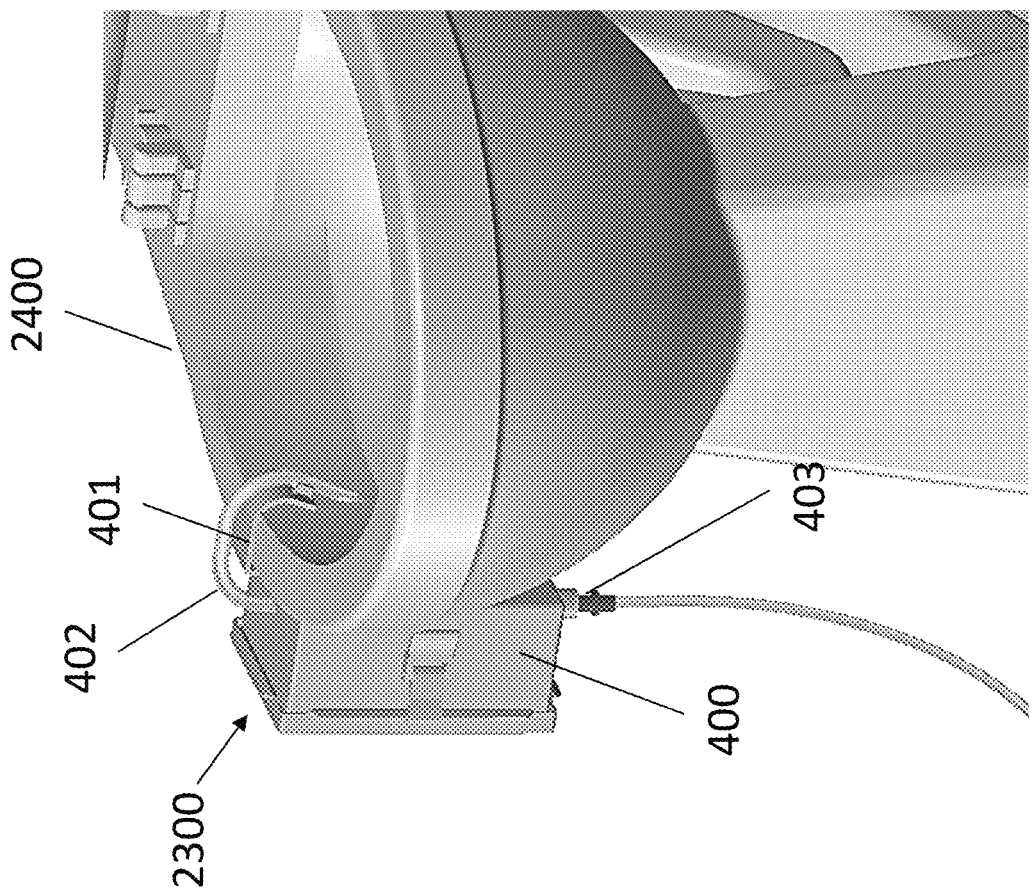
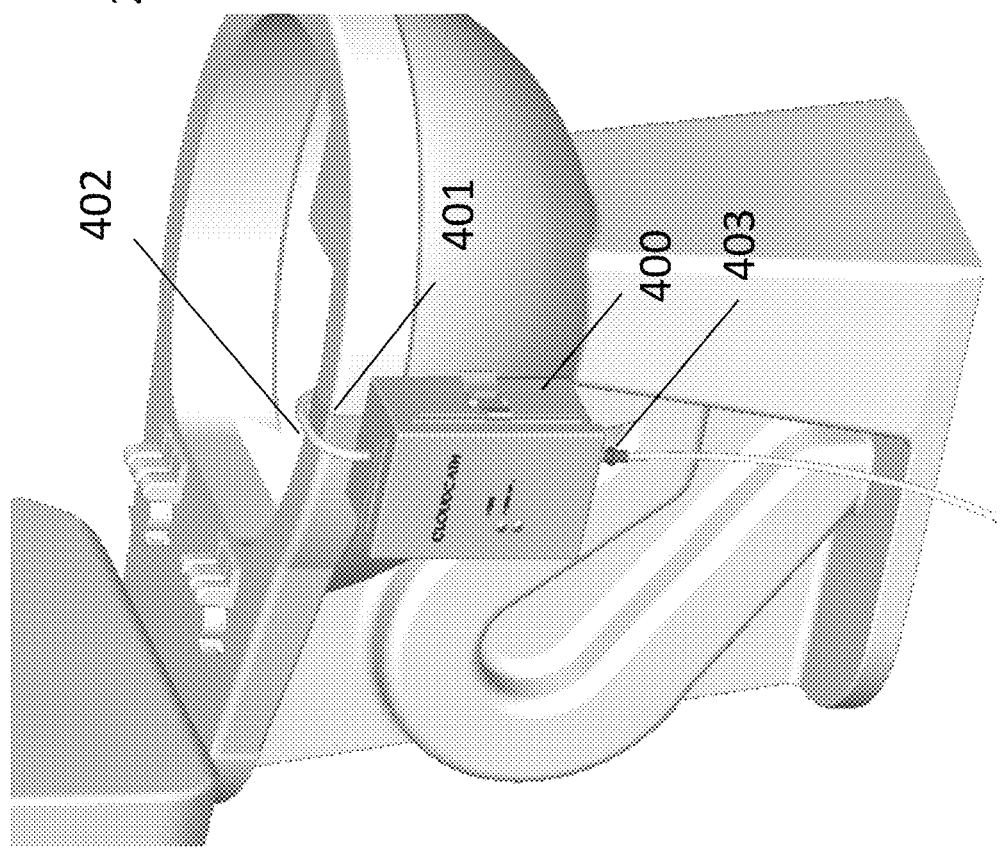
Figure 24B
Figure 24A

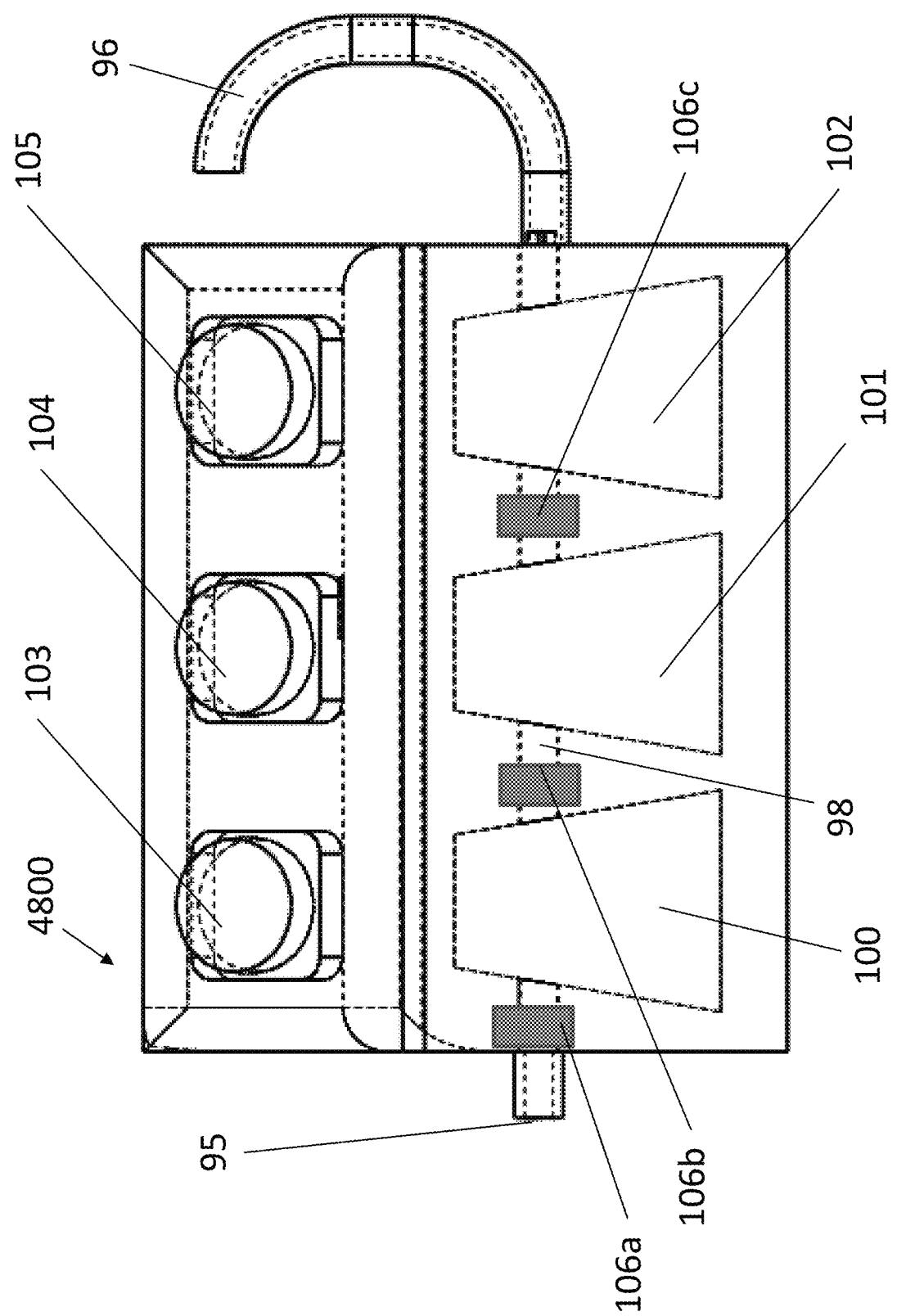

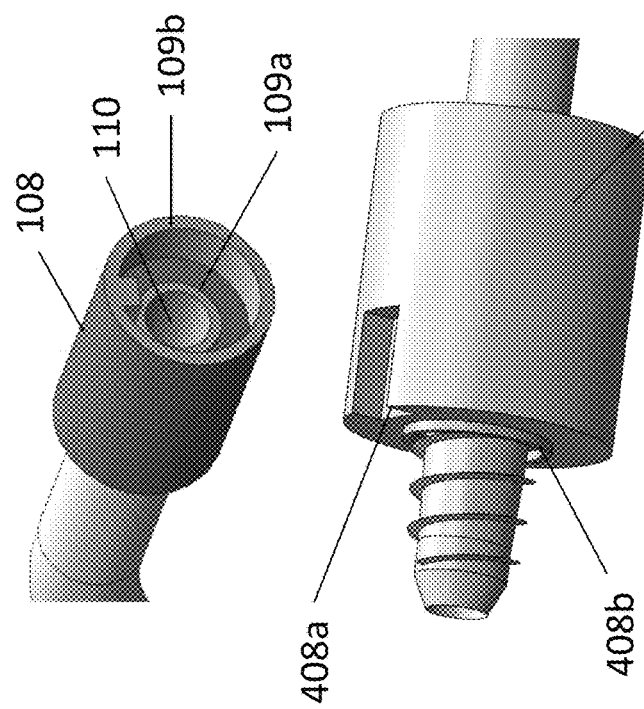
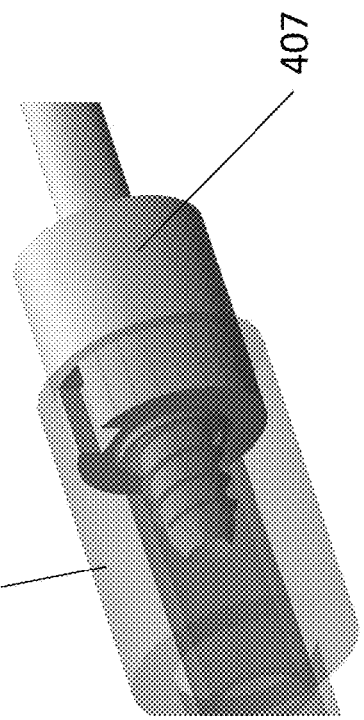
Figure 48C
Figure 48D
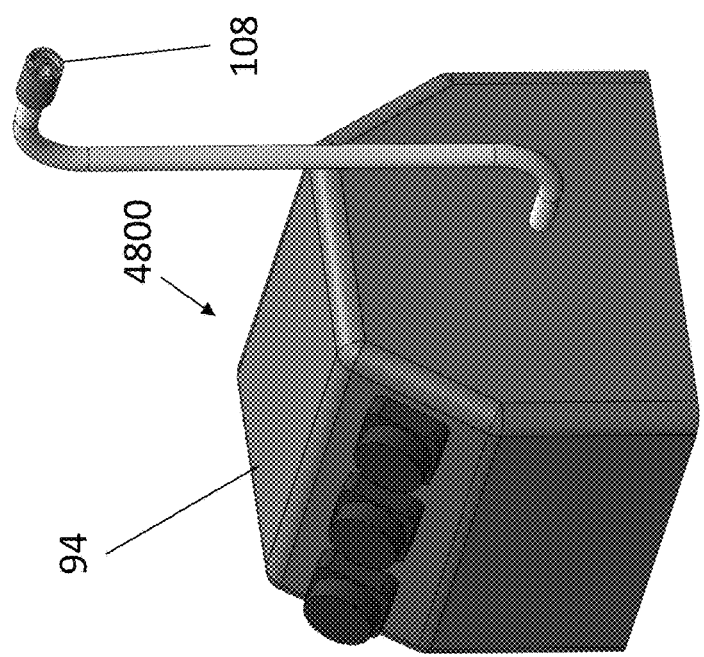
Figure 48B

Figure 60

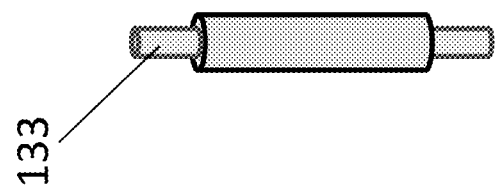
Figure 63C
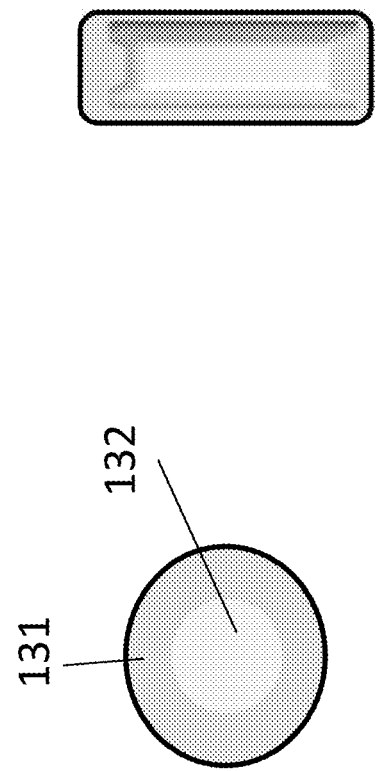
Figure 63B
Figure 63A

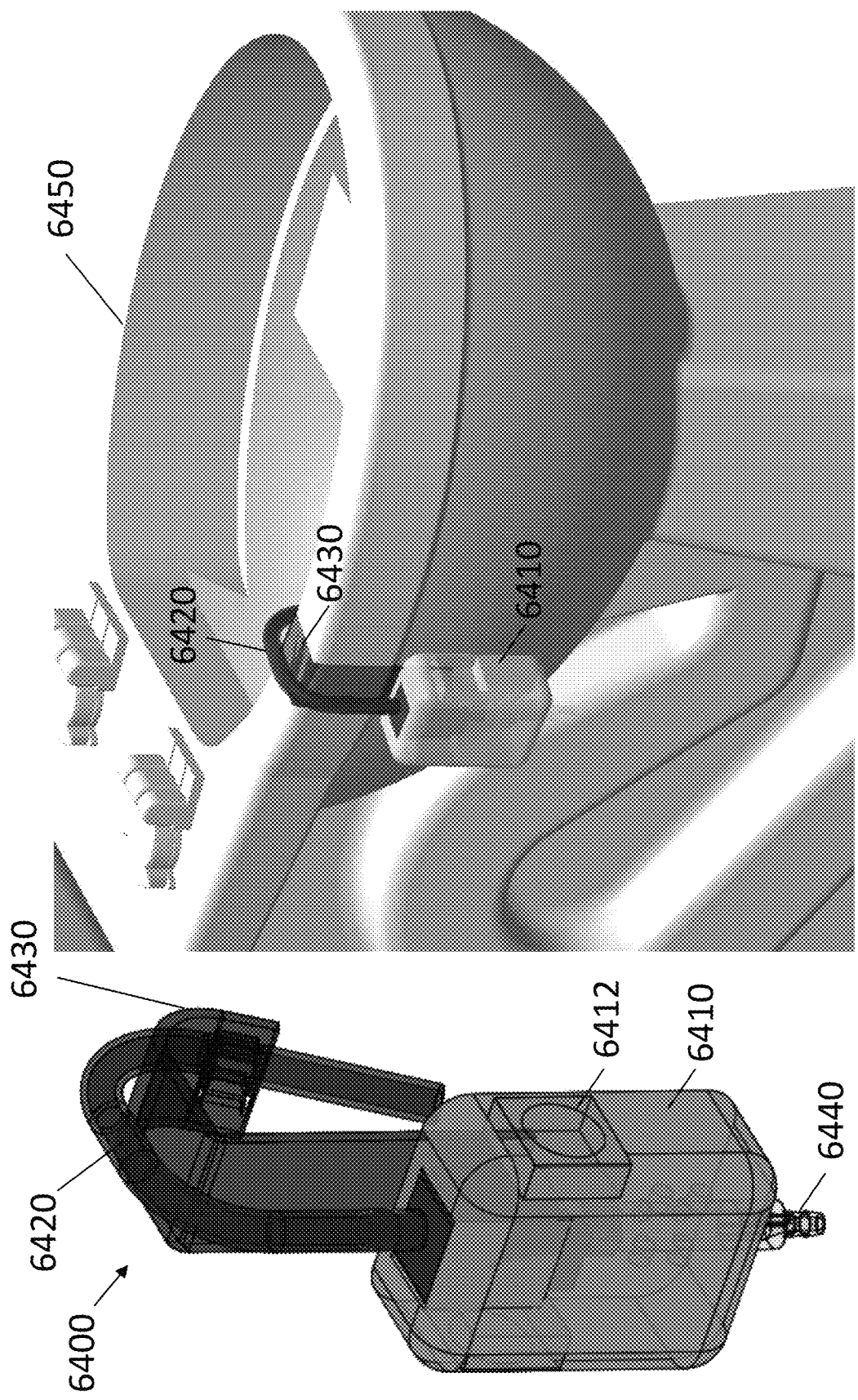

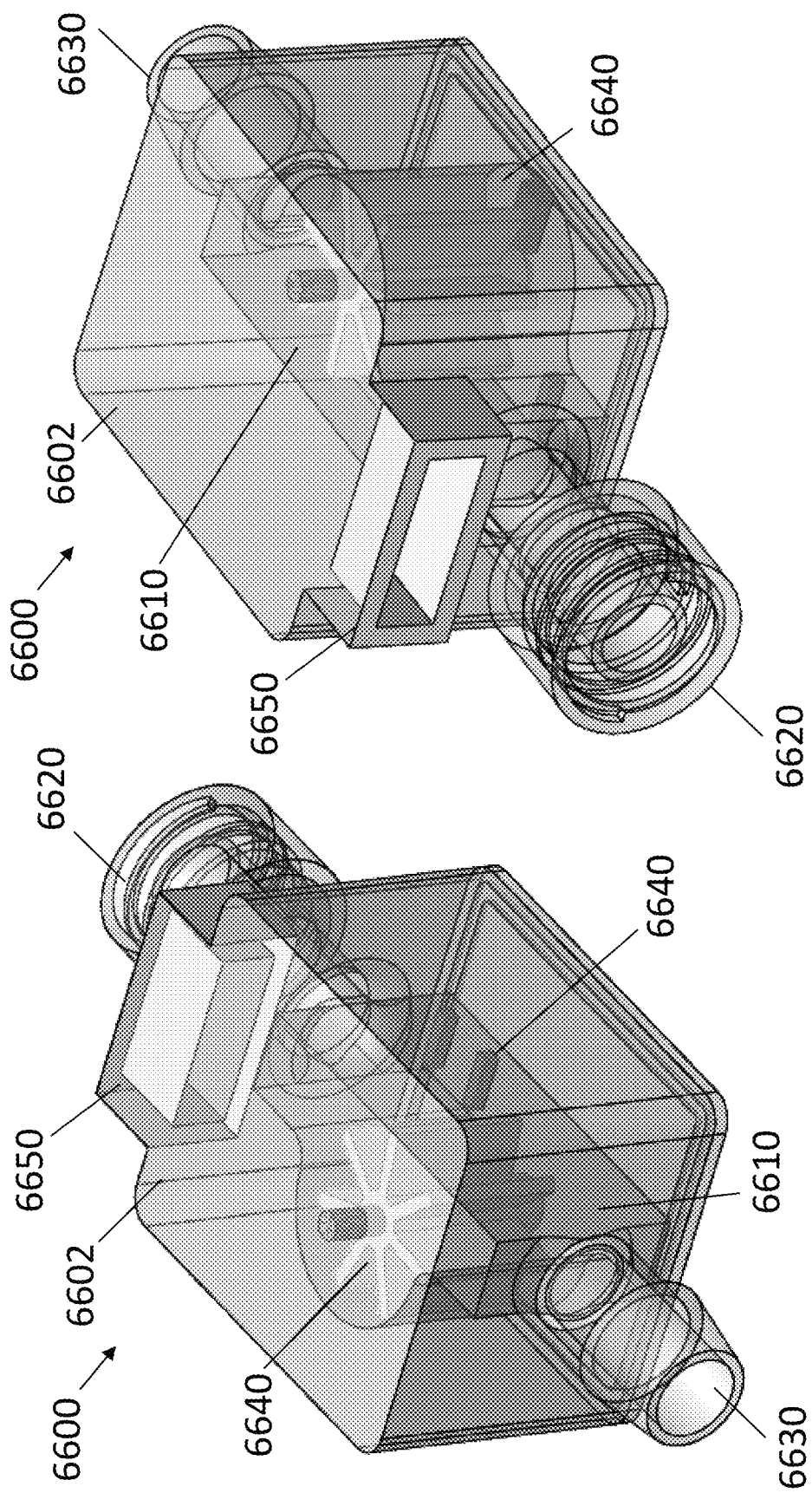

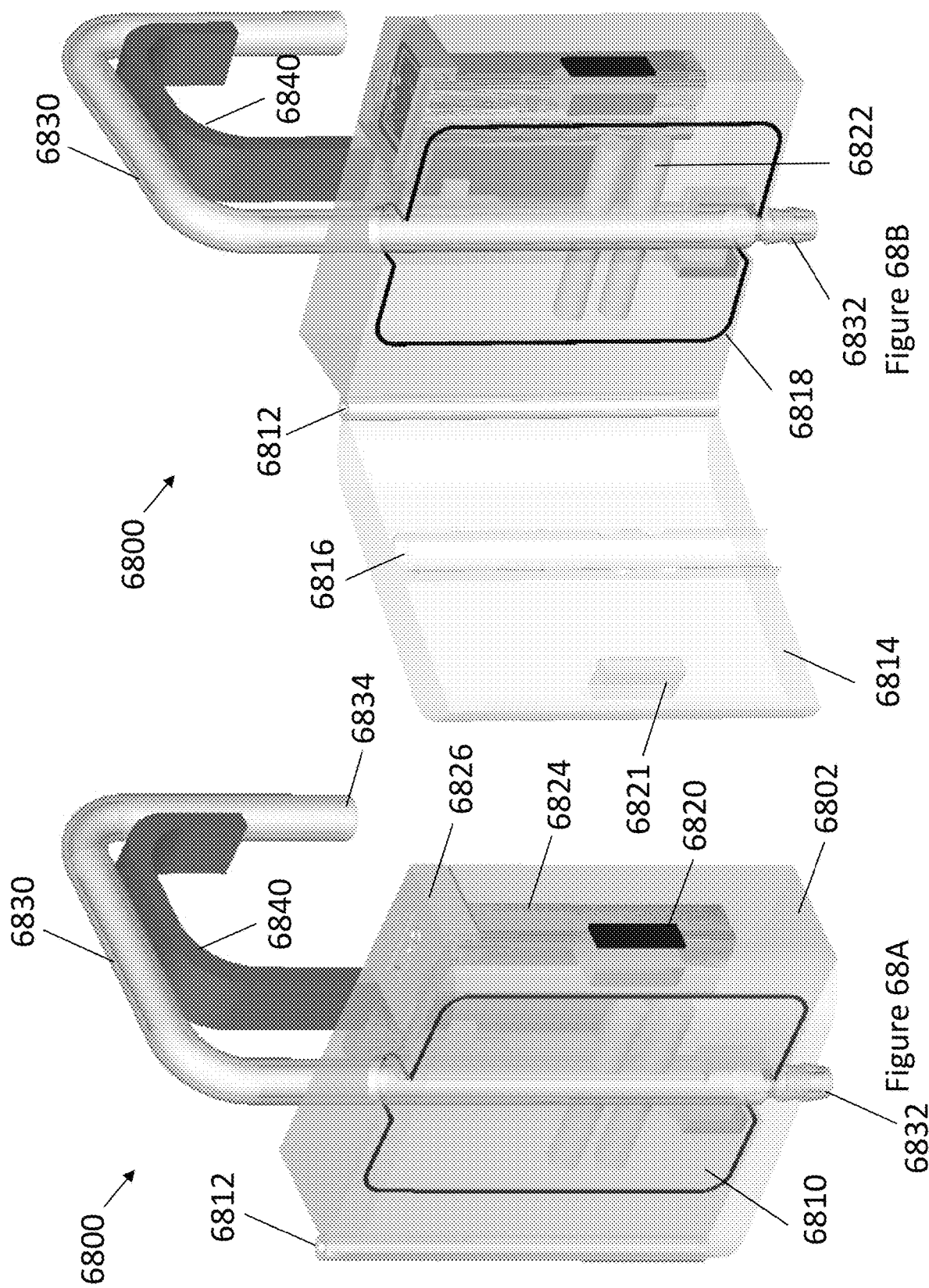

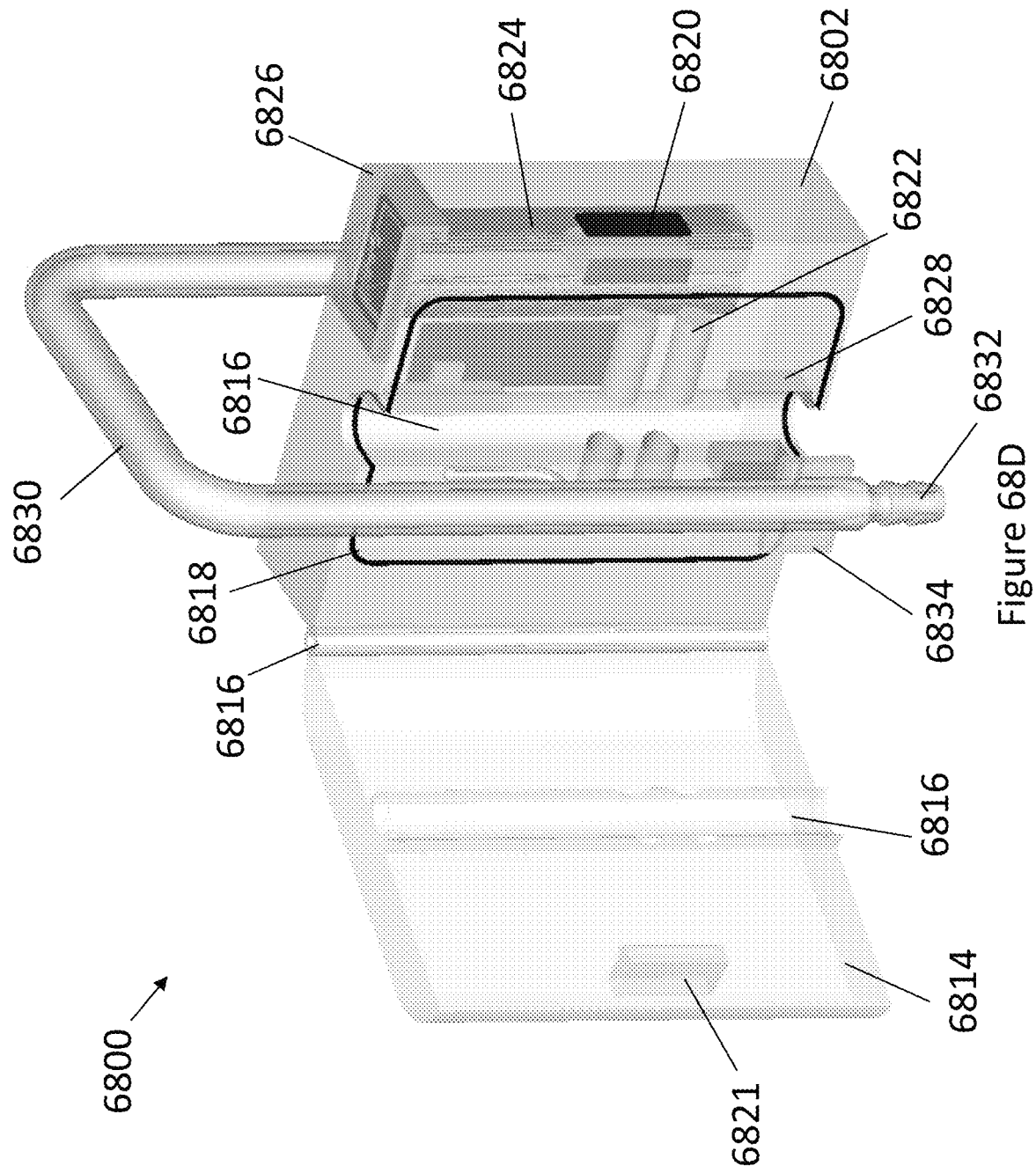

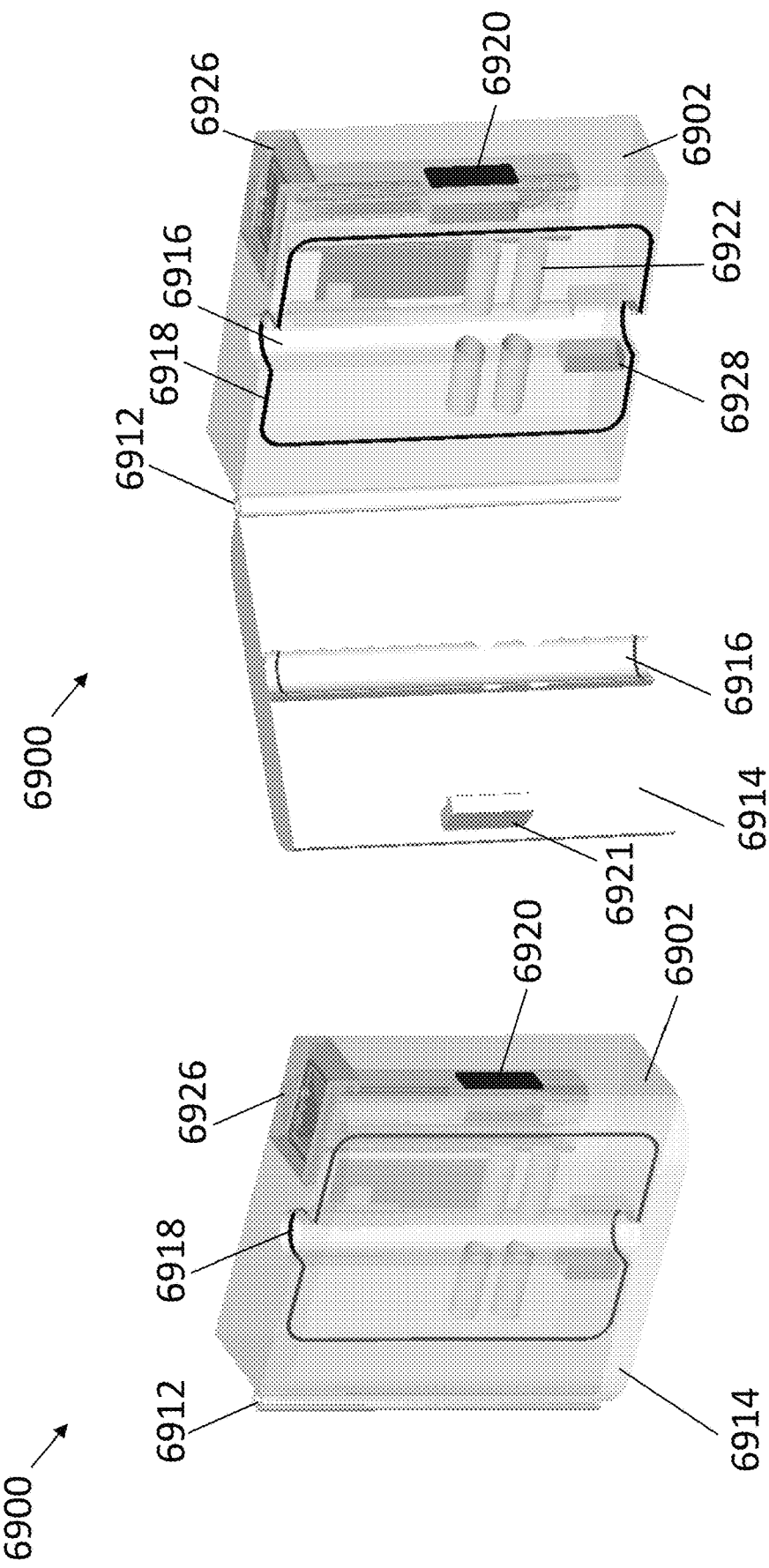

SENSOR MONITORING SYSTEM FOR IN-DWELLING CATHETER BASED TREATMENTS

CROSS-REFERENCE TO RELATED APPLICATIONS

This application claims priority to U.S. Provisional Application Ser. No. 62/599,619, filed on Dec. 15, 2017, and to U.S. Provisional Application Ser. No. 62/731,339, filed on Sep. 14, 2018, the content of each of which is hereby incorporated by reference in its entirety.

BACKGROUND

Several chronic diseases rely on patient self-administration or home caretaker administration of treatment in outpatient settings, including infusion into and/or drainage of fluids from the body via catheters or tubes. Examples of these treatments include but are not limited to permanent in-dwelling catheters for peritoneal dialysis in end stage renal disease patients, urinary catheters, catheters used with insulin pumps in diabetic patients, permanent or temporary feeding tubes, ascites drainage catheters, hydrocephalus drainage catheters, and a wide array of central venous line delivered treatment applications. For treatments that have an in-center alternative treatment modality, such as hemodialysis for peritoneal dialysis, the recent shift from a fee-for-service model to value-based bundled payment systems structure by CMS, has led to providers being financially incentivized to have as many of their patients as possible to be treated via outpatient modalities to avoid the high overhead associated with in-center treatment. In those outpatient treatment settings, there are high indirect costs shifted to providers, such as compliance assurance and infection-related hospitalizations. With peritoneal dialysis (PD), for example, dialysis providers pay more than $200 MM annually in salaries for outpatient PD nurses and more than $1Bn annually in infection related hospitalizations. Patients currently visit dialysis clinics 1-3 times a month on average with the main purpose of the visits being a visual inspection for originating infections, compliance assurance via patient manual recorded data or computer memory cards with records of night cycler collected data for continuous cycling peritoneal dialysis patients, and treatment efficacy monitoring via blood draws. Therefore, additional devices, systems, and methods for monitoring patient complications such as infection, catheter blockages, and ultrafiltration failure may be desirable.

SUMMARY

A sensor monitoring system is provided that may be used with existing catheters to monitor the infusion and drainage of any solution into the human body. The system may be used, for example, with in-dwelling catheters for peritoneal dialysis in end stage renal disease (ESRD) patients, urinary catheters, hydrocephalus shunts, ascites drainage catheters, insulin pumps in diabetic patients, feeding tubes, central venous line catheters, and the like. The sensor monitoring system includes one or more fluid pathways for infusing into and/or draining solutions out of the catheter, and one or more sensors to monitor the fluid and/or the patient (e.g., at an area adjacent to a catheter exit site). The sensor monitoring system transmits the patient monitoring data to a database, which may, for example, allow data storage, processing, and/or access through graphical user interfaces to patients and providers via device applications or browser-based web access portals.

One variation of the system includes devices and methods for monitoring dialysis therapy relating to a) patient compliance to prescribed dialysis therapy, b) dialysate solution ultrafiltration (UF) efficacy, and/or c) dialysis-related complications such as infection and/or catheter blockages. The system provides an array of sensors with a multitude of sensing mechanisms contained in a housing and fluidically connected to the dialysate solution. One or more patient parameters or signals are monitored, and in some variations, a combination of different signals and/or signals over time are generated from the sensor array and reported or analyzed to determine patient status.

As described in further detail below, the system may be used in an ambulatory or home-based setting as a first line of defense for providers to continuously monitor for the earliest signs of complications, including but not limited to infections, catheter leakages, and catheter blockages. Patient compliance with the prescribed treatment may be tracked and communicated to the patient and/or providers and the treatment adequacy/efficacy may also be assessed to indicate whether the body is responding to the treatment. These systems may permit an increase in the number of patients that each provider is assigned and may reduce the number of clinic visits, which may provide substantial cost reduction value propositions for outpatient management overhead reduction. In addition, early infection detection may allow capture of originating infections in a stage where it is treatable via an antibiotic course rather than escalation to a hospitalization stay. Once antibiotic therapy is initiated, the efficacy of the antibiotic treatment may also be monitored with the system.

The one or more patient parameters may be wirelessly transmitted through secure protocols to a database which stores and processes the data. A user interface for the patient allows retrieval of the database information and additional inputs from the patient that are stored in the database. A user interface for the provider allows remote monitoring of one or more patients through a visual interface displaying the monitored data, and a system of alerts, which can provide updates or indicate deviations in the patient's monitored data (e.g., decreased analyte levels, decreased patient physical activity, decreased pH value, increased body core temperature), and/or diagnosis of clinical outcomes (e.g., patient infection, catheter leakage, catheter blockage, patient non-compliance to therapy, decrease in treatment efficacy, etc.), for example. A provider user interface may also allow input of patient vital sign measurements, test results, and clinical events such as an acute infection to track the history of patient care and provide data for regression analysis, such as correlation of sensor-based data and infection complications.

In one variation, the system monitors patients with end-stage renal disease that are prescribed peritoneal dialysis. In this variation, a patient monitoring device comprises flow sensors connected to the patient's dialysis catheter. The flow sensor may be used to measure the fill volume (FV) of infused dialysate solution infused through the catheter and/or the drain volume (DV) of waste dialysate solution exiting the catheter to determine the FV/DV ratio. With the DV measurement alone measured from the sensors, the prescribed FV value may be input by the patient or provider, and thus the FV/DV ratio can also be calculated. After the initial ultrafiltration (UF) stabilization period, the FV/DV ratio baseline value (e.g., average, median, range, standard deviation) for the patient is established and provides a correlation metric to the ultrafiltration efficacy. As the patient is monitored, deviations to the FV/DV ratio from baseline beyond an established level (e.g., outside of one standard deviation) can trigger alerts to the provider. The provider can then log into the browser-based web portal or other software to review the recent data in the context of the historical data and adjust the dialysate therapy (e.g., dialysis solution type, infusion volume, and number of daily cycles), or potentially switch the patient to hemodialysis treatment if the patient reaches low levels of UF deeming them medically ineligible to receive peritoneal dialysis treatments.

In another example for peritoneal dialysis patients, in which the patient monitoring device is connected to the patient dialysis catheter, a combination of one or more of temperature, optical scatter/absorption of fluid, conductivity, flow, and pH sensors can be used to detect infection in patients. The multitude of sensors can detect the varied biological expressions of infection. Various sensor measurements can be used to trigger alerts to the provider regarding potential infection. For example, alerts may be triggered by an elevated temperature of the drainage dialysate solution beyond a standard biological range, increased optical scatter/absorption of the drainage dialysate solution (with or without normalizing to the drain volume or dwell time data from the flow sensor) from baseline values, increased variance of the drainage dialysate solution from baseline values, and/or changes in the conductivity of the drainage dialysate solution and/or changes in the FV/DV ratio. The provider can, in some variations, log into the browser-based web portal to review the recent data in the context of the historical data, initiate infection treatment, and monitor treatment adequacy.

For patients on peritoneal dialysis, the system can utilize a multitude of sensors including, but not limited to, flow, temperature, optical scatter/absorption, pressure, pH, conductivity, accelerometer, and gyroscopes to provide remote monitoring of a) dialysis-related complications (e.g., peritonitis, catheter obstruction, catheter leakage, hernia incidence), b) patient compliance to the prescribed dialysis therapy, and c) ultrafiltration adequacy of the dialysis therapy. Remote monitoring gives providers and patients more cost-effective and convenient dialysis treatment.

Another potential benefit of the monitoring system is to enable care providers to monitor patients more frequently than what may be practical through solely in-person clinic visits. The frequent monitoring of patients allows for providers to immediately address complications and/or poor treatment efficacy before problems exacerbate. For example, infections, when detected early, can be treated with an antibiotic regimen that, early in the infection onset, is much more effective and can therefore prevent patient hospitalization when detected late. Infection resolution can be monitored upon initiation of the antibiotic treatment. In another example, when treatment efficacy is poor, the prescribed medical therapy (e.g., drug, dosage, frequency) can be updated immediately.

Another potential advantage of the monitoring system is to provide additional data for the provider to use in the diagnosis of complications and determine optimal treatment options. Current standard of care often relies on a combination of patient visual appearance, blood tests, and vital measurements. The data provided from the monitoring system can supplement the traditional data sets and provide additional insights into patient status, and account for a patient's historical (e.g., baseline) status. The system can also aggregate data over a period of time in a manner that allows for data trending visualization.

It should be appreciated that the systems and methods can be used in a variety of different dialysis therapies to treat kidney failure. Dialysis therapy can include and encompass any and all forms of therapies that utilize fluids (e.g., patient's blood, dialysate) to remove waste, toxins and excess water from the patient. Such therapies include, for example, hemodialysis, hemofiltration, hemodiafiltration and peritoneal dialysis, including automated peritoneal dialysis, continuous ambulatory peritoneal dialysis, and continuous flow peritoneal dialysis. Such therapies can also include, where applicable, both intermittent therapies and continuous therapies used for continuous renal replacement therapy. Patients treated with dialysis therapies may include patients with chronic renal failure, as well as those with acute renal failure, whether resulting from renal or non-renal disease.

In one variation, a method of detecting infection of a patient includes the steps of receiving patient fluid through a fluid conduit, measuring an optical characteristic of the patient fluid at two or more wavelength ranges, estimating a leukocyte concentration based at least in part on the optical characteristic measurement at the two or more wavelength ranges, and detecting an infection state of the patient based at least in part on the estimated leukocyte concentration.

In some variations, the optical characteristic comprises one or more of optical scatter and absorption. In some variations, the optical characteristic may be measured at a first wavelength range corresponds to a total particle concentration of the patient fluid and the optical characteristic may be measured at a second wavelength range corresponding to a leukocyte concentration of the patient fluid. The first wavelength range may be different from the second wavelength range. In some variations, the first wavelength range is between about 700 nm and about 1 mm and the second wavelength range is between about 260 nm and about 550 nm.

In some variations, measuring the optical characteristic at a first wavelength range corresponds to a total particle concentration of the patient fluid and measuring the optical characteristic at a second wavelength range corresponds to a non-leukocyte particle concentration of the patient fluid. The first wavelength range may be different from the second wavelength range. In some variations, homogeneity of the patient fluid may be measured using the sensor. A set of the optical characteristic measurements may be excluded from the leukocyte concentration estimation based at least in part on the measured homogeneity.

In some variations, dialysate fluid may be received through the fluid conduit. The optical characteristic of the dialysate fluid may be measured using the sensor. The dialysate fluid may be infused in the patient and the patient fluid may be drained from the patient. The estimated leukocyte concentration may be based at least in part on the optical characteristic measurement of the dialysate fluid. In some variations, an optical characteristic differential between the patient fluid and the dialysate fluid may be estimated. The infection state of the patient may be updated based at least in part on the optical characteristic differential.

In some variations, one or more of a flow rate and total flow volume of the patient fluid may be measured using a flow sensor coupled to the fluid conduit. The optical characteristic measurement may be normalized based on one or more of the flow rate and total flow volume measurement. In some of these variations, one or more of an obstruction and flow direction may be detected based at least in part on the flow rate measurement. In some of these variations, one or more of an infusion volume, drainage volume, infusion time, drainage time, and dwell time may be estimated based at least in part on the flow rate measurement. One or more of a dialysis efficiency and dialysis adequacy may be estimated based at least in part on the estimated infusion volume, drainage volume, and dwell time. In some variations, one or more of an infusion state, dwell state, and drainage state of the patient fluid may be detected without user input.

In some variations, the method may comprise one or more of the steps of measuring pH of the patient fluid using a pH sensor, wherein the detected infection state is based at least in part on the pH measurement, measuring a lactate concentration of the patient fluid using a lactate sensor, wherein the detected infection state is based at least in part on the lactate concentration measurement, counting cells of the patient fluid using a cell counter, wherein the detected infection state is based at least in part on the cell count, measuring leukocyte esterase of the patient fluid using a test strip, wherein the detected infection state is based at least in part on the leukocyte esterase measurement, measuring a chemiluminescence of the patient fluid using a chemiluminescence sensor, wherein the detected infection state is based at least in part on the chemiluminescence measurement, measuring a color of a patient skin using an image sensor, wherein the detected infection state is based at least in part on the color measurement, measuring a conductivity of the patient fluid using a conductivity sensor, estimating a solute concentration of the patient fluid based at least in part on the conductivity measurement, measuring urea of the patient fluid using an electrochemical sensor, estimating urea concentration of the patient fluid based at least in part on the urea measurement and at least one of the conductivity and a flow rate measurement, measuring creatinine of the patient fluid using an electrochemical sensor, estimating a creatinine concentration of the patient fluid based at least in part on the creatinine measurement and a flow volume measurement, measuring glucose of the patient fluid using a glucose sensor, and estimating a glucose concentration of the patient fluid based at least in part on the glucose measurement and at least one of the conductivity and the flow volume measurement.

In some variations, at least one alert may be output comprising one or more of the infection state of the patient, patient compliance with a prescribed therapy, therapy efficacy, sensor calibration, fluid conduit maintenance, and sensor data. In some of these variations, an alert sensitivity may be modified based on one or more of a set of patient clinical events and a patient profile.

In some variations, a prompt may be output to input patient data in response to detecting a positive infection state of the patient. The input patient data may be received. The detected infection state may be classified as a false positive based at least in part on the input patient data. In some variations, an alert corresponding to fluid conduit obstruction may be output based at least in part on a pressure measurement and an acceleration measurement. In some variations, the infection state of the patient may be transmitted to a health care provider. A prescription for a therapeutic agent may be received from the health care provider. The therapeutic agent may be dispensed without user input.

In some variations, a sample of the patient fluid may be collected in a sample container releasably engaged to the fluid conduit based at least in part on the detected infection state of the patient. The sample container may be disengaged from the fluid conduit. In some variations, a sample container alert may be output to one or more of the patient, a health care provider, and a courier based at least in part on the infection state and a location of the sample container. In some variations, the sensor may be coupled between a drainage line and a drainage vessel or the sensor may be coupled between an infusing line and an infusing dialysate vessel.

In some variations, a patient monitoring device may comprise an optical sensor arrangement comprising at least one emitter and at least one detector. The emitter may be configured to transmit light at one or more wavelength ranges through a patient fluid flowing through a fluid conduit. The at least one detector may be configured to receive the light transmitted through the patient fluid and generate signal data based on the received light. A controller may be configured to estimate total particle concentration and leukocyte concentration using the signal data. In some variations, the device may comprise a housing enclosing the optical sensor arrangement. The fluid conduit may be configured to releasably engage to the housing. In some of these variations, the housing may be configured to transition between an open configuration with an exposed interior cavity and a closed configuration with an enclosed interior cavity.

In some variations, at least one non-fluid-contact sensor comprises one or more of a pressure sensor, image sensor, accelerometer, gyroscope, temperature sensor, and magnetic field transducer. In some variations, the fluid conduit comprises at least one transparent portion that is substantially transparent to at least one of ultraviolet light, visible light, and infrared radiation. In some variations, the fluid path comprises an inlet configured to couple to at least one of an in-dwelling catheter and a drain line for peritoneal dialysis, and an outlet configured to open towards a drainage vessel.

In some variations, one or more portions of the fluid conduit may be composed of one or more of acrylic, polycarbonate, cyclic olefin copolymers (COC), polystyrene, acrylonitrile butadiene styrene (ABS), polyethylene glycol-coated silicone, zwitterionic coated polyurethane, polyethylene oxide-coated polyvinyl chloride, and polyamphiphilic silicone. In some of these variations, the fluid conduit is a first fluid conduit, and a second closed-end fluid conduit branches from the first fluid conduit. A flow sensor may be further configured to measure a fluid level of the second fluid conduit. In some variations, the fluid conduit may comprise a ball, and a flow sensor configured to measure the ball. In some variations, the fluid conduit may comprise at least one fluid-contact sensor comprising one or more of a flow sensor, conductivity sensor, temperature sensor, pH sensor, lactate sensor, test strip, chemiluminescence sensor, electrochemical sensor, and glucose sensor. In some variations, one or more portions of the fluid conduit are composed of a material susceptible to bacteria fouling. In some variations, a mount may be configured to releasably attach the housing to a drainage vessel.

In some variations, the housing may comprise a therapeutic agent container configured to store a therapeutic agent. The controller may be configured to receive a prescription from a health care provider and release the therapeutic agent based on the received prescription. Release of the therapeutic agent may comprise one or more of unlocking the therapeutic agent container and dispensing the therapeutic agent into the fluid conduit. In some variations, the controller may be configured to open a valve to fill a sample container with the patient fluid upon detecting a positive infection state of the patient. In some variations, a mount may comprise an adhesive layer comprising one or more of a silicone adhesive and an acrylate adhesive. In some variations, one or more of a temperature sensor and skin color sensor may be located at a mounting surface.

In some variations, a patient monitoring device may comprise a housing configured to releasably engage a fluid conduit. At least one sensor may be configured to measure at least one characteristic of fluid flow through the fluid conduit. A controller may be configured to generate patient data comprising an infection state of the patient based at least in part on the at least one characteristic. In some of these variations, the characteristic may comprise one or more of optical scatter, absorption, color, flow rate, conductivity, temperature, pH, lactate concentration, cell count, leukocyte esterase concentration, chemiluminescence, glucose concentration, urea concentration, and creatinine concentration.

In some variations, the housing may comprise a hinge and the housing is configured to surround at least a portion of the fluid conduit. In some variations, the fluid conduit may comprise a stiff curved end configured to releasably attach the fluid conduit to a drainage vessel such that the housing is separated from the drainage vessel. In some variations, the at least one sensor is configured to clamp over a portion of the fluid conduit transparent to at least one of ultraviolet light, visible light, and infrared radiation. In some variations, the at least one sensor is a fluid-contact sensor. In some variations, the device may comprise a limited-use sensor configured to releasably engage one or more of the fluid conduit and the housing. In some of these variations, the controller may be configured to detect an expiration of the limited-use sensor based at least in part on the measured flow rate.

In some variations, the fluid conduit may be coupled to one or more of an in-dwelling catheter for peritoneal dialysis, a urinary catheter, hydrocephalus shunt, percutaneous abscess drainage catheter, ascites drainage catheter, insulin pump, feeding tube, central venous line catheter, tunneled catheter, and implanted access port. In some variations, a docking station may comprise at least one fluid chamber, a pump coupled to the at least one fluid chamber, a fluid port coupled to the at least one fluid chamber, an engagement feature mateable with a patient monitoring device, an engagement sensor configured to generate a sensor signal when the engagement feature is mated with the patient monitoring device, and a controller configured to circulate a fluid through the patient monitoring device using the fluid pump based at least in part on the sensor signal.

In some variations, the fluid is circulated at one or more of a predetermined flow rate, conductivity, optical scatter, absorption, and temperature, and the controller is configured to calibrate at least one sensor of the patient monitoring device using the circulated fluid. In some variations, the at least one fluid chamber comprises a first chamber and a second chamber, the first chamber fluidically separated from a second chamber. In some variations, the docking station comprises a UV light source configured to optically couple to a fluid conduit of the patient monitoring device. The controller may be configured to emit UV light into the fluid conduit using the UV light source. In some variations, the engagement feature may comprise a fluid connector and an electrical connector. The fluid connector may be configured to mate with a fluid conduit of the patient monitoring device. The electrical connector may be configured to mate with one or more of an electronic communication device and a power source of the patient monitoring device.

In some variations, at least one sensor may comprise one or more of a flow sensor, conductivity sensor, image sensor, pressure sensor, accelerometer, and magnetic field transducer. In some variations, the controller may be configured to receive, store, and transmit one or more of sensor data, calibration data, patient data, and device data of the patient monitoring device. In some variations, the docking station may comprise a battery charging port configured to power a battery of the patient monitoring device.

In some variations, a method of monitoring infection of a patient may include the steps of measuring at least one characteristic of a patient fluid over a first time period and a second time period after the first time period. The at least one characteristic may comprise one or more of optical scatter, optical absorption, flow rate, conductivity, temperature, pH, lactate concentration, cell count, leukocyte esterase concentration, chemiluminescence, glucose concentration, urea concentration, and creatinine concentration. Patient data comprising a baseline range of the at least one characteristic may be generated over the first time period. A patient state based at least in part on the baseline range and the measured characteristic may be monitored over the second time period.

In some variations, a set of patient clinical events may be measured during the first time period and the second time period after the first time period. A relationship may be estimated between the set of patient clinical events and the at least one characteristic over the first time period. A patient state based at least in part on the estimated relationship and the measured characteristic may be monitored over the second time period. In some variations, an alert to a predetermined contact may be output when the measured characteristic over the second time period deviates from the baseline range.

In some variations, an alert sensitivity may be modified based on one or more of a number of deviations from the baseline range and a number of patient clinical events. In some variations, the patient state may comprise one or more of an infection state of the patient, patient compliance with a prescribed therapy, therapy efficacy, device maintenance, sensor calibration, and sensor data. In some variations, a communication channel may be established between the patient and a health care professional in response to the alert corresponding to the patient being in a high risk condition.

BRIEF DESCRIPTION OF THE FIGURES

FIGS. 6A, 6C, 7A, and 7C are schematic top views and FIGS. 6B, 6D, 7B, and 7D are schematic cross-sectional views.

FIGS. 10A-10C illustrates top views of exemplary variations of an optical sensor system. FIG. 10A illustrates a top view of a sensor system. FIG. 10B illustrates a variation of a sensor system including a fluid conduit. FIG. 10C illustrates a variation of an optical reader clamped to a fluid conduit.

FIGS. 20A and 20B illustrate respective side and perspective views of an exemplary variation of a patient monitoring device configured to clamp to a fluid conduit such as a connector tube.

FIGS. 21A, 21B, and 21C illustrate respective side and perspective views of another exemplary variation of a patient monitoring device configured to clamp to a connector tube.

FIGS. 24A and 24B illustrate perspective views of an exemplary variation of a patient monitoring device attached to a toilet.

FIG. 48A illustrates a schematic diagram of an exemplary variation of a docking station. FIG. 48B illustrates a perspective view of the docking station depicted in FIG. 48A. FIGS. 48C and 48D illustrate perspective views of exemplary connectors of the docking station depicted in FIG. 48B.

FIG. 60 illustrates an exemplary graphical user interface for patient monitoring by a provider.

FIGS. 63A, 63B, and 63C illustrate various views of exemplary variations of a subcutaneous sensor variation device.

FIG. 64A is a perspective view of an exemplary variation of a patient monitoring device. FIG. 64B is a perspective view of the patient monitoring device depicted in FIG. 64A attached to a toilet.

FIGS. 66A and 66B are perspective views of an exemplary variation of a disposable component of a patient monitoring device.

FIGS. 68A, 68B, 68C, and 68D are perspective views of an exemplary variation of a patient monitoring device.

FIGS. 69A, 69B, 69C, and 69D are perspective views of an exemplary variation of a durable component of a patient monitoring device.

DETAILED DESCRIPTION

Figure 1A:
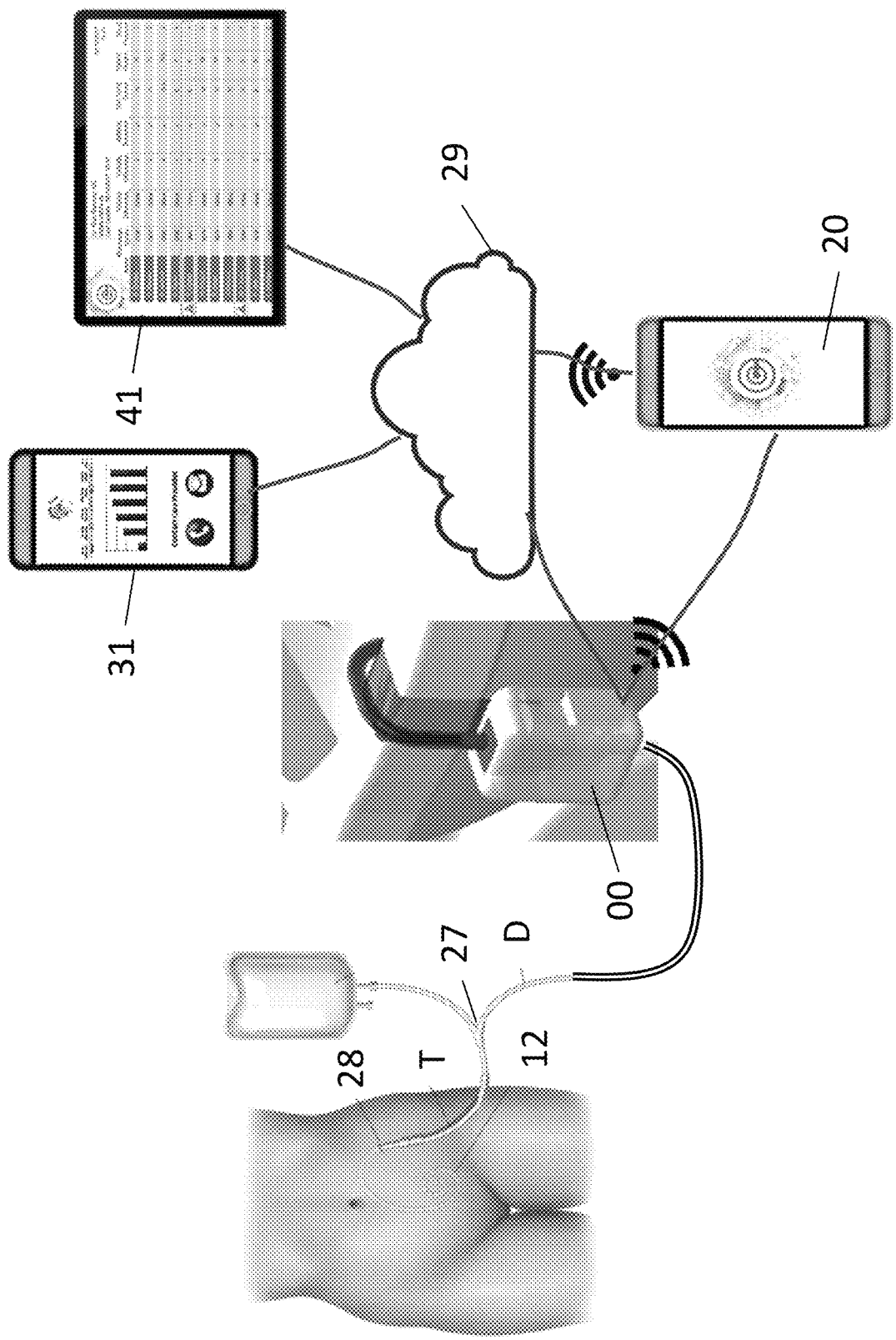
FIG. 1A schematically illustrates an exemplary variation of a monitoring system.

The various examples herein relate to systems used to collect, measure, analyze, transmit, and/or store patient data related to the infused and/or drained solutions into the human body via catheters for the monitoring of various therapies. The systems described herein may comprise a patient monitoring device with one or more sensors connected in-between, onto, and/or within a patient's catheter, connector tubing, and the infusing solution and/or draining solution. The patient monitoring device collects and may process the sensor data. The system may include an integrated or separate transmitter to receive and transmit the patient monitoring device data to one or more computing devices such as a mobile device and a database server. The system may include a database server that receives and/or processes the data. The system may include user interfaces that receive data from the database server, summarize the data visually, provides alerts to one or more stakeholders (e.g., users, providers, family, partners, caregivers), and/or allows users to input additional monitoring data.

In one method of use, the system monitors patient compliance to prescribed therapy, patient complications, and/or treatment efficacy. Initially, the provider may set up the patient in the monitoring system by inputting the information via one or more applications on one or more computing devices, mobile devices, tablet devices, and/or browser-based web access portals. Information input could include the assigned patient monitoring device identification number, the assigned transmitting computing device identification number, the patient name, date of birth, initial vital signs (e.g., blood pressure, temperature, weight, oxygenation level, etc.), and/or the details of the prescribed therapy including drug type, dosage, and durations of each use cycle.

The patient may connect the patient monitoring device to their catheter or connector tubing. Patients may prepare the patient monitoring device by first assembling a disposable component of the housing to the durable component of the patient monitoring device. The patient could then charge the patient monitoring device by plugging a micro-USB cord into a power source and into a micro-USB port of the patient monitoring device. Additionally or alternatively, the patient monitoring device may be docked to a docking station that may be configured to charge a battery of the patient monitoring device, upload/download data to a memory of the patient monitoring device, clean and/or sterilize one or more components of the patient monitoring device (e.g., contact sensors, fluid conduit), and/or calibrate the patient monitoring device. To activate the system, the patient may hold a switch to turn the system on, indicated by an LED light on the patient monitoring device. The patient may pair the patient monitoring device with a separate computing device (e.g., tablet, smartphone) via Bluetooth connectivity by holding the switch on the patient monitoring device until a blue and red LED light flash, opening a unique application on the computing device for the system, finding the patient monitoring device on the computing device application, and entering a unique code provided (e.g., PIN, password, identifier). Once communication is established and the patient monitoring device is authenticated, the application confirms via a pop-up message for the patient to connect the patient monitoring device to the catheter.

In some variations, the patient monitoring device may be attached to a drain vessel (e.g., drain basin, toilet, sink, tub, waste bag, etc.) via a clip holder, hook, clamp, strap, adhesive, or other suitable mounting feature and/or device. Alternatively, patients may attach the patient monitoring device to their abdomen or other skin surface next to their catheter (e.g., via an adhesive backing, after removing a release layer from the adhesive backing). The patient may flush the patient monitoring device tubing with sterile saline by connecting a saline-filled syringe to the inlet tubing port and injecting the saline until all air is flushed out. The patient may connect the fluid connection fitting from the patient monitoring device to their catheter port or to the connector tubing. The patient may remove the syringe from the inlet tubing of the patient monitoring device.

During the prescribed durations, the patient may connect the opposite tube fitting from the patient monitoring device to the tubing line from the prescribed therapy (e.g., the dialysis tubing port for peritoneal dialysis patients, the intravenous drug tubing port for patients with PICC lines treating infection, etc.).

During use of the device, (e.g., at a frequency of around every 2-4 weeks), the patient may receive a push notification on the computing device tablet or text message on their mobile device to maintain/service the patient monitoring device. The service may require the patient to remove the patient monitoring device, detach the disposable component (e.g., fluid conduit, cartridge) of the housing, replace the disposable component of the housing with a new disposable component, charge the patient monitoring device, detach the hardware module connector from the catheter or tubing connectors, and flush the patient monitoring device fluid line with isopropanol for cleaning and disinfection.

In another variation, maintenance/service of the patient monitoring device may include the use of a docking system (e.g., docking station) to automate the cleaning, sterilization, data transfer, charging, and/or calibrating processes for the device. The docking system may be a separate hardware device that includes an inlet and outlet fluid conduit which may be configured to be in fluid communication with a fluid conduit of the patient monitoring device. At a predetermined interval, a user may disconnect the patient monitoring device from the catheter or tubing connectors, and then connect the patient monitoring device to the connections of the docking system. Once connected, the docking system may charge a power source, and/or pump various fluids to clean and sterilize one or more components of the patient monitoring device. While connected, the docking system may calibrate the sensors with fluid, such as a clear fluid having known optical scatter/absorption characteristics for calibrating one or more sensors (e.g., spectroscopy sensor, optical scatter/absorption sensor), and/or fluid of known temperature for calibrating a temperature sensor, and/or fluid pumped at a known flow rate to calibrate a flow sensor, and/or fluid with known conductivity to calibrate a conductivity sensor.

The patient monitoring device may communicate sensor data to one or more processing devices (e.g., computing devices) such as a tablet computer, docking station, mobile device, and the like, using a wireless protocol (e.g., Bluetooth). The processing devices may receive and process the data and may further transmit the data to a server (e.g., database) via a wired or wireless network connection. When using a docking system, additional communication methods may be used, such as a wired Ethernet connection, or Wi-Fi. The redundant communication on the docking system may be used to transmit data when communication using the patient monitoring device otherwise fails.

In some variations, the patient may be provided access to their sensor data and/or analysis via a graphical user interface of a computing device (e.g., tablet, mobile phone, laptop, PC). The system may also allow the patient to input additional data into the user interface such as weight, blood pressure, oxygen saturation, energy/fatigue level, feelings of wellness, fever, and pain. Some of these inputs may be required at a specified frequency and patients may be prompted to input the data at these specified frequencies via push notification and/or text message.

In some variations, a provider (e.g., health care professional, care provider) may be provided access to the patient monitoring data via a graphical user interface on one or more computing devices such as a browser-based web access portal. The provider may, for instance, log in to the browser-based web access portal via a personal computer. The provider could review all of the monitored data from one or more patients. The provider could additionally input lab test results, notes from patient appointments, patient therapy changes, patient infections and complications, and any other findings into the system.

The system may also provide alerts to the patient and/or provider. An alert for the patient may be generated as a reminder to initiate a step in their prescribed therapy or warn the patient in the case there are delays in administering prescribed therapy or skipped therapies. Additionally, alerts may be generated for the patient and provider when there are anomalies in the data, such as when a potential complication is likely (e.g., a blocked catheter, patient infection event), or when a patient has skipped multiple doses of their therapy. In some variations, one or more alerts may be provided to a predetermined group of predetermined contacts (e.g., family, partner, caregiver, health care provider) based on predetermined criteria such as non-compliance or detected infection. The group of contacts may be selected, for example, by the patient or a caregiver, and may receive alerts or other communications via one or more of a telephone call, email, text message, push notification on a mobile device, web portal, and the like. In some variations, data communication may be initiated at predetermined intervals such as during docking with a docking station and/or when an infection state is detected.

Patient Monitoring System Configurations

FIG. 1A depicts an exemplary variation of a monitoring system for patients on peritoneal dialysis therapy. The patient may have an in-dwelling patient catheter (12) that is connectable to a transfer tubing set (T) that enables introduction and dialysate solution (27) into and from the patient through the patient catheter (12), such as in a dialysate exchange. Generally, a patient monitoring device (00) may be fluidically connected to the in-dwelling patient catheter (12) (e.g., via the transfer tubing set) so as to receive dialysate solution (e.g., drained dialysate solution). For example, the patient monitoring device (00) may be coupled in-line with a drainage line (D), such as to receive dialysate from the patient and pass it onto a drainage vessel (e.g., toilet). The patient monitoring device (00) may include one or more sensors to measure one or more parameters of the dialysate solution. The sensor data may be analyzed, such as described herein, to monitor one or more patient conditions.

The patient monitoring device (00) may include a microcontroller that, via firmware, may control one or more sensors, receive the signal output from the sensors, and/or optionally analyze the data from the sensors. The patient monitoring device (00) may store the data locally on a memory chip, encrypt the data, and send the data to a transmitter module (20) (e.g., docking station, patient mobile device). The transmitter module may transmit the data via wireless network connectivity to a database server (29) and/or network and other/or devices. Additionally, or alternatively, the patient monitoring device (00) may include a transmitter module for transmitting data directly to the database server (2) and/or network and/or other devices.

The database server (29) may receive the transmitted data, decrypt the data, analyze the data via a processor, and/or store the data on memory chips. The database server (29) may also upload the processed data via a secured access system to user interfaces on a desktop and/or mobile device application (31), and/or browser-based web access portal (41), or other software. The database server may also generate alerts directly, or through third party services, to a set of users (e.g., patient, provider, family, partner, caregiver, etc.) in the form of text messages, push notifications, automated phone calls, e-mails, and the like.

The user interface systems may include one or more browser-based web access portals (41) and/or device applications (31) that can be accessed by an authorized user (e.g., provider, patient, caregiver, partner). The user interface system may communicate user authentication data and data requests to the database server (29) and/or download the processed patient data from the database server (29) via a wired or wireless network connection and display the data in a graphical user interface (GUI). Additionally or alternatively, the user interface systems may include the GUI for the patient and provider to input additional data that are transmitted to the database server (29). The user interface system may also provide alerts to the patient and provider, such as push notifications and pop-up message boxes, and via the use of colored highlights of data deviations within the GUI.

A patient monitoring device may be fluidically connected to the catheter and infused or drained fluid in a variety of configurations. Like the patient monitoring device (00) described above with reference to FIG. 1A, variations of the patient monitoring device (00) may receive dialysate fluid and include one or more sensors for measuring one or more parameters of the dialysate fluid, and the sensor data may be communicated, stored, and/or analyzed as described above.

Figure 1B:
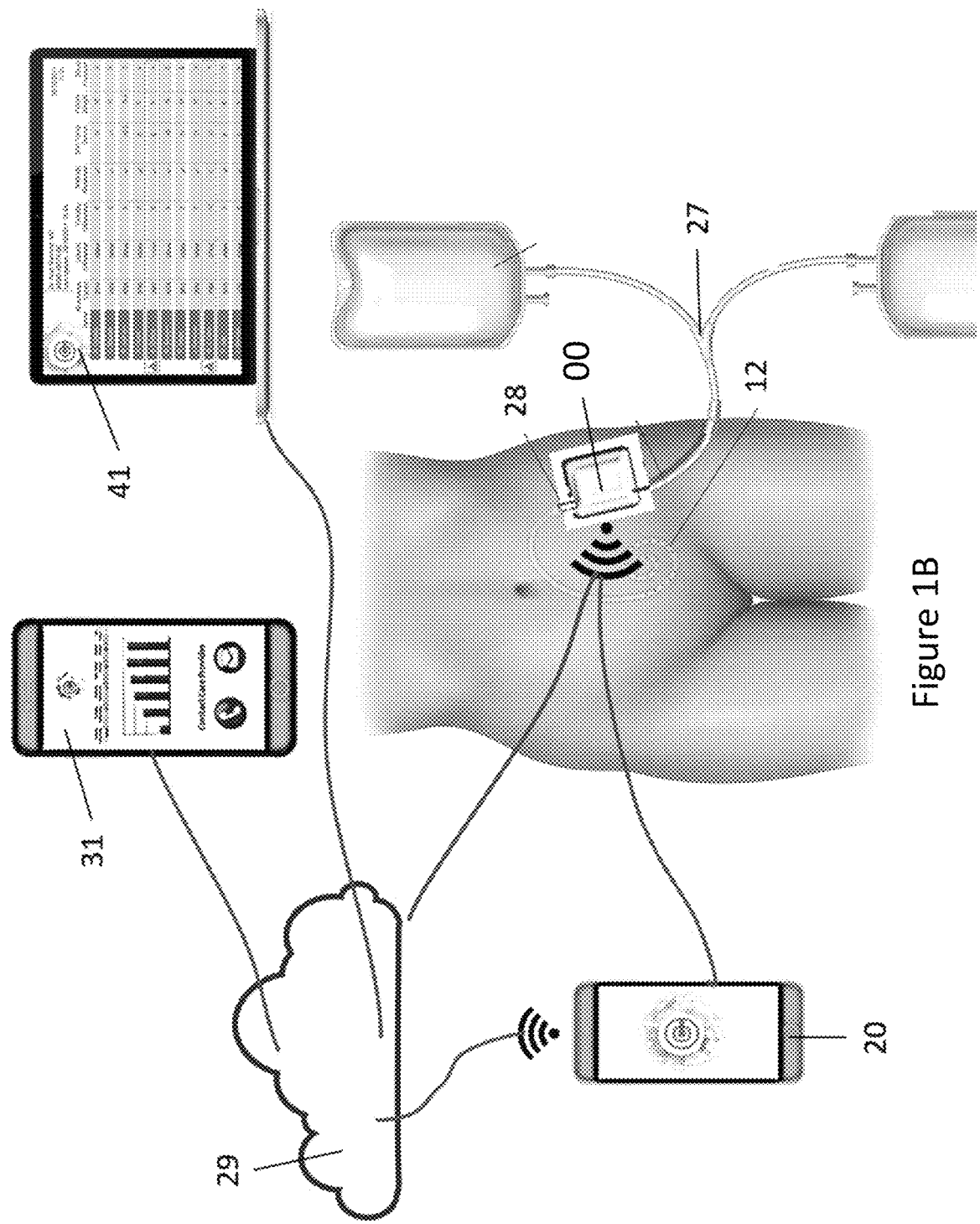
FIG. 1B schematically illustrates another exemplary variation of a monitoring system.

For example, FIG. 1B illustrates another variation in which a patient monitoring device (00) is coupled to a patient, such as at or near the exit site of the patient catheter (12). For example, the patient monitoring device (00) may include an adhesive patch, belt clip, or other device attached on or near the patient.

Figure 13:
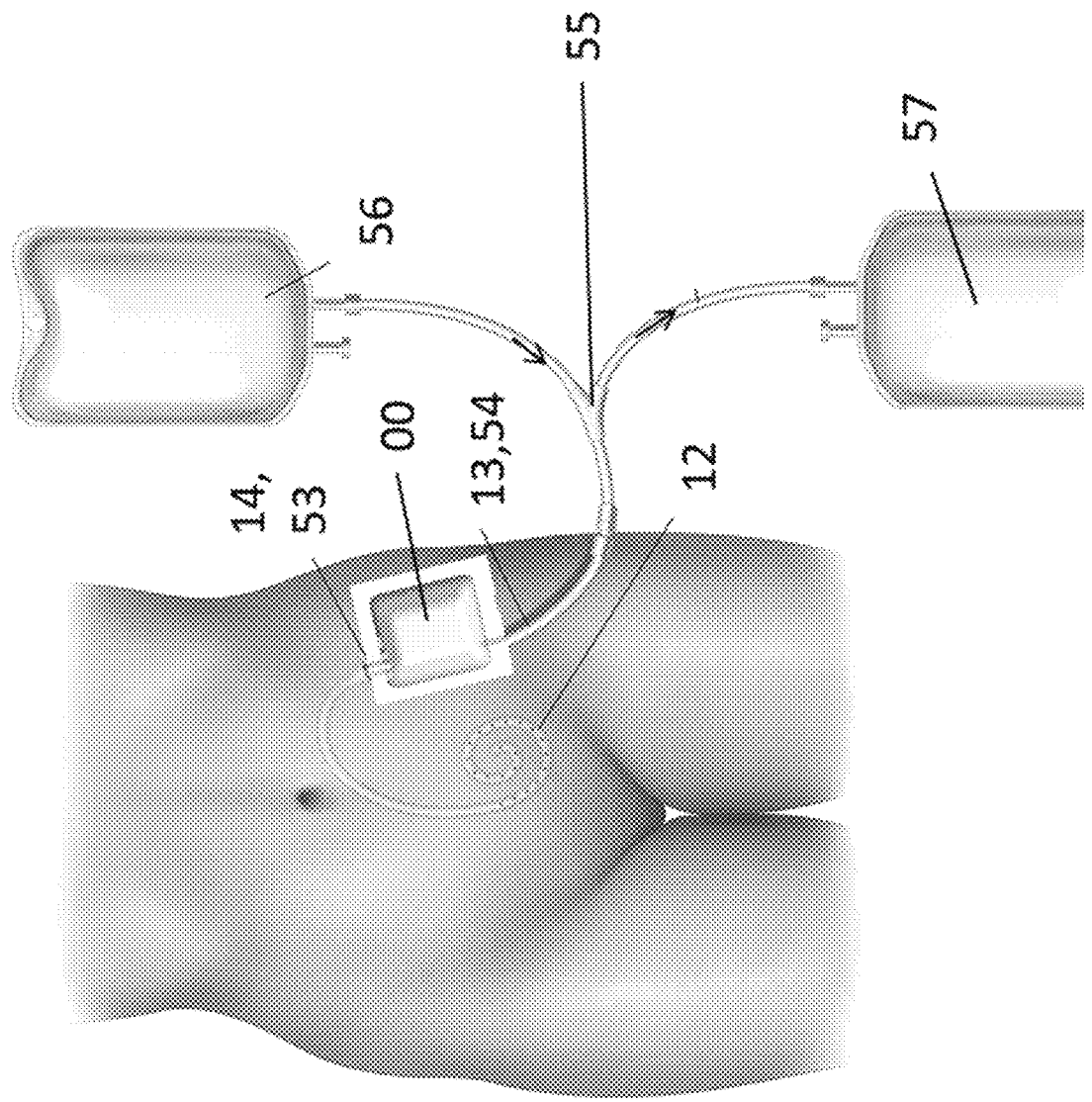
FIG. 13 illustrates an exemplary variation of a patient monitoring system including a patient monitoring device coupled to an in-dwelling catheter and connector tubing.

In one variation, where the system is used for patients on peritoneal dialysis, a set of fluid-detecting sensors may be in fluid communication with fresh dialysate infusing into the patient and waste dialysate draining out of the patient. For example, FIG. 13 depicts the patient monitoring device (00) connected via a connector (53) to the in-dwelling catheter connector (14) and a separate connector (54) connected to the dialysate tubing connector (13) after the junction (55) of the infusing dialysate vessel (56) and drainage dialysate vessel (57). In this variation, the waste dialysate and fresh dialysate both flow through the same set of sensors. In this variation, the direction of the flow may be determined by the use of a flow sensor and/or pressure sensor such that the system can differentiate between or recognize when infusion or drainage is occurring. In some variations, the flow sensors are configured or selected to detect both speed of flow and direction of flow. In other examples, a pressure sensor may be used, with or without sensor data from a flow sensor, to detect a higher pressure during the infusion and dialysate dwell cycle, and rapid drop in pressure during the drainage cycle. This system provides compatibility and usage with a variety of existing dialysis catheters and dialysate infusion systems, including continuous cycling peritoneal dialysis (CCPD) and continuous ambulatory peritoneal dialysis (CAPD) systems. Existing CCPD systems have some monitoring solutions, which the system can supplement. Current CAPD system have no monitoring solutions, which the systems described herein may supply.

Figure 14:
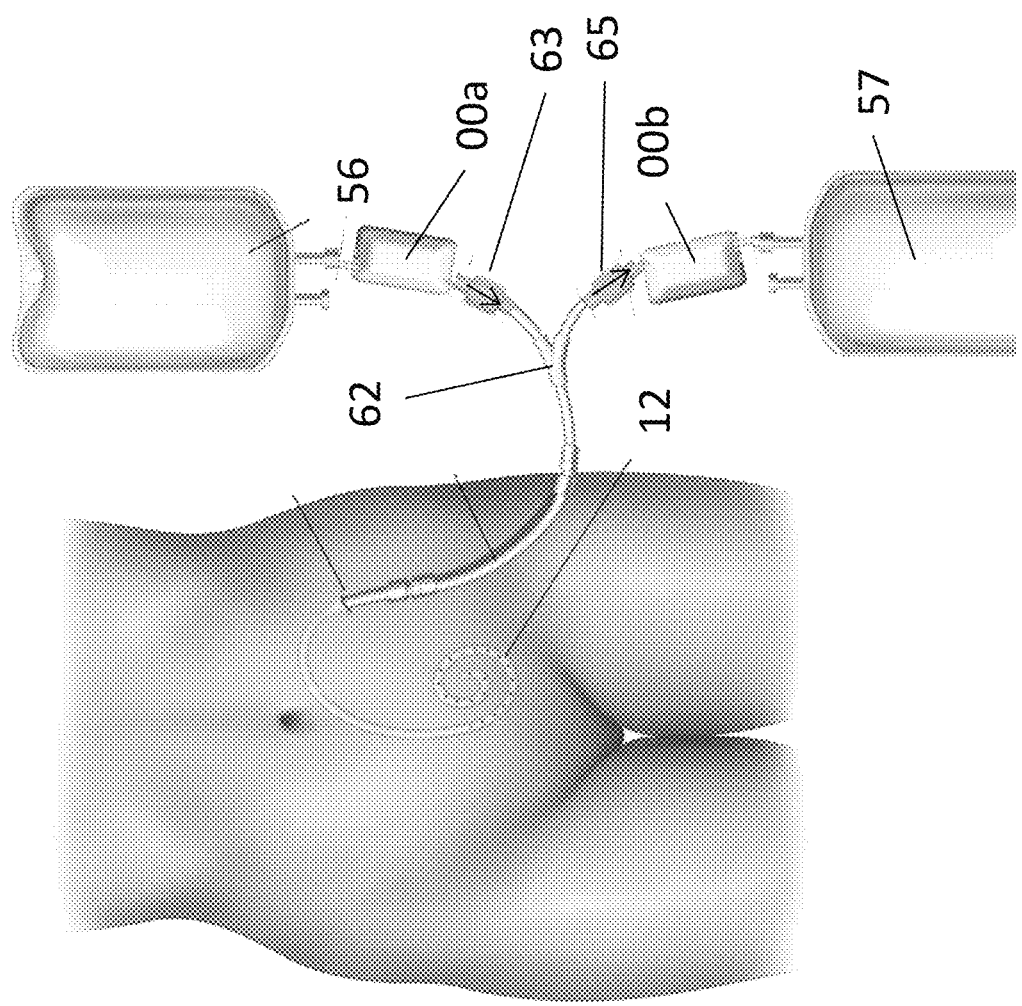
FIG. 14 illustrates an exemplary variation of a patient monitoring system including a set of patient monitoring devices coupled to connector tubing and, respectively, to a solution vessel and a drainage vessel.

In another variation, illustrated in FIG. 14, first the patient monitoring device (00b) is connected to the tubing (65) for the drainage dialysate vessel (57) and a second patient monitoring device (00a) is connected to the tubing (63) for the infusing dialysate vessel (56) before the junction (62) of the infusing dialysate vessel (56) and drainage dialysate vessel (57). The first and second patient monitoring devices (00b, 00a) may be wired or wirelessly connected to each other. At least one of the first and second patient monitoring devices (00b, 00a) may comprise one or more of the hardware processing, power, communication, and data storage components previously described.

Figure 15:
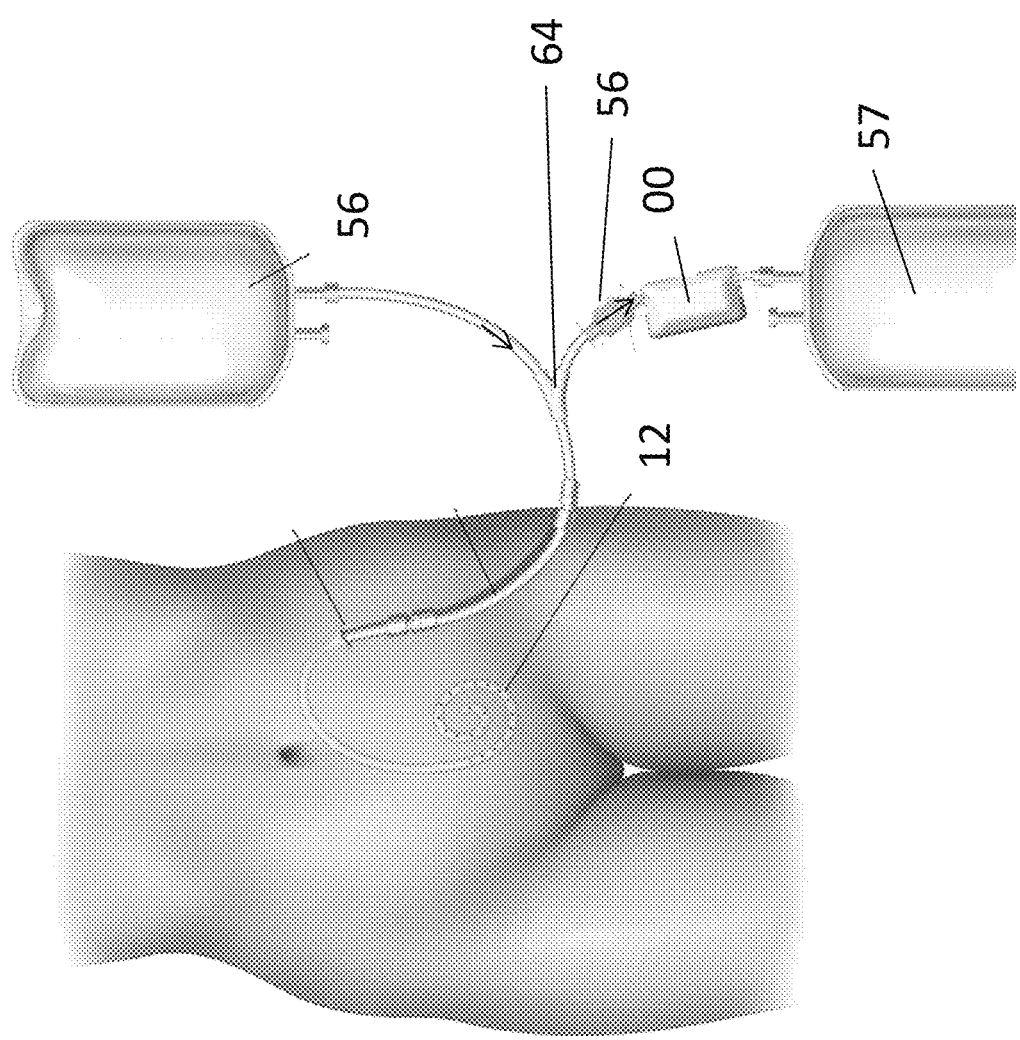
FIG. 15 illustrates an exemplary variation of a patient monitoring system including a patient monitoring device coupled to connector tubing and a drainage vessel.

In another variation illustrated in FIG. 15, a set of sensors is connected only to the waste dialysate solution port. FIG. 15 depicts the patient monitoring device (00) connected to only the waste dialysate solution vessel (57) (e.g., bag) tubing connector prior to the junction (64) of the infusing dialysate vessel (56) (e.g., bag) and drainage dialysate vessel (57). A drainage dialysate bag is not always used, and in those cases, the drainage line may be connected to a drainage vessel, such as a toilet, bathtub, sink, and the like. In this variation, the patient monitoring device monitors only the drainage dialysate solution. Likewise, for patients on CCPD, the patient monitoring (00) may be connected to the waste dialysate solution drainage tube that is typically connected to a toilet, bath tub, drain bucket, or similar vessel for disposal.

One or more portions of the fluid conduits as described herein may be composed of an optically clear material, with high optical transmission across wide wavelength ranges, that may maintain good optical clarity over time, such as one or more of glass, polyvinyl chloride (PVC), silicone, polycarbonate, fluorinated ethylene propylene (FEP), tetrafluoroethylene hexafluoropropylene vinylidene fluoride (THV), acrylic, or cyclic olefin copolymer (COC). Coating materials such as a Zwitterionic, and polyethylene glycol hydrophilic coating on silicone may also be used to prevent bio fouling of the fluid conduit. The fluid conduit may comprise of one or more materials. For instance, a glass tube segment may integrate with a non-fluid-contacting optical scatter and/or absorption sensor, and connect via an overlapped junction or adhesive to a separate PVC tube which integrates with the fluid-contacting sensors (e.g., pH, temperature, pressure, impedance, and conductivity).

Patient Monitoring Device

In some variations, the patient monitoring devices described herein may comprise two or more separate components that may engage with each other to provide full functionality. For example, a disposable component (e.g., fluid conduit, cartridge, drain line, tubing) may be configured to removably engage a durable component (e.g., housing, enclosure, sensor module) of a patient monitoring device. In some variations, a durable component may include at least one sensor and a processor to measure patient fluid and detect patient infection.

The disposable component may include fluid contacting components and the durable component may include a set of non-fluid contacting components. The disposable component may be replaced at predetermined intervals (e.g., daily, weekly) and/or predetermined criteria (e.g., patient infection event). The disposable component may, for example, be useful for short-term use since bacterial growth within the fluid conduit over time may result in an unacceptable number of false-positive and/or false-negative patient infection outputs. The durable component may provide long-term, multi-year functionality given proper calibration and maintenance (e.g., recharging, cleaning).

In some variations, fluid characteristics such as optical scatter, optical absorption, and/or fluid flow rate may be measured in a non-fluid contact manner using the durable component without separate sensors in the disposable component. As a result, manufacture of the disposable component may be simplified and provided at reduced cost. Furthermore, the disposable component may be configured to attach to existing drain line sets to provide additional functionality to existing peritoneal dialysis systems. In some variations, the disposable component may take the place of existing tubing set connectors. FIG. 67A depicts an exemplary variation of a patient monitoring device (6700) coupled to a drain line (6750) (e.g., tubing) and attached to a toilet (6760). The patient monitoring device (6700) includes a durable component (6710) (e.g., housing, enclosure) releasably coupled to a mounting feature (6730) such as a hanger clip configured to attach over a rim of the toilet bowl (6760). For example, the durable component (6710) may be coupled to the mounting feature (6730) via magnets, interlocking and/or complementary features, fasteners, and/or in any suitable manner. A disposable component (6720) (e.g., fluid conduit) may be releasably secured within an interior cavity of the durable component (6710). The durable component (6710) may include at least one lumen configured to allow fluid to flow through it. A proximal end of the disposable component (6710) may be coupled to a distal end of a drain line (6750) using a connector (6740) as described in more detail herein. For example, the inlet of the fluid conduit (6720) may comprise a tubing set connector (6740). A distal end of the disposable component (6720) may be configured to empty fluid (e.g., patient fluid) into a drainage vessel such as the toilet (6760). In some variations, a portion of the disposable component (6720) may follow a shape of the mounting feature (6730) (e.g., be similar in profile) so as to reduce an overall size and volume of the device (6700). The disposable component (6720) may comprise one or more portions such as a rigid distal end configured for connection to the tubing set connector (6740) and a flexible proximal end configured for releasable engagement with the mounting feature (6730). For example, a flexible end of the disposable component (6720) may wrap around the mounting feature (6730). In some variations, the disposable component (6720) may comprise a stiff curved end configured to releasably attach the fluid conduit to a drainage vessel such that the housing is separated from the drainage vessel and does not contact the drainage vessel.

Figure 67B:
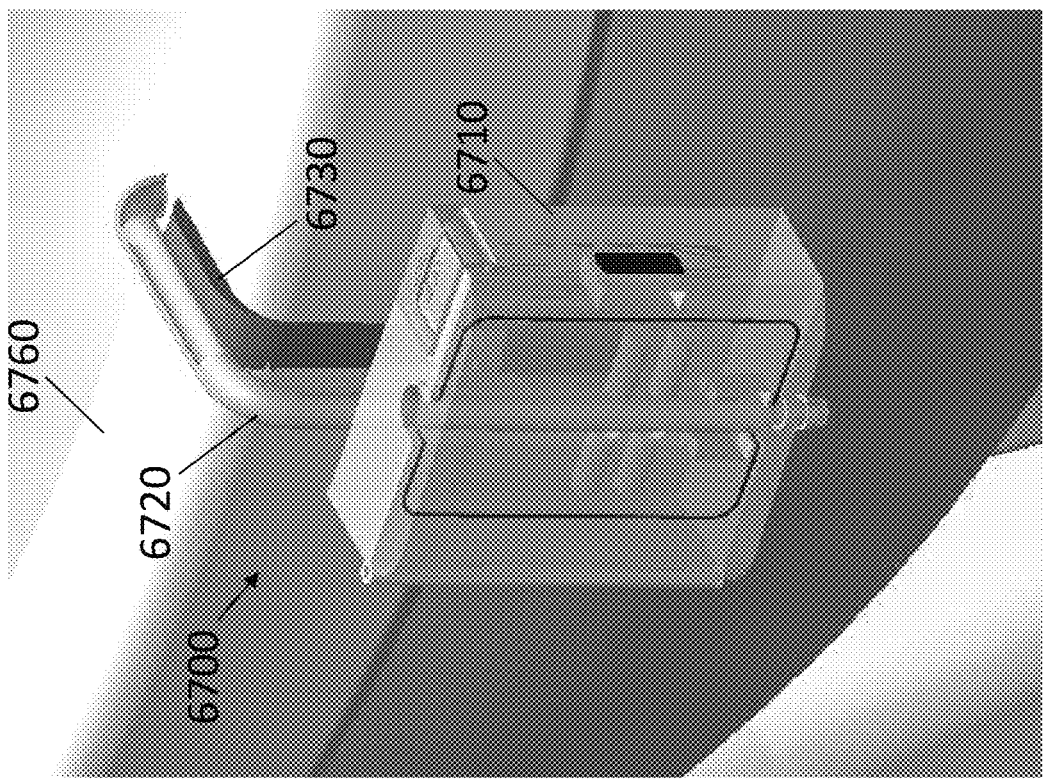
FIGS. 67A and 67B are perspective views of an exemplary variation of a patient monitoring device attached to a toilet.
Figure 67A:
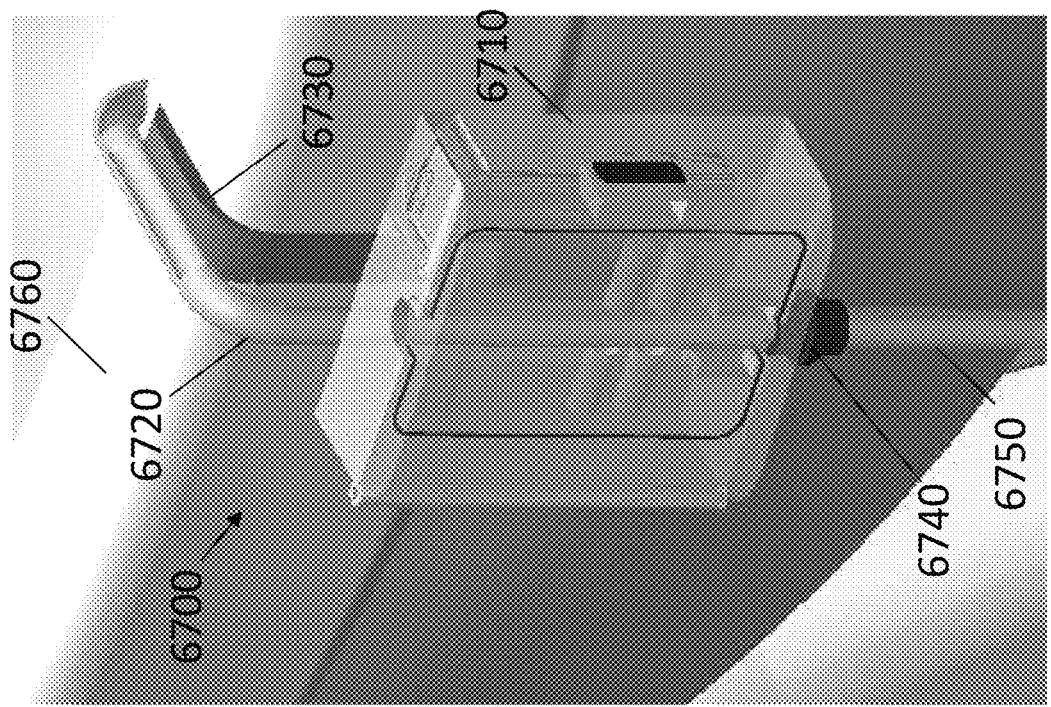

FIG. 67B illustrates the patient monitoring device (6700) without attachment to a drain line (6750) and connector (6740).

FIGS. 68A and 68B are perspective views of a patient monitoring device (6800) in respective closed and open configurations. A housing (6802) of a durable component may comprise a lid (6814) rotatable about a hinge (6812). The housing (6802) may define an interior cavity (6816) configured to hold a disposable component (6830) (e.g., fluid conduit). The fluid conduit (6830) may be configured to releasably engage to the housing (6802). For example, the disposable component (6830) may be snap-fit into the interior cavity (6816) of the housing (6802). The housing (6802) is configured to transition between an open configuration (FIG. 68B) with an exposed interior cavity (6816) and a closed configuration (FIG. 68A) with an enclosed interior cavity (6816). In the closed configuration shown in FIG. 68A, at least a portion of the fluid conduit (6830) may be shielded from external light and sealed from external fluid. A mounting feature (6840) may be removably attached to the housing (6802).

In some variations, the lid (6814) may be set of flaps, door, slit, cover, shield, latch, fastener or any other structure that allows a disposable component (6830) to be removably held in an interior cavity (6816). For example, a disposable component (6830) may be pushed through an opening between a pair of flaps to engage the disposable component (6830) with an interior cavity (6816) of the housing (6802). When a release mechanism is actuated (e.g., engagement feature (6820)), the disposable component (6830) may be released and/or pushed out of the interior cavity (6816) through the pair of flaps. In some variations, an opening of the interior cavity (6816) may face toward a drainage vessel. This may allow a user to first attach a disposable component to a drainage vessel and then allow the patient monitoring device to be pushed over the disposable component and against the drainage vessel. To uncouple the patient monitoring device from the disposable component, the user may actuate the release mechanism and pull the durable component away from the disposable component and drainage vessel.

The housing (6802) may comprise at least one non-contact fluid sensor (6822) configured to measure one or more parameters of fluid flow through the disposable component (6830). Sensor data measured using the sensor may be used to detect patient infection. For example, the housing (6802) may comprise at least one optical sensor arrangement (6822) arranged substantially perpendicular to a longitudinal axis of an interior cavity (6816) of the housing (6802). The optical sensor arrangement (6822) may comprise at least one emitter and at least one detector. As described in more detail herein, one or more emitters may be configured to transmit light at one or more wavelength ranges through a patient fluid flowing through the fluid conduit (6830). At least one detector may be configured to receive the light transmitted through the fluid conduit (6830) and the patient fluid. In some variations, one or more emitters transmits the light at a first wavelength range and a second wavelength range. The first wavelength range may be between about 700 nm and about 1 mm, and the second wavelength range may be between about 260 nm and about 550 nm. An emitter may comprise one or more of a light emitting diode, laser, collimator, lens, filter, and scintillator. A detector of the optical sensor arrangement (6822) may be oriented about 180 degrees around the fluid conduit relative to an emitter (e.g., on opposite sides of the fluid conduit (6830)). Additionally or alternatively, one or more detectors may be oriented about 10-179 degrees relative to an emitter to capture scattered light. The optical sensor arrangement (6822) may, for example, correspond to any of the optical sensors described herein such as in FIGS. 34, 43, and 44.

In some variations, the patient monitoring device (6800) may further comprise at least one non-contact sensor including one or more of a pressure sensor, image sensor, flow sensor, accelerometer, gyroscope, temperature sensor, and magnetic field transducer. The image sensor may comprise one or more of a cell counter and color sensor. For example, some sensors such as an accelerometer and gyroscope may be provided in the housing (6802) separate from the interior cavity (6812) and fluid conduit. One variation of a flow sensor is described in more detail with respect to FIG. 69D.

The housing (6802) may include controller comprising a processor and a memory (not shown) and which may be coupled to the optical sensor arrangement (6822). The controller includes the hardware and the firmware that, with the support of program memory and random access memory controls one or more sensors, receives the sensor data, processes the sensor data, stores the processed data in memory, communicates with a transmitter or directly to the database server system (not shown) via a communication device, and manages the power source. The memory may store the processed data until successful transmission to the data to the database server is confirmed. A power charging port may be controlled by the controller to charge the local power supply.

The controller may be configured to receive signal data corresponding to received light generated by the at least one detector. The controller may estimate total particle concentration data and leukocyte concentration data using the signal data as described in more detail herein. The patient monitoring device may further comprise an electronic communication device (e.g., wireless transmitter, transceiver) and a power source (e.g., battery) coupled to the controller.

In some variations, the patient monitoring device (6800) may comprise a user interface (e.g., FIG. 72) (e.g., visual indicator) configured to provide a patient monitoring device status, patient status, fluid monitoring status, disposable component status, communication status, combinations thereof, and the like. For example, a visual indicator may include an LED or LCD configured to display a battery life, operation status, and disposable component status (e.g., attachment status, replacement status). A visual indicator may be configured to notify the patient to contact their doctor or health care professional due to a detected patient infection event.

Figure 68C:
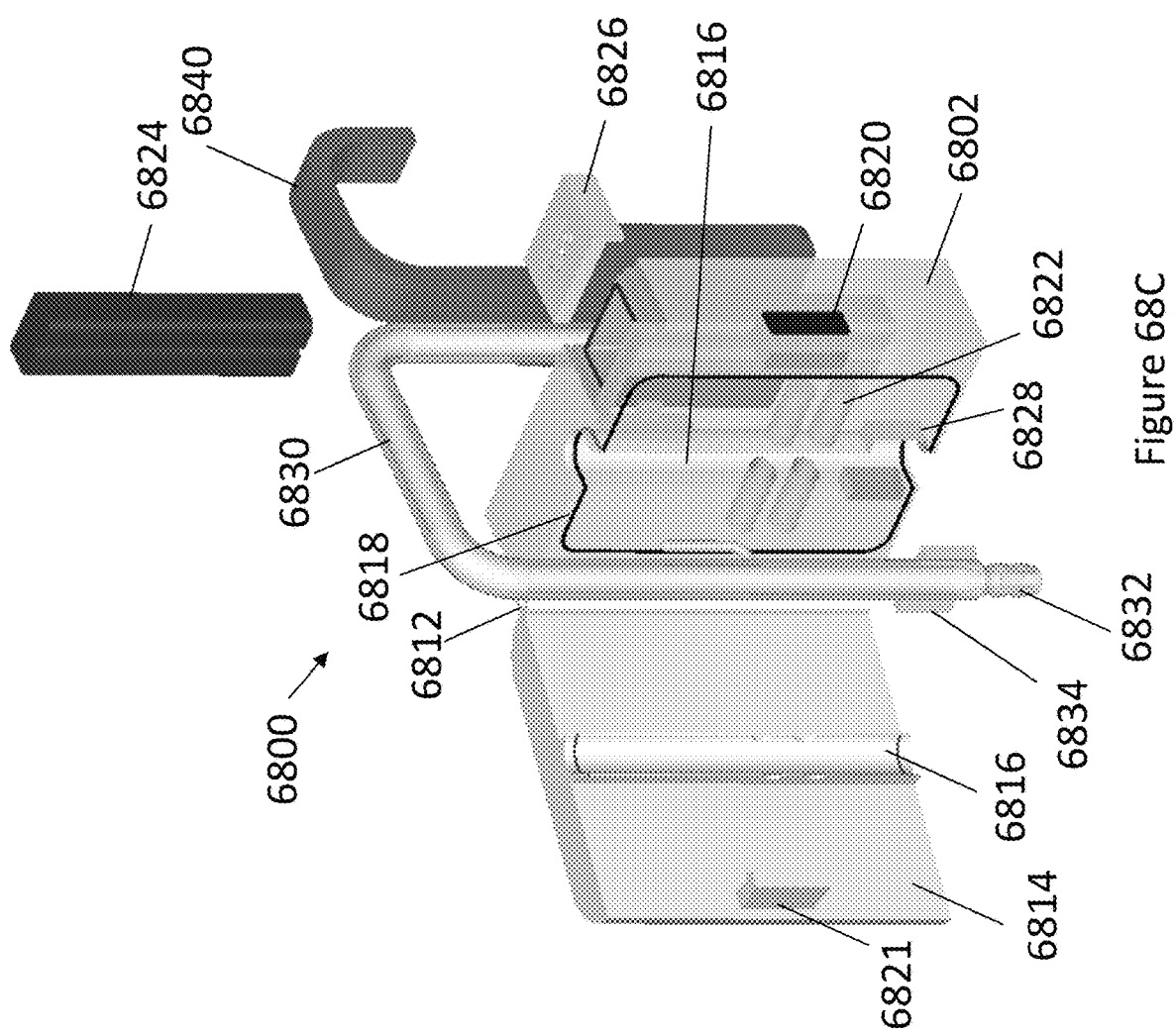

FIG. 68C is an exploded assembly view of the patient monitoring device (6800). The fluid conduit (6830) may be configured to be secured in the interior cavity (6816) by a friction fit and/or mechanical interfit. For example, the housing (6802) comprises a fluid conduit engagement feature (6828) (e.g., cradle or other recess) mateable with a corresponding housing engagement feature (6834) on the fluid conduit (6830). The housing (6802) may further comprise an engagement sensor (e.g., switch, optical sensor) configured to generate a sensor signal when the fluid conduit engagement feature (6828) is mated with its corresponding housing engagement feature (6834). The housing (6802) may comprise a seal (6818) configured to prevent fluid or gas ingress (i.e. hot humid air from the shower) into the interior cavity (6816) of the housing (6802) in the closed configuration. The seal (6818) may, for example, include a gasket, skirt or other suitable seal. The lid (6814) may comprise a housing engagement feature (6821) mateable with a corresponding lid engagement feature (6820) (e.g., spring-loaded latch release) of the housing (6802). For example, the lid (6814) may release and rotate about the hinge (6812) upon the pushing of a button (6820) on a side of the housing (6802). A power source (6824) (e.g., battery) may be removable from the housing (6804) and enclosed by a cover (6826). The mounting feature (6840) may be removably engaged to the housing (6802) as described in more detail herein. One or more components of the patient monitoring device (e.g., battery, lid, memory, sensors, fluid conduit) may be removable for ease of one or more of replacement, cleaning, data transfer, and charging. In some variations, redundant components may be provided such as a redundant battery and/or memory.

The fluid conduit (6830) may comprise an inlet (6832) configured to couple to at least one of an in-dwelling catheter and a drain line, and an outlet (6834) configured to open towards a drainage vessel. The fluid conduit (6830) is described in more detail herein with respect to FIGS. 70A and 70B.

Figure 69C:
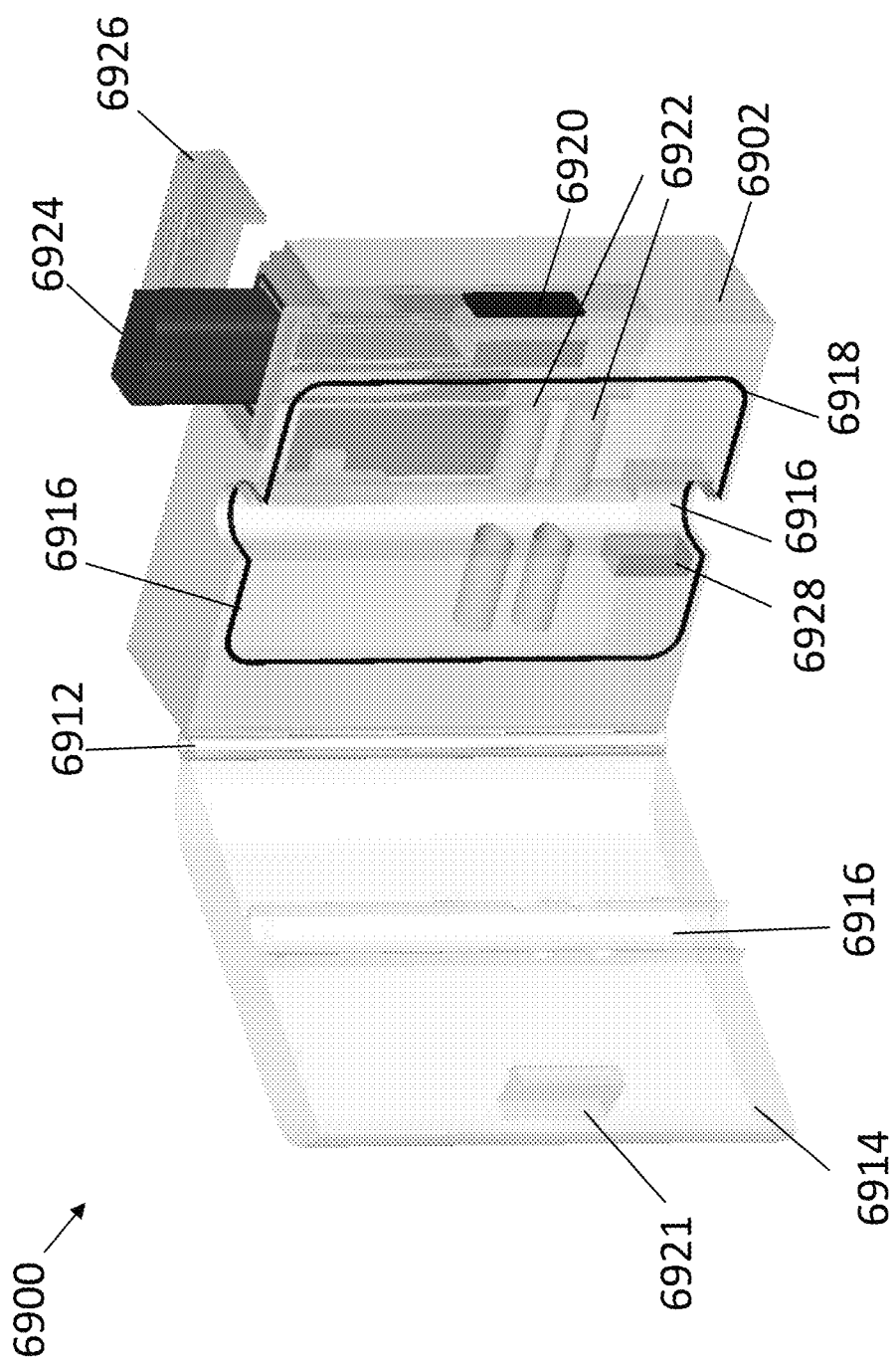

FIGS. 69A-69D are perspective views of a patient monitoring device (6900) similar to the patient monitoring device (6800) except that a disposable component and mounting feature are removed for the sake of clarity. A housing (6902) of a durable component may comprise a lid (6914) rotatable about a hinge (6912). The housing (6902) may define an interior cavity (6916) configured to hold a disposable component (e.g., fluid conduit). The housing (6902) is configured to transition between an open configuration (FIG. 69B) with an exposed interior cavity (6916) and a closed configuration (FIG. 69A) with an enclosed interior cavity (6916). The housing (6902) may comprise at least one non-contact fluid sensor (6922) configured to measure one or more parameters of fluid flow through a disposable component. For example, the housing (6902) may comprise at least one optical sensor (6922) arranged perpendicular to a longitudinal axis of an interior cavity (6916) of the housing (6902). FIG. 69C illustrates a pair of optical sensors (6922) (e.g., optical sensor arrangements) configured to transmit and receive light through an interior cavity (6916). For example, each optical sensor (6922) may comprise an emitter and two detectors arranged at about 90 degrees and about 180 degrees around the conduit relative to the emitter.

FIG. 69C illustrates an open configuration of the patient monitoring device (6900) including a power source (6924) and cover (6926). The cover (6926) may comprise a fluid seal (e.g., gasket) to prevent fluid ingress. The housing (6902) comprises a fluid conduit engagement feature (6928) mateable with a fluid conduit. The housing (6902) may further comprise an engagement sensor (e.g., switch, optical sensor) configured to generate a sensor signal when the fluid conduit engagement feature (6928) is mated a fluid conduit. The housing (6902) may comprise a seal (6918) configured to prevent fluid ingress into the interior cavity (6916) of the housing (6902) in the closed configuration. The lid (6914) may comprise a housing engagement feature (6921) (e.g., latch) mateable with a corresponding lid engagement feature (6920) (e.g., spring-loaded latch release) of the housing (6902).

Figure 69D:
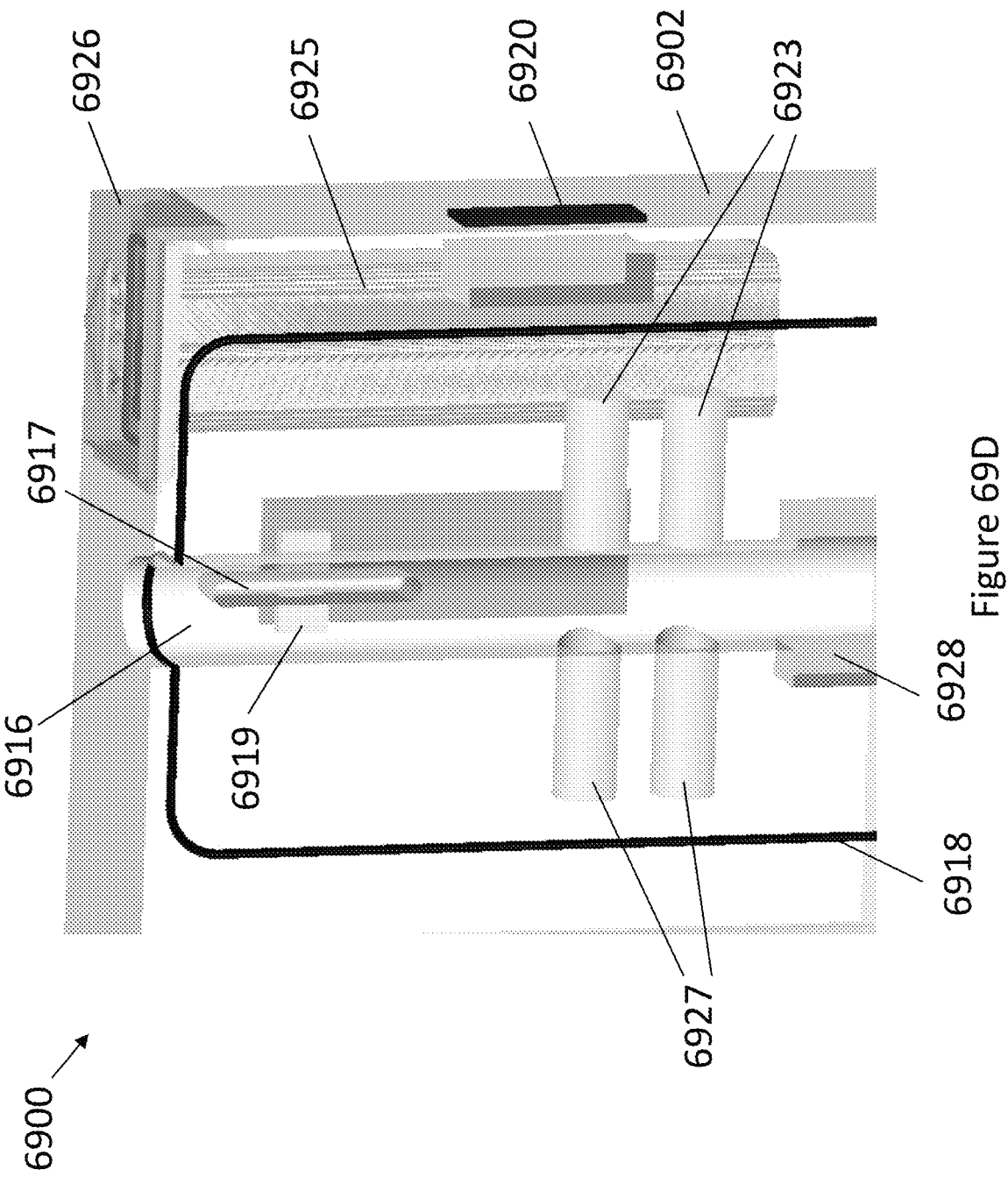

FIG. 69D is a detailed perspective view of the interior cavity (6916) of the patient monitoring device (6900). In some variations, the optical sensor arrangement may comprise one or more emitters (6923) and one or more detectors (6927). In FIG. 69D, the emitter (6923) and detector (6927) are oriented at 180 degrees separation around the circumference of the interior cavity (6916), though the emitter (6923) and detector (6927) may also be oriented at forward scattering angles (>90 degrees, <180 degrees), side scattering angle (90 degrees), or back-scattering angles (<90 degrees, >0 degrees). The interior cavity (6916) of the housing (6902) may further define other cavities (6917) configured to hold a second fluid conduit such as described with respect to FIGS. 70A and 70B.

At least one sensor (6919) such as an optical sensor comprising a light emitter and a light detector may be configured to measure a fluid level within the cavity (6917). The sensor (6919) may be configured to generate signal data corresponding to a fluid flow rate of patient fluid flowing through a disposable component (e.g., fluid conduit). The cavity (6917) may extend parallel to a longitudinal axis of the interior cavity (6916). At least a portion of the cavity (6917) may be shielded from external light and sealed from external fluid.

Figure 70B:
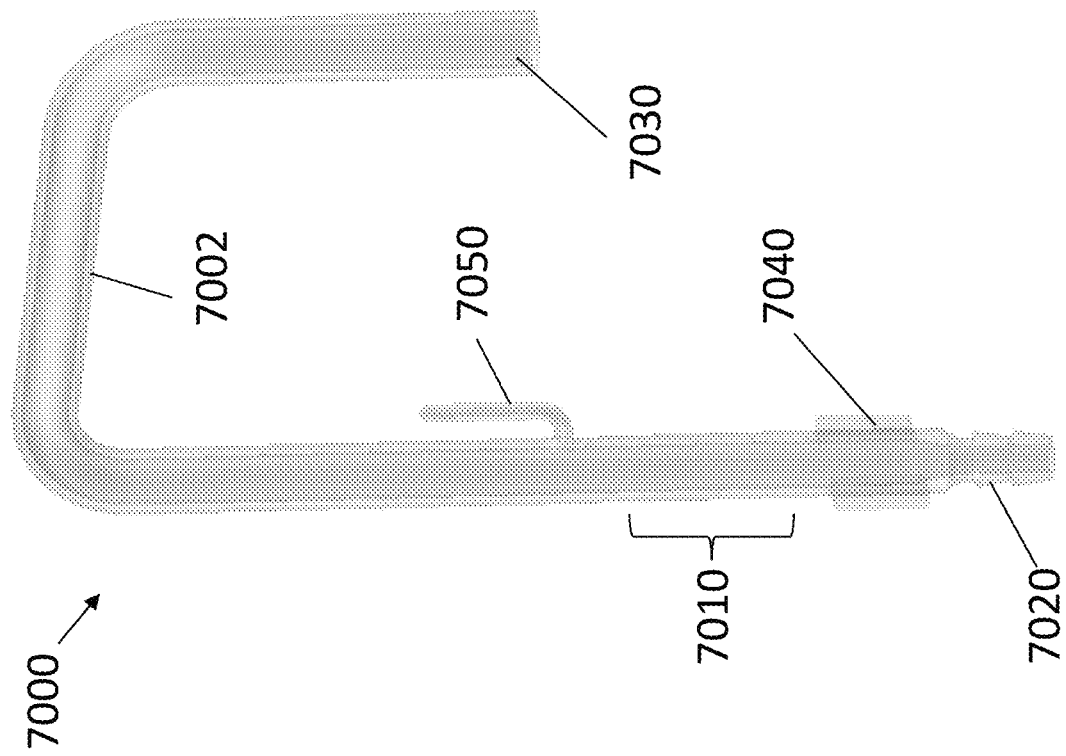
FIGS. 70A and 70B are perspective views of an exemplary variation of a fluid conduit of a patient monitoring device.
Figure 70A:
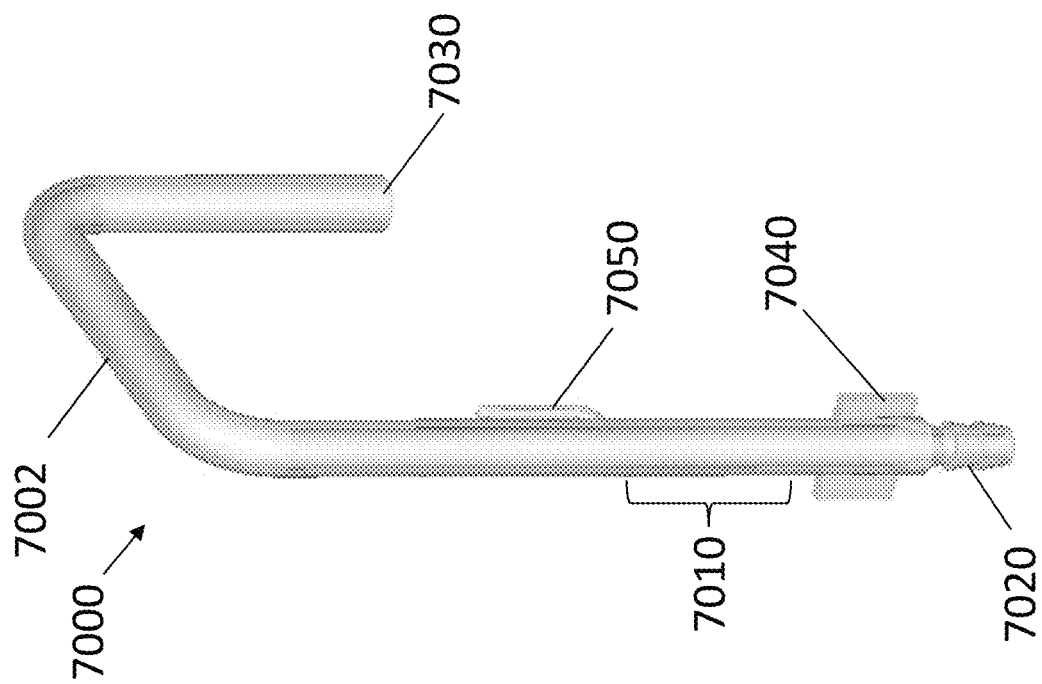

FIGS. 70A and 70B illustrate perspective views of a disposable component such as fluid conduit (7000) defining a lumen (7002) (e.g., fluid flow channel, fluid flow path). The fluid conduit (7000) may comprise an inlet (7020) and an outlet (7030). For example, the fluid conduit (7000) may comprise an inlet (7020) configured to couple to at least one of an in-dwelling catheter and a drain line, and an outlet (7030) configured to open towards a drainage vessel. The fluid conduit (7000) may have a curved shape such as a L-shape, J-shape, S-shape, U-shape, C-shape, combinations thereof, and the like, for example, to conform to and couple to a rim of a drainage vessel such as a toilet or sink. The shape and diameter of the fluid conduit (7000) may be configured to reduce clogging and obstruction from solid particles in the fluid such as fibrin.

In some variations, the inlet (7020) may comprise a connector which may, for example, have a thread and/or a taper. The inlet may comprise a barbed fitting configured to couple to standard tubing set drain lines. The fluid conduit (7000) may comprise one or more engagement features (7040) such as tabs configured to align the lumen (7002) of the fluid conduit (7000) with the interior cavity of the durable component. In some variations, the fluid conduit (6830) may comprise at least one fluid-contact sensor comprising one or more of a flow sensor, conductivity sensor, temperature sensor, pH sensor, lactate sensor, test strip, chemiluminescence sensor, electrochemical sensor, and glucose sensor.

In some variations, the fluid conduit (7000) comprises at least one optical sensing region configured to allow an optical sensor to optically measure a fluid characteristic of patient fluid flow. For example, the fluid conduit (7000) comprises at least one transparent portion (7010) disposed along any portion of the fluid conduit (7000) between the inlet (7020) and outlet (7030) suitable for an optical sensor arrangement to measure light passing through the transparent portion (7010). For example, the transparent portion may be located along a length of the fluid conduit (7000) such that external light is shielded from the transparent portion when the fluid conduit (7000) is held within an interior cavity of a durable component. In some variations, a transparent portion (7010, 7050) of the fluid conduit (7000) may be provided for each fluid characteristic to be measured (e.g., optical scatter, optical absorption, fluid flow rate).

The transparent portion is substantially transparent to at least one of ultraviolet light, visible light, and infrared radiation. One or more portions of the fluid conduit (7000) may, for example, be composed of one or more of acrylic, polycarbonate, cyclic olefin copolymers (COC), fluorinated ethylene propylene (FEP), tetrafluoroethylene hexafluoropropylene vinylidene fluoride (THV), polycarbonate, polystyrene, acrylonitrile butadiene styrene (ABS), polyethylene glycol-coated silicone, zwitterionic coated polyurethane, polyethylene oxide-coated polyvinyl chloride, and polyamphiphilic silicone. For example, the entire fluid conduit (7000) may be transparent or the portion of the fluid conduit (7000) held within an interior cavity of a durable component may be transparent. The transparent portion (7010) may be composed of a different material (and have different transparency) than other portions of the fluid conduit (7000).

In some variations, an exterior of the fluid conduit (7000) may comprise one or more handling interfaces (e.g., protrusion, grip) configured for manipulation by a patient. This may reduce patient contact with sensitive portions of the fluid conduit (7000) (e.g., inlet and transparent portions) that may otherwise alter sensor measurements. For example, a set of spaced apart protrusions may be provided around a circumference of the transparent portion that are not within a line of sight of any of the emitters and detectors. Furthermore, markings may be provided on the fluid conduit (7000) to indicate the handling interfaces and/or sensitive portions that should remain sterile (e.g., free from fingerprints and other contact).

In order to conserve the overall system power use, it is desirable for each sensor to operate only as necessary. In some variations, the patient monitoring device may perform patient complication detection only when fluid flows through the fluid conduit, thus reducing power consumption and unnecessary data generation. In some applications, such as continuous cycling peritoneal dialysis (CCPD), a cycle will include infusion, dwell, and drainage steps, where the patient monitoring device may only need to monitor the drainage step. The fluid conduit will initially be empty, from which the optical sensor arrangement may measure and determine when the initial drainage time begins. However, after completion of the first drainage cycle, the fluid conduit may have residual fluid that may not allow accurate measurement of initial drainage times of subsequent cycles. Therefore, on subsequent exchanges, measurement of fluid flow rate may be used to estimate an initial drainage time of a cycle. A fluid flow sensor may be used to determine when there is fluid flowing through the fluid conduit. When the fluid flow sensor indicates that fluid is flowing through the fluid conduit, one or more other patient monitoring sensors may begin to operate continuously, but otherwise operate on a relatively low duty cycle during times when the fluid flow sensor indicates there is no fluid flow. Generally, the patient monitoring device may operate in a low-power mode during period of no fluid flow (i.e. during infusion and dwell steps in the cycle). When fluid flow is detected, the sensors may be turned on and signal data generated.

Measurement of fluid flow may be performed by any suitable mechanism. For example, the patient monitoring system may generate a fluid flow signal using one or more of the optical sensors of the patient monitoring device. As another example, the patient monitoring device may comprise an accelerometer configured to detect vibrations corresponding to fluid pump activation and fluid flow. As another example, the patient monitoring device may comprise an audio device (e.g., microphone) configured to detect a sound pattern corresponding to one or more of fluid pump activation and fluid flow. Additionally or alternatively, a fluid flow signal may be received (e.g., via wireless communication) from a cycler and/or patient to indicate the onset or end of fluid flow (e.g., pumping) when a drain cycle begins. The patient monitoring devices described herein may comprise a non-fluid contact flow sensor configured to determine a fluid flow state within the fluid conduit. FIGS. 70 and 74-76 are exemplary variations of a fluid conduit comprising a portion configured to be measured by the flow sensor, as described below.

In some variations, as shown in FIGS. 70A and 70B, the first fluid conduit (7000) comprises a second fluid conduit (7050) (which may be closed-end) branching or diverging from a first (e.g., primary) fluid conduit (7000). Generally, the second fluid conduit (7050) may capture a volume of fluid that may be correlated to flow rate, as described below. The second fluid conduit (7050) may be formed parallel to the first fluid conduit (7000). Although the location of the second fluid conduit relative to the first fluid conduit (7000) is depicted as generally vertical, it should be understood that in other variations, the second fluid conduit and first fluid conduit may be oriented in any suitable direction. An end of the second fluid conduit (7050) may be sealed to prevent air/fluid leakage. A diameter of the second fluid conduit (7050) may be smaller than a diameter of the lumen (7002). The second fluid conduit (7050) may comprise at least one transparent portion similar to the transparent portion (7010) of the first fluid conduit (7000). As fluid flows through the lumen (7002), a volume of fluid fills a lower portion of the enclosure (7050) and a pocket of air becomes compressed and trapped within an upper portion of the enclosure (7050).

A fluid volume of the second fluid conduit (7050) (e.g., height to which fluid fills the enclosure (7050)) may correspond to a flow rate of patient fluid in the fluid conduit (7000). For example, when there is no fluid flow, there is minimal pressure in the fluid conduit (7000) such that the fluid level in the enclosure (7050) will be relatively low. When fluid flows through the fluid conduit (7000), a positive pressure in the fluid conduit (7000) will compress the air within the enclosure (7050) and increase the fluid level in the enclosure (7050). Accordingly, the greater the flow rate, the higher the fluid level in the enclosure (7000) (or generally for other second fluid conduit orientations, the greater the extent of fluid into the second fluid conduit). A sensor such as an optical sensor may be configured to measure the height of the fluid in the enclosure (7050), thus allowing a fluid flow rate to be estimated by a controller. In some variations, the fluid flow sensor may comprise an optical sensor arrangement including at least one emitter and at least one detector.

Figure 74:
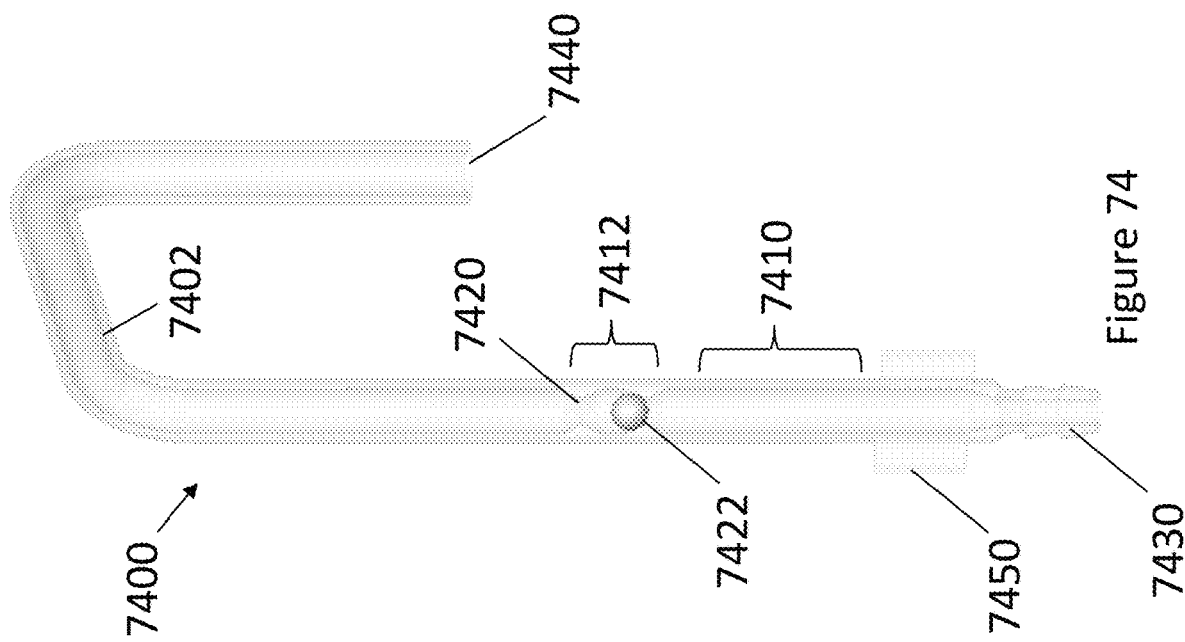
FIG. 74 is a perspective view of an exemplary variation of a fluid conduit of a patient monitoring device including a ball flow sensor.

In some variations, detection of fluid flow rate including an onset and/or an end (termination) of fluid flow may be used to determine when to initiate and end patient infection detection. FIGS. 74-76 depict further variations of a fluid flow detection mechanism. FIG. 74 is a perspective view of a disposable component such as fluid conduit (7400) defining a lumen (7402) (e.g., channel, path). The fluid conduit (7400) may comprise an inlet (7430) and an outlet (7440). For example, the fluid conduit (7400) may comprise an inlet (7430) configured to couple to at least one of an in-dwelling catheter and a drain line, and an outlet (7440) configured to open towards a drainage vessel. The fluid conduit (7400) may comprise one or more engagement features (7450) such as tabs configured to align the lumen (7002) of the fluid conduit (7000) with the interior cavity of the durable component. In FIGS. 70A and 70B, the fluid conduit (7002) comprises a first transparent portion (7010) configured for patient infection measurement (e.g., optical scatter and/or optical absorption), and a second transparent portion (7050) configured for measurement of fluid flow. The transparent portions (7010, 7050) are substantially transparent to at least one of ultraviolet light, visible light, and infrared radiation. The transparent portions (7010, 7050) may be composed of a different material (and have different transparency) than other portions of the fluid conduit (7002).

In some variations, as depicted in FIG. 74, the second transparent portion (7412) comprises a ball flow sensing portion (7420) including a ball (7422) arranged proximate one or more stops within the fluid lumen (7402). Generally, a height of the ball (7422) within the flow sensing portion (7420) will translate (e.g., rise) relative to the stops in response to increasing fluid flow rate. For example, the ball (7422) has neutral or slightly negative buoyancy and will rest at a bottom of the flow sensing portion (7420) when there is no fluid flow through the fluid conduit (7400). An optical sensor may be configured to detect the location of the ball (7422) and generate a fluid flow signal based on the ball location. In some variations, the fluid flow signal may be a binary signal such as fluid flow ON and fluid flow OFF.

Figure 75B:
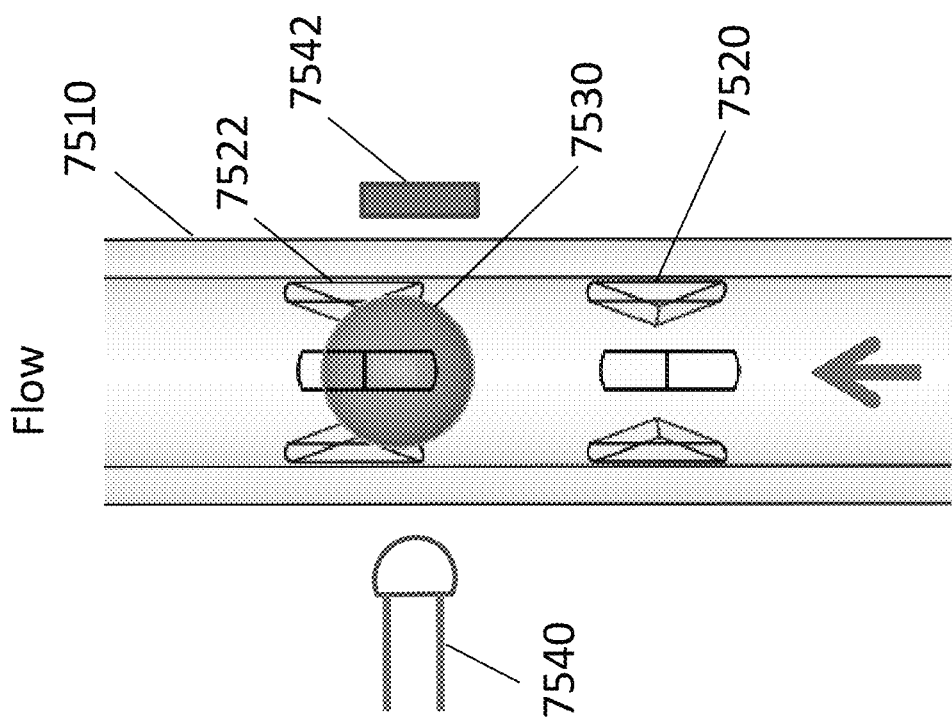
FIGS. 75A and 75B are detailed side views of an exemplary variation of a ball flow sensor of a fluid conduit.
Figure 75A:
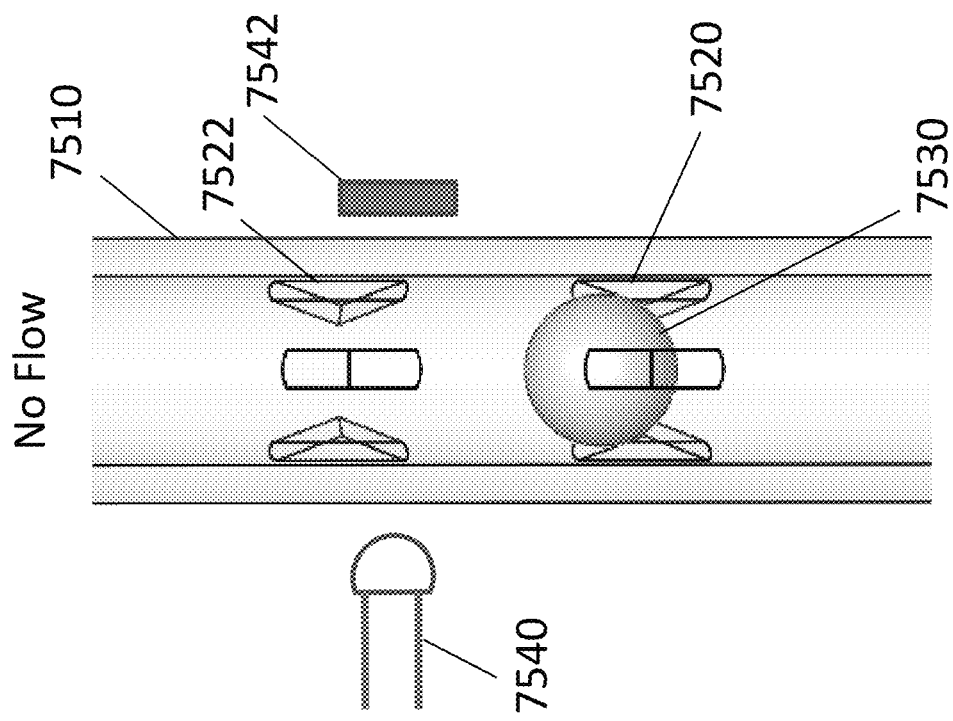

FIGS. 75A and 75B depict a first variation of an optical sensor and flow sensing portion (e.g., ball flow sensor). A fluid conduit (7510) comprises a flow sensing portion including a ball (7520) and a first internal radially-extending setting (7520) and/or a second internal radially-extending setting (7522). The first and second settings (7520, 7522) may be longitudinally or axially spaced-apart in the fluid conduit (7510). The ball may be arranged between the first and second settings such that the first and second settings are) configured to limit a range of motion of the ball (7520) within the fluid conduit (7510) (e.g., the ball's travel is limited in a proximal direction by one setting and in a distal direction by the other setting). For example, the An optical sensor arrangement comprising an emitter (7540) and a detector (7542) may be configured to transmit and receive light through a transparent portion of the fluid conduit (7510). For example, the ball (7530) rests on the first setting (7520) in FIG. 75A when fluid does not flow through the fluid conduit (7510). The light emitted by the emitter (7540) is substantially transmitted through a transparent portion of the fluid conduit (7510) and received by the detector (7542). When fluid flows through the fluid conduit (7510), the ball (7520) is pushed into the second settings (7522) in FIG. 75B. The light emitted by the emitter (7540) is substantially blocked by the ball (7530). The valve may be a one-way valve that prevents fluid flow toward an inlet of the fluid conduit. In some variations, the ball and flow sensing portion may be disposed within a parallel fluid conduit path.

Figure 76B:
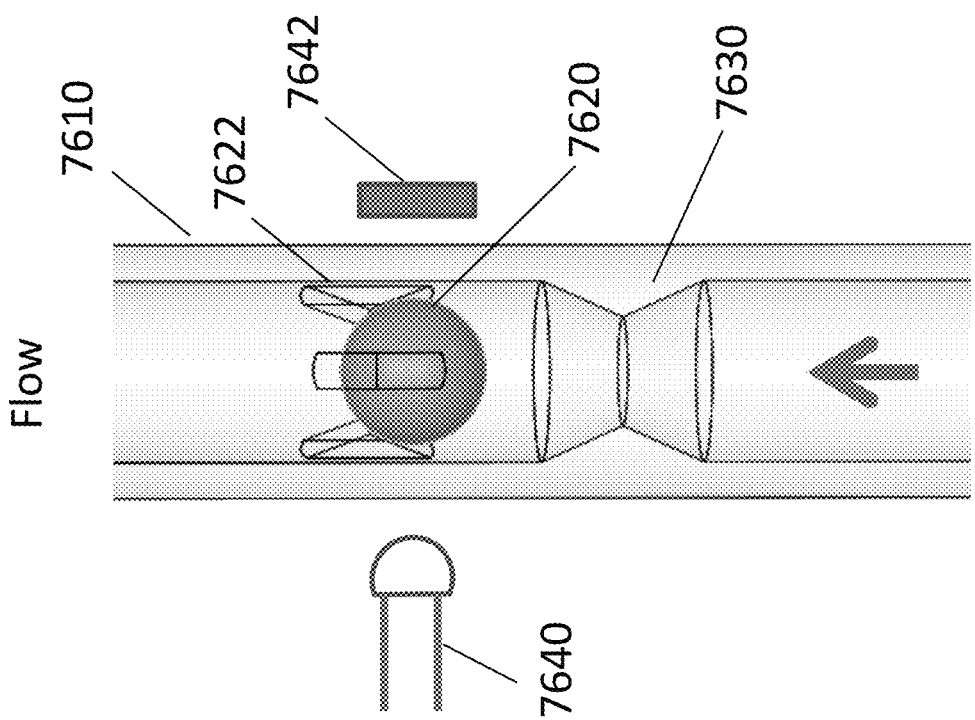
FIGS. 76A and 76B are detailed side views of another exemplary variation of a ball valve of a fluid conduit.
Figure 76A:
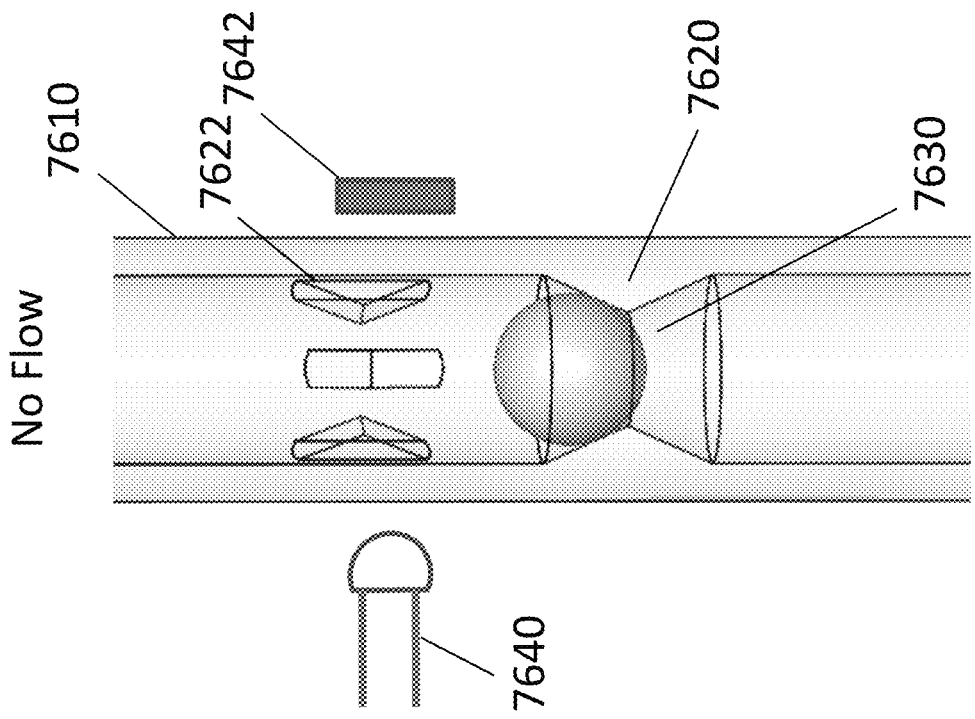

FIGS. 76A and 76B depict a second variation of an optical sensor and flow sensing portion. The configuration and operation of the fluid conduit (7610) is similar to that described in FIGS. 75A and 75B except that the first setting in a lumen of the fluid conduit (7610) may comprise a reduced-diameter or necked portion (7620) configured to receive or hold a ball (7620) and provide a fluidic seal when there is no fluid flow. This variation acts as a one-way valve that obstructs flow in the downward direction of FIGS. 76A and 76B. The fluid conduit (7610) further comprises a second setting (7622) (e.g., a set of one or more prongs) configured to limit a range of motion of the ball within the fluid conduit (7610), but still allow fluid flow in the upward direction of FIGS. 76A and 76B. An optical sensor arrangement comprising an emitter (7640) and a detector (7642) may be configured to transmit and receive light through a transparent portion of the fluid conduit (7610). The optical sensor may be located along any portion of the valve such that light obstruction by the ball (7620) corresponds to fluid flow and substantial light transmission corresponds to no fluid flow.

The fluid conduits described herein may be formed in one or more portions. For example, one or more transparent portions (e.g., optical sensing regions) of the fluid conduit may be formed separately from other portions and coupled together to form a single piece component via any suitable method including but not limited to molding, welding, bonding, adhesives, mechanical interfit, and the like.

Additionally or alternatively, one or more portions of the fluid conduit may be composed of a material susceptible to bacteria fouling. That is, one or more portions of the fluid conduit may be composed of a material that allows for improved growth of bacteria on an inner wall surface of the fluid conduit as compared to a surface not comprising the material. In some variations, the fluid conduit may comprise a plurality of parallel channels. In some variations, the fluid conduit may comprise one or more valves such as a one-way valve. In some variations, the fluid conduit may be configured to be replaced at a predetermined interval (e.g., daily, every two days, weekly).

Figure 71B:
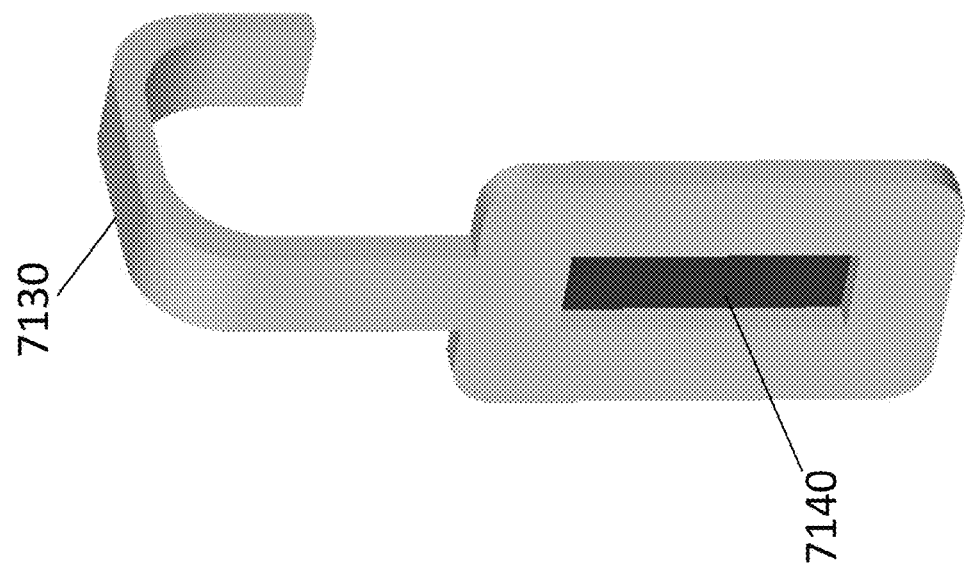
FIG. 71B is a perspective view of an exemplary variation of a mounting feature.
Figure 71A:
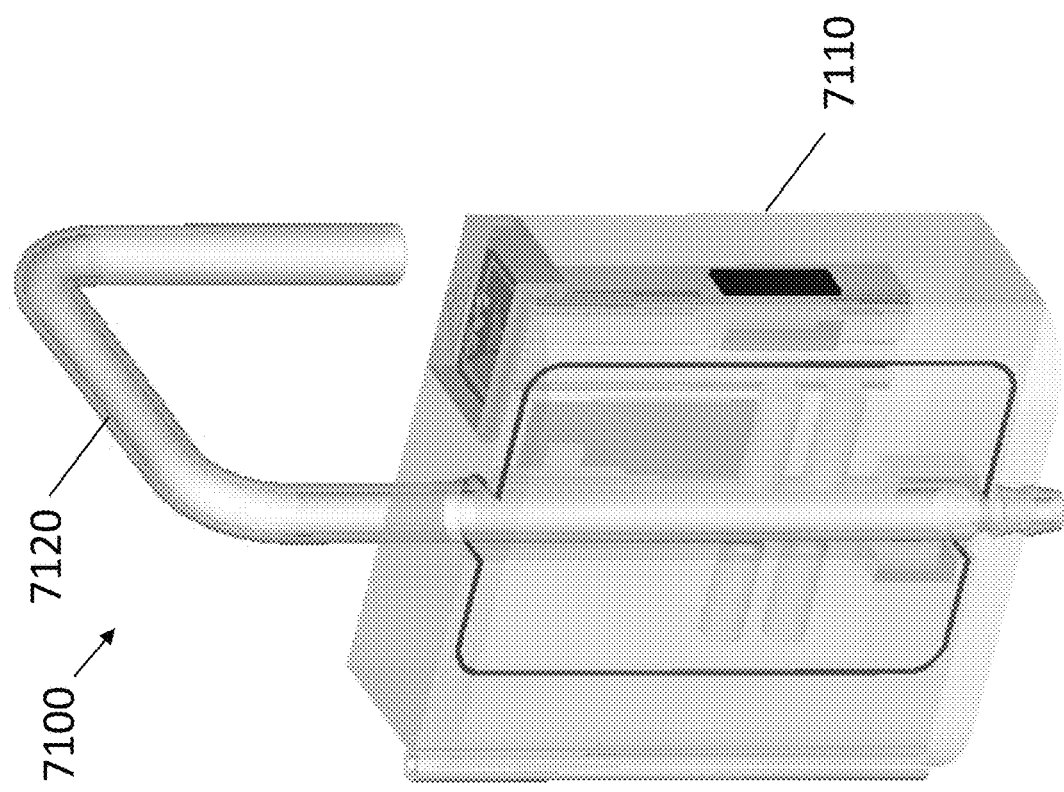
FIG. 71A is a perspective view of an exemplary variation of a patient monitoring device.
Figure 71D:
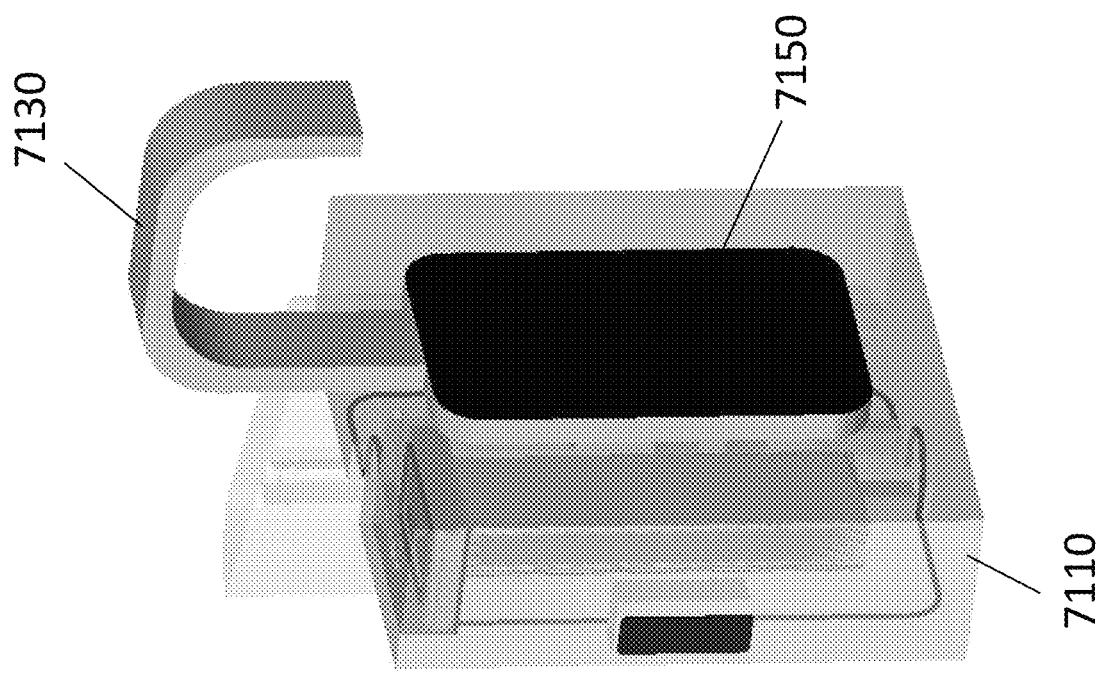
FIGS. 71C and 71D are perspective views of the patient monitoring device and mounting feature depicted in FIGS. 71A and 71B.
Figure 71C:
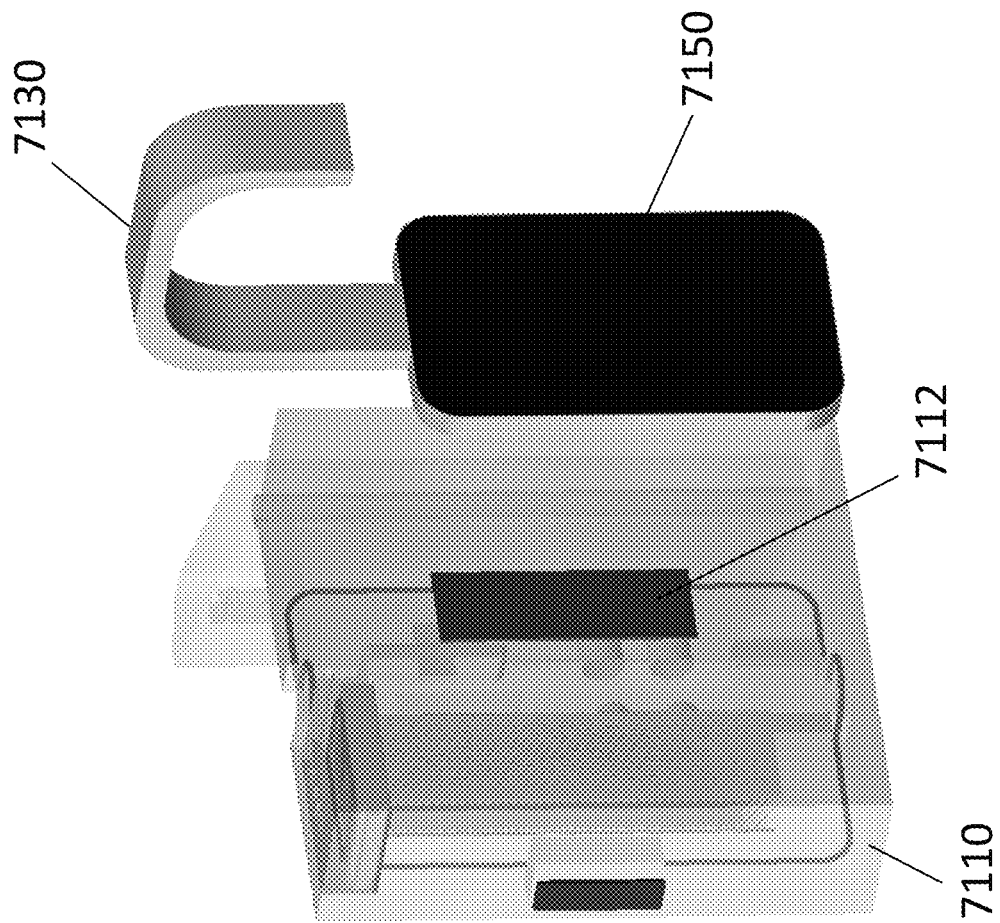

FIGS. 71A-71B illustrate perspective views of a mounting feature (7130) (e.g., mount) of a patient monitoring device (7100). FIG. 71A is a perspective view of a patient monitoring device (7100) including a durable component (7110) and disposable component (7120) such as those described herein. FIG. 71B illustrates a mount (7130) comprising a housing engagement feature (7140). In some variations, the housing engagement feature (7140) may comprise a magnet within a recess. The mount (7130) may be configured to releasably attach the housing (7110) to a drainage vessel such as a toilet. The mount (7130) may be curved in the shape of a clip so as to allow the patient monitoring device (7100) to conform or be removably hung over a drainage vessel. The mount may alternatively be composed of a semi-flexible material (e.g., polymer overmolded on an armature wire) to allow the curvature to be formed by the user. FIG. 71C illustrates the housing (7110) comprising a mount engagement feature (7112) that may comprise a magnet that in some variations may protrude from a surface of the housing (7110). FIG. 71D depicts the mount (7130) engaged to the housing (7110). In some variations, the mounting feature (7130) may comprise an adhesive (7150) configured to adhere to a drainage vessel. Although FIGS. 71A-71D depict the mount (7130) as disposed on a side of the housing (7110) opposite an interior cavity of the patient monitoring device, the mount (7130) may be disposed on any surface of the housing (7110). For example, the mount (7130) may be disposed on a same side of the housing (7110) as the interior cavity such that an interior cavity of the housing (7110) may face the drainage vessel when the mount (7130) couples the housing (7110) to the drainage vessel.

Method of Detecting Patient infection

In some variations, a method of detecting patient infection using a patient monitoring device such as those illustrated in FIGS. 67-71 and 74-76 may include the steps of attaching a mounting feature (e.g., clip) to a drainage vessel (e.g., toilet). A durable component of the patient monitoring device may be attached to the mounting feature. If necessary, a power source such as a battery may be inserted in the patient monitoring device (FIG. 69C). A disposable component (e.g., fluid conduit, drain line extension tube) may be connected to a tubing set drain line such as those manufactured by Baxter and Fresenius. The disposable component may be coupled to the durable component such that a transparent sensing portion of a fluid conduit is optically coupled to a sensor of the durable component. The durable component may then be activated and used to monitor fluid and/or patient parameters and used to generate data and/or alerts.

In another variation, a disposable component may be first coupled to a distal end of a tubing set drain line. The disposable component may then be attached to a drainage vessel. A durable component may be releasably engaged to the disposable component. For example, a patient monitoring device may be clamped onto a transparent portion of a disposable component.

In some variations, a calibration process may be performed upon engagement of the disposable component to the durable component. For example, one or more optical sensors may confirm detection of a fluid conduit upon reception of an engagement signal. Alternatively, a switch may be actuated when the fluid conduit is inserted. Once the fluid conduit is assembled, optical sensor data may be used to authenticate the fluid conduit and confirm fluid conduit parameters such as transparency and/or sterility. For example, the patient monitoring device may be disabled and/or an alert transmitted if incompatible tubing is placed within the interior cavity of the patient monitoring device. Even if the fluid conduit is authenticated, an error may be generated using the optical sensors if the fluid conduit does not fall within predetermined tolerances (e.g., wall thickness, color, transparency). This may prevent a patient from attempting to use a fluid conduit that is unacceptable due to reuse, bacterial fouling, loss of sterility (e.g., fingerprints), expiration, manufacturing error, combinations thereof, and the like. In some variations, optical sensor measurements of the patient fluid may be modified based on the calibration performed.

In some variations, patient fluid may be received through a fluid conduit coupled to or arranged proximate a sensor. A fluid flow signal may be received and used to initiate one or more fluid characteristic measurements. For example, a patient monitoring device may generate a fluid flow signal using an optical sensor arrangement and/or accelerometer. Additionally or alternatively, a cycler may output a fluid flow signal. In response to the fluid flow signal, a fluid characteristic such as optical scatter and/or absorption of the patient fluid may be measured at one or more wavelength ranges (bands) using the sensor. A particle concentration and/or leukocyte concentration of the patient fluid may be estimated based at least in part on the optical scatter and/or absorption measurement at one or more wavelength ranges. An infection state of the patient may be detected based at least in part on the estimated leukocyte concentration. The patient fluid is drained from the patient.

In some variations, a measurement of the optical scatter and/or absorption at a first wavelength range may be correlated to a total particle concentration of the patient fluid, and a measurement of the optical scatter and/or absorption at a second wavelength range may be correlated to a specific leukocyte concentration of the patient fluid, where the first wavelength range is different from the second wavelength range. For example, the first wavelength range may be between about 700 nm and about 1 mm, and the second wavelength range may be between about 260 nm and about 550 nm. In some variations, the second wavelength range may correspond to a non-leukocyte particle concentration of the patient fluid. For example, the second wavelength range may include specific particle type wavelengths (e.g., red blood cells, fibrin, triglycerides) and exclude wavelengths between about 260 nm and about 550 nm. The leukocyte concentration may be calculated by subtracting the total particle concentration from the non-leukocyte concentration.

In some variations, a first optical sensor arrangement may initially measure the optical scatter and/or absorption of fluid at a first wavelength range. If the measurements exceed a predetermined threshold (e.g., corresponding to a potential infection), then a second optical sensor arrangement may measure the optical scatter and/or absorption of fluid at a second wavelength range. A ratio of the signals from the first and second optical sensor arrangements may be calculated.

In some variations, the patient monitoring device may be configured to measure homogeneity of the patient fluid using the sensor. A set of the optical scatter and/or absorption measurements may be excluded from the leukocyte concentration estimation based at least in part on the measured homogeneity. For example, non-homogeneous fluid flow due to large and/or mixed particles (e.g., fibrin) may generate sensor measurements that form inaccurate concentration estimates. Excluding the sensor measurements of time periods of non-homogenous flow may increase the accuracy of fluid flow analysis such as leukocyte concentration estimates.

In some variations, the patient monitoring device may be coupled between a dialysate fluid vessel and a dialysate line so as to receive dialysate fluid through the fluid conduit where the dialysate fluid is to be infused in the patient. Optical scatter and/or absorption of the dialysate fluid may be measured using one or more sensors. The estimated leukocyte concentration may be based at least in part on the optical scatter and/or absorption measurements of the dialysate fluid. An optical scatter and/or absorption differential between the patient fluid and the dialysate fluid may be estimated by the patient monitoring device. The infection state of the patient may be updated based at least in part on the optical scatter and/or absorption differential or ratio.

As described herein, a flow rate, total flow volume, and/or flow direction of the patient fluid may be measured using a flow sensor coupled to the fluid conduit. The optical scatter and/or absorption measurements may be normalized based at least in part on the flow rate measurement or total flow volume. One or more of the patient fluid measurements may be normalized based at least in part on the flow rate or total flow volume measurement. One or more of an obstruction and flow direction may be detected based at least in part on the flow rate measurement. One or more of an infusion volume, drainage volume, infusion time, drainage time, and dwell time may be estimated based at least in part on the flow rate measurement. For example, a dwell time and a drain time may be estimated when a patient monitoring device begins measuring new fluid flow for cycling machines that measure multiple drain cycles with dwell cycles in-between. In some variations, fluid flow parameters may be determined using an ultrasonic flow sensor coupled to a fluid conduit, an accelerometer configured to detect vibrations corresponding to fluid pump activation, and data communication with a cycling machine.

One or more of a dialysis efficiency and dialysis adequacy may be estimated based at least in part on the estimated infusion volume, drainage volume, and dwell time. One or more of an infusion state and drainage state of the patient fluid may be detected without user input.

In some variations, at least one alert may be outputted comprising one or more of the infection state of the patient, patient compliance with a prescribed therapy, therapy efficacy, sensor calibration, fluid conduit maintenance, and sensor data. The alert may include notifying at least one predetermined contact comprising one or more of the patient, health care professional, a patient's partner, family member, and provider.

A communication channel may be established between the patient and a health care professional in response to the alert corresponding to the patient being in a high risk condition. At least one alert threshold may be set corresponding to turbidity, fluid flow, and conductivity based on user input. An alert corresponding to therapy efficacy may be output based at least in part on a flow measurement and a conductivity measurement. An alert corresponding to fluid conduit obstruction may be output based at least in part on a pressure measurement and an acceleration measurement. A patient infection alert may be output based on one or more of the patient fluid measurements.

Additional Patient Monitoring Devices

In some variations, a disposable component of a patient monitoring device may include a fluid conduit and one or more sensors that may be, for example, a limited-use sensor that may have a limited lifespan and may be replaced at the same time as the fluid conduit. For example, the disposable component may comprise at least one fluid contact sensor that may be configured to measure at least one fluid characteristic of patient fluid in the fluid conduit such as fluid ionic conductivity. Accordingly, the number of sensors in a durable component may be reduced, thus allowing the durable component to be reduced in size. Replacement of fluid-contacting components also negates the need for cleaning and servicing of fluid-contacting components, which are susceptible to bio-fouling and corrosion. In some variations, a set of disposable components compatible with a single durable component may be configured with different sensor arrangements for different applications and measurement requirements. FIG. 64A depicts an exemplary variation of a patient monitoring device (6400) configured to couple to a drain line (e.g., connector tubing) and attached to a toilet (6450). The patient monitoring device (6400) includes a durable component (6410) (e.g., housing, enclosure) releasably coupled to a mounting feature (6430) such as a hanger clip configured to attach over a rim of the toilet bowl (6450). A disposable component (6420) (e.g., fluid conduit) may be releasably secured within an interior cavity of the durable component (6410). The durable component (6410) may comprise an engagement feature (6412) (e.g., spring-loaded latch release) configured to release the disposable component (6420) from a cavity of the durable component (6410). The durable component (6420) may include at least one lumen configured to releasably engage and hold a fluid conduit. A proximal end of the disposable component (6420) may be coupled to a distal end of a drain line using a connector (6440) as described in more detail herein. For example, the inlet of the fluid conduit (6420) may comprise a tubing set connector (6440). A distal end of the disposable component (6420) may be configured to empty fluid (e.g., patient fluid) into a drainage vessel such as the toilet (6450). In some variations, a portion of the disposable component (6420) may follow a shape of the mounting feature (6430) so as to reduce an overall size and volume of the device (6400).

Figure 65:
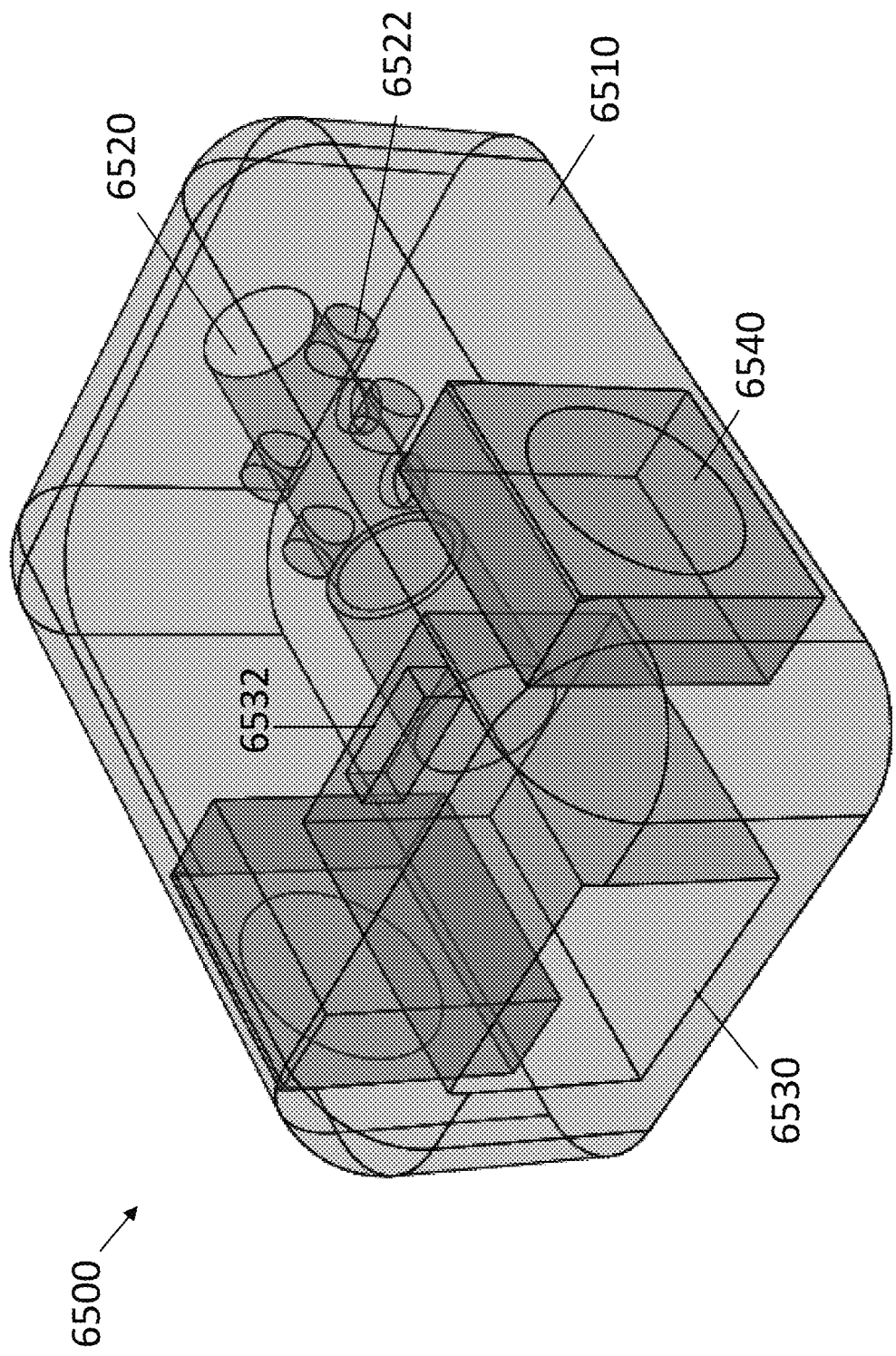
FIG. 65 is a perspective view of an exemplary variation of a durable component of a patient monitoring device.

FIG. 65 illustrates a durable component (6500) of a patient monitoring device. A housing (6510) of the durable component (6500) may comprise a lumen (6520) and cavity (6530) configured to hold and/or releasably engage one or more disposable components (6600, 6660) (see FIGS. 66A-66D) of the patient monitoring device. For example, as shown in FIGS. 66E and 66F, a first disposable component (6600) may be snap-fit into the cavity (6530) and the second disposable component (6660) may be screwed into the first disposable component (6600) and held in the lumen (6520) of the durable component (6500). The housing (6510) may further comprise a connector (6532) configured to provide an electrical connection (e.g., electronic contact points) to the first disposable component (6600) for charging and/or communication between the durable component (6500) and first disposable component (6660). For example, the connector (6532) may comprise a USB port or a proprietary connector configured to provide power and/or data transfer capabilities. The connector (6532) coupled to the first disposable component may further form a fluid seal (e.g., IP67 certified). At least a portion of the disposable components (6600, 6660) may be shielded from external light and sealed from external fluid when coupled to the durable component (6500). A mounting feature may be removably attached to the durable component (6500).

The durable component (6500) may comprise at least one non-contact fluid sensor (6522) configured to measure one or more parameters of fluid flow through the disposable components (6600, 6660). Sensor data measured using the sensor (6522) may be used to detect patient infection. For example, the durable component (6500) may comprise at least one optical sensor (6522) arranged substantially perpendicular to a longitudinal axis of the lumen (6520) of the durable component (6500). The optical sensor (6522) may comprise an emitter and at least one detector as described in detail herein. The optical sensor (6522) may correspond to any of the optical sensors described herein such as in FIGS. 34, 43, 44, 68, and 69.

In some variations, the patient monitoring device (6500) may further comprise at least one non-contact sensor including one or more of a pressure sensor, image sensor, flow sensor, accelerometer, gyroscope, temperature sensor, and magnetic field transducer. The image sensor may comprise one or more of a cell counter and color sensor. For example, some sensors such as an accelerometer and gyroscope may be provided in the housing (6510) separate from the lumen (6520) and cavity (6530).

The durable component (6500) may include controller comprising a processor and a memory (not shown) and which may be coupled to the optical sensor (6522). The controller includes the hardware and the firmware that, with the support of program memory and random access memory controls one or more sensors, receives the sensor data, processes the sensor data, stores the processed data in memory, communicates with a transmitter or directly to the database server system (not shown) via a communication device, and manages the power source. The memory may store the processed data until successful transmission of the data to the database server is confirmed. A power charging port may be controlled by the controller to charge the local power supply. The controller may be configured to receive signal data corresponding to received light generated by at least one detector. The controller may estimate total particle concentration data and leukocyte concentration data using the signal data as described in more detail herein. The patient monitoring device may further comprise an electronic communication device (e.g., wireless transmitter, transceiver) and a power source (e.g., battery) coupled to the controller. In some variations, the durable component (6500) may comprise a user interface (as shown and described with respect to FIG. 72) and described in more detail herein.

The first disposable component (6600) is configured to be secured in the cavity (6530) by a friction fit or mechanical interfit. For example, the housing (6510) comprises a disposable component engagement feature (6540) (e.g., spring-loaded pins) mateable with the first disposable component (6600). The housing (6510) may further comprise an engagement sensor (e.g., switch, optical sensor) configured to generate a sensor signal when the first disposable component (6600) is disposed in the cavity (6530). The engagement feature (6540) may be pushed inward to release the first disposable component (6600) from the cavity (6530). One or more components of the patient monitoring device (e.g., battery, memory, sensors) may be removable for ease of one or more of replacement, cleaning, data transfer, and charging. In some variations, redundant components may be provided such as a redundant battery and/or memory.

FIGS. 66A and 66B are perspective views of a first disposable component (6600) comprising a housing (6602) defining a first fluid conduit (6610) coupled to an inlet (6620) and an outlet (6630). An outlet (6630) of the first disposable component (6600) may be coupled to a proximal end of a drain line that opens towards a drainage vessel. For example, the outlet (6630) may comprise a barb fitting. An inlet (6620) of the first disposable component (6600) may be configured to couple to an outlet of a second disposable component (6660). For example, the inlet (6620) may comprise a female Luer-lock fitting. The first disposable component (6600) may comprise one or more fluid contact sensors (6640) such as a flow sensor, ionic conductivity sensor, and fluid temperature sensor. In some variations, the first disposable component (6600) may be configured to be replaced at predetermined intervals (e.g., weekly, bi-weekly, monthly). The housing (6602) may further comprise a connector (6650) configured to provide an electrical connection (e.g., electronic contact points) to a corresponding connector of the durable component (6500) for power and/or communication. The connector (6650) may be coupled to each of the fluid contact sensors (6640).

Figure 66C:
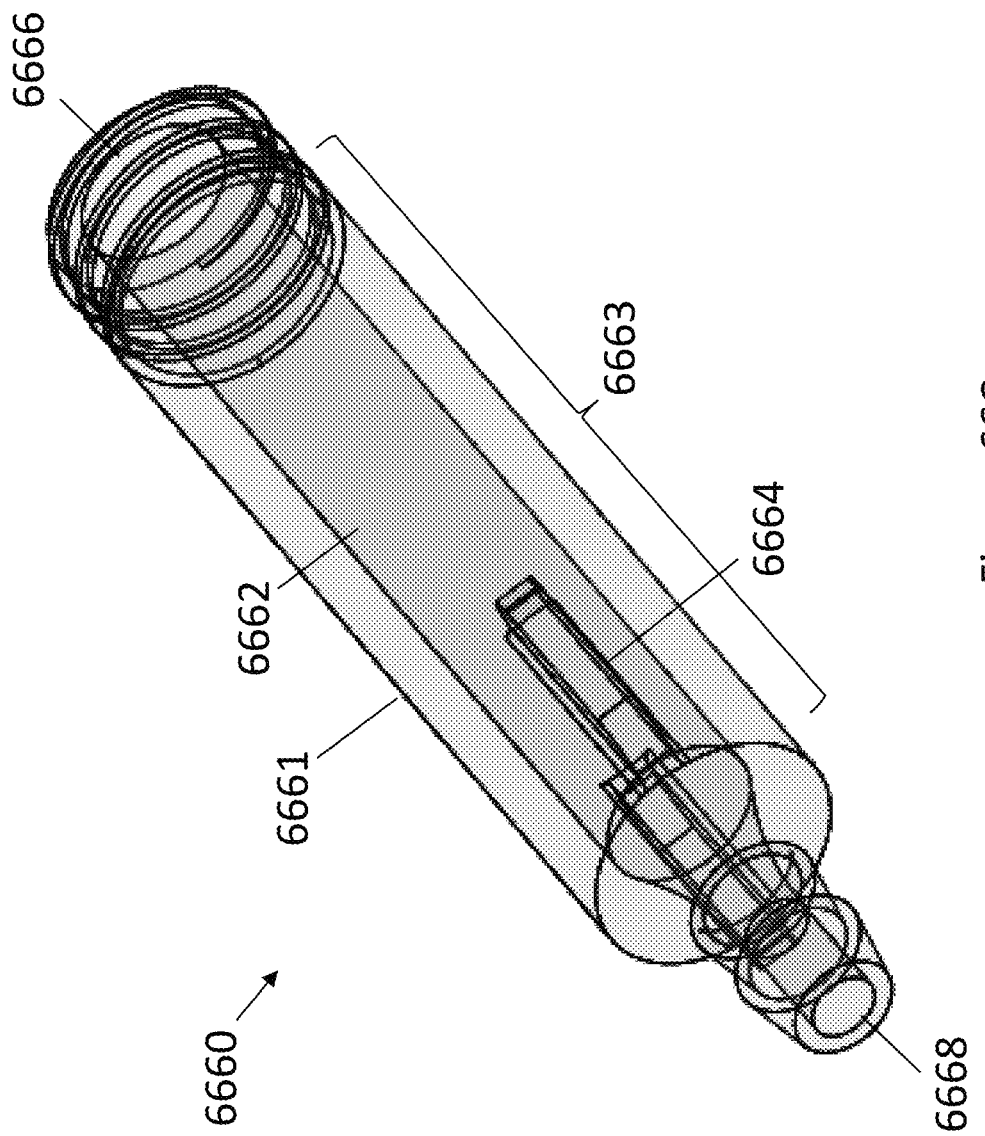
FIG. 66C is a perspective view of an exemplary variation of a disposable fluid conduit of a patient monitoring device.

FIG. 66C is a perspective of a second disposable component (6660) comprising a housing (6661) defining a second fluid conduit (6662) coupled to an inlet (6668) and an outlet (6666). An inlet (6668) of the second disposable component (6660) may be coupled to the end of a drain line. For example, the inlet (6668) may comprise a barb fitting (e.g., double-barb fitting) that may be configured to be difficult to remove once coupled. An outlet (6666) of the second disposable component (6660) may be configured to couple to an inlet of the first disposable component (6600). For example, the outlet (6666) may comprise a male Luer fitting. In some variations, the second disposable component may be configured to be replaced at a predetermined interval (e.g., daily, weekly, bi-weekly). The second disposable component may be replaced at a greater frequency than the first disposable component. For example, the second disposable component (6660) may be replaced daily with the cycling machine tubing set. The second disposable component (6660) may comprise an engagement feature (6664) configured to aid user rotation of the second disposable component (6660) into the first disposable component (6600). When the second disposable component (6660) is fully coupled to the first disposable component (6600), any thread or parting line of the second disposable component (6660) may be out of the field of view of an optical sensor (6522) of the durable component (6500).

The housing (6661) comprises at least one transparent portion (6663) that may be substantially transparent to at least one of ultraviolet light, visible light, and infrared radiation. For example, one or more portions of the housing (6661) are composed of one or more of acrylic, polycarbonate, cyclic olefin copolymers (COC), polystyrene, acrylonitrile butadiene styrene (ABS), polyethylene glycol-coated silicone, zwitterionic coated polyurethane, polyethylene oxide-coated polyvinyl chloride, and polyamphiphilic silicone. The transparent portion (6663) may be composed of a different material (and have different transparency) than other portions of the housing (6661). The second disposable component (6660) may be formed by injection molding and may be formed as a single piece or multi-piece component. The first and second disposable components may be sterile when supplied to the patient.

Figure 66D:
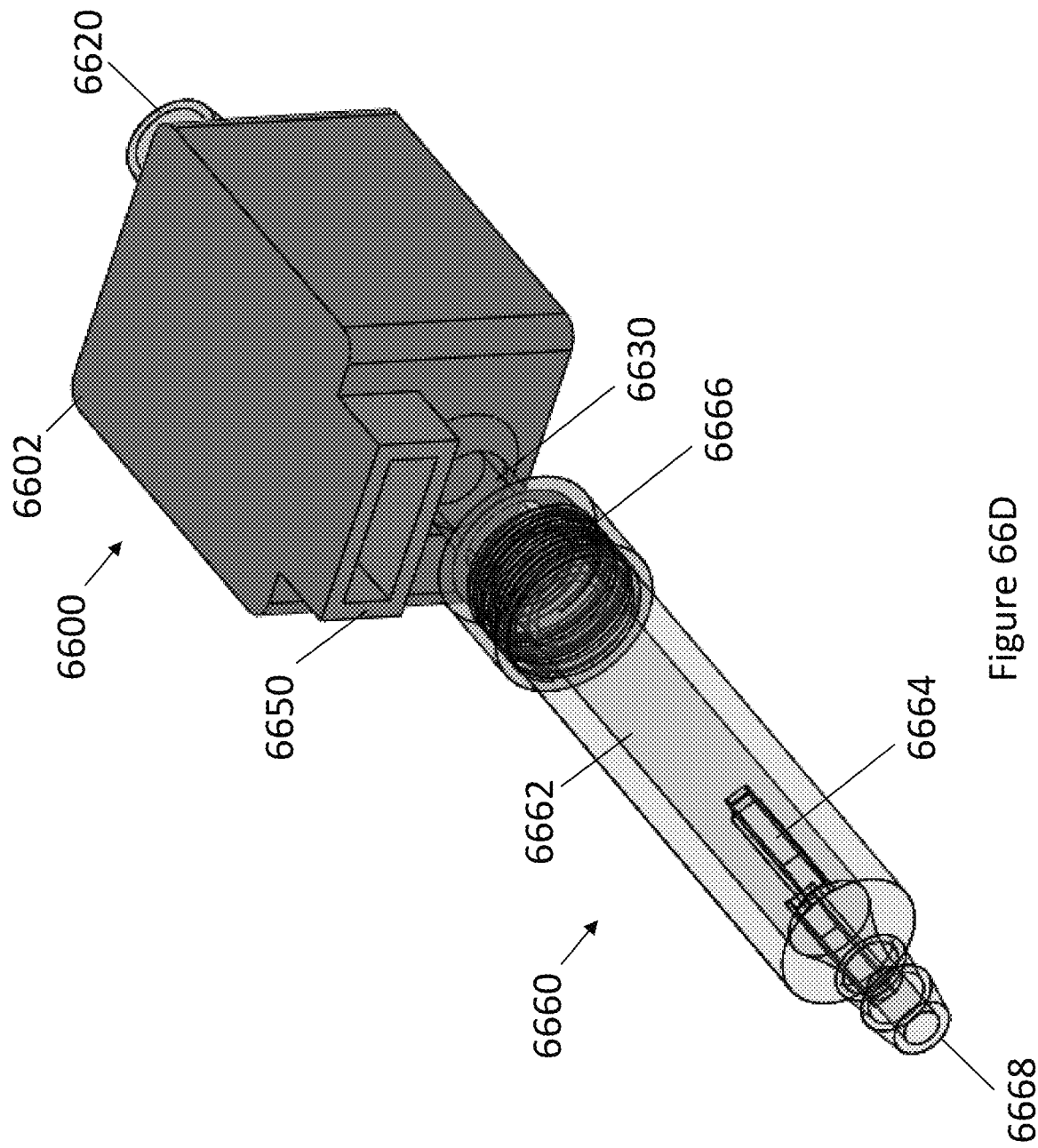
FIG. 66D is a perspective view of the disposable component and disposable fluid conduit depicted in FIGS. 66A-66C.
Figure 66F:
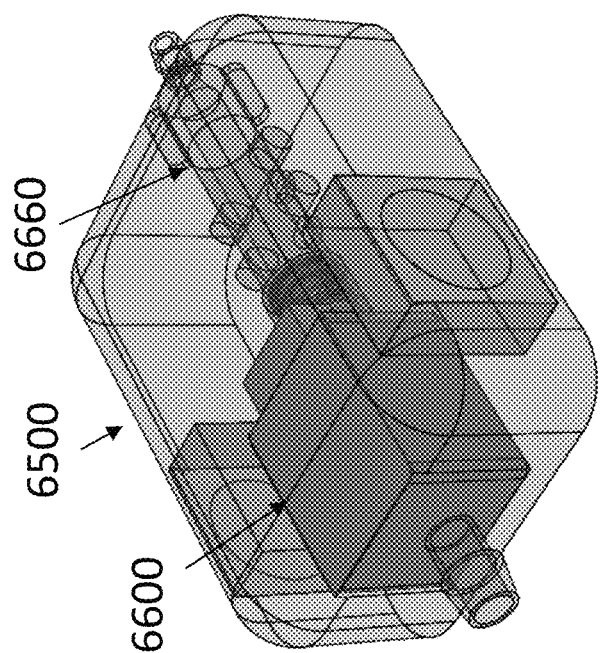
FIG. 66F is an assembled perspective view of a patient monitoring device.
Figure 66E:
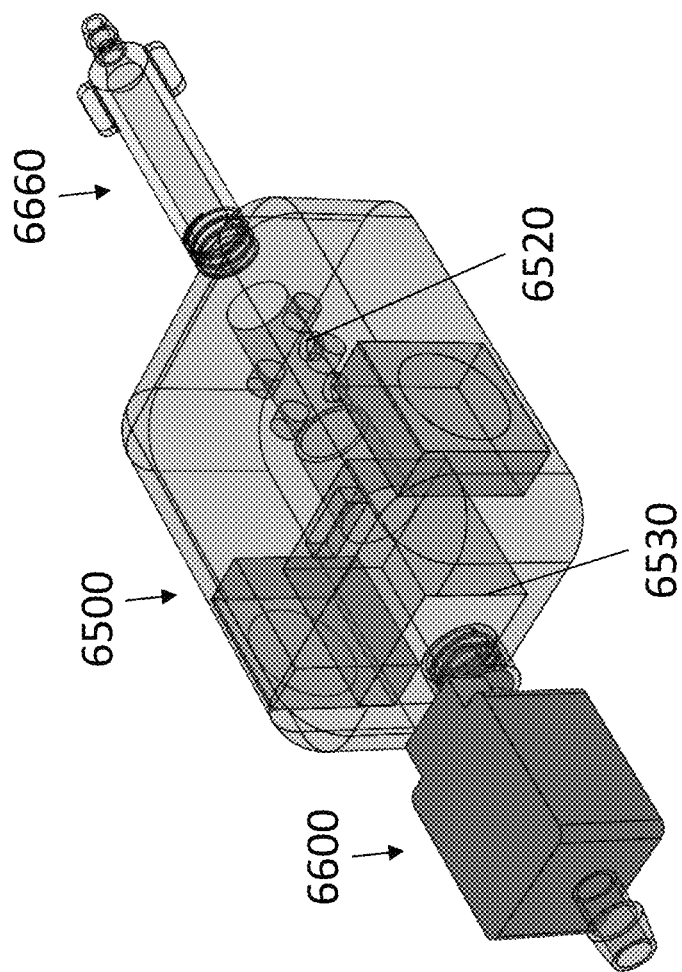
FIG. 66E is an exploded perspective view of the patient monitoring device.

FIG. 66D is a perspective view of the first disposable component (6600) coupled to the second disposable component (6660). In some variations, an inlet (6668) of the second disposable component (6660) may be coupled to the end of a drain line. An outlet (6666) of the second disposable component (6660) may be configured to couple to an inlet (6630) of the first disposable component (6600). An outlet (6620) of the first disposable component (6600) may couple to tubing configured to open towards a drainage vessel such as the toilet.

Figure 2:
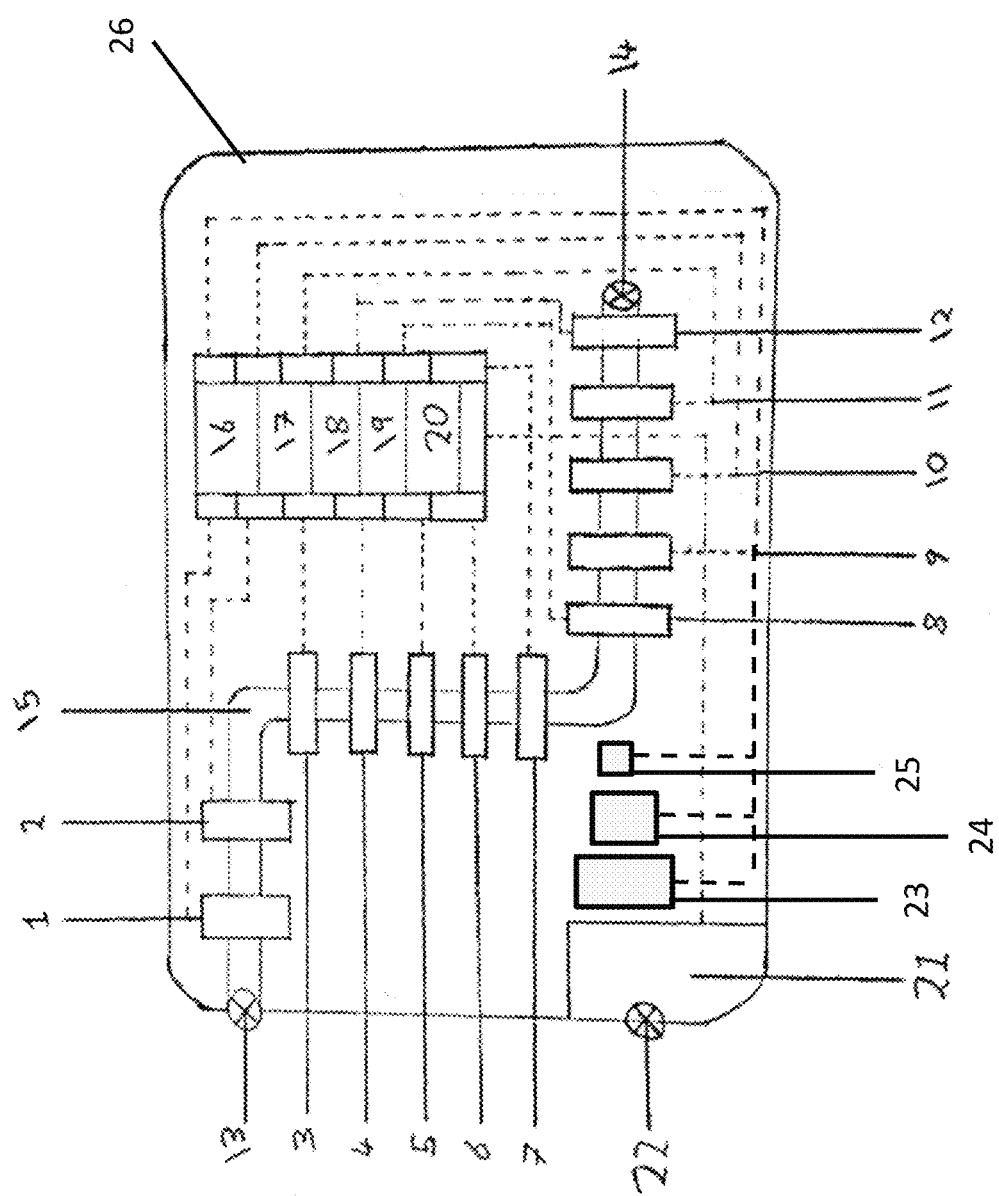
FIG. 2 schematically illustrates an exemplary variation of a patient monitoring device, depicting a patient monitoring device layout, and connections to an in-dwelling catheter and dialysate fluid.

FIG. 2 depicts one exemplary hardware configuration for the electrical layout of the hardware patient monitoring device. The various sensing technologies within the housing or enclosure (26), connections to the other electrical components, and fluid conduit (15) are illustrated. The set of sensors fluidically connected to the fluid conduit (15) may include a flow sensor (1), an optical sensor (2), a temperature sensor (3), a pressure sensor (4) a conductivity sensor (5), a pH Sensor (6), a glucose sensor (7), a lactate sensor (8), a cell counter (9), a urea sensor (10), and a creatinine sensor (11). In some variations, the patient monitoring device (00) may comprise one or more sensors configured to detect patient infection. A patient infection sensor may include a spectroscopy sensor such as an optical scatter/absorption sensor. For example, a fluid optical scatter/absorption sensor (2) may be optically connected to the fluid conduit (15) such that a light emitter and detector have sufficient optical clarity to measure the fluid in the fluid conduit (15). An accelerometer and gyroscope position sensor (23) may be fixed within the enclosure (26). A skin color sensor (24) and/or a skin surface temperature sensor (25) may be located such that the sensors are exposed to or in positioned against the skin surface, next to an in-dwelling catheter exit site. A first connector (13) configured to connect to one or more of an infused and drained dialysate containers (not shown in FIG. 2) and a second connector (14) configured to connect to the in-dwelling catheter (not shown) allow the system to detect all inflow and outflow fluids. The processor (16) includes the hardware and the firmware that, with the support of program memory and random access memory (17) controls the network of sensors, receives the sensor data, processes the sensor data, stores the processed data in the memory module (19), communicates with a transmitter (e.g., via Bluetooth, Wi-Fi) or directly (e.g. via LTE cellular) to the database server system (not shown) via the wireless communication module (18), and manages the local power supply (21). The local memory module (19) stores the processed data until successful transmission to the data to the database server is confirmed. A power charging port (22) is controlled by the processor (16) to charge the local power supply (21).

Figure 3:
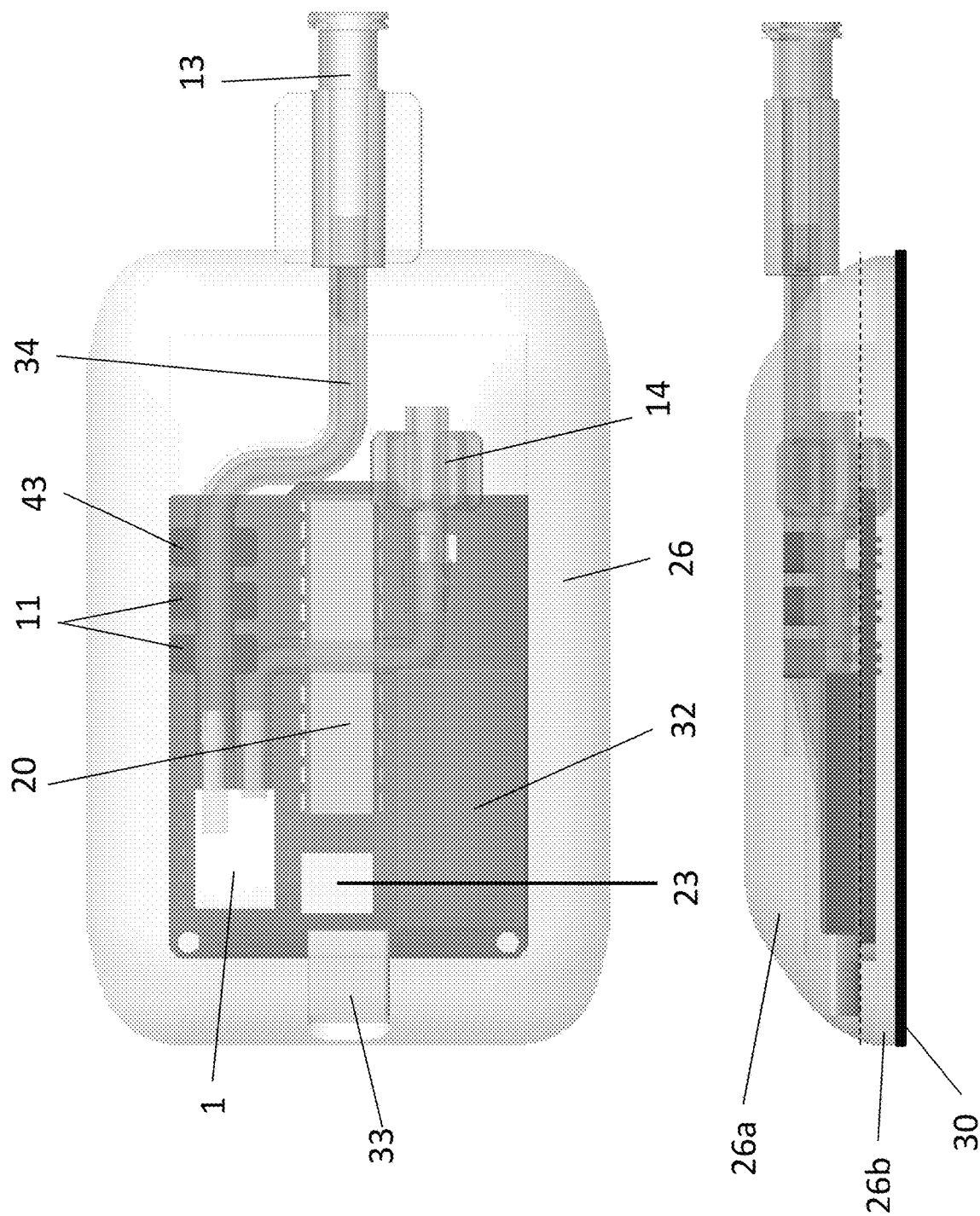
FIG. 3 illustrates a top and side view of an exemplary variation of a patient monitoring device housing and components.

FIG. 3 depicts one configuration of a patient monitoring device. The housing or enclosure (26) contains the patient monitoring device components. A first half of the enclosure (26a) may be a snap-fit into a disposable second half of the enclosure (26b), which is bonded to an adhesive layer (30) that can temporarily bond to the patient's skin. In other examples, the enclosure may be heat-welded or glued together, or may comprise a housing with a side opening and a side cap, or may comprise an assembly affixed with fasteners such as screws, or may comprise a spring-loaded latch release of one side, or a connection with one side internally threaded and the other side externally threaded. Tubing connectors (e.g., standard Luer connectors) may include one connection port (13) connected to the dialysate solution and one connection port (14) connected to the in-dwelling catheter. The connection port for the catheter (14) may be contained within the enclosure (26). In-between the connectors (13, 14), there is a fluid conduit (34) (e.g., tube) that enters through a sensor network which may comprise a multitude of non-fluid-contacting sensors (43) (e.g., optical scatter/absorption sensors), fluid-contacting sensors with no moving parts (11) (e.g., conductivity, impedance, and pressure sensors), and fluid-contacting sensors with moving parts (1) (e.g., Hall-effect flow sensor). A gyroscope/accelerometer motion sensor (23) may be in a fixed position and separate from the fluid conduit of the fluid conduit (34). The sensors (1, 43, 11, 23) are connected to a printed circuit board (PCB). A control device (e.g., microcontroller, firmware, memory storage module, wireless transmission module) (20) are also connected to the PCB. Via the PCB, the control device (20) may be connected to each sensor for power supply to the sensor and data output from each sensor to the control device (20). For local power supply, a battery (32) may be connected to the PCB, and a charging/communication port (22). A USB port (33) or other suitable port may connect to an external power source and/or function as a wired communication channel. The control device (20) may be connected to the battery (32) and the charging port (22) via the PCB. The microcontroller, memory storage module, and wireless transmission module are depicted as connected on one chipset in FIG. 3 but can be separate components connected via the PCB.

Figure 4:
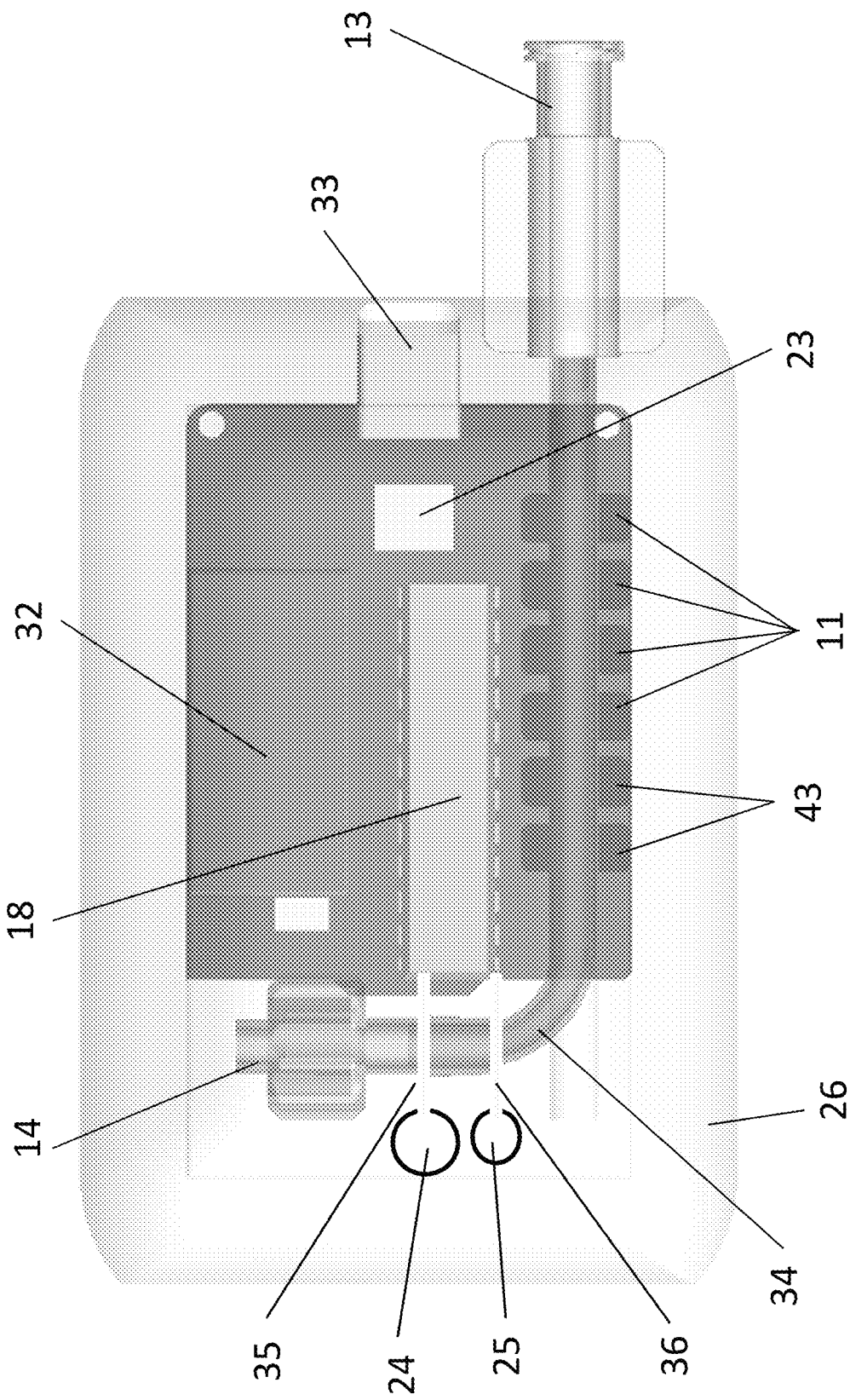
FIG. 4 illustrates a cross-sectional top view of another exemplary variation of a patient monitoring device housing and components.

FIG. 4 depicts an alternate configuration of the patient monitoring device. The housing or enclosure (26) contains at least a portion of the patient monitoring device components. Connectors include a first connector (13) connected to the dialysate solution and a second connector (14) connected to the catheter. The second connector may be enclosed within the enclosure (26). Between the connectors (13, 14), a fluid conduit (34) may couple to one or more non-fluid-contacting sensors (43) (e.g., optical scatter/absorption and optical cell-counter sensors), and fluid-contacting sensors with no moving parts (11) (e.g., conductivity, impedance, pressure, pH, temperature sensors). A gyroscope/accelerometer motion sensor (23) may also be provided, separate from the fluid conduit (34). A color sensor (24) may be positioned by a catheter exit site directly above the skin surface, and/or a skin temperature sensor (25) may be positioned directly against the skin surface. The sensors (43, 11) next to the fluid conduit (34), are connected to a printed circuit board (PCB). The sensors (24, 25) measuring the skin surface are connected to the PCB via wire leads (35, 36) (e.g., flexible circuit). A control device (e.g., microcontroller, firmware, memory storage module, wireless transmission module) (18) are also connected to the PCB. Via the PCB, the control device (18) may be connected to each sensor for power supply to the sensor and data output from each sensor to the control device (18). For local power supply, a battery (32) is connected to the PCB, as well as a charging and/or communication port (33). For example, a USB port (33) may also act as a connection to an external power source or wired communication channel to access the data. The control device (18) may be connected to the battery and the charging port via the PCB. The microcontroller, memory storage module, and wireless transmission module are depicted as connected on one chipset in FIG. 4 but can be separate components connected via the PCB.

Disposable-Durable Component Interfaces

In the variations depicted in FIGS. 3 and 4, the network of sensors is combined with the rest of the hardware system and embedded with the PCB which contains the battery (32), control device (18), charging port (33), connectors (13,14), and enclosure (26). In another variation, depicted in FIG. 5, one set of permanent or semi-permanent sensors (1, 43) are connected to the first enclosure half (26a). Another set of disposable sensors (11) (e.g., enzyme-based electrochemical sensors, test indicator strips) may be connected to the second enclosure half (26b) which also contains the adhesive layer (30) in contact with the patient. In this variation, the second enclosure half (26b) and components coupled thereto may be referred to as a cartridge. The adhesive layer replacement cycle may coincide with the sensor replacement cycle such that the cartridge may be replaced together. The two halves of the assembly (26a, 26b) may be removably coupled such as via snap fittings and/or an electrical connector. Different cartridges may comprise different configurations, such as different sensor packages. In some variations, a cartridge may comprise an enclosed housing such that fluid-contacting components are sterile until the cartridge is properly loaded into the durable component interface (e.g., first half (26a)).

Figure 5:
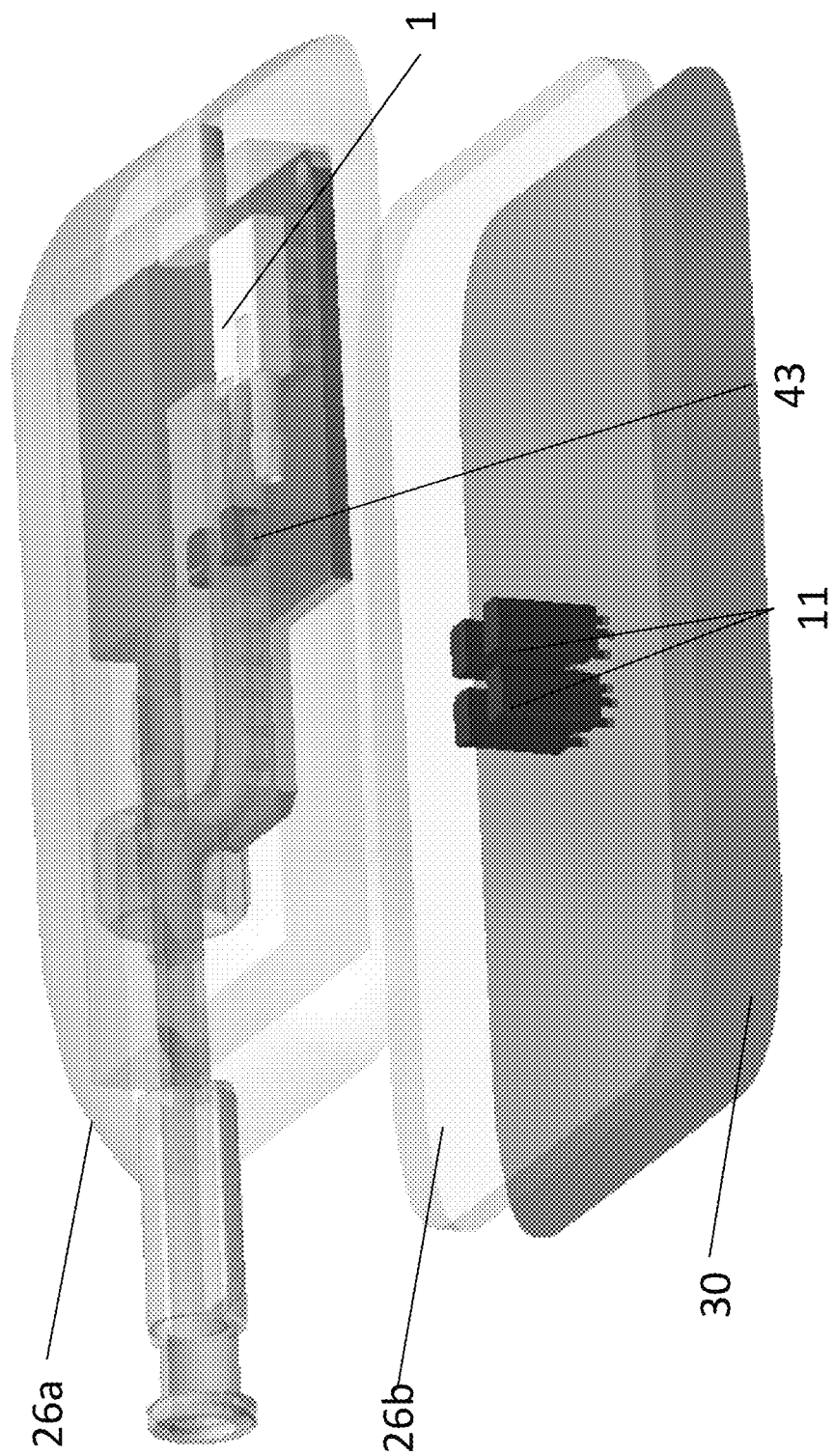
FIG. 5 illustrates an assembly view of an exemplary variation of a patient monitoring device of disposable and permanent components.

In each variation described in FIGS. 3, 4, and 5, one or more components of the patient monitoring device (e.g., battery, memory, sensors, fluid conduit) may be removable for ease of one or more of replacement, cleaning, data transfer, and charging. In some variations, redundant components may be provided such as a redundant battery of equal or different capacity used as a "backup" power supply in the case the primary battery has been exhausted.

In some variations, the patient monitoring device may be two or more separate components that can be attached to each other to provide full functionality. For example, a cartridge-based device may comprise a disposable cartridge configured to removably attach to a durable component interface (e.g., permanent enclosure/housing) of the patient monitoring device. The cartridge may comprise a set of fluid-contacting components (e.g., fluid conduit, fluid contact sensors) and the durable component interface may comprise a set of non-fluid contacting components (e.g., non-fluid contact sensors, control device, battery, transmitter). In some of these variations, the fluid-contacting components may be removed and replaced as needed. For example, fluid-contacting components of the patient monitoring device may require replacement due to one or more of regulatory requirements, biofouling, use, wear, degradation, and other changes over time. Also, if a patient requires the device for only a short-term period of time, replacement of the fluid-contacting components allows the device to be safely used for multiple patients by swapping out the fluid-contacting components. In some variations, the disposable cartridge may comprise two or more portions that may be removably attached to form the disposable component.

Additionally or alternatively, one or more of the durable component and cartridge of the patient monitoring device may be cleaned and sterilized using devices, fluids, and/or mediums such as ethylene oxide (EtO), an autoclave, solvent soak, cleaning agent soak, and the like at predetermined intervals. For example, the cartridge may be configured to be cleaned, sterilized, and re-used at predetermined intervals rather than being disposed of. For example, the cartridge may be replaced or sterilized using an autoclave whenever an infection is detected or once every 28 days. Furthermore, in between these replacement or sterilization steps, the cartridge may be cleaned daily or weekly with a fluid (e.g., acid, alcohol rinse). In some variations, the durable component may comprise a set of fluid-contacting components and non-fluid contacting components. For example, the first and second connectors may be attached to the durable component and may connect to a fluid conduit of the cartridge that may receive fluid.

Fluid Conduit

Figure 16A:
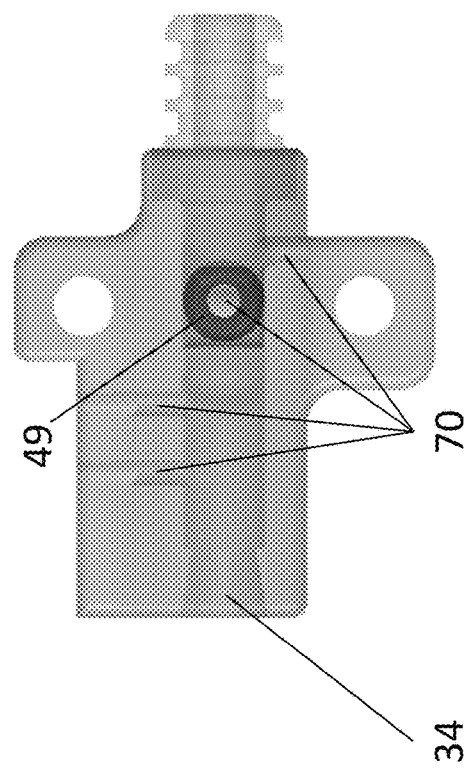
FIG. 16A illustrates a plan view of an exemplary variation of a fluid conduit.
Figure 16C:
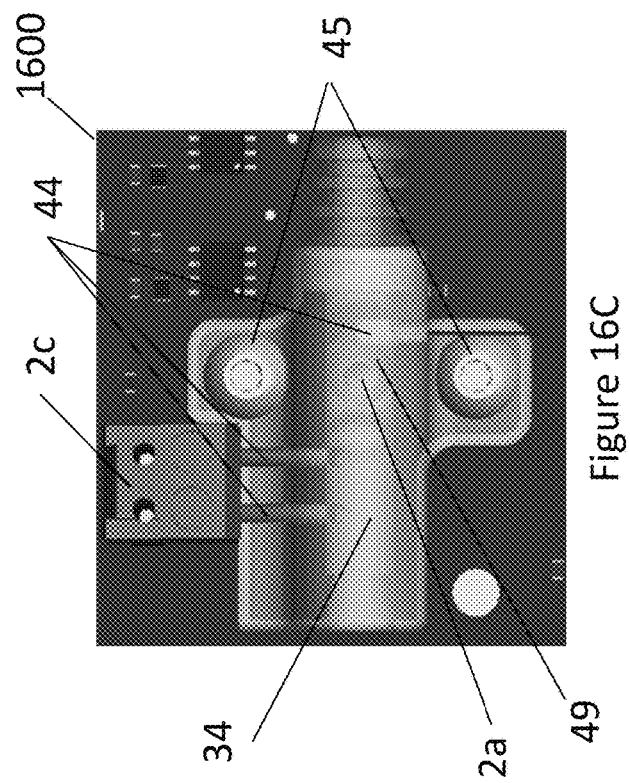
FIG. 16C is a plan view of an exemplary variation of the fluid conduit and PCB interface depicted in FIGS. 16A and 16B.
Figure 16B:
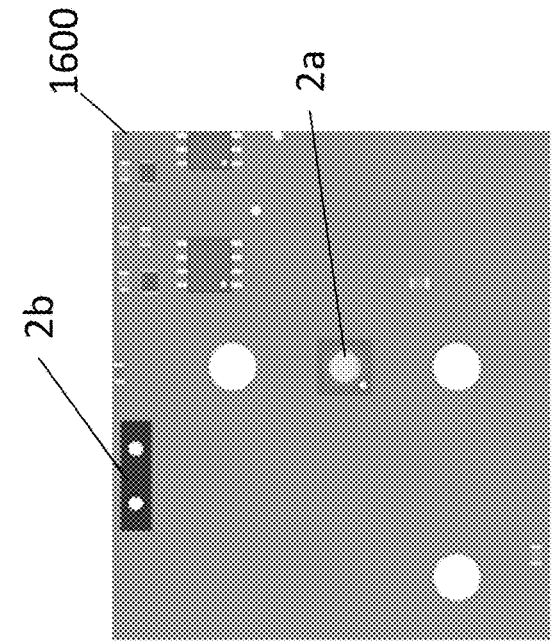
FIG. 16B is a plan view of an exemplary variation of a PCB interface.

FIGS. 16A-16C illustrate one variation of a fluid conduit coupled to a printed circuit board that may comprise a set of sensors configured to determine one or more characteristics of the fluid flowing through a fluid conduit. FIG. 16A depicts a fluid conduit (34) (e.g., formed using molded PVC) defining one or more holes (70) covered by one or more respective sealing elements (49) (e.g., silicone O-rings, adhesive, glue). FIG. 16B illustrates a printed circuit board (PCB) interface (1600) comprising a surface-mount device (SMD) sensor (2a) and a printed circuit board (PCB)-mounted connector (2b). In FIG. 16C, a set of fluid-contacting sensors (44) are disposed within a corresponding set of holes (70). SMD sensor (2a) may be sealed within a hole (70) via sealing gasket (49) and compression fitting with screws (45). A sensor terminal (2c) may connect to the printed circuit board-mounted connector (2b). The SMD sensor (2a) may be, for example, a non-contact sensor.

Figure 16D:
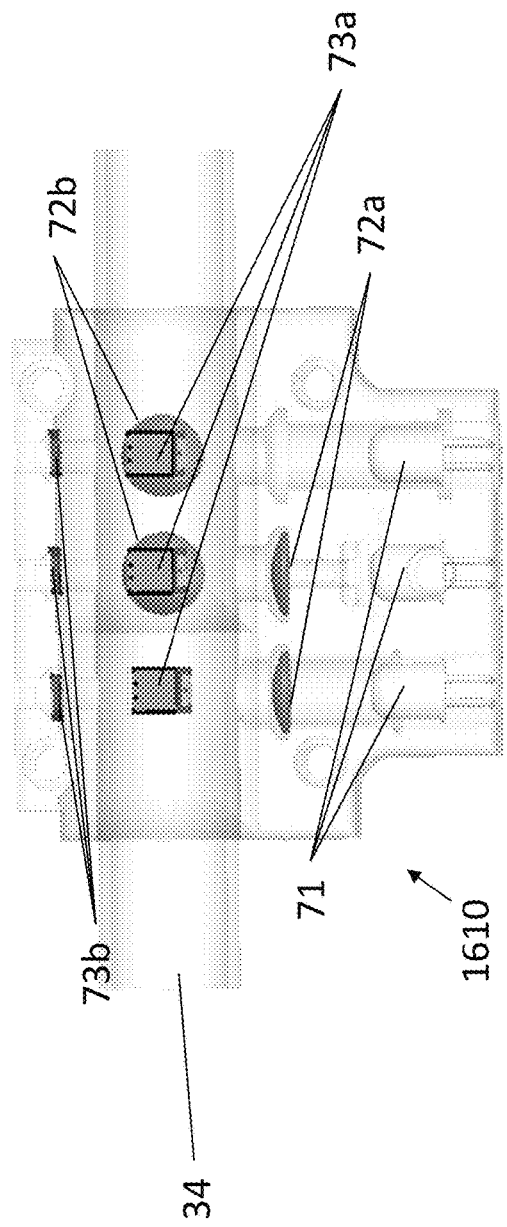
FIG. 16D is a top view of an exemplary variation of a fluid conduit and patient monitoring device.
Figure 16E:
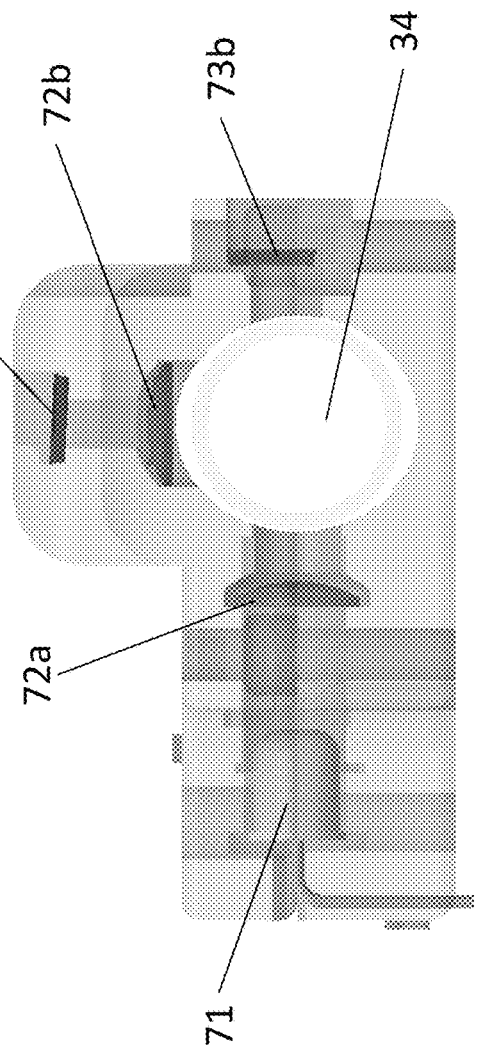
FIG. 16E is a side cross-sectional view of an exemplary variation of the fluid conduit and patient monitoring device depicted in FIG. 16D.

FIG. 16D illustrates a top cross-sectional view and FIG. 16E represents a side cross-sectional view of a patient monitoring device such as an optical scatter/absorption measurement system (1610). The system (1610) may include a spectroscopy sensor comprised of a set of light emitters (71) and light sensors (73). The set of light emitters (71) may be configured to transmit light into a fluid conduit (34). In some variations, a lens or filter (72a) may be disposed between the lighter emitters (71) and fluid conduit (34). The set of light sensors (73b, 73a) may be oriented at respective predetermined light absorption angles and scatter angles relative to the set of light emitters (71). In some variations, a lens or filter (72b) may be disposed between the set of light sensors (73b, 73a) and fluid conduit (34). As further described herein, the spectroscopy sensor need not contact fluid flowing through fluid conduit (34), but instead the fluid conduit (34) may be substantially optically transparent (or close, with a high total transmittance of wavelengths used in the measurement) such that the spectroscopy sensor may measure contents of the fluid conduit (34). In some variations, the fluid conduit (34) may define a set of holes configured to hold a corresponding set of fluid-contacting sensors while maintaining a fluid seal (e.g., with sealing gaskets (40)).

Figure 17:
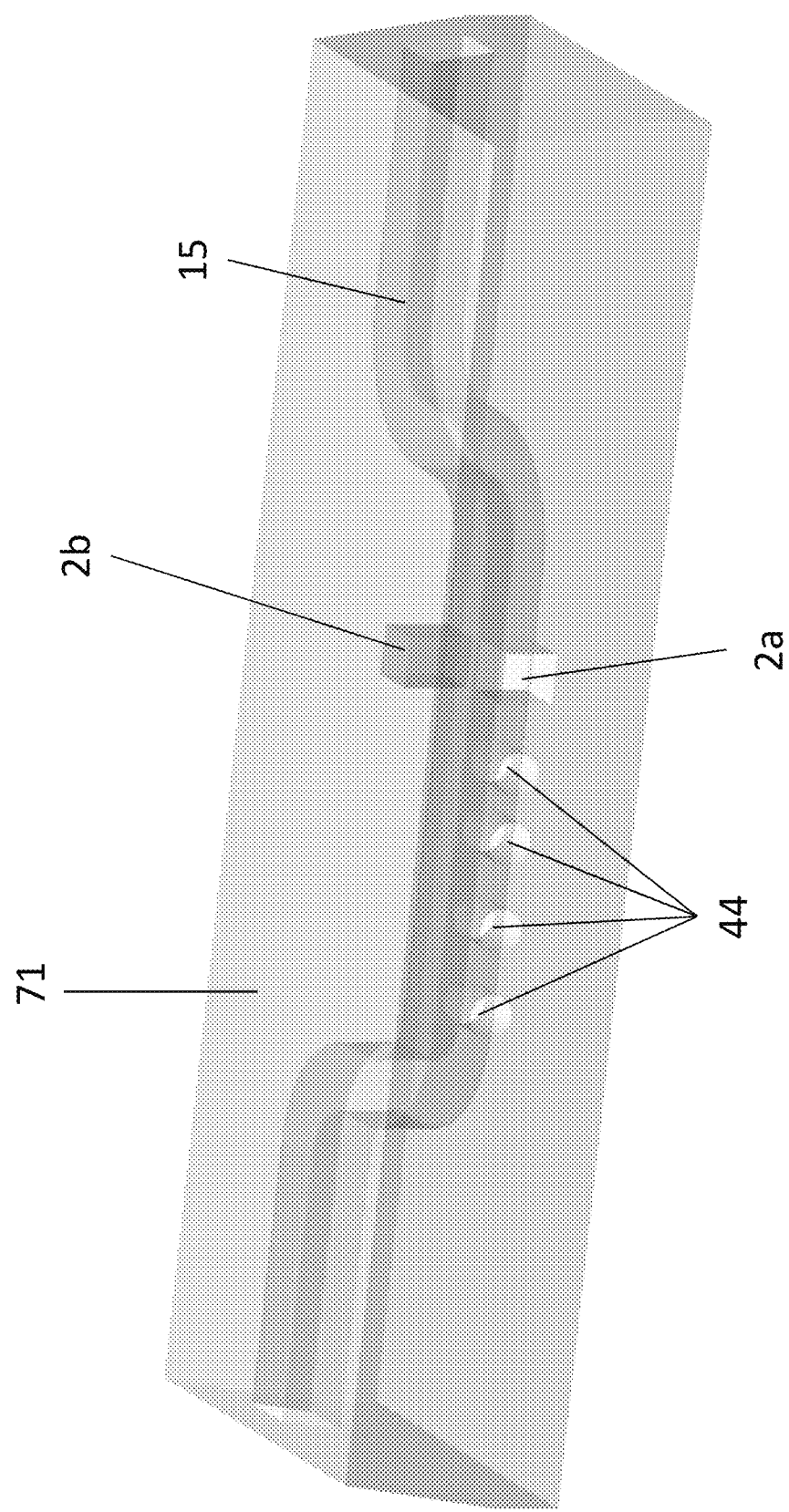
FIG. 17 illustrates a perspective view of an exemplary variation of a fluid conduit.

In some variations, the fluid conduit may have a circular cross-sectional shape. The fluid conduit may define a lumen (e.g., having a circular or square cross-section) within a rigid or semi-rigid material. In other variations, the fluid conduit may have any suitable shape. For example, FIG. 17 illustrates a square cross-section fluid conduit (15) in a structure (71) (e.g., housing) with holes configured to hold a set of fluid-contacting sensors (44) and a hole for an optical scatter/absorption sensor emitter (2b) and a hole for an optical scatter/absorption sensor detector (2a). The emitter (2b) and detector (2a) are shown as oriented 90 degrees apart from each other around the fluid conduit. Additionally or alternatively, the sensors may be molded directly into the structure (71) to ensure a fluid-tight seal. In some variations, the set of sensors (2, 44) may be held in the holes using an adhesive to ensure a fluid-tight seal. In some variations, a transparent layer may be provided between the sensor and lumen. For example, a glass interface may be disposed between a sensor (2, 44) and fluid in the fluid conduit (15). In some variations, the structure (71) may be formed by, for example, one or more of injection molding, machining, ultrasonic welding, and 3D printing techniques.

In the systems and devices described herein comprising a plurality of sensors, upstream sensors may be configured to alter the properties of the particles within the fluid conduit and therefore affect the measurements performed by downstream sensors. For example, chemi-resistor sensors may chemically react to the particles, which may change, for example, the optical scatter/absorption of fluid in the fluid conduit. In another example, an optical sensor may include light emitters emitting light in the ultraviolet wavelength range, which may kill cells and/or pathogens, thereby affecting downstream optical measurement of the cells and/or pathogens. Conductivity measurements that apply electrical current through the fluid may also damage cells or pathogens, thereby affecting downstream optical measurement of the cells and/or pathogens. Furthermore, conductivity measurements may also heat the fluid, which may alter downstream temperature measurement. As such, the order of the sensors may be important in a sensor system having a plurality of sensors. In particular, sensors which may react with the fluid and or particles within the fluid conduit should generally be placed downstream such that their effects do not affect the measurements performed by sensors in the system.

Figure 26:
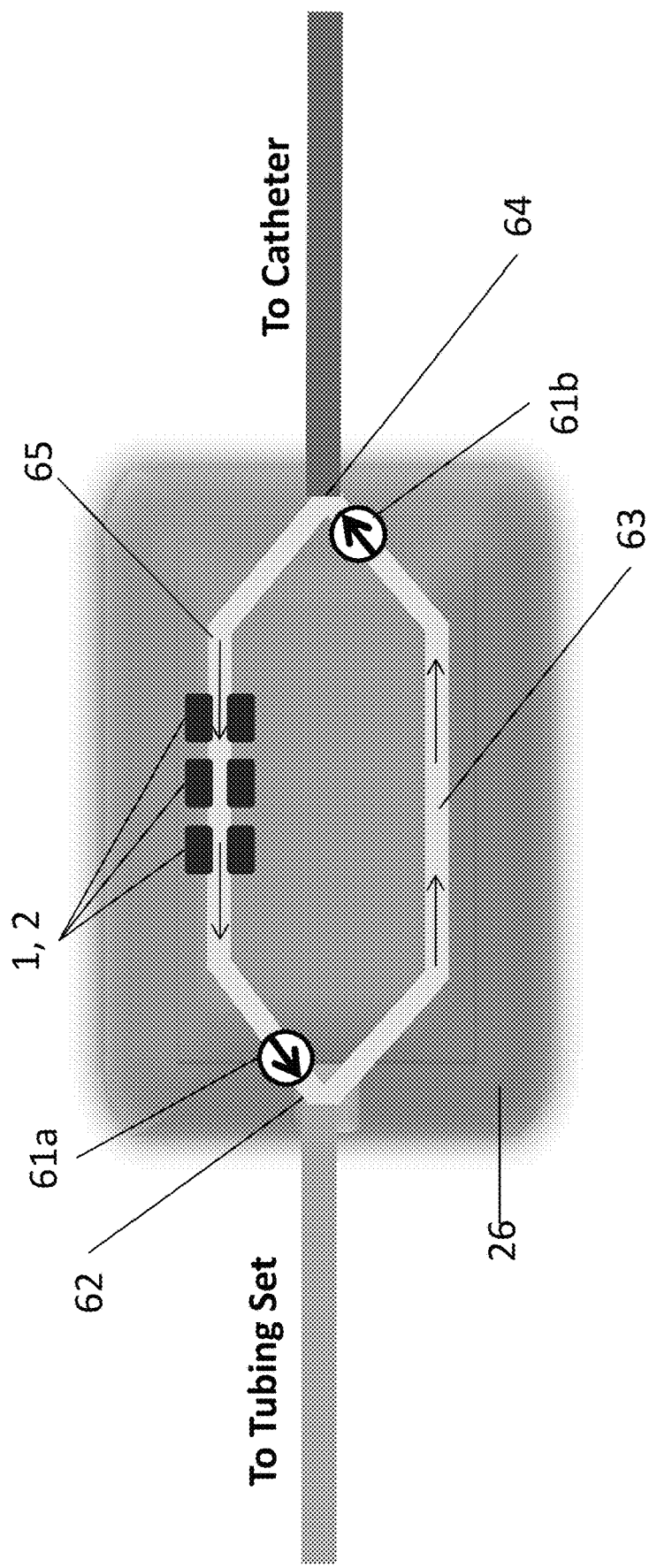
FIG. 26 illustrates a schematic diagram of an exemplary variation of a patient monitoring device comprising a set of fluid conduit and a set of one-way valves.
Figure 29:
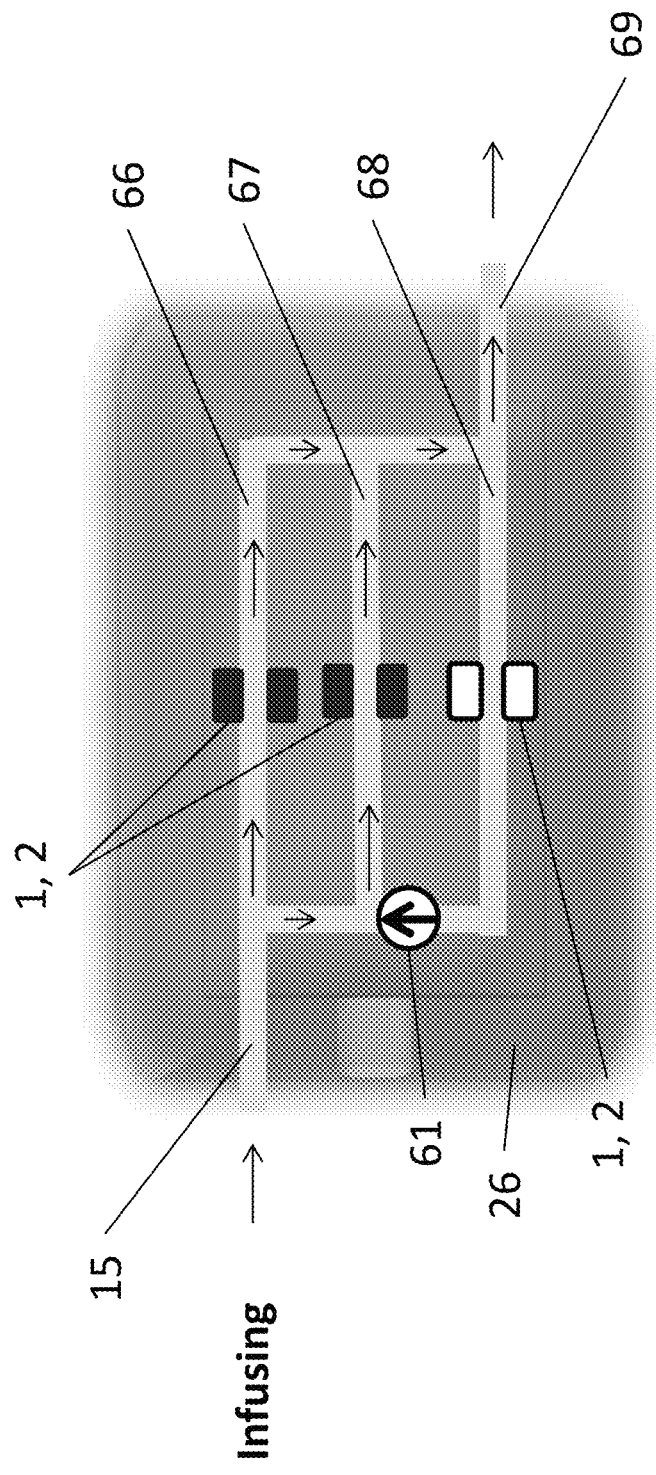
Figure 30:
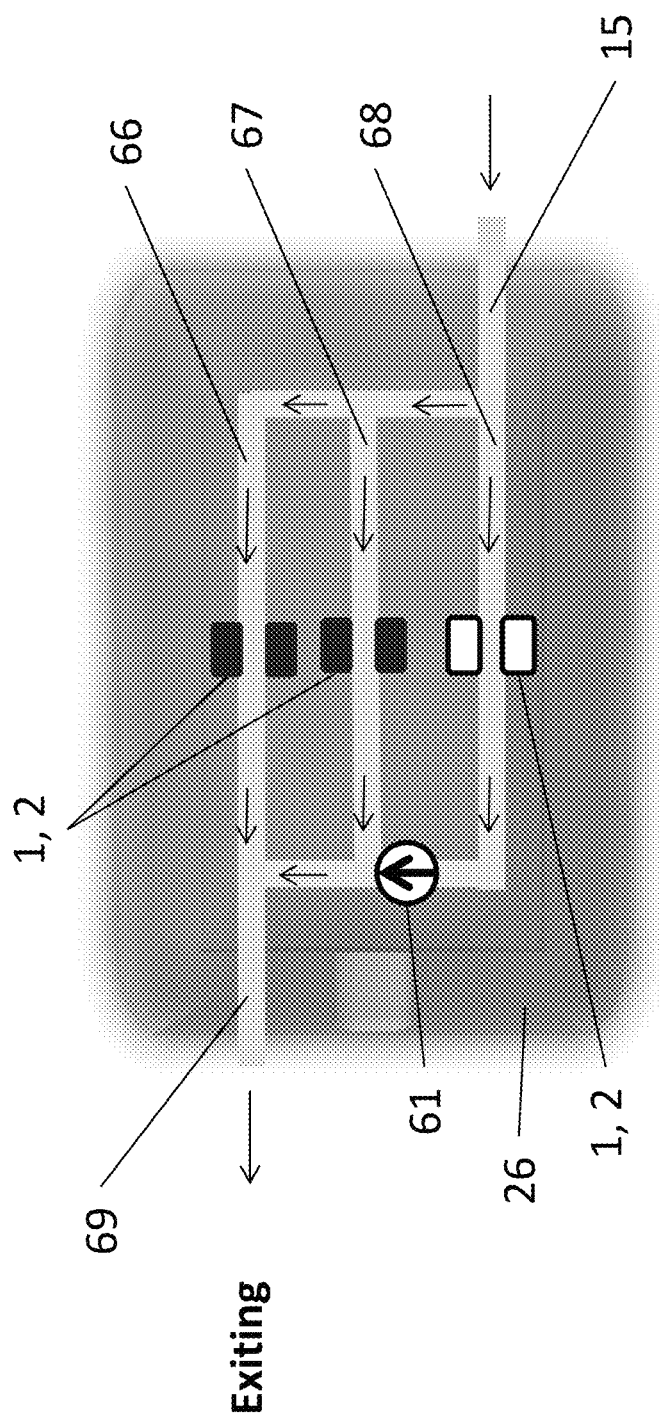

In some variations, such as in the example of FIGS. 26, 29, and 30 in which the fluid flow conduit is unidirectional through the patient monitoring device, one or more one-way valves (61) can be used to ensure fluid flow is limited to the intended direction. One-way valves, such as Qosina part #80107 (Ronkonkoma, NY), self-seal when flow goes in the direction opposite to the intended direction. The check valve can be permanently attached to the patient monitoring device or used as a separate accessory. The check valve can be used in addition to the Luer-activated valve.

The network of sensors may be configured to measure the fluid flowing in or out of the catheter. There are multiple configurations of the sensors and fluid conduits. In one variation as shown in FIGS. 2 and 3, there are one or more sensors in a singular fluid conduit.

In another variation, depicted in FIG. 26, the fluid conduit bifurcates between a sensor fluid conduit and an infusing fluid conduit. When fluid is infused from the tubing set, a one-way valve (61a) at the junction (62) to the tubing set prevents the fluid from entering the sensor fluid conduit (65). The infusion fluid all passes through the infusion fluid conduit (63), and then through the catheter junction (64), into the catheter. When fluid is drained from the catheter, a one-way valve (61b) at the junction (64) to the catheter prevents the drained fluid from entering the infusion fluid conduit (63). The drainage fluid all passes through the drainage fluid conduit (65) and then through the tubing set junction (62) into the drain line. By isolating the infusing fluid conduit, there is a lower risk of entrapped pathogens that can be infused into the patient.

Figure 27:
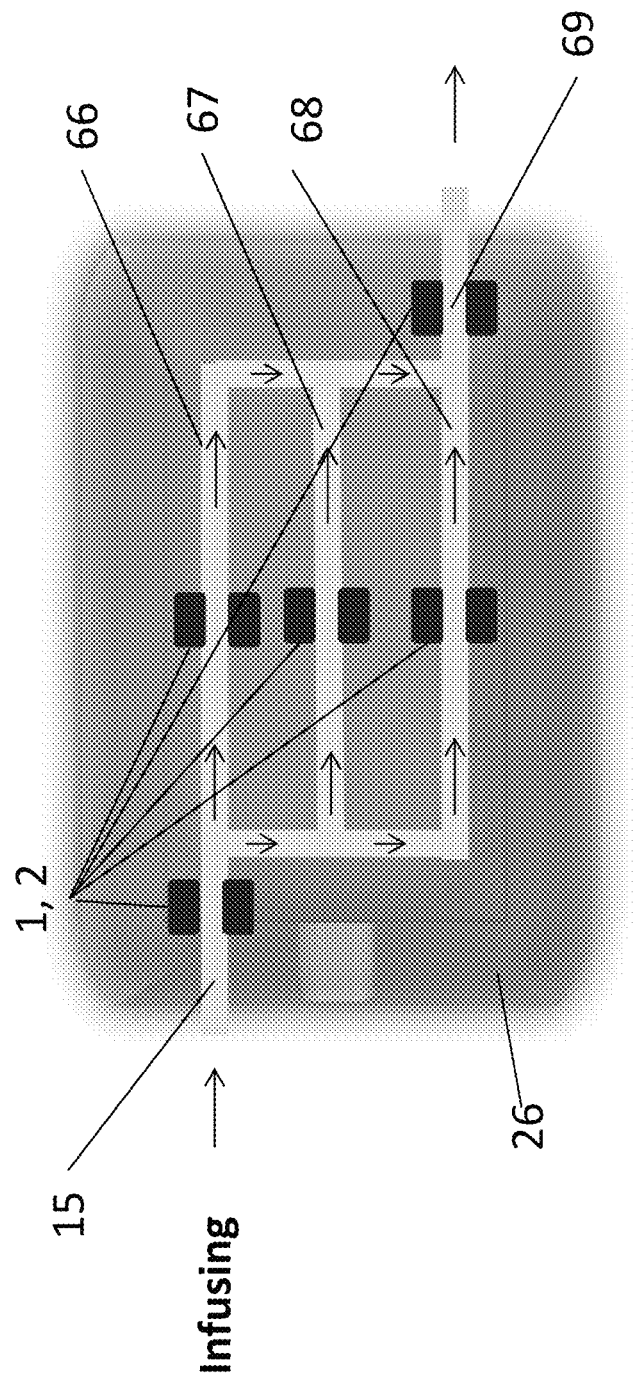
FIGS. 27, 28, 29, 30, 31, and 32 illustrate schematic diagrams of exemplary variations of patient monitoring devices comprising fluid conduit and sensors.
Figure 28:
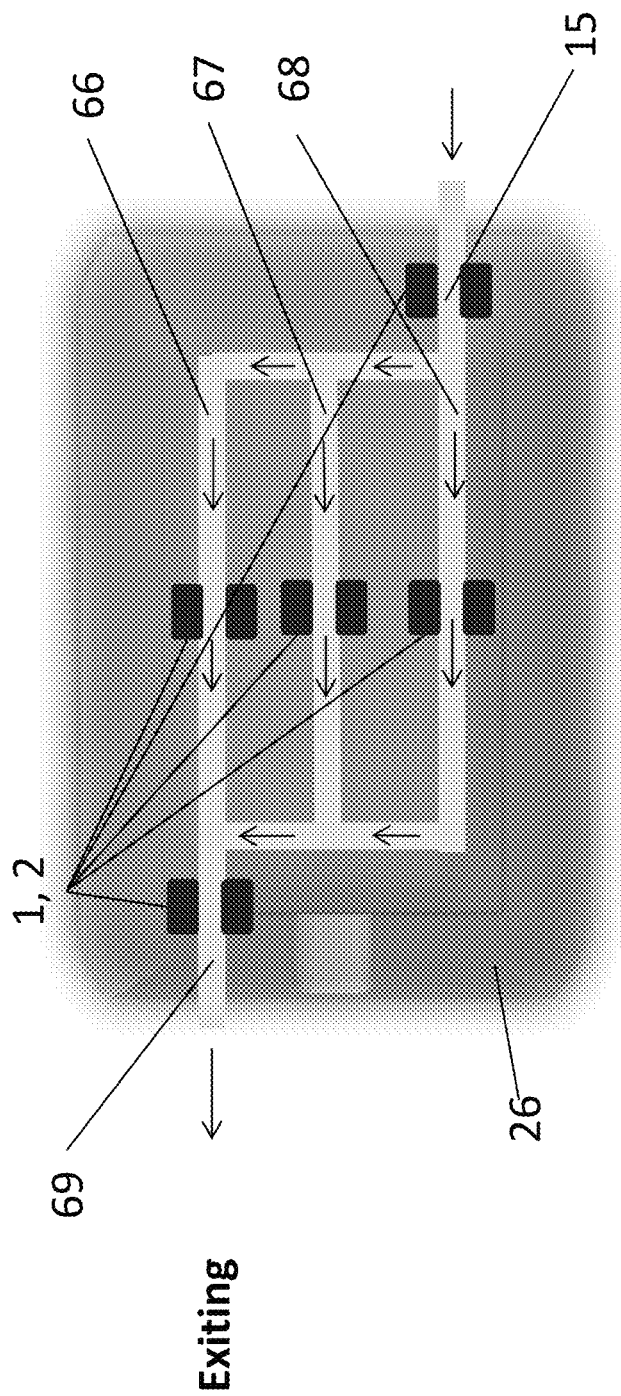

In another variation, depicted in FIGS. 27 and 28, there are a plurality of parallel fluid conduits, where different sensors (1, 2) reside on different fluid conduits. With multiple optical-based sensors, for example, it may be desirable to isolate sensors such that interference between sensors can be minimized. In-between each fluid conduit, there may be electrical and/or light shielding materials to isolate the sensors. Each of the fluid conduits can also have unique cross-sectional areas. In the case of chemi-resistor mechanism-based sensors, where a long fluid dwell time is desirable, the cross-sectional area of the measurement channel can be relatively small (e.g., about 100 to about 500 um diameters) to reduce the flow velocity via an increase in back-pressure from the lumen reduction. FIGS. 27 and 28 depict a fluid conduit (15) that splits into three fluid conduits (66, 67, 68), with sensors (1, 2) monitoring each fluid conduit. After passing through the three fluid conduits, the fluid re-converges into a fluid conduit (69) connected to the catheter. FIG. 27 depicts fluid flow direction with arrows showing when fluid is being infused into the catheter, and FIG. 28 depicts fluid flow direction with arrows showing when fluid is exiting from the catheter.

In another variation, depicted in FIGS. 29 and 30, a one-way valve (61) may be used such that the only infusing or exiting solution is measured by the sensors in one or more fluid conduits. FIGS. 29 and 30 depict a fluid conduit (15) that splits into three fluid conduits (66, 67, 68) with sensors (1, 2) monitoring each fluid conduit. The fluid conduits re-converge into a fluid conduit (69) connected to the catheter. Between the fluid conduit (15) and fluid conduit (69), there is a one-way valve (61). FIG. 29 depicts fluid flow direction with arrows showing when fluid is being infused into the catheter and FIG. 30 depicts fluid flow direction with arrows showing when fluid is exiting the catheter. During the infusing state, the one-way valve (61) prevents fluid from flowing into fluid conduit (68), but when fluid is exiting the catheter, the one-way valve allows fluid to flow into fluid conduit (68). An example of such mode of operation is during the use of an active sensor that may react with the fluid, such as enzyme-based electrochemical sensors, which produce by-products from the enzymatic reaction that the system can avoid entering the patient, and would only be activated when fluid is exiting from the patient.

Figure 31:
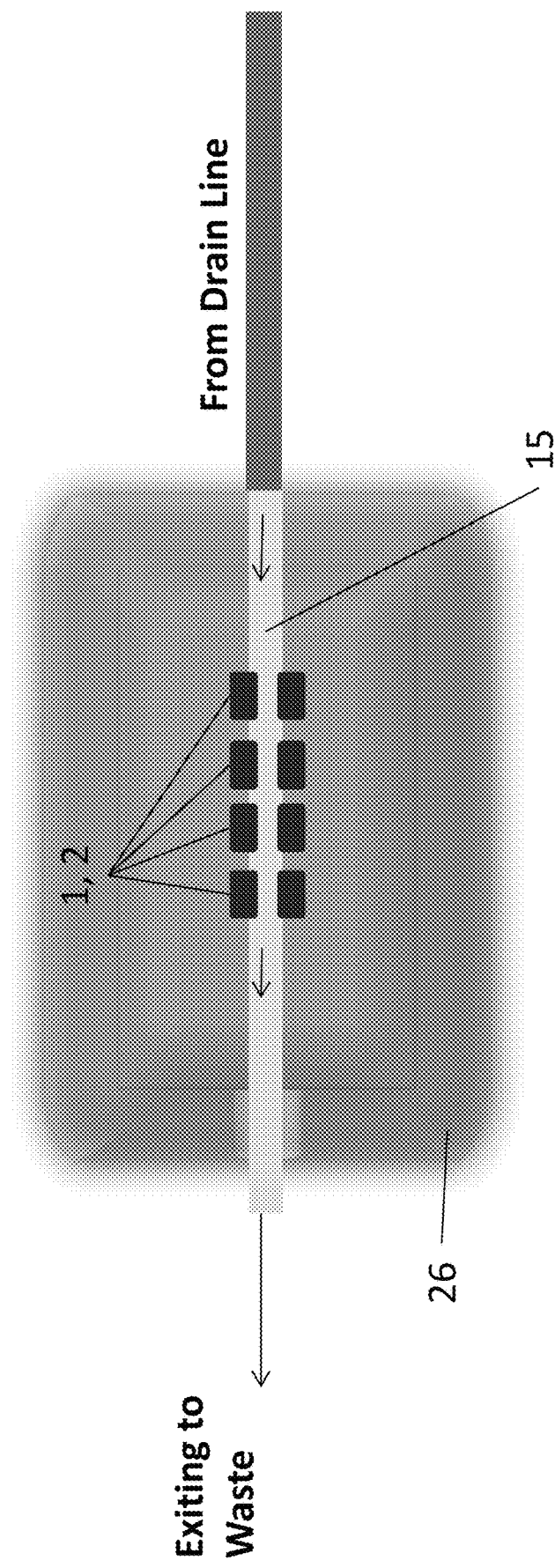

In another variation, the device only interfaces with the drainage fluid. FIG. 31 depicts this in the most basic configuration. The drain line is attached to the primary conduit (15) which passes through the patient monitoring sensors 1, 2, and exits to the waste receptacle.

Figure 32:
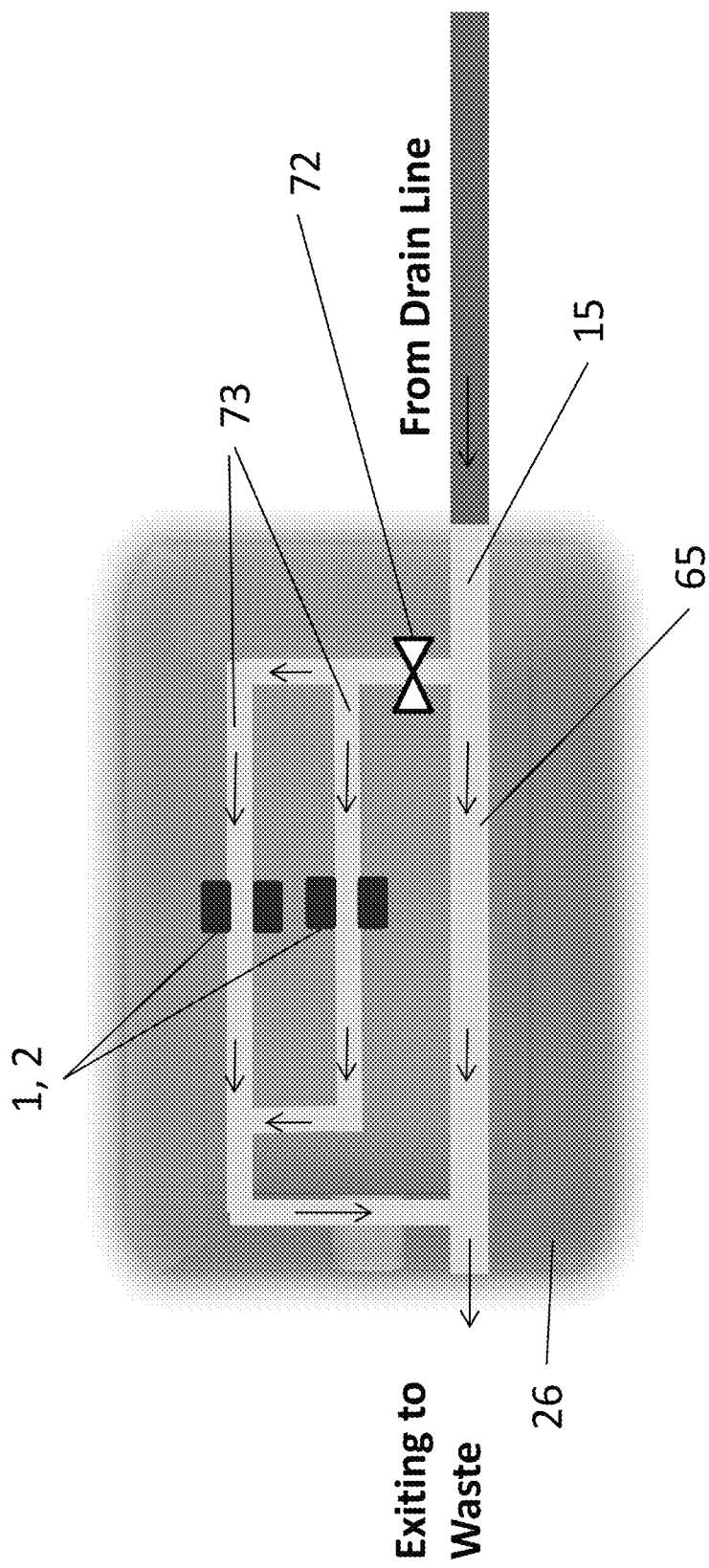

In another variation of a device connected to the drain line, FIG. 32 depicts the fluid conduit. The drain line is attached to the primary drain conduit (15) and a valve (72) diverts flow to one or more sensing channels (73) while the remainder of the fluid flow continues through the waste channel (65). After the fluid passes through the sensing channel, the sensing fluid channel may reconnect to the primary drain conduit (65). Alternately, after the fluid passes through the sensing channel, the sensing fluid channel may drain out directly to the waste receptacle.

Cartridge

FIGS. 6 and 7 illustrate examples of patient monitoring devices comprising cartridge loading mechanisms. FIGS. 6A and 6B depicts a top and front view of the durable component of a patient monitoring device without a cartridge loaded. There is a recess (e.g., track) (37) configured for coupling with the cartridge (not shown). In some variations, a switch (38) may be disposed in or adjacent to the recess (37).

Figure 6B:
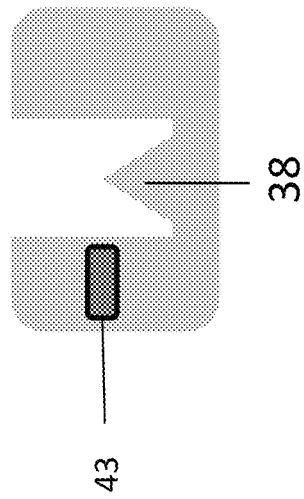
FIGS. 6A-6D and 7A-7D illustrate various exemplary patient monitoring device and disposable component configurations. In particular.
Figure 6D:
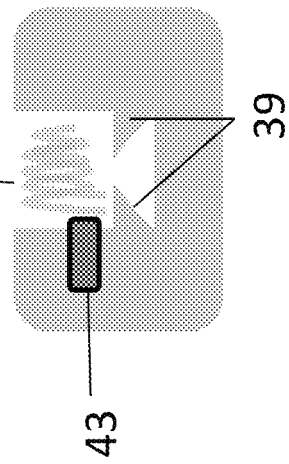
Figure 6A:
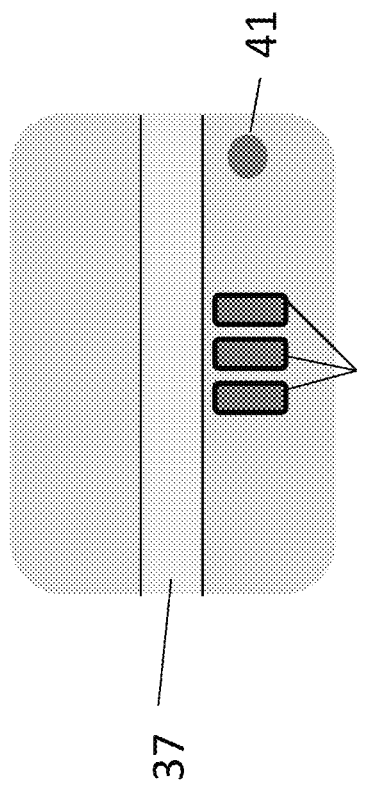
Figure 6C:
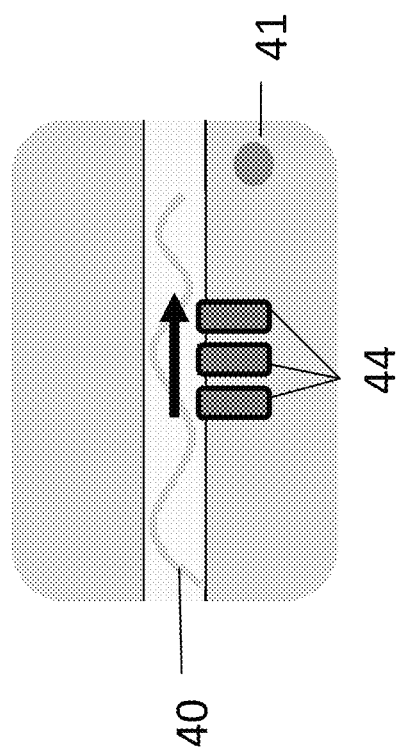

FIGS. 6C and 6D illustrate a top and side view of the patient monitoring device with the disposable cartridge (40) loaded. Loading of the cartridge (40) into the recess (37) may activate a switch (38) configured to transmit an installation signal. A locking mechanism such as a set of spring-loaded flanges (39) may be configured to advance toward the cartridge (40) and hold it in place, as shown in FIG. 6D. Additionally or alternatively, a set of fluid-contacting sensors (44) may be advanced toward the cartridge (44) upon loading, permitting the sensors (44) to have contact with fluid that flows through a fluid conduit of the cartridge (40), as shown in FIG. 6C. In some variations, a visual indicator (41) may be provided to indicate a status of the cartridge. For example, the indicator (41) may be red when the cartridge is not loaded (e.g., switch OFF) or loaded incorrectly and may be green when it is properly loaded (e.g., switch ON).

Figure 7A:
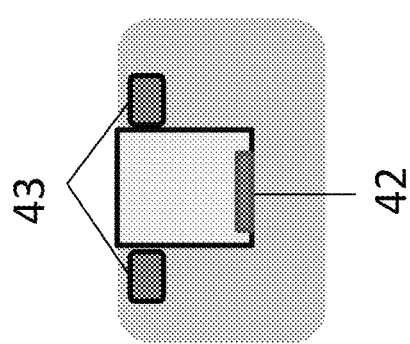
Figure 7B:
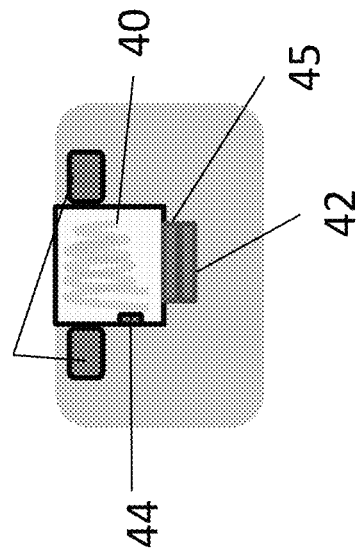
Figure 7C:
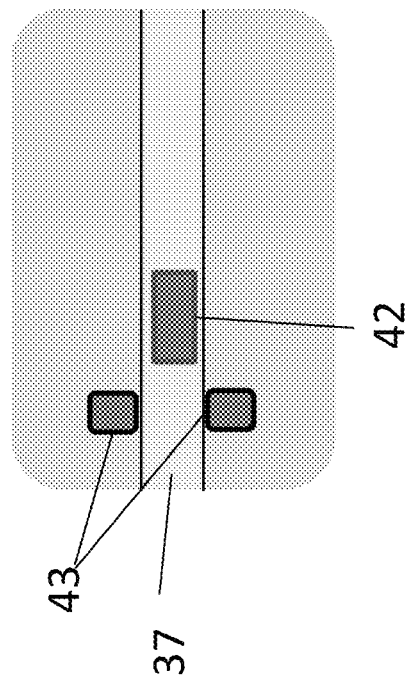
Figure 7D:
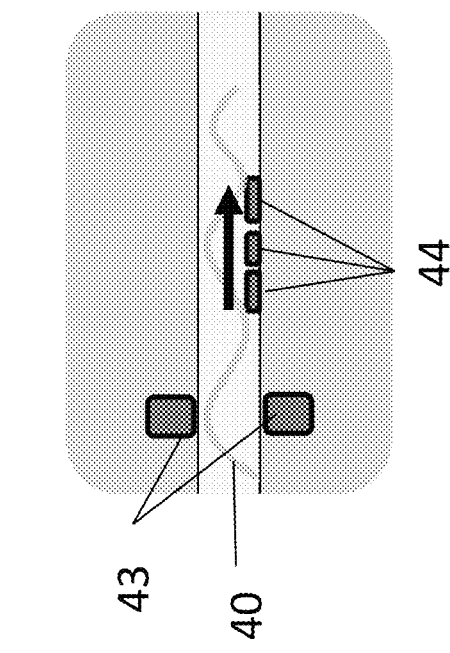

As another example, FIG. 7A depicts the top and front view of the patient monitoring device without the cartridge (40) loaded. A durable component defining a recess (e.g., track) (37) may comprise an electrical connector (42) configured for coupling with the cartridge (40). In some variations, the cartridge (40) may comprise a printed circuit board and a connector (45) configured to mate with the electrical connector (42) of the durable component. Non-fluid contacting sensors (43) reside in the reusable module, and fluid-contacting sensors (44) reside in the disposable cartridge. In this example, all fluid-contacting components, including the sensors, are part of the disposable cartridge (40).

The components may be fitted together through a number of mechanisms. For example, the components may be held together through a set of latches, a set of magnets and magnetic counterparts, screws with threaded holes, a nut that holds the pieces together through pressure, combinations thereof, and the like. Additionally or alternatively, one or more components may twist into each other and seal like that of a Luer lock or lock into each other through an axis lock, frame lock, liner lock, or lock back mechanism that can be released by pushing on the locked piece, a separate button, or other fixture. The interfaces listed above are examples that are inclusive, and other interfaces may be used to fix the components together for use.

The components may be released from one another through pushing a button on the locking feature but may alternatively employ other mechanical and/or electrical means. One method to release the disposable from the durable component is through a user interface on the patient monitoring device or on a separate mobile, tablet, or browser-based user interface. The patient could select to swap out the disposable cartridge due to an automated prompt, prompt from the provider, or through their own agency. The cartridge would be released or unlocked and able to be removed from the durable component of the device after the action. Alternatively, an employee of the device manufacturer, provider, or third-party service could be prompted to change the disposable component. The employee may have a special key, which could be physical or electronic, to unlock the device and also release the durable component. Through this method, the patient would not have any interaction with the interior of the device. A combination of patient and provider permissions could also be employed to facilitate changing the cartridge. An example is the provider prompting the patient to change the disposable component, an authentication code is sent to the patient through their profile on the unique application for the device, and the code is inputted physically or digitally to the device, unlocking it. In some variations, the disposable component may be unlocked automatically under predetermined criteria such as regulatory requirements, time, use, wear, biofouling, and the like.

In some variations, one or more of the components of the cartridge and durable component may be disabled under predetermined conditions. For example, if one or more sensors lose calibration due to bacteria fouling, low battery, or predetermined time interval, loss of calibration, then a signal may be received by one or more of the cartridge and durable components to disable patient monitoring.

Sterility

Any of the cartridges described herein may be configured to maintain the sterility of its fluid channel(s) between manufacturing and installation. In some variations, the ends of a fluid channel of the cartridge may be sealed using a thin membrane to maintain the sterility of the fluid channel. The membrane may be composed of silicon, hydrogel, polyvinyl alcohol (PVA), combinations thereof, and the like. In some of these variations, the fluid conduit may be inserted within a lumen of a connection port (e.g., tubing connector) where the connection port is configured to fluidically couple to a dialysate solution or in-dwelling catheter. In these variations, the membranes may remain intact until fluid flows through the connection port to contact. For example, fluid flow through the connection port can contact and then dissolve the membranes (e.g., PVA membrane), thus fluidically coupling the fluid conduit to the connection port. Additionally or alternatively, the membrane seals may be broken by applying sufficient external force to the ends of the fluid conduit (e.g., squeezing the fluid channel). In other variations, an end of the connection port may be inserted into a lumen of the fluid channel sealed by a set of membranes, thereby puncturing the membrane seals and fluidically connecting the fluid conduit to the connection port.

In some variations of the disposable cartridge, the fluid channel material may composed of materials with known fouling properties that are factored into the sensor readings affected by the fluid channel clarity, to calibrate the sensor readings. Manufacturer calibration may form an initial calibration and then use a test period to see how the fouling progresses over time with a specific individual. Thereafter, the typical fouling dynamics can be known and accounted for. The device can record metrics such as the total time the fluid-contacting material has been in the device and the total fluid that has been in contact to refine the corrections for fouling and also to determine how often to change the disposable component.

In one variation, materials with high anti-fouling properties, such as polyethylene glycol (PEG)-coated silicone with hydrogel coated silicone, zwitterionic (phosphorylcholine, sulfobetaine) coated polyurethane, polyethylene oxide-coated polyvinyl chloride (PVC), and polyamphiphilic silicone, may be used to maintain consistent optical clarity over the duration of usage. The anti-fouling materials may be incorporated into one or more fluid contacting components of the patient monitoring device (e.g., fluid channels, connector tubes, sensor interfaces). For example, a sensor may include a fluid flow sensor comprising a hall effect sensor and a rotating turbine composed at least in part of an anti-fouling material. The anti-fouling material may reduce clogging and drag of the rotating turbine.

Sensor Infection Prevention

All parts fluidically connected to the catheter are designed to avoid or reduce potential infection transmission. For example, the sensor surfaces that interface with the infused fluid, and any accessories or connectors, may be configured or selected to minimize space or surface area in which bacteria or biofilm can accumulate. Flow sensors, for example, may be configured or selected to utilize ultrasound or optical measurement which have no moving parts, as opposed to Hall-effect sensors which have a rotating or other movable sensor element in contact with the infused fluid. However, a Hall-effect sensor may be used, which contains anti-microbial surface treatment such as silver coating, and with all fluid-flowing cavities which do not have any static fluid. The Hall-effect sensor may also be used in cases where fluid only drains from catheters and never enters patients.

Sensor materials may be selected such that contact surfaces are corrosion resistant, and biocompatible. In one example, borosilicate glass can be the interface between the dialysate fluid and infrared sensors. The hardware system comprises of materials that can be sterilized through common sterile methods such as steam sterilization, chemical soak (e.g., isopropanol), ultraviolet (UV) germicidal irradiation, E-beam or Gamma irradiation. In one use case, during a prescribed maintenance period, the patient sterilizes the hardware sensor system utilizing a commercially available in-home steam sterilization unit or the chemical sterilization in the docking system described herein.

In other variations, a fluid conduit may be composed of a material susceptible to bacterial and/or other biofouling to exacerbate the reduction in light received by the optical scatter/absorption sensor. This may promote one or more of cleaning, sterilization, and replacement of the fluid conduit at predetermined intervals. In some of these variations, one or more portions of the patient monitoring device composed of the biofouling susceptible material may be replaced upon detection of patient infection. This may allow the system to "reset" and monitor the progress of the patient infection or detect a new infection. Fouling materials include high surface energy materials, polycarbonate, Nylon, polyethylene terephthalate (PET).

Materials can also be designed for frequent cleaning. Materials with high hardness and solvent resistance such as quartz, borosilicate, or sapphire glass, can be used for abrasive and/or solvent cleaning. Other materials with high lubricity and solvent resistance, such as fluoropolymers (FEP, PTFE), can be used for cleaning via flushing with solvents and/or with mild abrasion.

Patient Monitoring Device Housing and Mounting

The patient monitoring devices described herein may comprise a housing (e.g., enclosure) that may vary based on application and patient needs. For example, the enclosure of a patient monitoring device may be flexible, rigid, or both, and comprise components with different flexibility and/or rigidity. For example, the enclosure for a patient monitoring device worn by the patient may include one or more parts that are flexible in nature to accommodate movement of the contact skin area, improve comfort for the patient, and reduce stress on the adhesive. The enclosure parts may be manufactured (e.g., injection molded, machined, 3-D printed) from flexible materials such as silicone, thermoplastic polyurethane (TPU), and the like. The enclosure may also include a rigid base material, such as polycarbonate, and acrylonitrile butadiene styrene (ABS), with one or more flexible materials over-molded. The housing may comprise a mounting feature configured to attach to a structure such as drainage vessel or a patient.

In some variations, the enclosures described herein may be coupled to the patient in a variety of ways. In one example, the enclosure attaches to the patient's skin via an adhesive. A double-sided adhesive layer may comprise a specific adhesive interfacing with the enclosure, and a separate adhesive interfacing with the patient skin. In one example, the enclosure may comprise silicone walls or include a silicone outer layer. The adhesive may be a silicone adhesive such as Dow Corning (Midland, MI) Silastic medical adhesive. Various adhesives may be used on the skin surface side including hydrocolloid adhesives, which can sufficiently seal a skin surface for 2-4 weeks. The adhesive can be replaceable and may be done so in a period matching the maintenance cycle of battery charges, cartridge replacements, cleaning/sterilization cycle, patient infection detection, combinations thereof, and the like.

The enclosure, such as that previously described and illustrated in FIG. 3, may contain one or more components and openings. In order to protect the internal hardware components in various environmental conditions, the enclosure design may include seals (e.g., silicone sealing gaskets) between components that provide a water-tight seal. In order to reduce light noise for optical-based sensors (e.g., spectroscopy sensor, optical scatter/absorption sensor, color sensor), the enclosure design may also contain light-shielding features, such as opaque colorant additives into the raw enclosure material, or reflective paint on the external surface, over a sub-section or over the entire enclosure. In order to allow detection of air or liquid leaks into the fluid conduit by the user, a section of the enclosure around the fluid conduit tubing may be optically clear or translucent.

Figure 18:
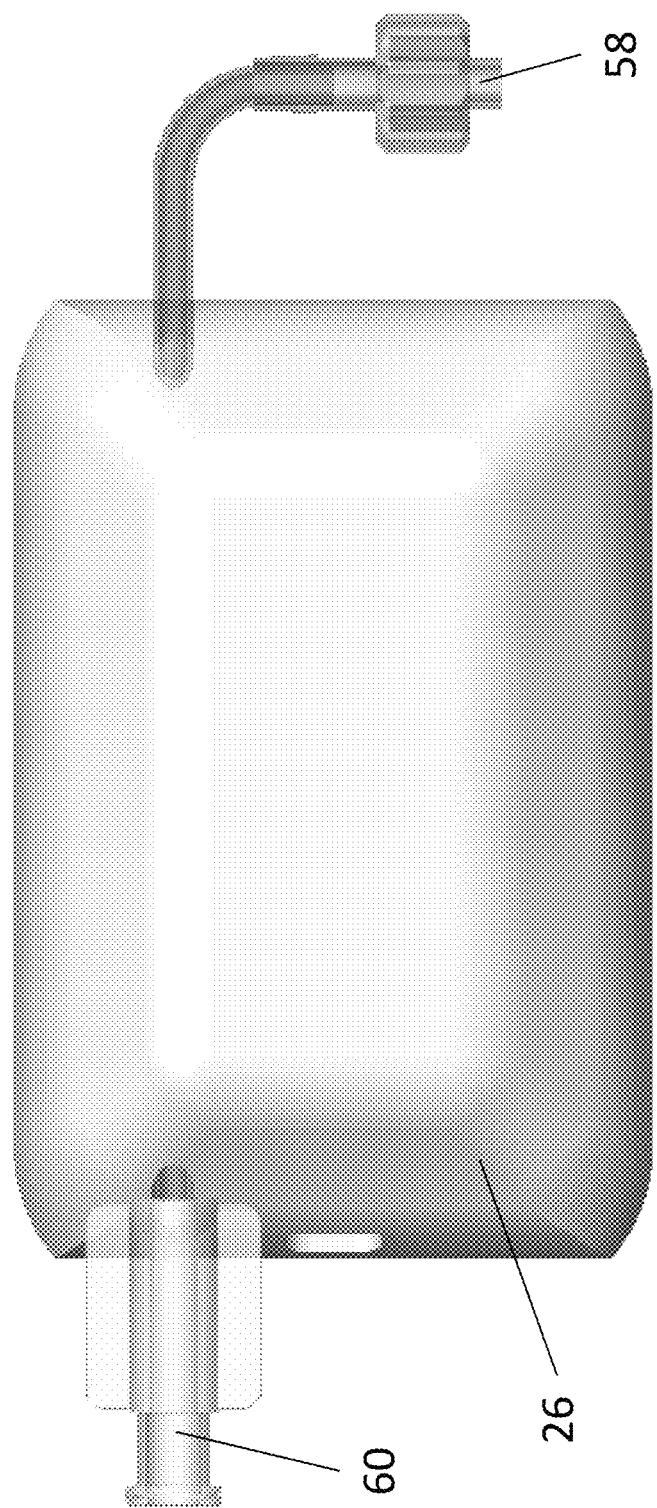
FIG. 18 illustrates an exemplary variation of an inlet and an outlet of a patient monitoring device.
Figure 19:
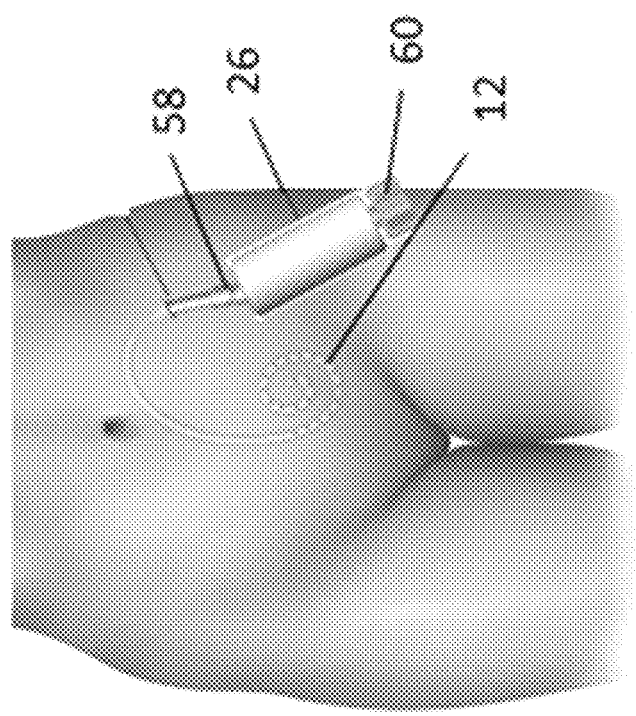
FIG. 19 illustrates an exemplary variation of a patient monitoring system including a patient monitoring device coupled to an in-dwelling catheter.

In the variations depicted in FIGS. 3, 4, and 5, the enclosure may enclose the port (14) (e.g., connector) connected to the catheter in addition to the catheter exit site from the patient skin, which may offer protection against infection at the catheter exit site. Typically, the port (14) can be connected to the enclosure via tubing, but in other examples, the port (14) may be integrated into the wall of the enclosure. The patient monitoring device may alternately have both port ends exit from the enclosure, such as in the variation depicted in FIG. 18. FIG. 18 depicts an alternate variation of the patient monitoring device form factor in which the enclosure has two exposed ports for the fluid conduit external to the enclosure body. One port (58) connects to the catheter (not shown), and another port (60) connects to the infusion/drainage fluid tubing port (not shown).

In another variation, depicted in FIG. 14, the patient monitoring devices are disposed in place of conventional transfer sets used for quick connection of the tubing sets for peritoneal dialysis therapy. Thus, the patient monitoring devices described herein may be referred to as a "smart" transfer set.

In another variation, the patient monitoring devices described herein may be disposed in place of conventional drainage lines used for drainage fluid flow to a disposal vessel. In some of these variations, the patient monitoring device may include a length of tubing connected to a CCPD or CAPD. The tubing may be used for one or more drainage cycles. Thus, the patient monitoring devices described herein may herein be referred to as a "smart" drainage line.

In another variation, depicted in FIG. 20A, a patient monitoring device (301) may be clamped over a sensor portion of a fluid conduit (34) (e.g., tubing set, connector tubes). In some variations, one or more portions of the fluid conduit (34) may comprise a sensor portion (302) and tubing connections (34). In particular, the patient monitoring device (301) may be configured to clamp over the sensor portion (302) to measure one or more properties of the fluid without direct fluid contact. For example, the patient monitoring device (301) may comprise one or more sensors configured to measure one or more parameters such as fluid optical scatter/absorption, fluid temperature (via infrared sensing), and fluid pressure (via distension of the sensing region material). In some variations, the sensor portion (302) may be composed of an optical grade silicone (Nusil MED-6033) with a thin wall (i.e., 0.020 inches) that may be molded with the fluid conduit (34).

In some variations, a patient monitoring device may be clamped over a conventional tubing set and be configured to puncture a fluid conduit such that the patient monitoring device may be in direct contact with fluid within the fluid conduit. FIG. 21A illustrates one variation in which a fluid conduit (34) may be scored with a set of punch-out holes (303) within a sensor portion (302) of the channel (34). As shown in FIG. 21B, the patient monitoring device (301) may include a set of protruding sensors (304) that may be configured to align with the punch-out holes (303). The protruding sensors (304) may be further configured to penetrate the punch-out holes (303) when the patient monitoring device (301) is clamped over the sensor portion 9302) of the fluid conduit (34) with a predetermined force, as shown in FIG. 21C. In this manner, the set of sensors (304) of the patient monitoring device (301) may directly contact the fluid in the fluid conduit (34) while maintaining a fluidic seal.

In some variations, two of the protruding sensors (304) may comprise electrodes configured to measure fluid conductivity, and a third sensor may comprise a pressure sensor. In other variations, one or more of the sensors (304) may comprise a temperature sensor. In some variations, the sensor portion (302) may not include a set of scored punch-out holes. In some variations, the set of protruding sensors (304) may include a set of protrusions configured to penetrate a wall of the sensor portion (302). For example, the set of protrusions may comprise a set of sharp needle-like ends. In some variations, the sensor portion (302) may be formed of rigid material such as PVC or nylon that may be easily punctured using a protrusion.

Figure 22:
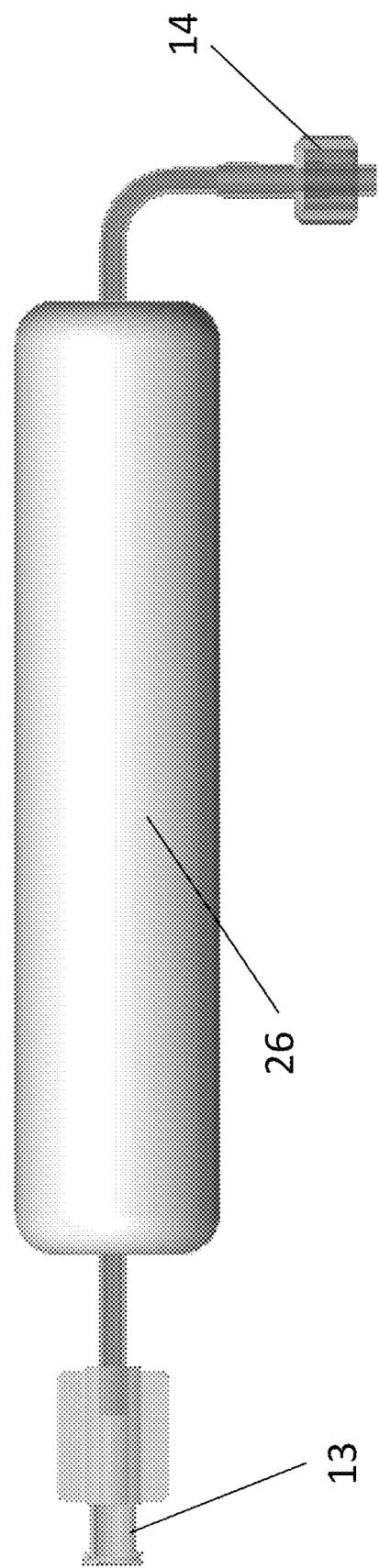
FIG. 22 illustrates a side view of an exemplary variation of a patient monitoring device.

In another variation, the patient monitoring device may be configured to be worn with a separate strap, belt loop, within pockets, or temporarily held in place with tape. FIG. 22 depicts an alternate form factor of the patient monitoring device in which the housing (26) is cylindrical in shape, with reduced footprint compared to the variation shown in FIG. 18 and has both connection ports (13, 14) external to the enclosure.

Figures 23A, 23B:
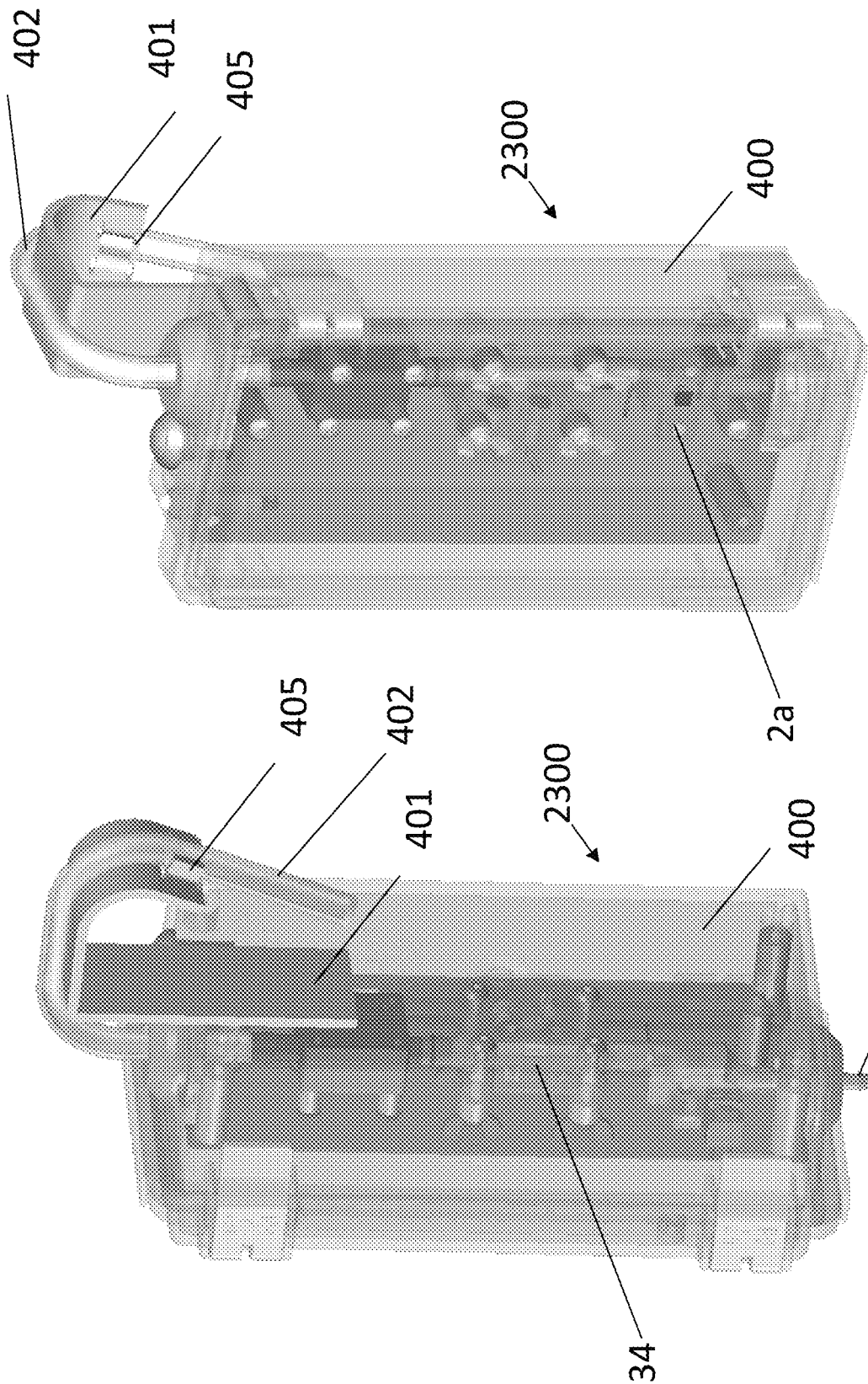
FIGS. 23A and 23B illustrates a schematic perspective view of an exemplary variation of a patient monitoring device having a mounting feature.

In another variation, depicted in the cross-sectional perspective views of FIGS. 23A and 23B, a patient monitoring device (2300) may comprise a housing (400) having a mounting clip (401) designed to attach to a drainage vessel, such as a toilet, drain pan, waste bucket, waste bag, bath tub, and the like. A tubing set drain line (402) may be connected to an inlet connector (403). After fluid passes through the patient monitoring device (2300), fluid may drain through the drain line (402) which may have a connection point (405) to the mounting clip (401). In other variations, the patient monitoring device (2300) may be coupled to the drainage vessel in any suitable manner such as with a hook, strap, adhesive, clamp, magnetic attachment, combinations thereof, and the like. In some of these variations, a user may connect the drainage tubing from the existing cycling equipment to the device inlet connector (403) via any of a barbed, Luer, compression or similar fitting. The fluid conduit (34) may extend past a set of sensors (2a) and through the housing (400) through a section of tubing connected to the mounting clip (401) to drain the fluid into a drainage vessel such as a toilet, drain pan, waste bucket, waste bag, bath tub and the like.

FIGS. 24A and 24B depicts one variation of a patient monitoring device (2300) attached to the side of a toilet (2400). Standard Luer-type connectors (regular or large-bore size) may be used as the interface of the patient monitoring device flow line to the existing Luer-type connector of most catheters, and Luer-type connector of the connection tubing for most infused pharmaceutical solutions or drainage bags. In another example, a barb fitting may be used. In other examples, however, a different or proprietary connector interface may be used.

Figures 25A, 25B:
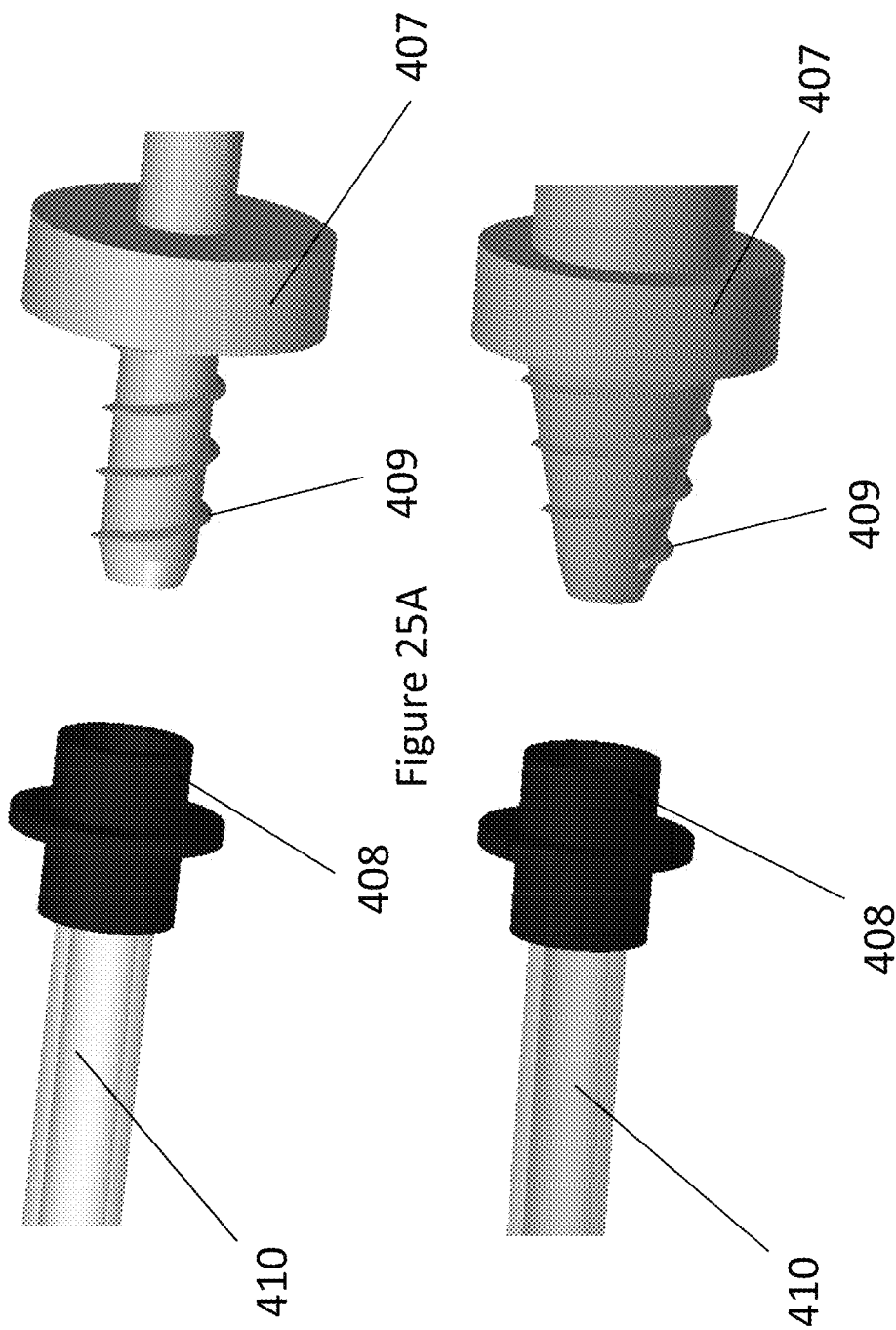
FIGS. 25A and 25B illustrate perspective views of exemplary variations of a tubing connector set.

In one variation, a threaded connector as shown in FIGS. 25A and 25B may be used as a universal connector to connect to various manufacturers' drain line. For example, a first connector (407) may comprise a thread (409) configured to mate with the internal diameter of a drain line tubing end (408) of a second connector (410) via twisting on the drain line tubing for a leak-free assembly. The first connector (407) may be sized for a predetermined inner diameter size of tubing as illustrated in FIG. 25A or a plurality of tubing sizes via a tapered design illustrated in FIG. 25B. These first connectors (407) may be coupled to an inlet/outlet connector of the patient monitoring device.

In some variations, one or more fluid conduit connectors of a patient monitoring device may include a Luer-activated valve. The valve may open to allow fluid flow when an in-dwelling catheter or connector tubing are connected and closed to seal off liquid and air when the in-dwelling catheter or connector tubing are disconnected. The Luer-activated valves, such as Qosina part #80114 (Ronkonkoma, NY) are bi-directional self-sealing when not connected, and activate when the stem of the male Luer lock connection to allow fluid flow in either direction. The valve can be permanently attached to the patient monitoring device, or used as a separate accessory, which allows for detachment during system sterilization, and easy replacement during maintenance cycles.

Test Indicator Strips

In some variations, a disposable cartridge of a patient monitoring device may include a set of test indicator strips. The test indicator strips may be one-time use or have a limited number of uses, where the system monitors the number of uses before indicating or signaling replacement. In some variations of test strips that provide a positive-only reaction, the test strips may be used until a positive reaction is obtained or until a non-specific binding of particles to the receptors reaches a predetermined non-specific binding threshold (e.g., 30% of receptors). For example, a non-specific binding threshold may correspond to a predetermined volume of drained fluid that flows over the set of test strips. Assuming that a positive reaction does not occur, the set of test strips may be used continuously until the predetermined volume of drained fluid has been detected by, for example, a fluid flow sensor. In some variations, a control device (e.g., processor) of the system may analyze fluid flow generated by a fluid flow sensor to generate a signal indicating that the set of test strips should be replaced. As described in more detail herein, an optical reader may be used to read the set of test strips.

In some variations, the test indicator strips may detect specific solutes that would be indicative of complications (e.g., leukocyte esterase for general infections, pH for urinary tract infections, hemoglobin for bleeding). The test strips may be based on methods such as immune-assays (e.g., ELISA) or enzymatic assays. The test strips can be used in conjunction with other sensors in the device. For example, a sensor may indicate when fluid flow has initiated, and the test strip would be activated, coordinating the time in which the test strip would be subsequently analyzed. For example, once the pressure sensor and/or flow sensor detects fluid flow through the fluid conduit corresponding to fluid flow over the test strip, a control device may initiate a test strip timer configured to indicate a time when the test strip is ready for analysis. The test strip may be optically analyzed by one or more of an optical reader (e.g., color sensor for a colorimetric assay) coupled to the fluid conduit and test strip, and a user observing the test strip through an optically clear region (e.g., sensing window) in the fluid conduit.

Figure 8A:
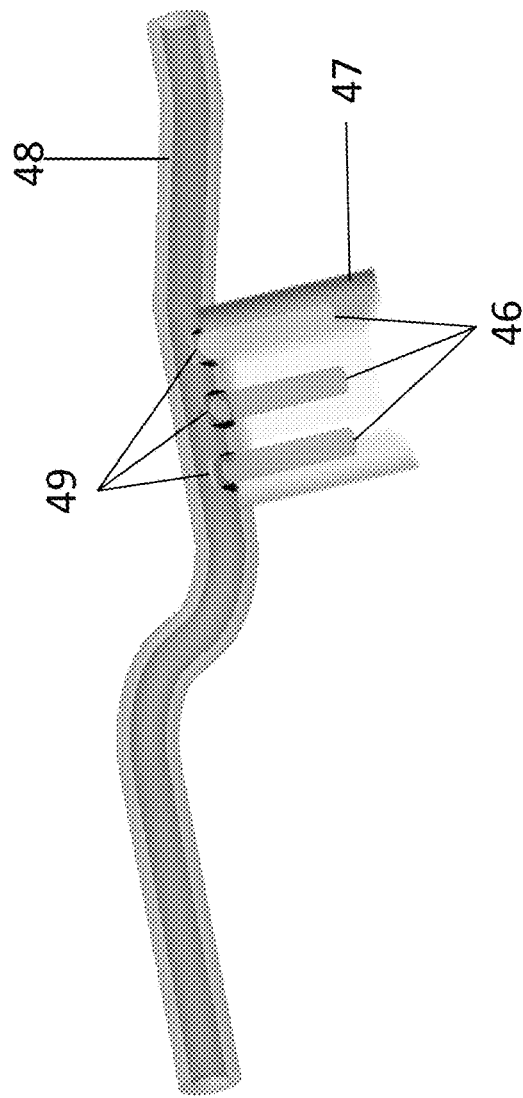
FIG. 8A illustrates a perspective view of an exemplary variation of a disposable component of a patient monitoring device coupled to a fluid conduit.
Figure 8B:
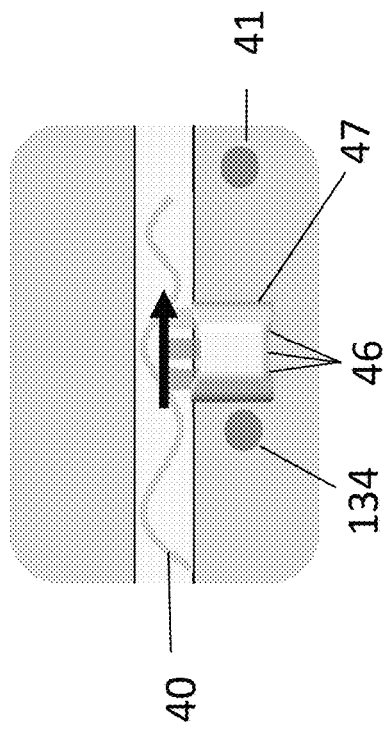
FIGS. 8B and 8C are schematic top views of the disposable component and fluid conduit depicted in FIG. 8A.
Figure 8C:
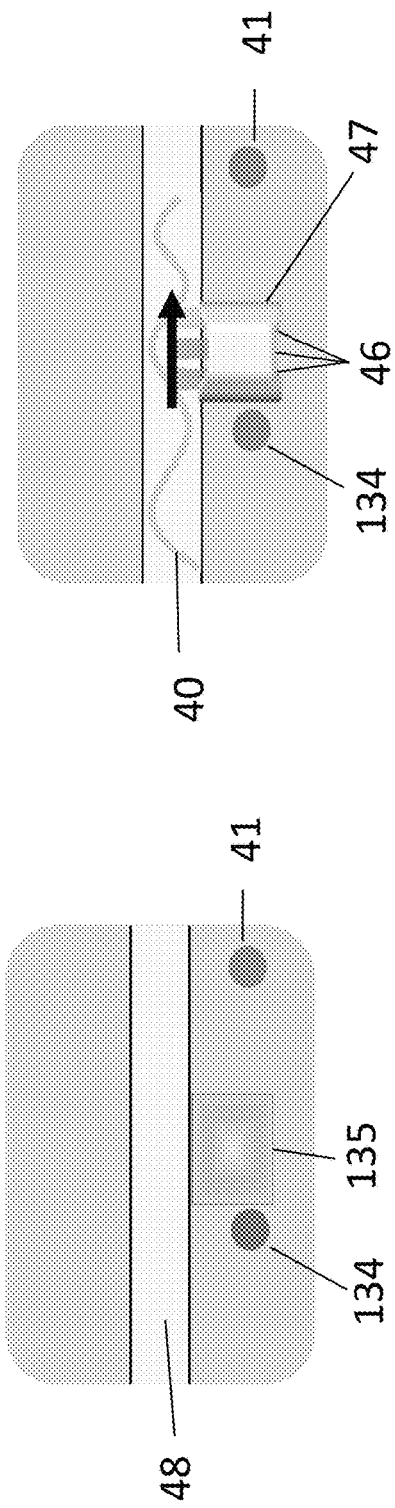

FIGS. 8A and 8C depict variations of the device in which disposable test strips are used to assess the presence and or concentration of specific solutes. In some variations, a set of test strips housed in a removable sensor may be removably attached to a disposable cartridge comprising a fluid conduit. The strips (46) are fixed to a cartridge (47) and are in direct contact with the fluid being analyzed. For example, a cartridge (47) may be removably attached to a cartridge having a fluid conduit (48). For the sake of clarity, only the fluid conduit (48) of the disposable cartridge is illustrated in FIG. 8A. As illustrated in FIG. 8A, the cartridge (47) may be inserted through sealing gaskets (49) disposed in a wall of the fluid conduit (48), which allows the cartridge (47) to be replaced at a different frequency than the fluid conduit (48) and corresponding disposable cartridge. FIG. 8B illustrates a durable component coupled to a fluid conduit (48) of a disposable component. When the cartridge (47) is not attached to the fluid conduit (48), as shown in FIG. 8B, an indicator light (134) may indicate an attachment status of the cartridge (47) (e.g., red corresponds to an unattached cartridge state and green corresponds to an attached cartridge state). The recess (135) may be configured for receiving the test strip module (47). Upon attachment of the cartridge (47) to the fluid conduit (48), as shown in FIG. 8C, the indicator light (134) may indicate an attached cartridge state green light) where the set of test strips (46) are inserted through the sealing gaskets (49) and into the fluid conduit (48).

In another variation, the disposable fluid conduit (6830) depicted in FIGS. 68A-D may integrate the test strips in the lumen. The test strips would then be part of the disposable assembly, which could facilitate ease of replacement.

Some test indicator strips have specific exposure times, and in some variations, a set of test strips may be exposed to only a portion of the test fluid volume and analyzed at a specific time after exposure to fluid. For example, the Multistix 10 SG Reagent Strip by Siemens works optimally when the glucose and bilirubin tests are read at about 30 seconds post-exposure, the ketone test is read at about 40 seconds post-exposure, the specific gravity test is read at about 45 seconds post-exposure, the pH test, protein test, urobilinogen test, blood test, and nitrite tests are read at about 60 seconds post-exposure, and the leukocyte test is read at about 2 minutes post-exposure. The exposure, incubation, and reading steps may be performed by the device, a user, or a combination of both. For example, an audible alert (e.g., beep, voice) may be outputted to a user when one or more test strips are ready for visual analysis.

Light emission or color change are two of the possible readouts for the test strips, may be measured by the user or through an optical instrument such as the Clinitek Status+ Analyzer by Siemens. Alternatively, an optical test strip reader may be integrated within the patient monitoring device (e.g., durable component, disposable cartridge) or as a separate removable optical sensor.

Exposure and reading of the test strips using the systems and devices described herein may provide systematic monitoring as well as more sensitive and consistent analysis (e.g., optical readout and non-optical readouts (e.g., chemical byproducts)) of a test strip than provided by a patient. The test indicator strips may not be used for every fluid test, but only when there is a suspicion of complication indicated by another sensor. For example, if optical scatter/absorption data indicates a spike in optical scatter/absorption levels, one or more test indicator strips may be used to detect the presence of leukocytes or blood to determine the specific source of the optical scatter/absorption. The exposure may happen automatically using the patient monitoring device or by the patient themselves by inserting the strips into the solution as it leaves the drain line, for example.

Figure 9A:
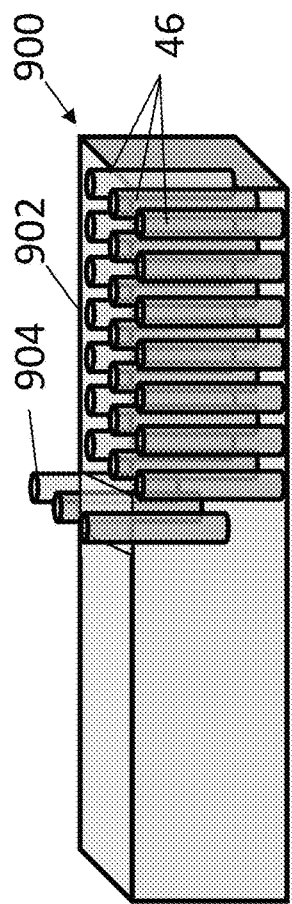
FIGS. 9A-9D illustrate a schematic perspective view of an exemplary variation of a removable disposable component in different states.

A set of test strips may be provided in a cartridge (e.g., test strip module) that may be removably attached to one or more of the patient monitoring device and/or disposable component. In some variations, the cartridge may be removably attached to a disposable component (e.g., cartridge) and the disposable component may be removably attached to a durable component of the patient monitoring device. In some variations, the device may automatically swap out the strips in the loaded cartridge, reducing the need for the patient to be responsible for replacement and intervention with the patient monitoring device. FIGS. 9A-9D illustrate one variation of a cartridge (900) comprising a set of test strips (46). In FIG. 9A, a first subset of test strips may be disposed in a first position (902) where the test strips are stored and ready to be exposed to fluid flow. A second subset of test strips may be disposed in a second position (904) where one or more test strips may be advanced into and out of the cartridge (900). The cartridge (900) may define one or more openings (e.g., test strip slits) configured for advancement of the second subset of test strips out of the cartridge (900). For example, in a manner similar to that shown in FIGS. 8A and 8C, the test strips (46) may advance out of the cartridge (900) and through one or more gaskets in a wall of a fluid conduit (not shown) and subsequently contact fluid flowing within the fluid conduit. In some variations, the set of test strips (46) in the second position (904) may be exposed to half or less of the fluid conduit width in order to reduce the effect of the laminar flow of the set of test strips (46) on the fluid conduit.

Figure 9B:
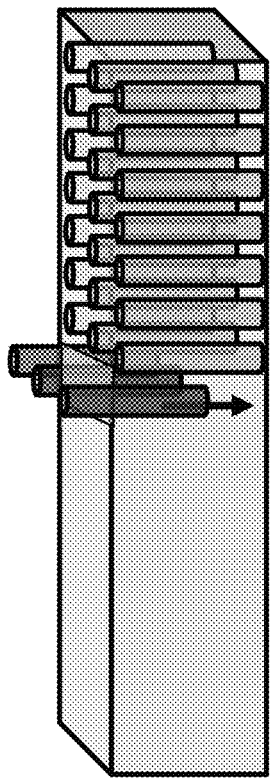
Figure 9C:
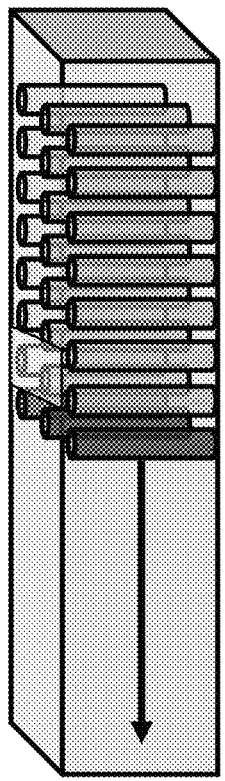
Figure 9D:
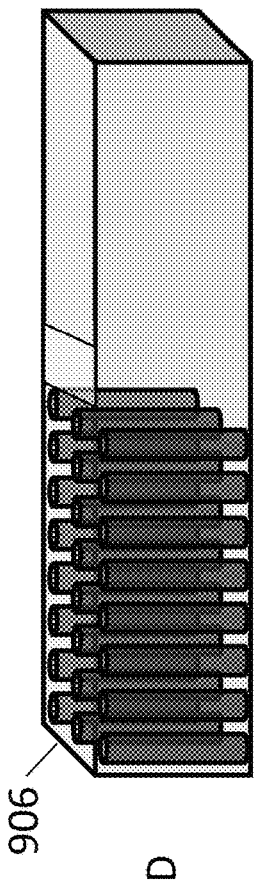

After the set of strips in the second position (902) are used, the set of test strips (46) in the second position (902) may be retracted back into the cartridge (900), as shown in FIG. 9B. The entire set of test strips (46) may then be advanced (FIG. 9C) toward the third position (906) (FIG. 9D) thereby aligning an unused set of strips (46) to the second position (904). FIG. 9D illustrates all of the test strips (46) as used and advanced into the third position (906), and ready for replacement. In some variations, the cartridge (900) may comprise one or more springs (not shown) configured to advance the second subset of test strips in and out of the cartridge (900). Furthermore, the set of test strips (46) may be coupled to a movable track within the cartridge (900). The track (not shown) may be coupled to a chain and gear configured to incrementally advance the set of test strips (46) toward the third position (906). In some variations, one or more of the springs and track may be coupled to a motor and a control device of a durable component of the patient monitoring device.

In some variations, a test strip reader if either a durable or disposable component may be located adjacent the fluid conduit to read the test strips held in the second position (904). In some variations, the test strip reader may be disposed between an outer surface of the fluid conduit and a surface of the cartridge (900) such that the test strip reader may read the test strips (46) as they are retracted into the cartridge (900). In other variations, a test strip reader may be disposed within the cartridge (900) and configured to read the retracted test strips (46) in the third position (906) within the cartridge (900).

In some variations, one or more test strips may be integrated directly into the disposable fluid line or drainage vessel. For example, one or more test strips may be disposed along an inner wall of a connector tube (e.g., fluid line, drain line) and drainage vessel. Peritoneal dialysis may include disposable drainage lines and vessels that may be replaced at predetermined intervals (e.g., after each exchange cycle, daily). A test strip reader may be coupled (e.g., clamped) to the connector tube and/or drainage vessel and configured to read the test strips. Fluid flowing through the connector tube and/or drainage vessel may contact the test indicator strips and be read by a test strip reader. The connector tube and/or drainage vessel may be discarded after use once the test strip reader is removed. The connector tube and/or drainage vessel may be composed of a material with high optical clarity that may be molded or otherwise shaped, such as silicone, PVC, polyurethane, and nylon. In some variations, the test strips may be coupled to an inner wall of a connector tube and/or drainage vessel using one or more of an adhesive, an injection molding process, an ultrasonic bond, laser bond, and the like. In some other variations, a set of test strips may be disposed in a separate conduit (e.g., fluid conduit and/or container) connected to a connector tube and/or drainage vessel. The conduit may be coupled to one or more of the patient monitoring device, connector tube, and drainage vessel. Fluid flow may be controlled into the conduit. For example, the conduit may be coupled to one or more of a valve, permeable membrane, and dissolvable obstruction (e.g., polyvinyl alcohol). The valve may be controlled by a user and/or the patient monitoring device.

Figure 12:
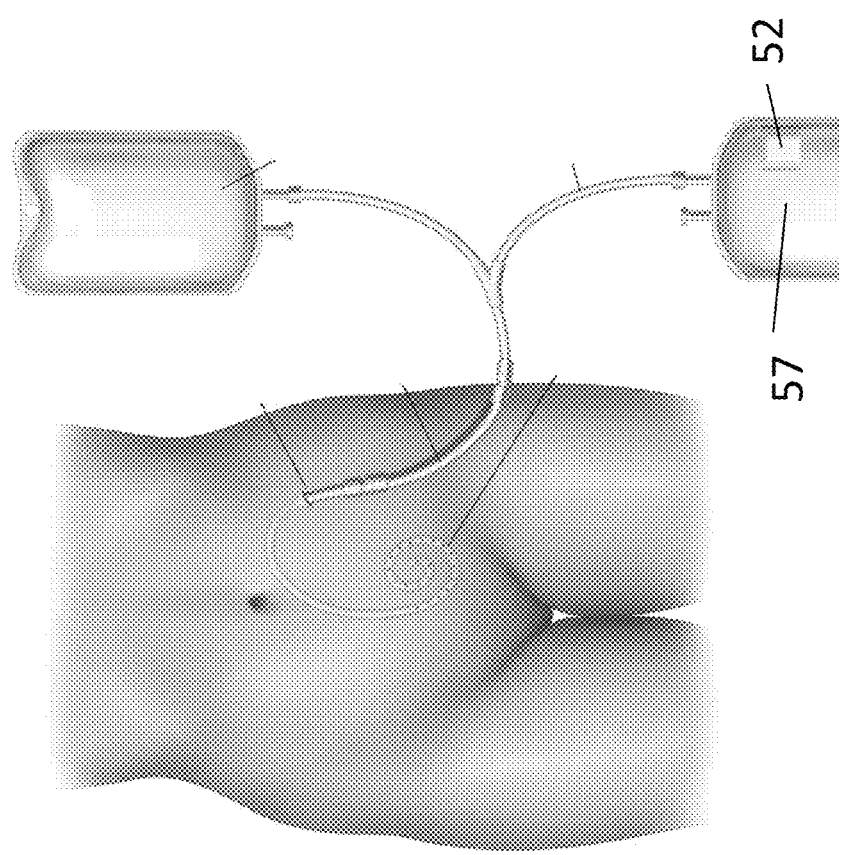
FIG. 12 illustrates an exemplary variation of a patient monitoring system including a patient monitoring device coupled to a drainage vessel.

In one variation, FIG. 12 illustrates an optical reader (52) coupled to an inner wall of a drainage vessel (57). In this configuration, the vessel (57) and reader (52) may be discarded together. In some variations, the optical reader (52) may be coupled to the inner wall of the vessel (57) or tubing in the same manner as the test strips (e.g., adhesive, injection molding, ultrasonic bonding, laser bonding). In some variations, the optical reader (52) may comprise a battery, processor, memory, and wireless transmitter and may process and transmit sensor data in a manner similar to the patient monitoring devices described herein. The optical reader (52) may form a wired connection to a patient monitoring device (not shown) for data communication and/or control.

In other variations, one or more test strips may be disposed in a separate test strip module connected to an inlet and/or outlet of the patient monitoring device and/or the disposable tubing. The independent test strip module allows the test strips to be flexibly connected at different locations to a variety of tubing sets from different manufacturers. The patient monitoring device may also be replaced at a different frequency from the other components of the system. FIG. 10A depicts one variation in which a set of test strips (46) are attached within internal fluid flow conduit of a test strip module (1000). The inlet connector (50) or outlet connector (51) may mate with connector tubes (1010). The connectors (50, 51) may be one or more of a barbed-type, standard quick disconnect, universal Luer-type connectors, and custom connector types. The system is shown assembled to the tubing in FIG. 10B, and together with the clamp-on test strip reader (52) in FIG. 10C.

Figure 11A:
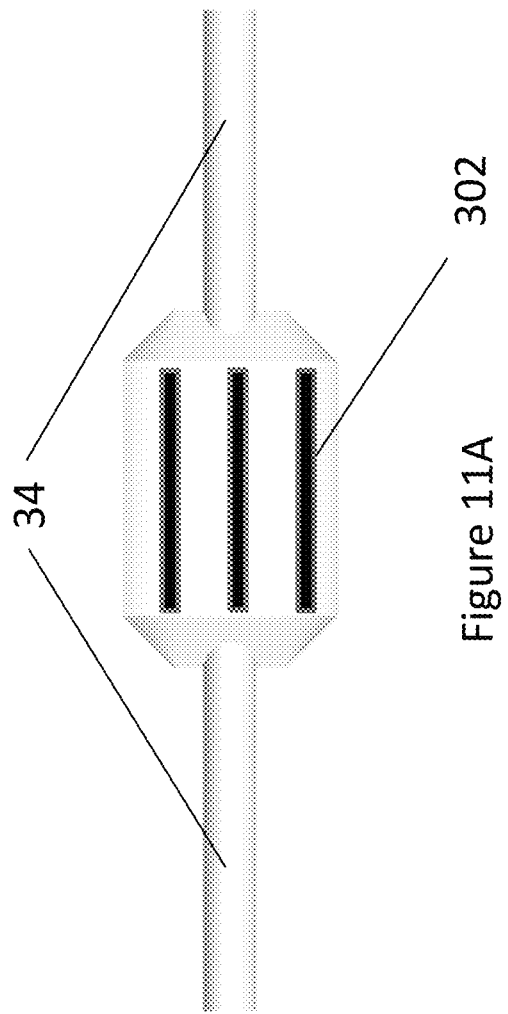
FIGS. 11A and 11B illustrate respective side and perspective views of an exemplary variation of a patient monitoring device configured to clamp to a fluid conduit.
Figure 11B:
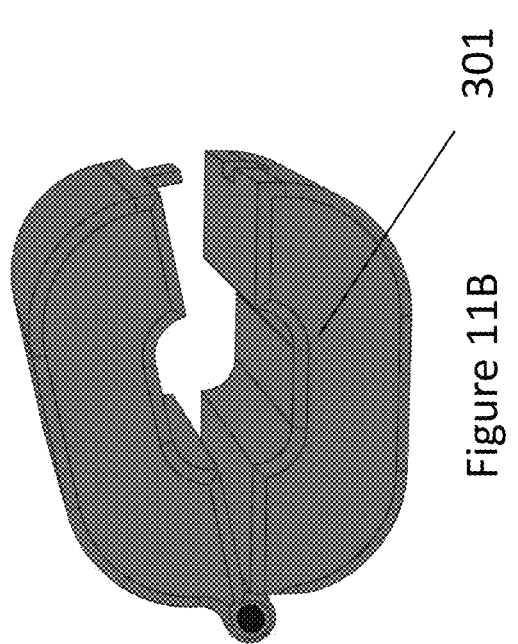

Another variation of the clamp-on test strip reader with the test strips is shown in FIGS. 11A and 11B. FIG. 11B is a perspective view of a patient monitoring device (301) (e.g., test strip reader) that may comprise one or more sensors configured to read a set of test strips (302) clamped therebetween. FIG. 11A illustrates a sensor portion (302) of a fluid conduit (34) (e.g., drain tubing). For example, the sensor portion (302) may comprise a set of test strips aligned to an optically transparent window for a clamp-on optical reader (301) to measure the set of test strips. The patient monitoring device (301) may be configured to clamp over the sensor portion (302) to read the color of the set of test strips (302).

Sensors for Infection Detection

In-dwelling patient catheters are susceptible to infection complications. In the case of peritoneal dialysis patients, an in-dwelling catheter is used to infuse and drain dialysate solution, and peritonitis is a common complication. In the example of peritoneal dialysis patients, infection detection can be monitored with at least one patient infection detector such as one or more sensors configured to measure a suitable parameter including, but not limited to, patient core body temperature, patient skin temperature, drainage dialysate pH, drainage dialysate optical scatter/absorption, drainage dialysate white blood cell count or activity, drainage dialysate lactate content, and catheter exit site skin discoloration (e.g., due to rash), etc.

Clinically, one of the signs of infection is fever. Body temperature typically ranges between 36.1 to 37.2° C. Body temperature exceeding this range is indicative of fever. For temperature monitoring, an infrared sensor, thermocouple, or thermistor may be used to monitor the skin surface or in the case of peritoneal dialysis patients, the sensor can directly measure the drainage dialysate solution immediately upon exiting the body.

Figure 33:
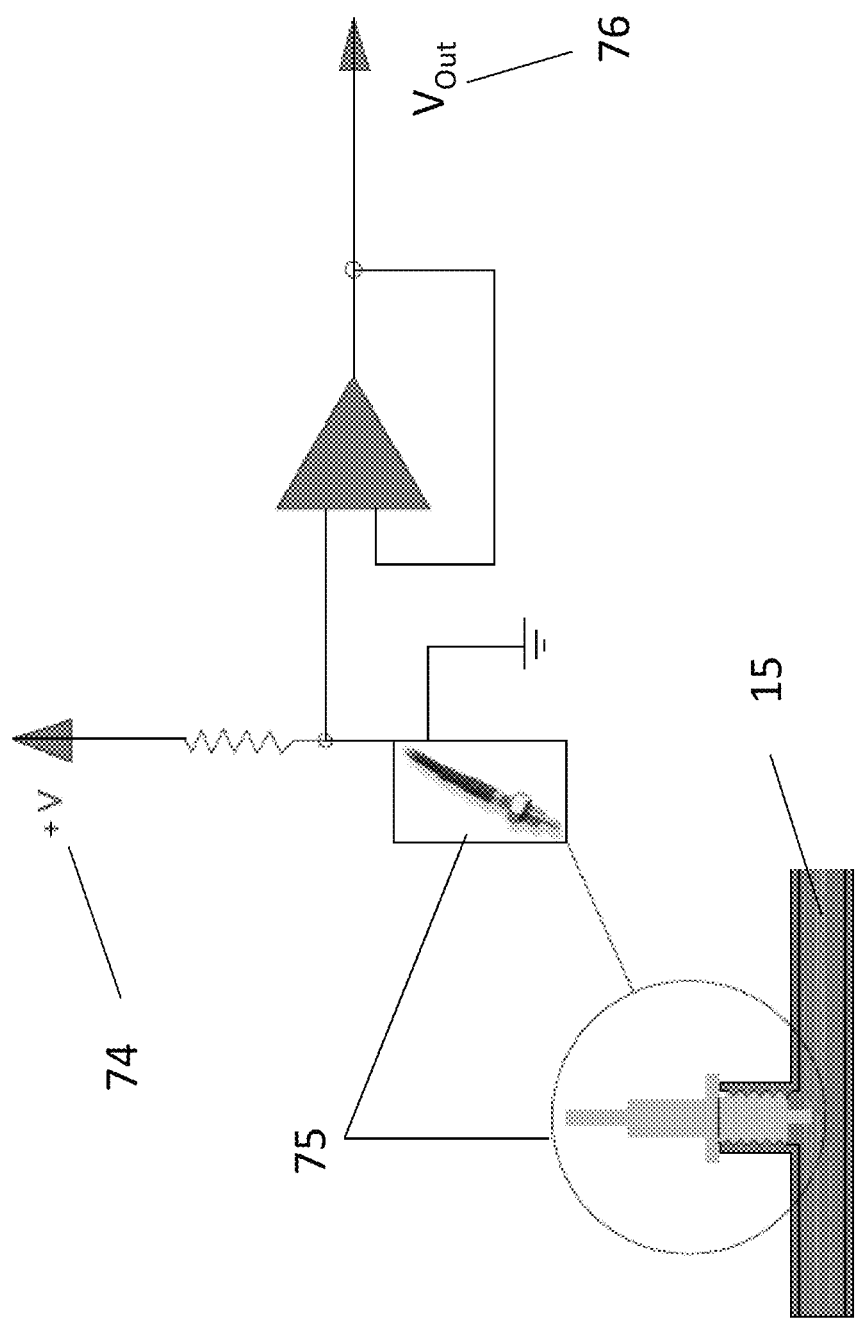
FIG. 33 illustrates a schematic circuit diagram of an exemplary variation of a thermistor.

Thermistors are usually two-terminal semiconductor devices made from semi-conductive materials that have an electrical resistance that varies non-linearly with temperature. FIG. 33 depicts one circuit design for a thermistor, in which power (74) is supplied by the microcontroller to the sensor (75) which is placed such that the sensing surface is in direct contact with the fluid conduit (15) for optimal heat-transfer, and the sensor outputs a voltage (76) to the microcontroller. In thermistors, the temperature variation results in resistance changes, causing varying voltage output.

In the use of the thermistor for peritoneal dialysis patients, the thermistor sensor can be positioned to measure the dialysate drainage fluid flow conduit immediately exiting the catheter/body, which would allow readings of drainage dialysate solution coming directly out of the body. Drainage dialysate temperature should be equal to body temperature after the long dwell time inside the abdomen. However, depending on the distance from the thermistor position and the body, which is driven primarily by the length of the in-dwelling catheter extending outside the body, a temperature offset may be required to account for heat loss or gain. For example, a separate ambient temperature sensor and fluid flow meter may be used in combination with the fluid temperature sensor. With the measurement of flow rate and ambient temperature, heat loss may be estimated to a reasonable degree of accuracy. As an alternate to offsetting the thermistor values based on the thermal loss in the tubing and using the temperature value in absolute terms, relative temperature changes to the temperature measured of the drainage dialysate, as measured over time, may be used.

In another method, thermistors can also be placed directly against the skin to measure the skin surface temperature for monitoring patients using various catheter types. In this use case, the thermistor can be supported by the fixed enclosure to allow pressure to push the sensing surface against the skin for optimal heat transfer. Besides monitoring onset of infection, temperature measurement can also provide feedback on patient response to treatment of infection. For example, when infection is detected, an antibiotic regimen can be prescribed to the patient. The patient temperature change can be monitored during treatment as a method of assessing the efficacy of the antibiotic treatment.

Optical scatter/absorption measurement of fluid exiting the catheter can also be used for infection detection. In the case of peritoneal dialysis patients, fresh dialysate delivered into the patient is a clear solution prior to introduction into the body. Upon drainage of the dialysate solution, cloudy dialysate solution can be indicative of infection, specifically peritonitis. White blood cells, also referred to as leukocytes, concentrate in areas of infection and are mixed into the dialysate solution during the peritoneal dialysis session, thereby producing a turbid drainage dialysate solution. The system may utilize a spectroscopy sensor (e.g., optical scatter/absorption sensor) to analyze infusing and drainage dialysate solution as one method of detecting patient infection.

An optical scatter/absorption sensor is used to quantitatively measure the suspended particles in a fluid. This is done by measuring light scattering and/or light absorption imposed by the suspended solids in a fluid. Notably, optical scatter/absorption measurement may be used to determine the composition of particles within a fluid. As used herein, optical scatter/absorption can mean the light absorption or scattering at particular wavelengths or ranges that may give differential signals based on the substance.

Figure 34:
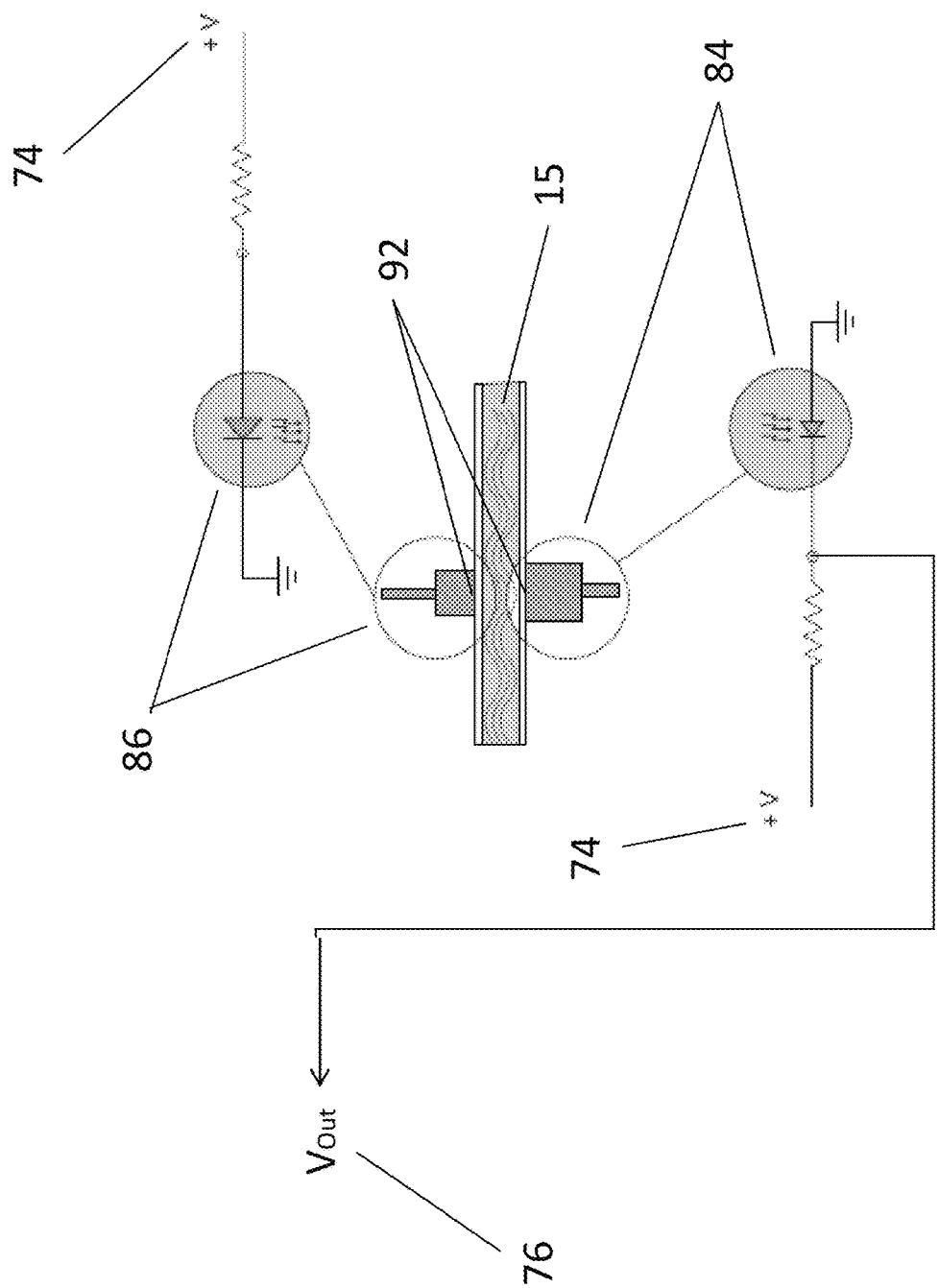
FIG. 34 illustrates a schematic circuit diagram of an exemplary variation of an infrared optical scatter and/or absorption sensor.

FIG. 34 depicts an exemplary infrared optical scatter/absorption sensor. A microcontroller supplies power (74) to a light emitter (86) and a detector (84). The emitter (86) transmits light through the fluid-interfacing surface (92) and fluid conduit (15). The detector (84) detects the scatter of the light transmitted through, and outputs a corresponding voltage (80) based on the quantity of the detected light to the microcontroller. As shown in FIG. 34, the emitter and detector are oriented at 180 degrees separation around the circumference of the fluid conduit (15), though the emitter and detector can also be oriented at other forward scattering angles (>90 degrees), side scattering angle (90 degrees), or back-scattering angles (<90 degrees). To add specificity of the detected particles, additional light absorption and scattering patterns can be used at different wavelengths and/or scattering angles with multiple emitter/detector systems based on unique absorbance and scattering patterns of different particle types (both cellular and non-cellular).

Figure 77:
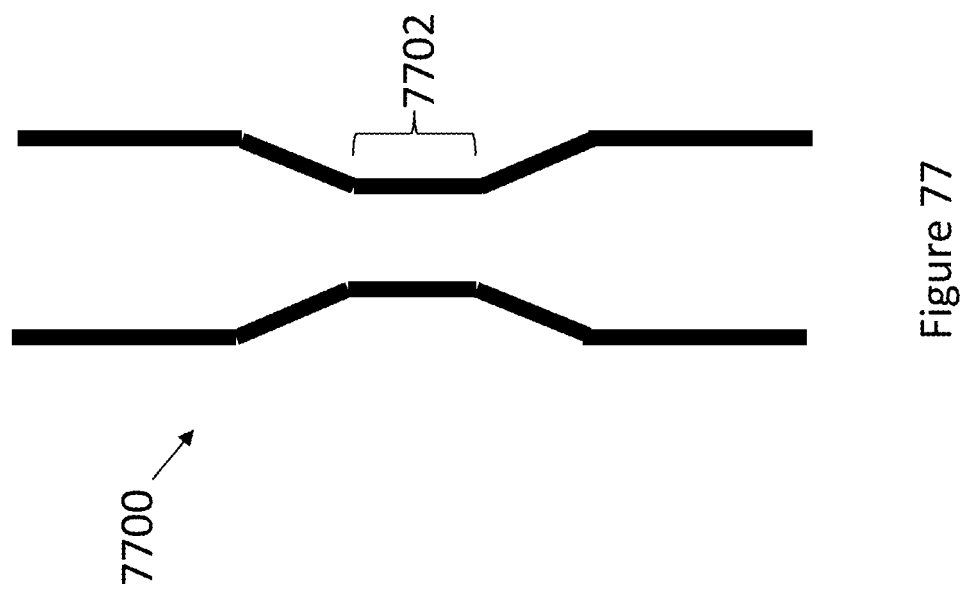
FIG. 77 is a schematic cross-sectional side view of another exemplary variation of a fluid conduit of a patient monitoring device.
Figure 78B:
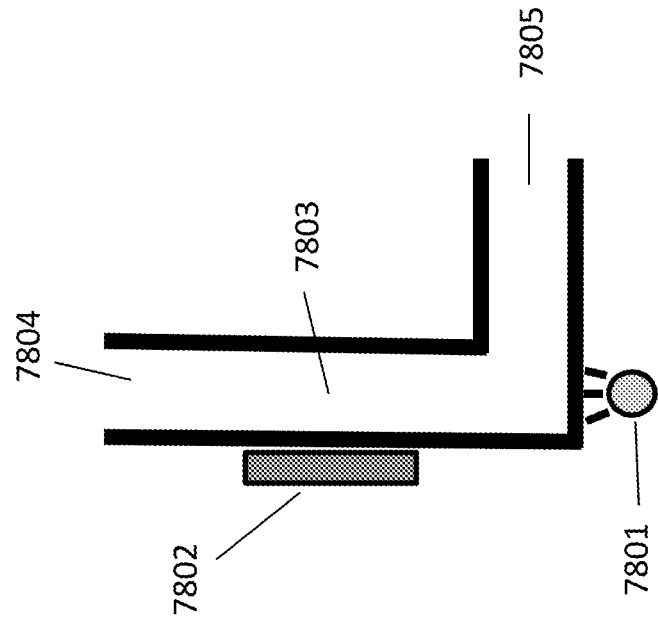
FIGS. 78A, 78B, 78C, and 78D are schematic cross-sectional side view of exemplary variation of an optical sensor and fluid conduit configuration of a patient monitoring device.
Figure 78A:
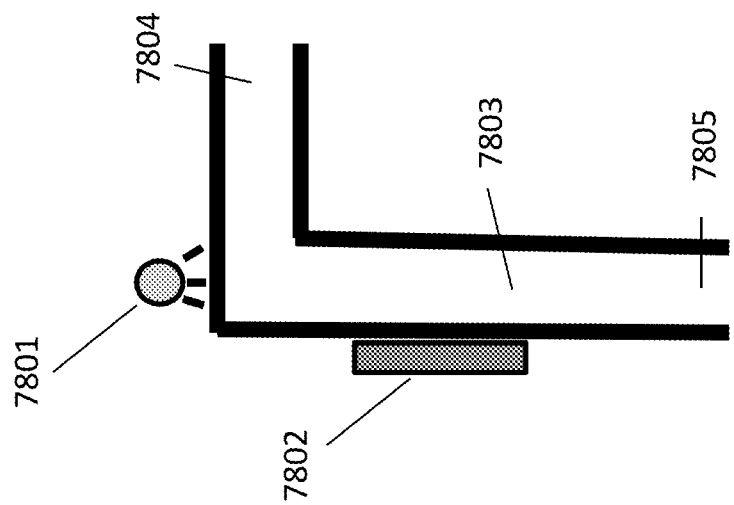
Figure 78D:
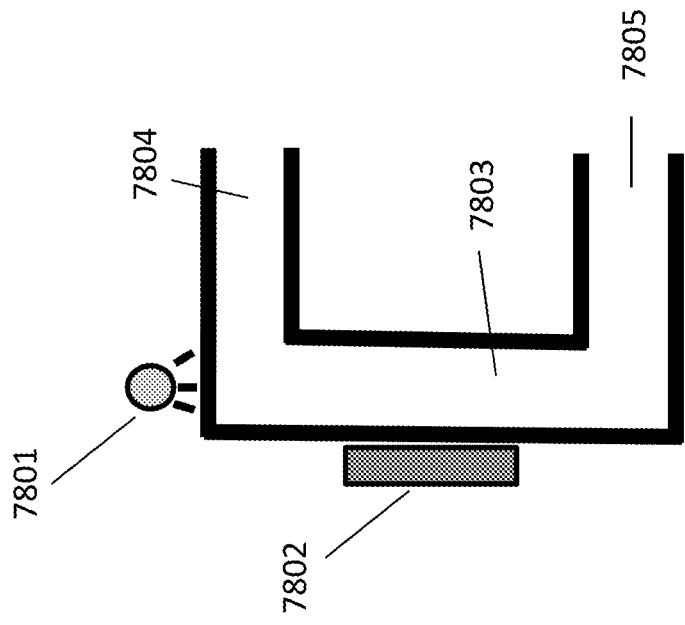
Figure 78C:
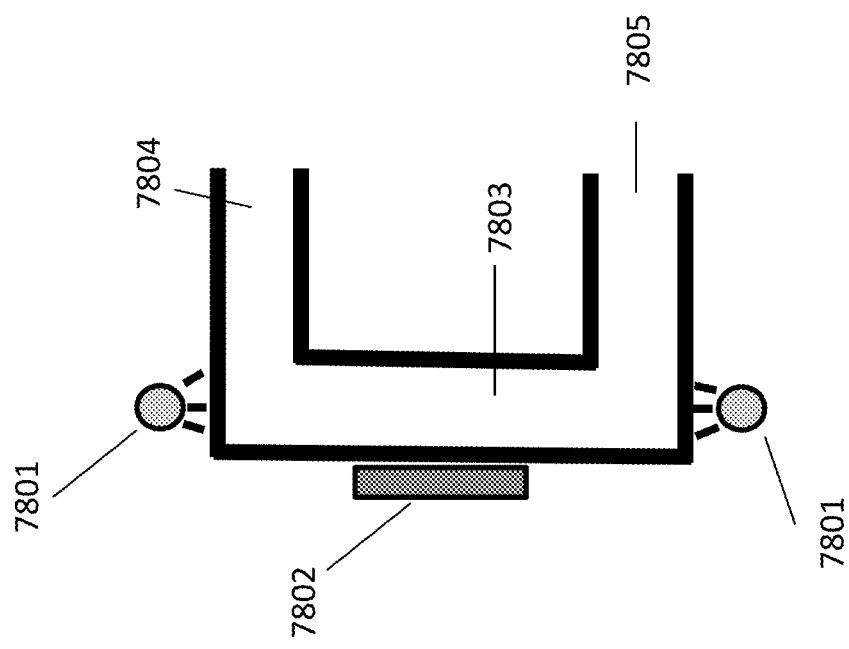

The fluid conduit, light emitter, and detector may have various configurations. FIGS. 77A-77D depict variations of orientations in which at least one detector (e.g., photosensor) (7802) is oriented along a longitudinal axis of the fluid conduit (7803). A light emitter (7801) may be oriented closer to the distal end (7805) of the fluid conduit (7803) (FIG. 78B), or closer to the proximal end (7804) of the fluid conduit (7803) (FIG. 78A). One or more detectors (7802) may be oriented radially around the fluid conduit (7803). To align the light emitter (7801) longitudinally to the fluid conduit (7803), a 90 degree bend in the fluid conduit (7803) is depicted, but variations of the angle, or an inset cavity may be used to position the light emitter (7801). FIGS. 78A and 78B depict portions of a fluid conduit (7803) having a single bend while FIGS. 78C and 78D depict fluid conduits (7803) having a bend on either side of a detector (7802). In FIG. 78C, a pair of light emitters (7801) are aligned along a longitudinal axis of the fluid conduit (7803) on opposite sides of a detector (7802).

In some variations, the accuracy of optical signal measurements may be improved by reducing the presence of bubbles (micro-sized and larger) that adhere to the surface of a fluid conduit during measurement. Some variations of the fluid conduit may comprise one or more of hydrophilic materials configured to prevent bubbles from adhering to a conduit surface, and a filter may be placed upstream of an optical sensor arrangement. For example, the filter may be an air filter, such as Hydrophilic Filter (Qosina, P/N 28216).

Additionally or alternatively, a pressure differential within the fluid conduit may reduce the presence of bubbles. In some variations, the fluid conduit may have a non-uniform profile, in which a transparent portion optical sensing region) has a reduced cross-sectional area that generates a pressure differential configured to evacuate bubbles from the transparent portion. For example, FIG. 77 depicts a cross-sectional view of a fluid conduit (7700) having a transparent portion (7702) with a reduced cross-sectional area relative to other portions of the fluid conduit (7700). In the reduced cross-sectional area, fluid flow velocity increases abruptly, which facilitates release of bubbles binding to the surface of the fluid conduit (7700) in the transparent portion (7702). A variety of profiles may be used to increase turbulence in the transparent portion (7702) to promote air bubble release. In some variations, the fluid conduit may be coupled to one or more of a vibrator and solenoid configured to displace air bubbles at predetermined intervals.

In some variations, the accuracy of optical signal measurements may be improved by reducing and/or compensating for external light noise (such as from ambient light sources) using one or more of the mechanisms described in detail herein. For example, a transparent region (e.g., optical sensing region) of a fluid conduit may be shielded from external light using an enclosure (e.g., opaque housing, lid, cover, flaps, door) during measurement. In some variations, a collimator located in front of a detector may be configured to reduce detection of external light noise (e.g., stray light). Additionally or alternatively, the fluid conduit may comprise one or more light absorbing portions (e.g., opaque portions, rings) proximal and/or distal to the transparent portion. The light absorbing portions are configured to reduce conduction of light from light sources external to the patient monitoring device. In some variations, an optical sensor arrangement may be configured to measure an amount of external light such that optical characteristic measurements and/or calculations may be modified to compensate for the measured external light. For example, an emitter of an optical sensor arrangement may be configured to generate light in a pulsed manner. Optical characteristics may be measured by at least one detector when the emitter pulses light and an amount of external light may be measured by at least one detector when the emitter does not emit light and is "in the dark".

Figure 43:
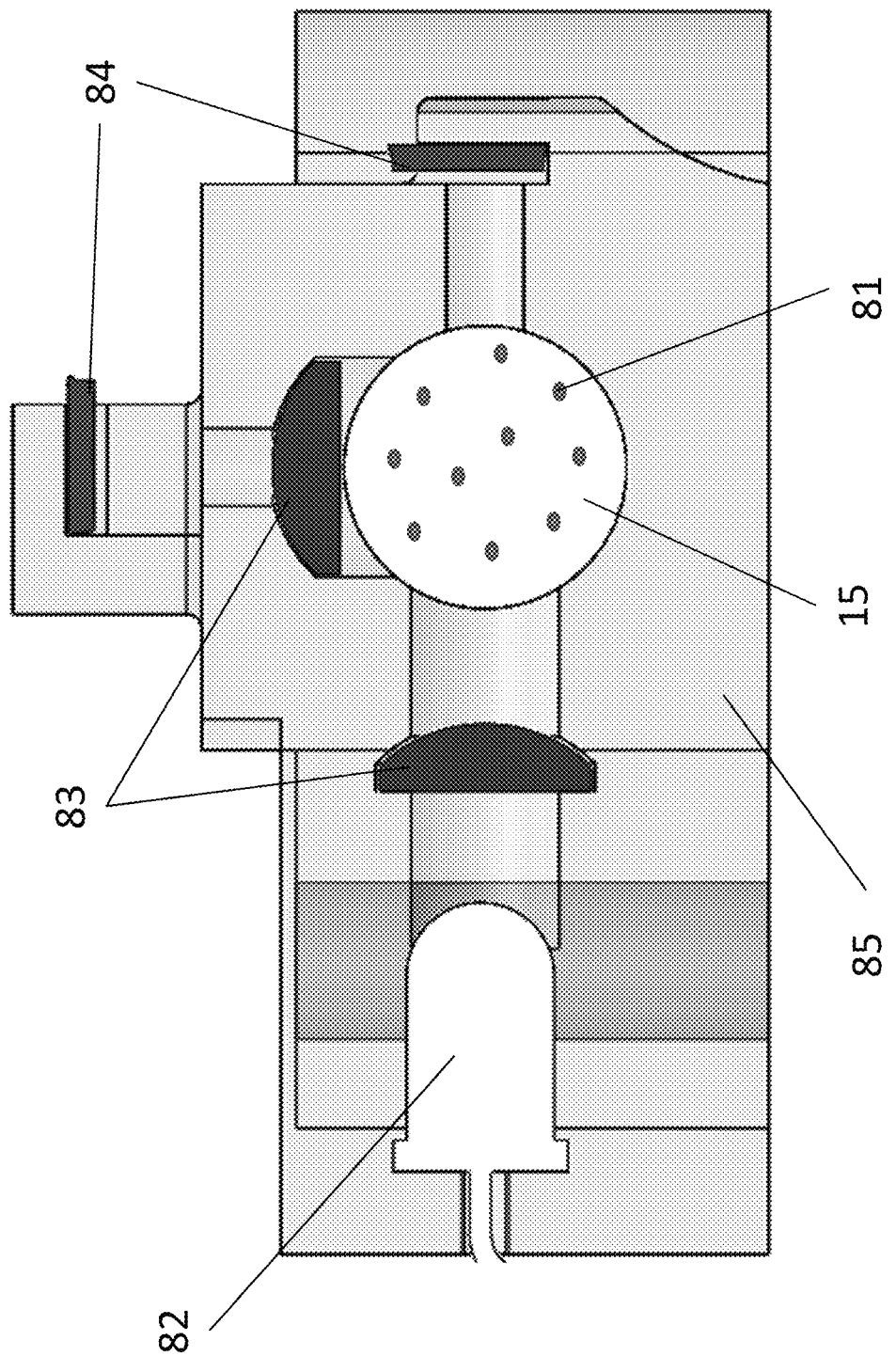
FIG. 43 illustrates a schematic cross-sectional view of an exemplary variation of an optical scatter and/or absorption sensor.

FIG. 43 depicts a cross-sectional view of one stage of an optical scatter/absorption system. The fluid flows through the fluid conduit (15) with particles (81). Light source (82), convex-plano lenses (83), light detectors (84), and fluid conduit are assembled into a fixture (85). The light source (82) emits light, and a convex-plano lens (83) collimates the light waves. One of the detectors (84) oriented 180 degrees relative to the emitter (86) receives the remainder of the light after it has passed through the conduit (15). Another convex-plano lens (83) oriented at 90 degrees relative to the emitter, receives the side-scattered light. This convex-plano lens collimates the received light before it reaches the light detector (84) oriented at the 90 degree position.

Additional lens types (equi-convex, bi-convex, converging meniscus, positive meniscus) may be used to focus the light source from the light source or from the scattered light to the detector. Wavelengths of light may be transmitted in phase or out of phase. From the relatively wide band of a light source, filters may be used for discrete wavelength transmission.

In some variations, a scintillator may be used to improve the signal strength of the light detector (84). In some variations, a light detector (84) may have a larger surface area to capture more light. The light detectors (84) as depicted in FIG. 43 are oriented perpendicular to the radial direction of the fluid conduit (15). Additionally or alternatively, the light detectors (84) may be provided at an angle (<90 degrees or >90 degrees) relative to the radial direction of the fluid conduit (15) to effectively increase the surface area in the light path for receiving additional light and/or to prevent reflection of light back to the fluid conduit (15).

Figure 44:
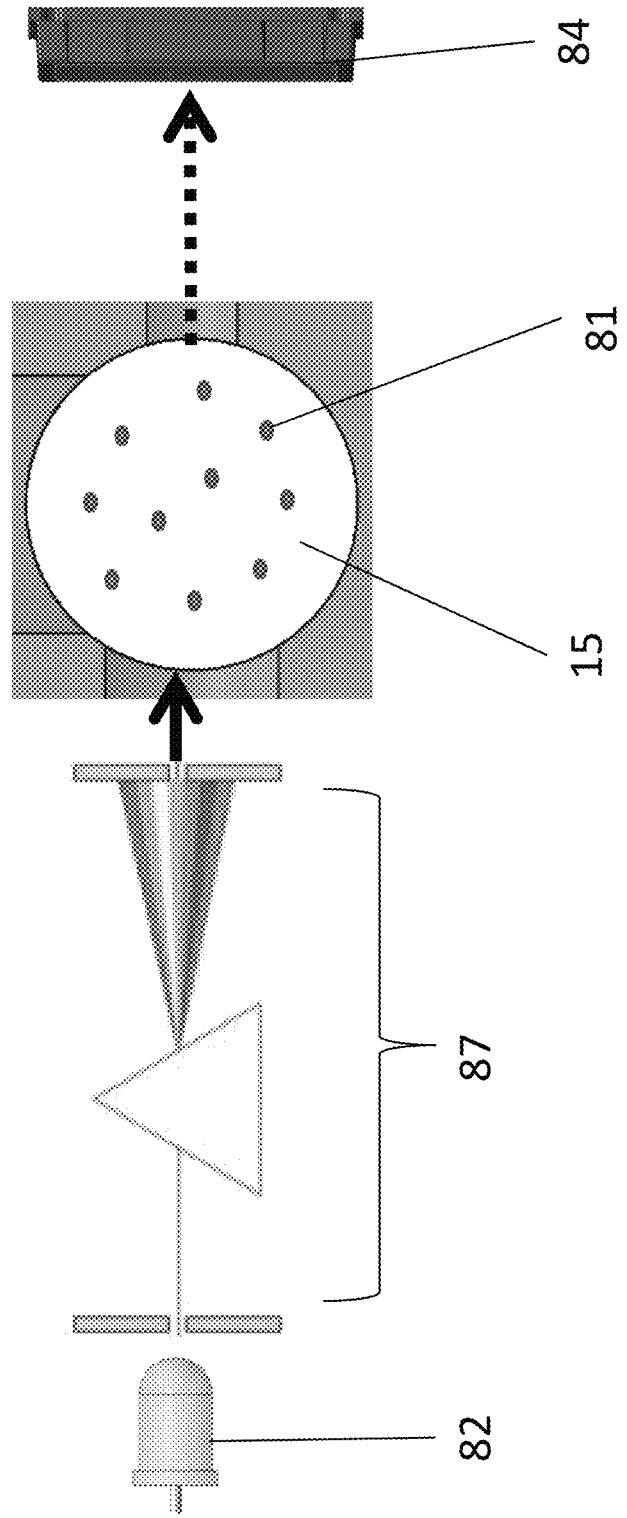
FIG. 44 illustrates a schematic diagram of an exemplary variation of a forward optical system.

As an alternate, or supplement to the optical scatter/absorption system described, a spectroscopy system can be integrated for a wide-band wavelength absorbance analysis to determine specific constituents within the fluid. A forward optical system is depicted in FIG. 44. A white light source (82) transmits a wide band of wavelengths to a monochromator (87). Discrete wavelengths are transmitted through the fluid channel (15) and the constituents within the fluid (81) absorb different wavelengths in the spectrum of light, with the resultant light measured by the detector (84). A reverse optical system could similarly be integrated.

In the use of the optical scatter/absorption sensor within the system, the material of the fluid-interfacing surface could comprise of material with high optical clarity, such as one or more of acrylic, cyclic olefin copolymer, and a material that combines high heat conductivity, such as Pyrex glass, or glass-filled nylon, or a material with high anti-fouling properties, such as polyethylene glycol (PEG)-coated silicone, hydrogel coated silicone, zwitterionic (phosphorylcholine, sulfobetaine) coated polyurethane, polyethylene oxide-coated polyvinyl chloride (PVC), and polyamphiphilic silicone, to maintain consistent optical clarity over the duration of usage.

Materials susceptible to bacterial fouling can also be utilized to amplify optical scatter/absorption level changes. At light absorption angles (180 degrees), increased optical scatter/absorption related to infection will generally reduce the light received by the detector. Bacterial fouling of the tubing material can further reduce the amount of light received by the detector, thus amplifying the signal. Alternately, any biofouling of the material resulting in a reduction in the light received by the detector of the optical scatter/absorption system can be used to signal one or more of replacement, cleaning, and maintenance of the fluid channel.

Figure 35:
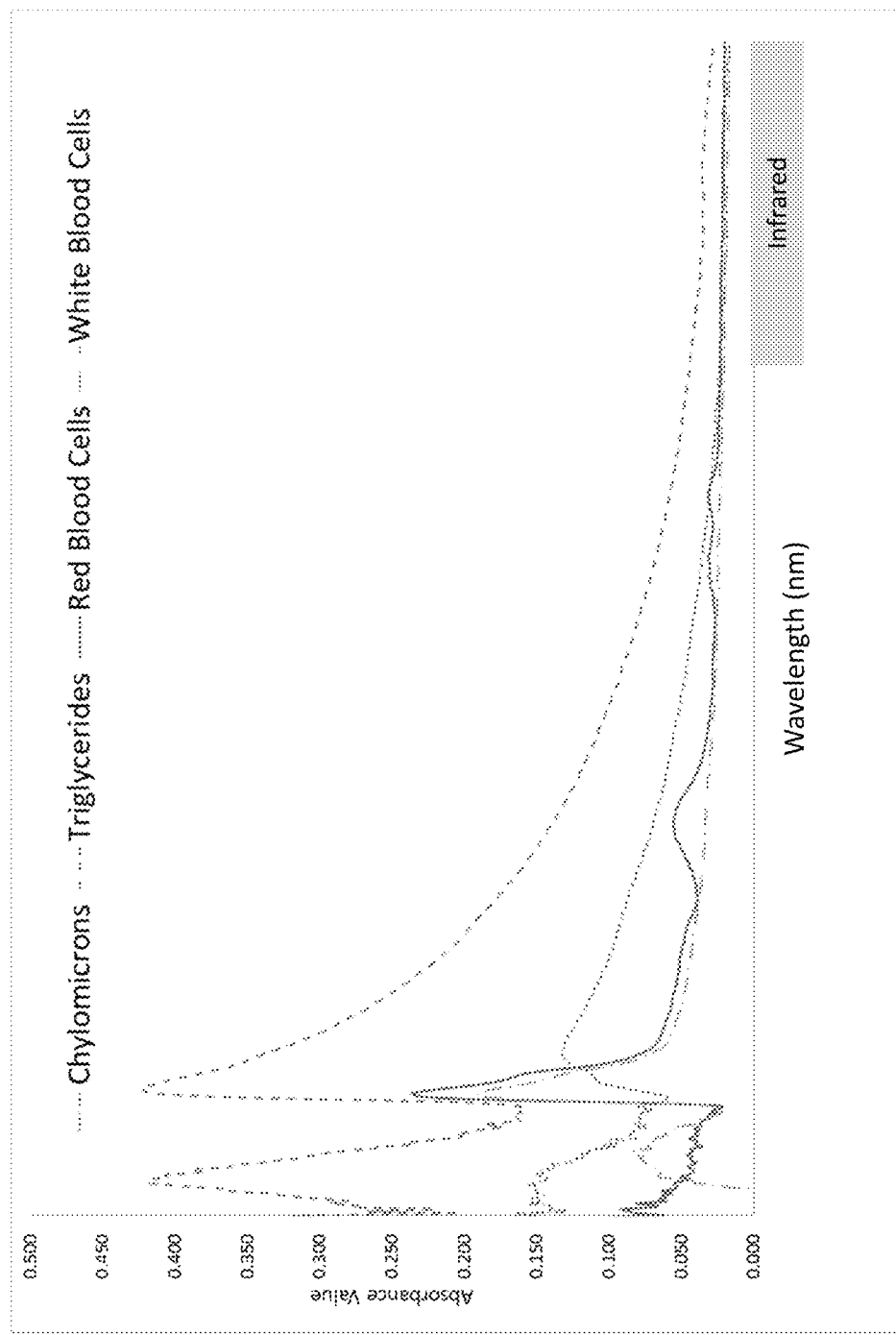
FIG. 35 illustrates an exemplary variation of an absorption spectrum of components of effluent.

Identification of particles indicative of a specific complication is challenging in complex fluids such as blood, urine, ascites, and peritoneal dialysis drainage. As shown in FIG. 35, different particle types (red blood cells, chylomicrons, triglycerides, white blood cells) may have unique, distinguishable optical absorbance spectrums. In some variations, a sensor may be sensitive to a wide range of wavelengths and configured to measure the entire absorbance spectrum to identify the unique optical absorbance spectrum signatures of the particles present, but such systems may be relatively bulky and expensive in some contexts. Measurements in certain selected wavelength ranges (e.g., the infrared range), may enable minimal differentiation of the different particle types based on their optical absorbance behavior, making it difficult to distinguish between different particle types (e.g., red blood cells, chylomicrons, triglycerides, white blood cells) when measuring optical characteristics in the infrared range. Accordingly, in some variations, the optical measurements of a fluid at a specific wavelength range or band may indicate the presence of any one or more of a plurality of particle types in the fluid, which may lead to ambiguity as to which particle type(s) are present in the fluid based on a given sensor signal. For example, optical measurements for a wavelength range may correspond to a cell concentration of red blood cells, or white blood cells, or a combination of both.

In some variations, measurements at a set of different (e.g., discrete) wavelengths or wavelength ranges may be performed by at least one sensor to differentiate between particles present in the fluid and their characteristics. Multiple stages of optical scatter/absorption measurements can be used. For example, based on the differentiation of absorbance spectrum between particle types, a first stage of the optical scatter/absorption measurement can utilize a first wavelength range such as an infrared wavelength range to detect general increases in particle concentration within the fluid (the first wavelength or wavelength range may be a "non-specific" wavelength or wavelength range). Additionally, a second stage optical scatter/absorption measurement using a second wavelength range than the first stage measurement, such as in the near-UV spectrum, may be used to differentiate between particle types (the second wavelength or wavelength rang may accordingly be a "specific" wavelength or wavelength range). Additional stages for various wavelength ranges may also be used to differentiate additional specific particle types. For each stage of the optical scatter/absorption measurement, one or more light emitters, and one or more detectors can be used to measure the scatter or absorption of the light. Additional detectors may be used to measure data from another scattering angle and may be used to, for example, improve signal strength. The set of detectors may also be used to validate data generated from a primary sensor in order to eliminate any erroneous data points. For example, photodetectors angled at about 90 and about 180 degree relative to a single emitter may be expected to have similar ratios. However, if the ratio deviates by a predetermined threshold, the deviation may be erroneous and may be filtered out. In some variations, the emitters and detectors may have either a narrow or wide wavelength emission/detection band with or without the use of filters.

Figure 36:
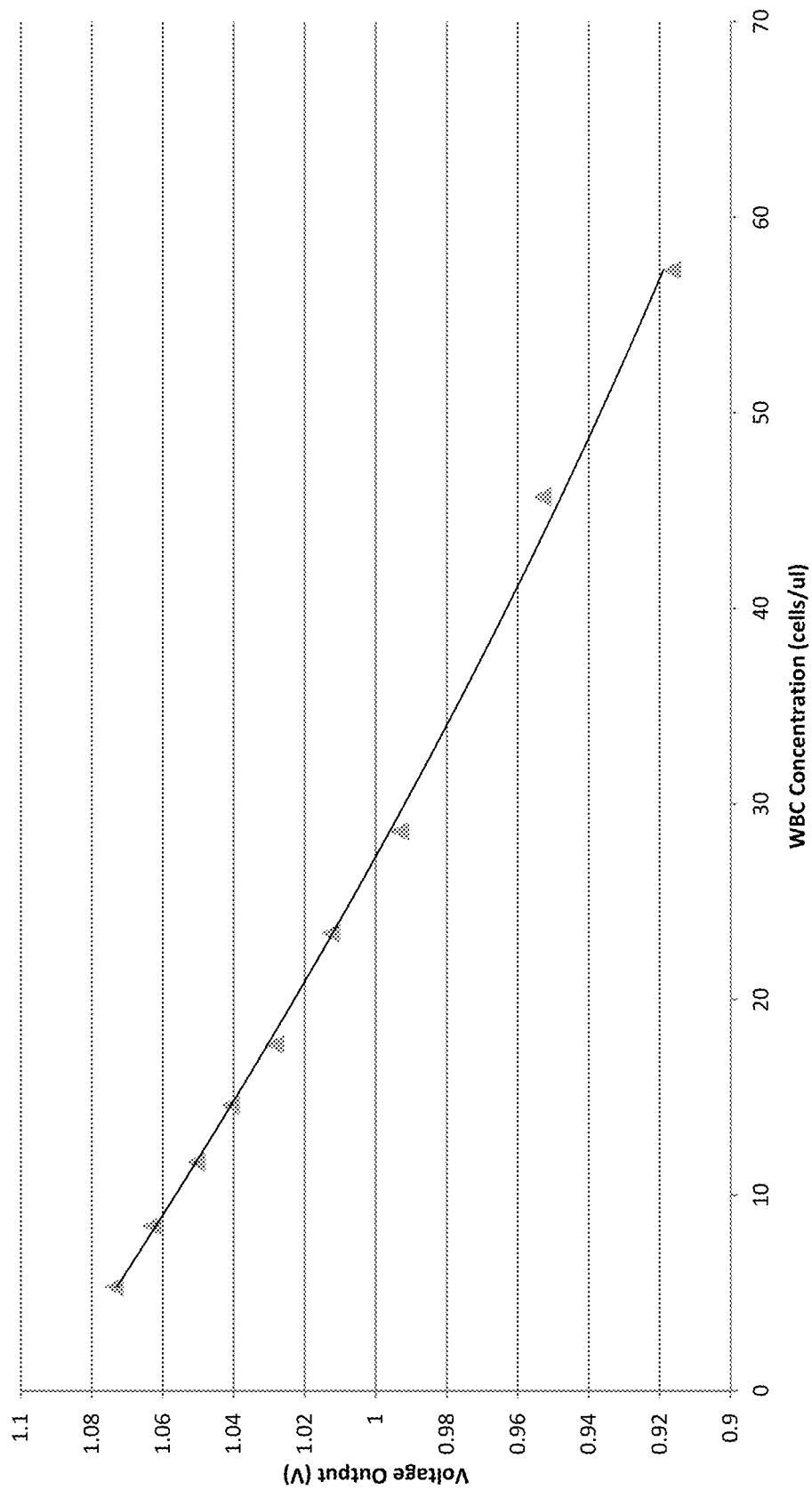
FIG. 36 illustrates an exemplary variation of a plot of cellular concentration and voltage output from an optical scatter and/or absorption sensor.

Sensor data from the multiple stages may, in some variations, be analyzed to identify particle type(s) based at least in part on one or more correlation plots for possible particle types. In some variations, a correlation plot may be generated for each measurement stage based on the concentration of each particle type, derived empirically or theoretically. For example, FIG. 36 illustrates an exemplary sensed output voltage of an optical scatter/absorption sensor versus white blood cell concentration plotted. FIG. 36 illustrates a relationship based, for example, on empirical data for one or more sensors in controlled conditions with varying white blood cell concentration in measured fluid. The relationship between white blood cell concentration and sensor signal may be characterized and/or accessible by a parametric equation, a lookup table, etc. As another example, another sensed output voltage plot versus red blood cell concentration (or other suitable fluid characteristic) may similarly be generated and demonstrate a unique profile (e.g., with a corresponding relationship which may be characterized and/or accessible, for example, by a parametric equation, a lookup table, etc.). Accordingly, a measured sensor signal (e.g., voltage) may be correlated to a white blood cell concentration and/or red blood cell concentration in the measured fluid (or other fluid characteristic) using the respective curves or correlation plots for white blood cells and red blood cells. Depending on the wavelength band selected and the particle type's absorbance within a wavelength band, the correlation plot may be unique for different particles. For example, a concentration plot for red blood cells and white blood cells may be substantially the same for a non-particle-differentiating (e.g., 850 nm-870 nm wavelength band) optical sensor. In contrast, a concentration plot for red blood cells and white blood cells may be clearly differentiable for a particle differentiating (e.g., 400 nm-420 nm wavelength band) optical sensor.

Figure 37:
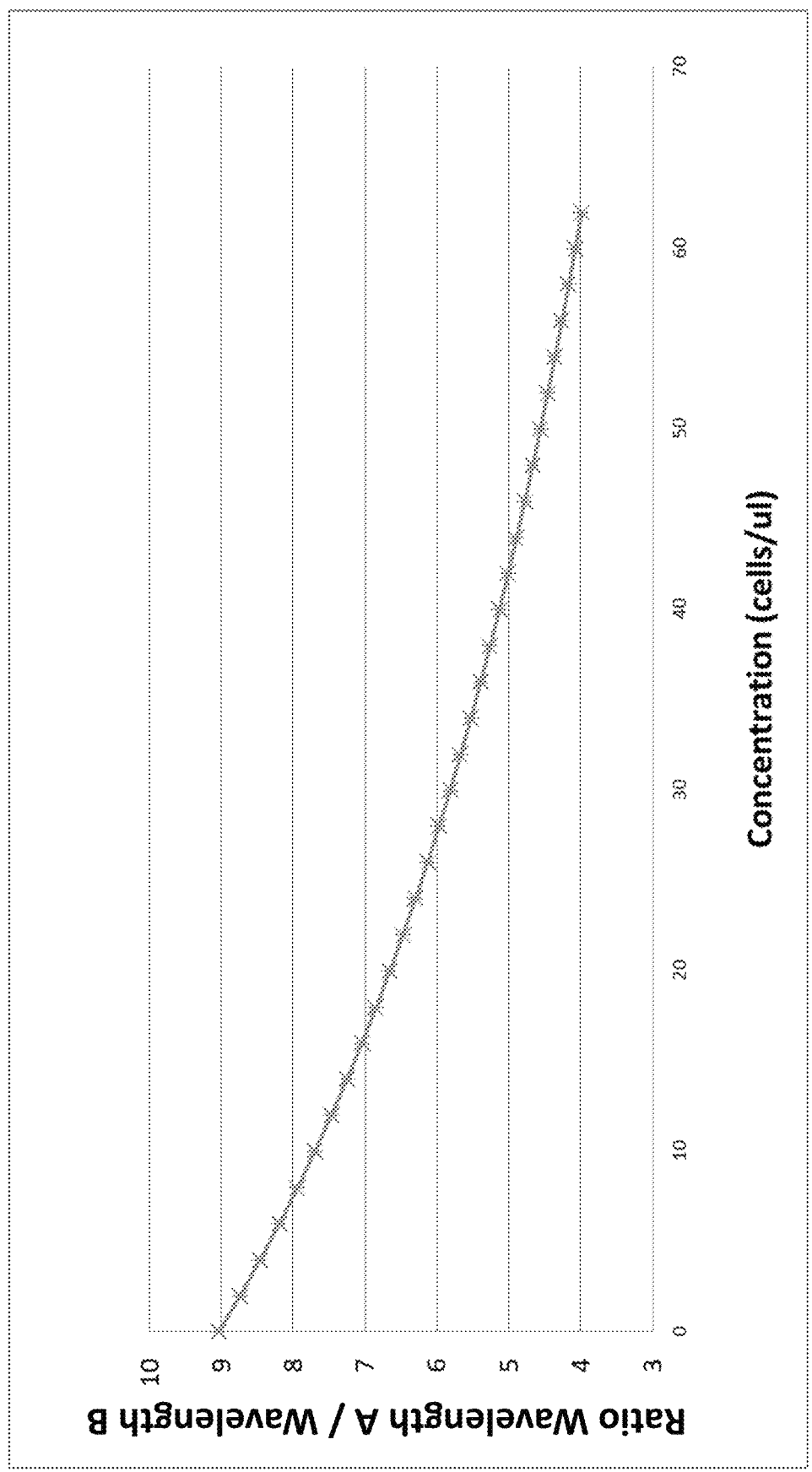
FIG. 37 illustrates an exemplary plot of cellular concentration and signal ratio.

Additionally or alternatively, based on correlation plots such as those described above, one or more ratios of sensor data associated with the different stages (e.g., measurements at different wavelength bands) may be calculated and plotted against particle type concentration to derive additional correlation plots. For example, FIG. 37 is a correlation plot of the sensor data measured from the first and second stage sensor systems (e.g., voltage from a first stage sensor system described above, relative to (e.g., divided by) voltage from a second stage sensor system described above) for varying white blood cell concentrations. A similar correlation plot using the sensor data measured from the first and second stage sensor systems can be created for red blood cells. Due to the unique absorbance characteristics of the WBC and RBC particle types at the second stage wavelength band, the ratios may be different for each particle type.

The correlation plot data generated at different stages (e.g., discrete wavelength ranges or bands) may allow particle types within a fluid to be differentiated (e.g., identified). This may be useful in situations in which the optical measurements of a fluid at a specific wavelength range or band may indicate the presence of any one or more of a plurality of particle types in the fluid, which may lead to ambiguity as to which particle type(s) are present based on a given sensor signal. For example, optical measurements for a wavelength range may correspond to a cell concentration of red blood cells, or white blood cells, or a combination of both. Furthermore, a particle type may be dominant (e.g., have a higher concentration) than other particle types in the fluid.

Generally, an optical sensor may be configured to measure fluid at two or more wavelength ranges. The measurements at the different wavelength ranges may be separately plotted for different particle types against known concentration relationships. A set of possible particle type concentrations may be estimated from these plots. The estimated concentrations may then be compared to each other to find substantially matching values. When the estimated concentration values for a particle type match across the different plots, then the particle type may be estimated. For example, the concentration of the unknown dominant particle type may be identified in a set of one or more known (or predetermined) correlation plots (e.g., concentration curves). The set of correlation plots may, for example, include a specific particle correlation plot (e.g., similar in concept to the correlation plot shown in FIG. 36 which relates (i) signal at one wavelength to (ii) a specific particle type such as white blood cells) and one or more ratio-based correlation plots (e.g., similar in concept to the correlation plot shown in FIG. 37 which relates (i) a ratio of signal data for multiple wavelengths to (ii) a specific particle type such as white blood cells). Generally, sensor signals and a ratio of sensor signals for measurements at different wavelengths can be correlated to specific particle types using the set of correlation plots in a multi-step process, as illustrated in the examples below.

Example 1: A first stage (e.g., non-particle-differentiating) optical sensor may be configured to measure fluid at between about 850 nm and about 870 nm wavelength band and a second stage (e.g., particle-differentiating) optical sensor may be configured to measure fluid at between about 400 nm and about 420 nm wavelength band. The first stage optical sensor measures a sensor output voltage of 0.95 V. The second stage optical sensor measures an output voltage of about 0.15 V.

Figure 38A:
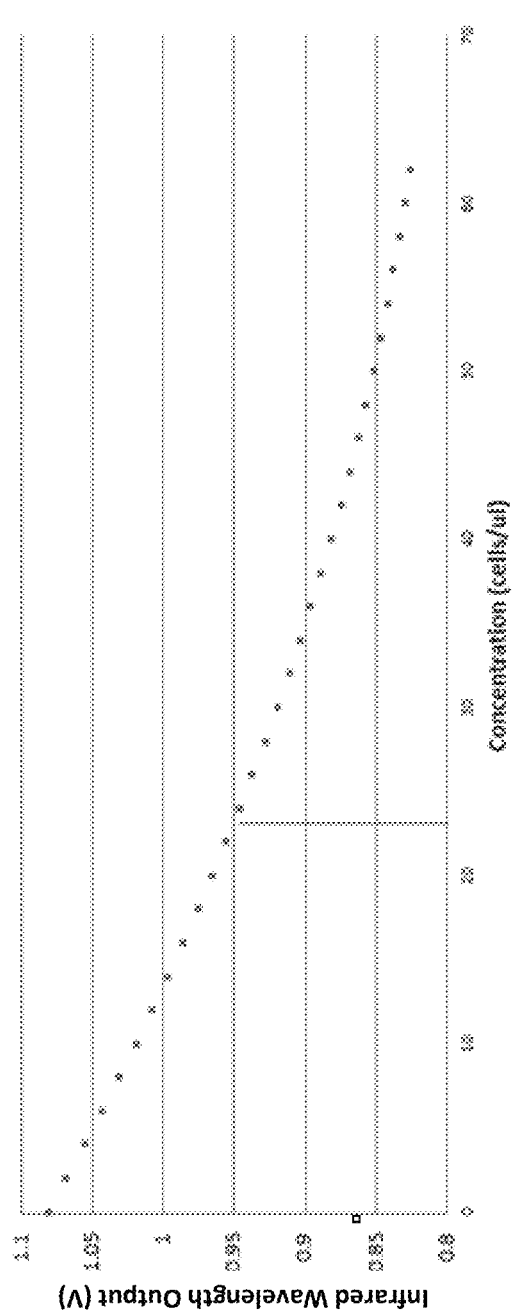
FIGS. 38A and 38B illustrate an exemplary plot of cellular concentration and signal output from a two-stage optical scatter and/or absorption system where the second stage utilizes a differentiating wavelength range.
Figure 38B:
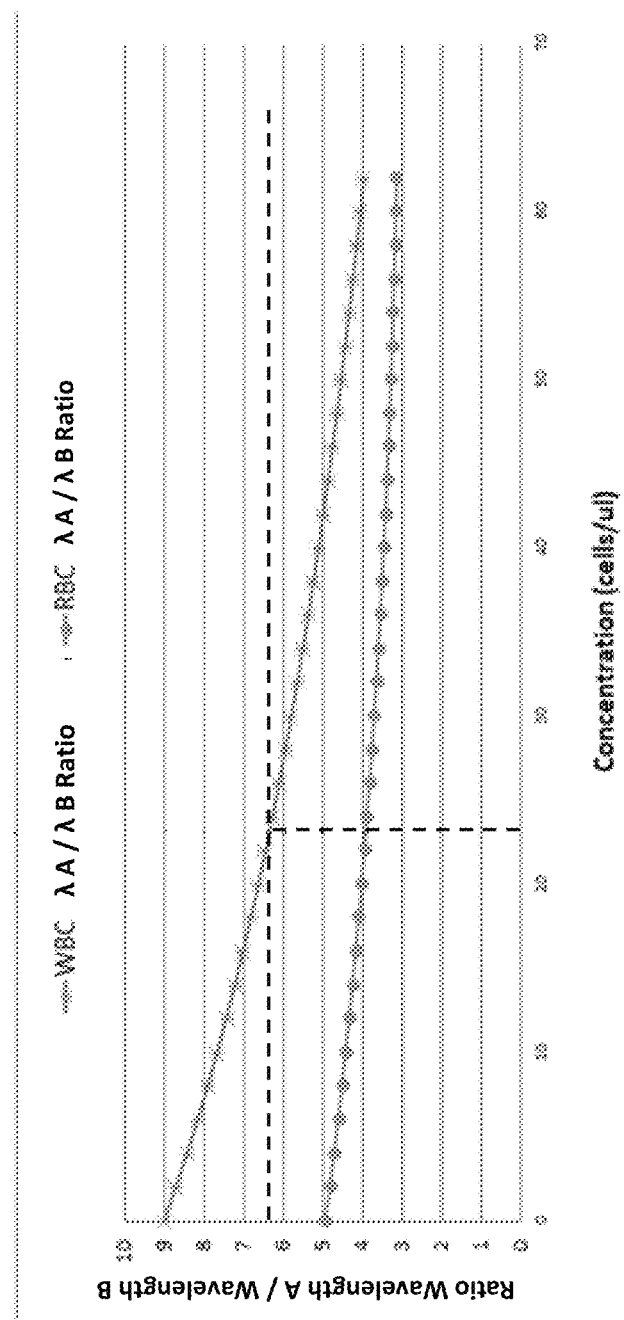

FIG. 38A and FIG. 38B depict the application of correlation plots to identify the particle type and concentration from these two signals output from the first and second stage optical sensors. FIG. 38A is a predetermined correlation plot of sensor signal (e.g., optical measurement at a wavelength within a first wavelength range or band, such as infrared) versus white blood cell concentration, overlaid with a predetermined correlation plot of sensor signal versus red blood cell concentration (the curve is substantially the same for both white and blood cell concentrations) Specifically, the sensor signal was derived from a first stage optical sensor configured to measure fluid at between about 850 nm and about 870 nm. In this example, the first stage optical sensor provided a signal output of about 0.95 V, which (based on correlating this value to cell concentration in FIG. 38A) suggests that the measured fluid has a concentration of about 23 cells/µL concentration of an unknown particle type (either white blood cells or red blood cells). To help determine whether the fluid has a concentration of 23 white blood cells/µL or 23 red blood cells/µL, a second step analysis using one or more ratio-based correlation plots, such as that shown in FIG. 38B, may be performed.

FIG. 38B is an overlay of ratio-based correlation plots for white blood cells (WBC) and for red blood cells (RBC). Specifically, the WBC and RBC curves in FIG. 38B correspond to known concentration relationships of a ratio of the measured sensor outputs at the first wavelength range ("Wavelength A") divided by a second wavelength range ("Wavelength B") (measurements in the first stage relative to measurements in the second stage). In this example, the ratio of the first stage to the second stage ($\lambda A/\lambda B$) is calculated as 0.95/0.15=6.33. The measured ratio of 6.33 intersects the WBC curve at 23 cells/µL and does not intersect the RBC curve at all. Accordingly, the ratio-based correlation plot of FIG. 38B indicates that the measured cell concentration of 23 cells/µL, is of white blood cells. In other words, since the estimated WBC concentration values match over different correlation plots, the optical scatter/absorption measured by the first and second stage optical sensors is largely due to WBC particles and minimally from RBC particles. The WBC concentration values measured may then be used to determine patient infection, as described in more detail herein.

Example 2: In this example, both stages of the optical scatter/absorption may be at wavelengths that have differentiating absorbance characteristics for different particle types. A first stage (e.g., non-particle-differentiating) optical sensor may be configured to measure fluid at about a 260 nm wavelength (Wavelength C) and a second stage (e.g., particle-differentiating) optical sensor may be configured to measure fluid at another cell-specific wavelength (Wavelength D). The first stage optical sensor measures a sensor output voltage of about 0.950 V. The second stage optical sensor measures an output voltage of about 0.194 V.

Figure 39A:
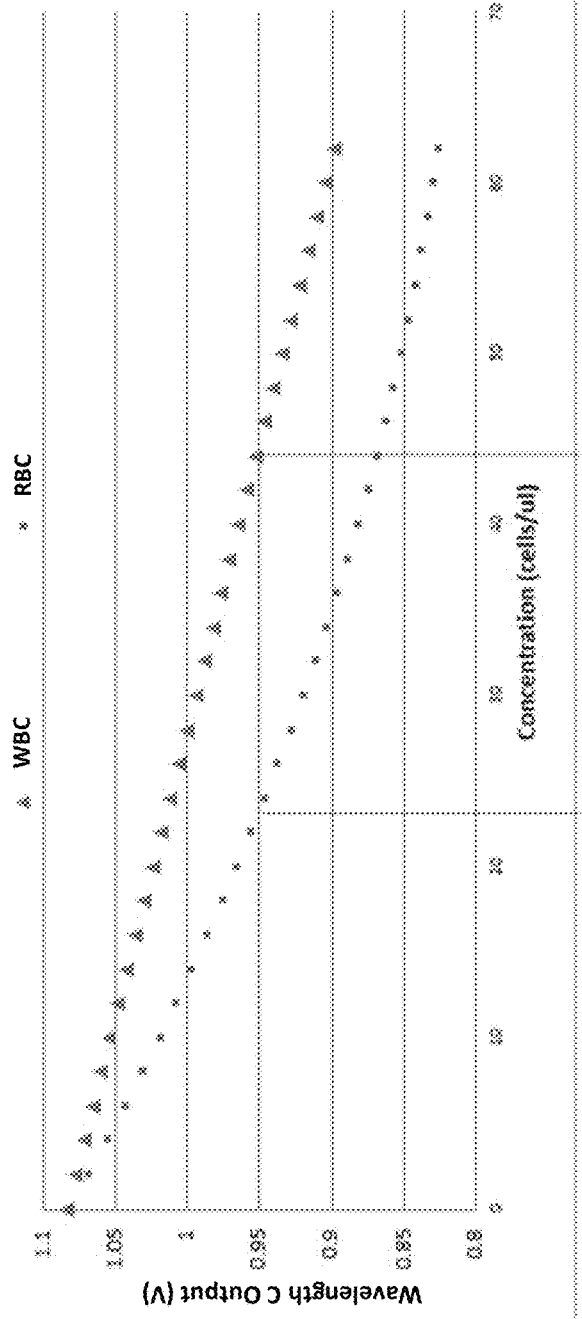
FIGS. 39A and 39B illustrate other exemplary plots of cellular concentration and signal output from a two-stage optical scatter and/or absorption system where the first and second stage utilize differentiating wavelength ranges.
Figure 39B:
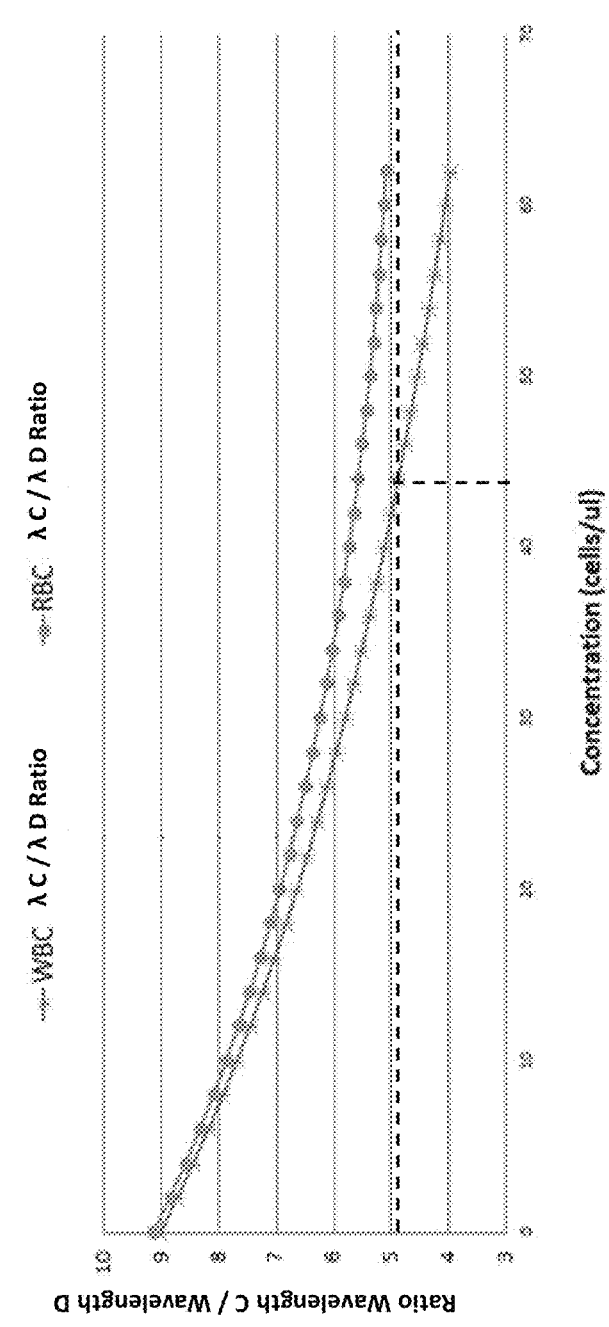

Similar to Example 1, correlation plots as shown in FIGS. 39A and 39B for different particle types may be used to analyze the first and second stage sensor data. Specifically, FIG. 39A includes an overlay of a predetermined correlation plot for sensor signal output measured at Wavelength C versus WBC, and sensor signal output measured at Wavelength C versus RBC. In this example, the first stage optical sensor provided a signal output of about 0.950 V, which (based on correlating this value to cell concentration in FIG. 38A) suggests that the measured fluid has either about 44 cells/µL concentration of WBC or about 23 cells/µL concentration of RBC. However, it is unclear from FIG. 39A alone whether the first stage sensor signal should be correlated to such a WBC concentration or such a RBC concentration. Accordingly, a second step analysis using one or more ratio-based correlation plots, such as that shown in FIG. 39B, may be performed.

Like FIG. 38B, FIG. 39B is an overlay of ratio-based correlation plots for white blood cells (WBC) and for red blood cells (RBC). Specifically, the WBC and RBC curves in FIG. 39B correspond to known concentration relationships of a ratio of the measured sensor outputs at the first wavelength range ("Wavelength C") divided by a second wavelength range ("Wavelength D") (measurements in the first stage relative to measurements in the second stage). Here in this example, the Wavelength C/Wavelength D ratio is calculated as 0.950V/0.194V=4.9. This measured ratio of 4.9 is plotted against a known WBC ratio curve and a RBC ratio curve. The ratio of 4.9 intersects the WBC curve at 44 cells/μL but does not intersect the RBC curve shown in FIG. 39B. Because FIGS. 39A and 39B both indicate an estimated WBC concentration of 44 cells/μL, the measured cell concentration may be identified as primarily associated with WBC (at a concentration of about 44 cells/μL).

Figures 40A, 40B:
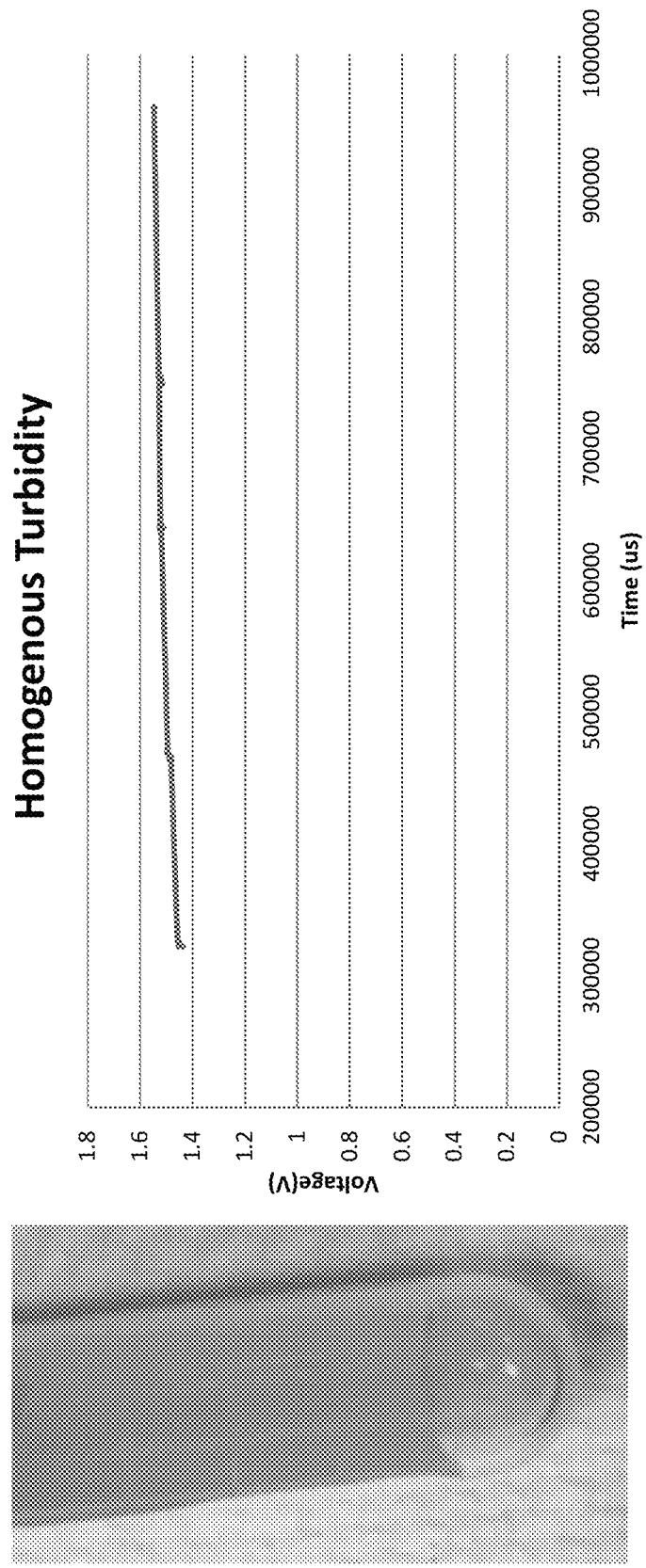
FIG. 40A illustrates an exemplary plot of homogenous optical scatter/absorption.
FIG. 40B is an image of a homogenous mixture of particles in a solution.

In another method to distinguish particle types, non-homogeneous and homogeneously-mixed particles can be distinguished. The optical scatter/absorption sensor can sample at a frequency high enough (e.g., 50 Hz) to detect particles as they flow through the sensors. Homogeneous fluid will exhibit relatively low variance in each measurement, as shown in FIG. 40A.

Figure 41A:
FIG. 41A illustrates an exemplary plot of non-homogenous optical scatter/absorption.
Figure 41B:
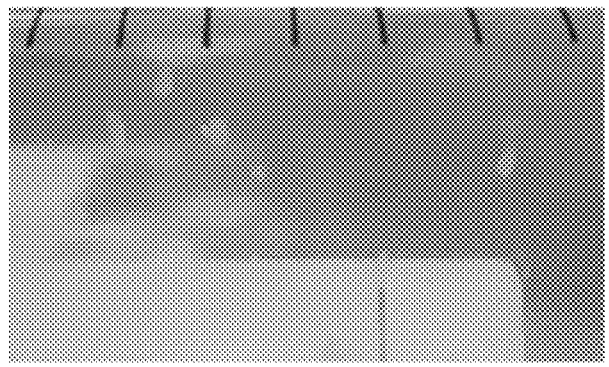
FIG. 41B is an image of non-homogenous particles suspended in a solution.

In the case where multiple, discrete particles are passing through, the optical scatter/absorption sensor will pick up spikes in the measurement output as the particle passes through, and a corresponding high variance in the data may result, as shown in FIG. 41A.

Figure 42A:
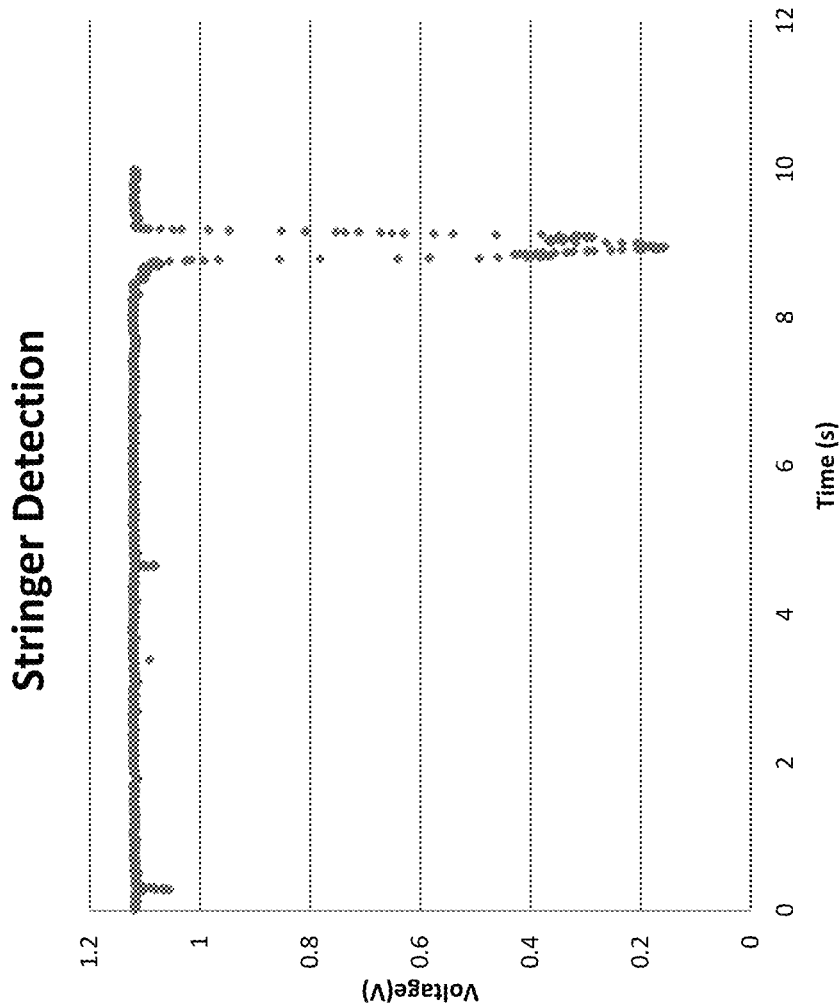
FIG. 42A illustrates an exemplary plot of large particle flow over time.
Figure 42B:
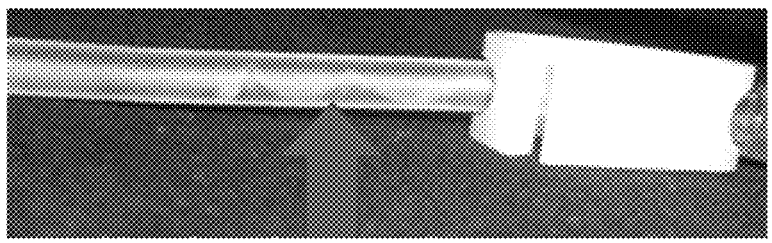
FIG. 42B is an image of a stringer (e.g., fibrin) in a fluid conduit.

The sensors described herein may also detect single strands (e.g., fibrin stringers). As the stringer (see FIG. 42B) passes by the optical scatter/absorption sensor, a large change in the measured optical scatter/absorption value will be generated, as shown in FIG. 42A, after which, the signal should return to the measurements corresponding to the bulk fluid optical scatter/absorption. In some variations, the stringers and non-homogenous particles may be excluded from subsequent data analysis. The light emitter may be a light emitting diode (LED) source, or laser. The light emitter may include additional optics, such as a convex-plano lens to collimate the light source. The light source may also integrate filters to narrow the band of wavelengths.

The integration of the optical scatter/absorption light emitter and detector within the housing should include light-shielding via an opaque enclosure surrounding the optical scatter/absorption sensor emitter and detector in order to exclude environment light noise and optimize optical scatter/absorption sensor performance.

Optical scatter/absorption sensor output voltage values can be converted to Formazin Turbidity Units (FTU) to be used directly, or as a differential. Optical scatter/absorption of the fresh infused dialysate solution before entrance into the body could be measured by the sensor and compared to the optical scatter/absorption of the drainage dialysate solution exiting the body in order to determine an optical scatter/absorption differential or ratio. For example, drained dialysate optical scatter/absorption levels (typically in the 5-100 FTU range) can be monitored alone, or a unit-less ratio can be calculated of drained dialysate optical scatter/absorption to infused dialysate optical scatter/absorption. Alternately, because optical scatter/absorption is usually associated with the elevated white blood cell concentration of an infection event, the optical scatter/absorption values may be converted to a specific white blood cell count. Besides monitoring onset of infection, dialysate optical scatter/absorption measurement can also provide feedback on patient response to treatment. For example, when infection is detected, an antibiotic regimen is typically prescribed to the patient. A successful antibiotic therapy should result in gradual reduction of the infection and white blood cell concentration present in the drainage fluid. The dialysate optical scatter/absorption differential throughout treatment can be monitored as a method of assessing the efficacy of the antibiotic treatment.

Optical scatter/absorption measurements also can be used in conjunction with other data inputs. In one example, the optical scatter/absorption system is used in conjunction with a flow sensor. The flow sensor determines the overall drainage fluid volume. In the case of peritoneal dialysis, the flow sensor may also determine the dialysis dwell time. The particle concentration may vary based on the fluid drain volume, and/or the dwell cycle time. Hence, it may be important to normalize the optical scatter/absorption value measurements with the drainage volume and/or the dwell cycle time.

The pH of fluid exiting catheters can vary due to the onset of patient acidosis, which is one patient symptom related to infections. In one use case, pH sensors can monitor acidosis in peritoneal dialysis patients. Many dialysate solutions utilized for peritoneal dialysis have a neutral pH at 7.0. A known body response to infection, like peritonitis, is acidosis, indicated by a pH less than 7.0. The system may utilize a pH sensor as a method to detect infection. A pH sensor measures the acidity or alkalinity of a solution by measuring the difference in electrical potential. Exemplary pH sensors that may be used include, but are not limited to, Analog Devices EVAL-CN0326-PMDZ-ND (Norwood, MA) and Vernier Software and Technology PH-BTA (Beaverton, OR). A pH sensor fluidically connected to the dialysate fluid flow conduit would monitor dialysate pH for both fresh dialysate and drainage dialysate. Calibration of the pH sensor can be conducted with a known pH of the fresh infused dialysate. The sensor analog output values can be converted directly to a value, or alternately, the relative difference between the outputs from the pH sensor of the fresh dialysate and drainage dialysate can be used. For example, the measurement of the drainage dialysate produces an output of 3.2V from a pH sensor, and based on the linear calibration curve, may correspond to a pH of 6.5, which may trigger an alert due to the acidity of the drainage dialysate solution. Alternatively, the infused dialysate produces an output of 3.5V and the drainage dialysate produces an output of 3.0V. Based on the sensor design where the output voltage directly correlates to pH values, it would be derived that the drainage dialysate is more acidic than the infused dialysate, and an alert would be triggered.

For peritoneal dialysis patients, an ascites lactate level of more than 25 mg/dL can be indicative of active peritonitis. Lactate monitoring using an amperometric sensor, such as Zimmer and Peacock model A-AD-GG-106-L (Royston, United Kingdom) allows for another early diagnostic method for peritonitis. A lactate sensor functions by producing a current when a potential is applied between three electrodes. Analysis of the potential and current produced determines lactate presence in the ascites solution. In the system, the electrodes of the lactate sensor may be immersed or in direct fluid communication within one section of the dialysate fluid flow conduit such as configurations depicted in FIGS. 45 and 46.

The presence of a high concentration of white blood cells in fluid exiting catheters can be indicative of infections. Higher concentrations of white blood cells may generally be correlated to greater degrees of infection. A portion of these white blood cells diffuse into the dialysate fluid, and concentrations exceeding about 100 cells/ml are highly indicative of peritonitis. Fresh dialysate solution is a dextrose solution with a few substrates, and prior to entering the body, has no cells. Patients with peritonitis will build up white blood cells in the peritoneum to fight the infection, and the drainage dialysate solution from the body will have a number of these leukocytes. Therefore, peritonitis may be detected with cell counter sensors which can distinguish between one or more types of leukocyte cells. Commercially available cell counters include Millipore Sigma PHCC40050 (Burlington, MA). Utilizing a combined approach of flow sensing as well as cell counting can produce data in diagnosing peritonitis as well as other infections. In the system, a leukocyte cell-counting microsensor can be fluidically connected to the fluid flow conduit of the dialysate drainage fluid such that the sensing surface area is continuously in contact with the drainage dialysate solution. The cell-counter sensors contain a microfabricated, cell-sensing zone that enables discrimination by cell size and cell volume to specify cell type. Leukocyte cells can be counted by the sensor. In combination, the flow sensor can provide data on the volume of fluid measured by the cell counter, in order to normalize the cell concentration per unit of fluid volume.

In another method, the cells may be counted via optical imaging and image data analysis to determine the cell count of leukocytes and/or other cells. A micro camera, such as commercially available Lumenier CP-520 Pico-520TVL Nano Camera 1460 (Sarasota, FL), may be aligned to an optically clear length of the dialysate fluid flow conduit, and would capture high-magnification, high-resolution images. In the system, the camera could be combined with an optical zoom lens next to a clear length of the dialysate fluid conduit, include a light source, and have light shielded from external light in the camera section, which would affect the image taken. The images would be sent to the database server system and analyzed by a microprocessor. Leukocytes have a distinct size from other cell types and can be distinguished via image analysis with the microprocessor in order to count the total number in any provided image.

Additionally, the increased presence or activity of white blood cells due to infections can be determined using a proxy known to be associated with white blood cells. One example is leukocyte esterase, which can be determined using a test strip such as the Siemens Multistix 10 SG. This test is based on the esterase activity of polymorphonuclear leukocytes. High esterase activity is suggestive of an infection through the high activity or concentration of polymorphonuclear leukocytes. Another proxy-based test to determine the onset of infection involves chemiluminescence, which exploits phagocytosis. Chemiluminescence ties the luminescent signal to the phagocytic activity of the cells, which indicates high concentration of certain types of white blood cells or phagocytic activity. Thus, a high chemiluminescent signal can indicate an increased activity or concentration of certain white blood cells.

Patients with infections can develop rashes next to the catheter exit site, which would result in skin redness and other discoloration. A micro camera may also be provided and directed at the skin area next to the catheter exit site to monitor for rash. In another method, an RGB color sensor, such as the Texas Advanced Optoelectronic Solutions model TCS3472 (Plano, TX) may be used directed at the skin area next to the catheter exit site to monitor for rash. In either method described, light shielding around the measurement site could be used in combination with a light source to optimize the precision of the sensors.

Pressure Sensing

Pressure sensing of in-dwelling catheters can provide valuable information about potential catheter dislocation, leakage or blockage while administering therapies when fluid is infused or exiting the catheter. For example, pressure measurement during a period in which solution is infused via a pumping system can detect sudden drops in pressure indicative of a leak, or a sudden rise in pressure indicative of a blockage in the fluid conduit.

When therapies are not being delivered, catheter pressure sensing can also provide valuable insights for patient vital system monitoring. For central venous lines, for example, catheters are positioned within the patient venous where the ends are close by the right atrium of the heart. When the system is connected to central venous catheters, pressure measurement can provide patient vital information including central venous pressure, heart rate, and respiratory rate.

Pressure sensors have a variety of mechanisms of operation including but not limited to piezoresistive, capacitive, electromagnetic, optical, resonant, thermal, ionization, and potentiometric. Commercially available pressure sensors include Omega PX26-005GV fluid pressure sensor (Norwalk, CT).

Figure 45:
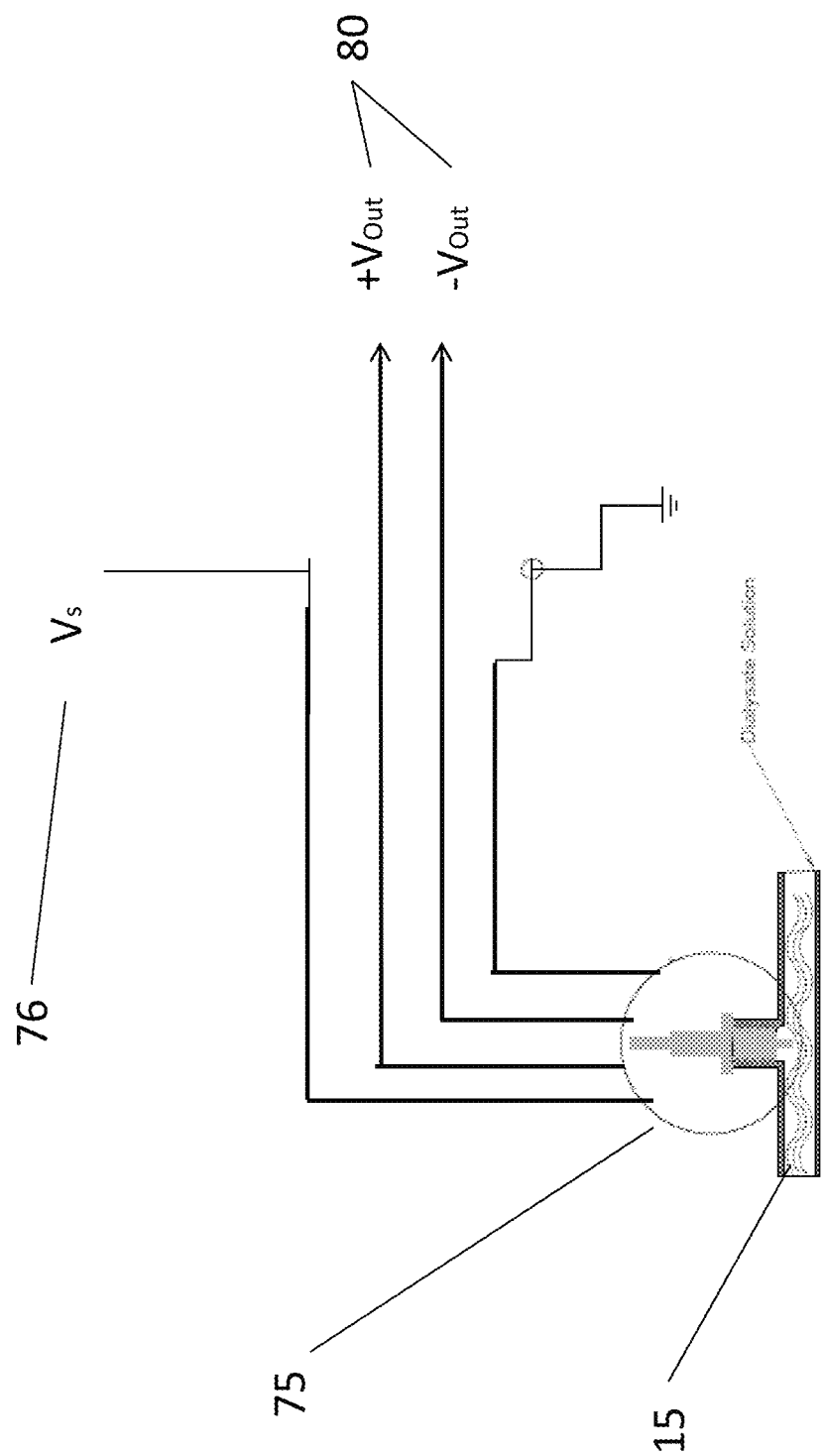
FIG. 45 illustrates a schematic circuit diagram of an exemplary variation of a pressure sensor mechanism.

FIG. 45 depicts the use of a pressure sensor. Voltage (76) is supplied and grounded by the microcontroller, and the sensor (75) has the sensing surface fluidically connected to the fluid conduit (15). The signal outputs from the sensor (80) are measured by the microcontroller.

In the system, the pressure sensor can be fluidically connected to the catheter, via the patient monitoring device as in the configuration depicted in FIGS. 16A-16C, in which the pressure sensor could be placed as one of the sensors (44) in the fluid conduit. During the infusing and/or drainage cycles of the dialysate solution, changes in the pressure may indicate potential complications. For example, elevated pressure during infusing or drainage suggest potential clogging of the catheter. During infusing, if there are sudden drops in pressure, the system may detect a catheter or connection leakage, or hernia of the patient's abdominal cavity.

In the case of peritoneal dialysis patients, in which the catheter is implanted within the peritoneal cavity, the system can monitor the intra-peritoneal pressure. There is a relationship between intra-peritoneal pressure (IPP) and some known complications associated with peritoneal dialysis including hydrothorax, abdominal wall hernias, and gastroesophageal reflux. In addition, pressure changes during dialysate infusion cycles may indicate blockages, dislocations, or leaks of the in-dwelling catheter. Pressure sensors can be used to detect these complications.

During dwell cycles, or after completion of a dialysis cycle, the dialysate tubing may be disconnected, in which case, the sensor system still remains attached to the in-dwelling dialysis catheter when positioned in the configuration depicted in FIG. 13. In the dialysate dwell phase, if there are sudden drops in pressure, the system may detect a catheter or connection leakage, or hernia of the patient's abdominal cavity. In-between dialysis cycles, when there is no dialysate solution in the patient and the hardware sensor system is connected to the in-dwelling dialysis catheter, the pressure measured directly correlates to the intra-peritoneal pressure (IPP), which can be utilized for patient vital system monitoring. IPP can correlate to respiration cycles, blood pressure, and cardiac output. In one use case, signal processing by the microprocessor in the patient monitoring device or by the database server central processing unit can isolate respiration waveforms from the pressure data. Because poor dialysis efficacy can cause shortness of breath, the IPP may show changes in the respiratory waveform, which would trigger an alert for potential ultrafiltration efficacy reduction. The respiration cycles can thus be utilized as another method of patient monitoring.

Sensors for Patient Movement

Patient physical movement and position are important indicators of patient well-being. The overall well-being of the patient can be used by itself or in tandem with other patient monitoring data. Accelerometers and/or gyroscopes with one or more axis can measure patient movement and position via the force generated from a mass within the sensor that is displaced by gravity during linear or rotational acceleration. Any of variety of accelerometers, e.g., the NXP p/n MMA8453QT (Eindhoven, Netherlands) and gyroscopes, e.g., the InvenSense ITG-3200 (San Jose, CA) may be used. In the system, the accelerometer and/or gyroscope can be embedded anywhere within the patient monitoring device in form factors where the patient monitoring device is fixed to the patient. While the patient monitoring device is fixed to the patient, patient position and movement directly translate to the accelerometer and/or gyroscope measurements.

Gyroscope data can be used to monitor patient position. The gyroscope data may be used to quantify the duration a patient is lying down. The total daily duration that the patient is not lying down can be monitored as a metric for patient activity. Any significant deviations to the duration may trigger an alert.

In another use case, the combination of the gyroscope and accelerometer may be used to detect a patient fall event. Patient falls, related or not related to dialysis therapy could trigger an alert.

Sensors for Flow Differential

A flow sensor can track the flow rate and direction of a fluid or gas along a channel. In the system, a flow sensor could be fluidically connected to the catheter where the cross-sectional area of the conduit is constant in the length which the flow sensor is contained. The speed at which fluid is infused and exits is tracked by the flow meter. Given the fixed channel cross-sectional area, volumetric data can also be derived.

In the use case of flow sensors for peritoneal dialysis patient monitoring, the flow meter would operate throughout the duration of infusing and draining cycle. The overall flow volume of infusing solution and drainage solution can be quantified. The dialysate infusing volume (Vi) and dialysate drain volume of waste (Vw) can be used to determine a Vw/Vi ratio. Vw/Vi ratios are indicative of the permeability of the peritoneum to water primarily, but also of other dialysis solutes from ultrafiltration. The Vw/Vi ratio typically stabilizes within the first 6 weeks of a patient's peritoneal dialysis treatment. Therefore, the Vw/Vi ratio can be used as one metric to determine dialysis efficacy.

The flow sensor can also be used to monitor patient compliance assurance. When fluidically coupled to the catheter, the flow sensor can use the flow directionality data to determine if flow is infusing of draining. In the system, the flow meter can be coupled with time data. When the flow sensor detects non-zero flow velocity and directionality of flow in the infusing direction, the microprocessor can record an infusing start time. When the flow sensor detects that flow velocity is zero after initial infusion, the microprocessor can record a dwell start time. When the flow sensor detects non-zero flow velocity and the directionality of flow is in the drainage direction, the microprocessor can record a drainage start time. In this manner, infusing, dwell, and drainage times can all be recorded for every cycle of various therapies to determine the patient's compliance to their prescribed therapy.

The flow sensor(s) can also be used to detect catheter obstructions. In the use of the system with peritoneal dialysis, for CAPD, and even some steps of CCPD cycles, flow is infused or drained via hydrostatic fluid pressure differentials. During dialysate infusion, a stand holds the dialysate fluid at an elevation above the patient, which creates a relatively constant positive pressure gradient and the dialysate fluid flows into the patient. During dialysate drainage, the drain tube is positioned close to or on the floor at an elevation below the patient, which creates a relatively negative pressure gradient and the dialysate fluid flows out of the patient. Because the pressure gradients during each of these cycles is fairly consistent (depending on patient position), the average fluid flow rates should be fairly consistent cycle to cycle. However, slowing fluid flow rate between cycles would suggest an obstruction somewhere in the fluid flow line. Increasing fluid flow rate would suggest potential leakage of the system. To determine either condition, average flow rate could be measured and recorded for each cycle, or simply the total duration of each cycle could be measured and recorded.

There are a multitude of flow sensor mechanisms including, but not limited to mechanical flow meters, pressure-based meters, Doppler flow meters, optical flow meters, open-channel flow meters, ultrasonic flow meters and electromagnetic flow meters. For example, a compact ultrasonic flow meter, such as the Parker CFM1 flow meter (Parker Hannifin; Cleveland, OH), may be used. In another example, the flow sensor is a microfluidic chip with a microsensor. This sensor enables measurement of liquid flow inside a cost-efficient planar glass substrate. The digital microsensor chip provides the full signal processing functionality for a fully calibrated, temperature compensated, and linearized digital output. In addition, this sensor provides real time detection of failures such as clogging, air bubbles or leaks. This can give data on catheter leakage, line clogging, or even a possible diagnostic for hernia in the patient.

Sensors for Solute Measurement

Figure 46:
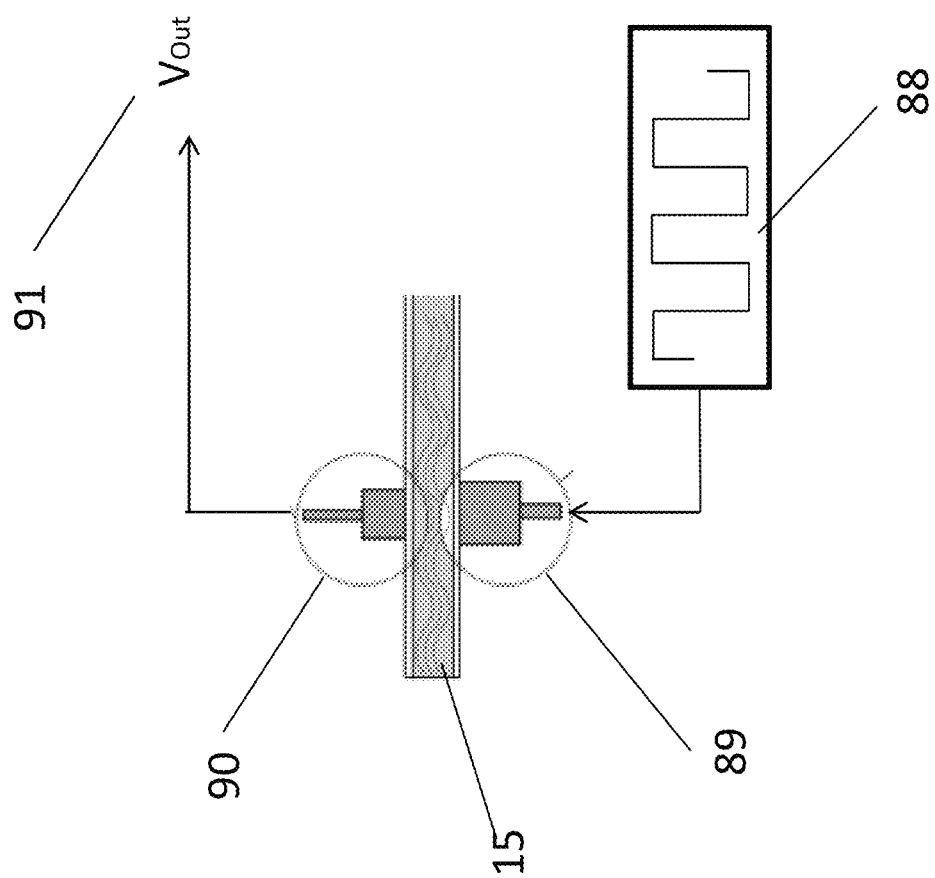
FIG. 46 illustrates a schematic circuit diagram of an exemplary variation of a conductivity sensor.

In the case of dialysis patients, analyte measurements of solutions indicate the efficacy of the dialysis treatment. For example, salt, urea, and creatinine are critical solutes diffused to the dialysate solution in peritoneal dialysis treatments. To monitor treatment efficacy, these analytes can be measured. In one method, salt content can be measured with an ionic conductivity sensor. FIG. 46 depicts one mechanism for conductivity measurement. A square wave voltage input (88) is generated by the microcontroller and transmitted to the transmitting electrode (89). The transmitted electrical current conducts across the dialysis conduit (15) through the fluid medium and conducts to the second electrode (90). In the system, both conductivity electrodes are immersed in a section of the dialysate fluid line, and maintained at a constant separation distance between electrodes to measure the conductivity of the dialysate solution. Additionally or alternately, a patient monitoring device may comprise a non-fluid contacting toroidal conductivity sensors. The amplitude of the received voltage (91) is measured by the microcontroller, and varies depending on the conductivity and presence of fluid in the fluid conduit. Because salt content in fluids affects conductivity, the dialysate salinity can be measured by the conductivity mechanism described. Both infusing and draining dialysate solution conductivity can be measured. Dextrose concentration is inversely related to ionic conductivity, and when analyzed together with salt concentrations as part of the overall fluid ionic conductivity measurement, ultrafiltration adequacy may be monitored. Values of drainage dialysate solution conductivity may be monitored alone or relative differences between infusing and drainage dialysate solution conductivity may be monitored. Conductivity measurement varies with temperature, and therefore, measurements are combined with temperature measurements, and standardized to a reference temperature, typically 25 degrees Celsius. Ionic conductivity measured values can be used alone, or in combination with fluid flow differential (via the flow sensors) to characterize both analyte and fluid extraction of the ultrafiltration process.

Urea is a colorless crystalline compound that is the main nitrogenous breakdown product of protein metabolism in mammals and is excreted in urine. Because kidneys help humans break down key toxins and nutrients in our body, patients with acute to chronic kidney failure require dialysis. The success or adequacy of dialysis treatment can be quantified by tracking urine clearance. Urea concentrations should decrease in the patient and rise in the dialysate solution. Common techniques of measuring small solute clearance include urea clearance normalized by the total body water. A urea sensor measures the concentration of urea in a fluid sample. Utilizing an electrochemical sensor, urea levels can be tracked at a relatively high specificity and resolution. A urea sensor is usually constructed by coupling one hydrophilic polymeric membrane containing immobilized urease to a commercial ammonia electrode which in turn consists of a pH glass electrode covered by internal electrolyte and a gas permeable hydrophobic membrane. Allowing this sensor to sense inlet dialysate solution for urea, in which there should not be, and comparing it to drained dialysate solution exiting the peritoneum, creates a strong metric to determine dialysis efficacy. To best utilize this sensor, high specificity would require a small reserve of dialysate solution to be slowed down by a reserve conduit for best sensor readings of urea concentration. In the system, the urea sensor measurement surface would be fluidically connected to both the infusing dialysate solution and drainage dialysate solution.

Another technique used in evaluating dialysis efficacy is peritoneal creatinine clearance (CCr). Creatinine clearance is used to estimate the overall small solute clearance during dialysis. Enzyme-catalyzed polymer transformation with electrochemical AC impedance detection is employed for the measurement of creatinine in serum samples. Similar to the design of a urea sensor, the urease is replaced with creatinine deiminase. The poly(methylvinyl ether)/maleic anhydride is screen-printed onto interdigitated screen-printed carbon electrodes and the electrodes overlaid with absorbent pads containing the relevant enzyme. Application of serum samples with creatinine, result in rapid polymer transformation, and resultant changes in the capacitance of the polymer-coated electrodes that are analyte-concentration dependent. As a result, a creatinine sensor is created. The same system can be used for urea or other serum detection. This sensor is dependent on a pH change, catalyzing the reaction, and thus can be used for a measure of as well for infection detection. In the system, the creatinine sensor measurement surface would be fluidically connected to both the infusing dialysate solution and drainage dialysate solution.

Dialysis efficacy can further be monitored via glucose concentration in the dialysate solution. The dextrose in dialysate solution is equivalent to the D-isomer, D-glucose. Common dialysate concentrations of dextrose include 1.5%, 2.5%, and 4.5% levels. During PD cycles, the permeability of the peritoneum allows for some dextrose diffusion into the patient. Therefore, measurement of glucose concentration can correlate to peritoneum permeability, which represent permeability of other solutes as well. In the system, the glucose sensor measurement surface would reside in a fluid conduit connected to both the infusing dialysate solution and drainage dialysate solution. The fluid conduit would also include a flow sensor. The combined flow rate data, fluid conduit cross-sectional area, and glucose concentration measurement would allow a calculation of glucose concentration/volume of dialysate. Because the concentration of dextrose and salts affect the fluid ionic conductivity, the combination of a glucose monitor with the ionic conductivity sensor can be used to calculate both the glucose and salt concentrations individually.

In addition to monitoring peritoneum permeability to solutes, glucose measurements can also help prevent hyper or hypoglycemia during dialysis treatment. During dialysis, a portion of the dextrose is also absorbed into the abdominal cavity tissue and high numbers of dialysis patients are also diabetic. Thus, monitoring the dextrose content reduction in the dialysate post-treatment would be desirable.

There are a multitude of glucose-monitoring technologies commonly used for diabetes management. Exemplary glucose measurement sensors that may be used include the Zimmer & Peacock ZIP Glucose sensor (Napa, CA). In another sensor type, the combination of micro-dialysis with infrared spectrometry provides a calibration-free assay for accurate continuous glucose monitoring, as reference spectra of dialysate components can be a-priori allocated. This sensor directly measures glucose concentrations by amperometric detection of hydrogen peroxide.

In another variation, the solute measurement sensor(s) can also be used to determine if the correct dialysate solution is being infused, as a method of monitoring patient compliance. The dialysate solutions typically differ in the concentration of dextrose. To monitor dialysate concentration, a glucose sensor could be used.

Docking System

Figure 47B:
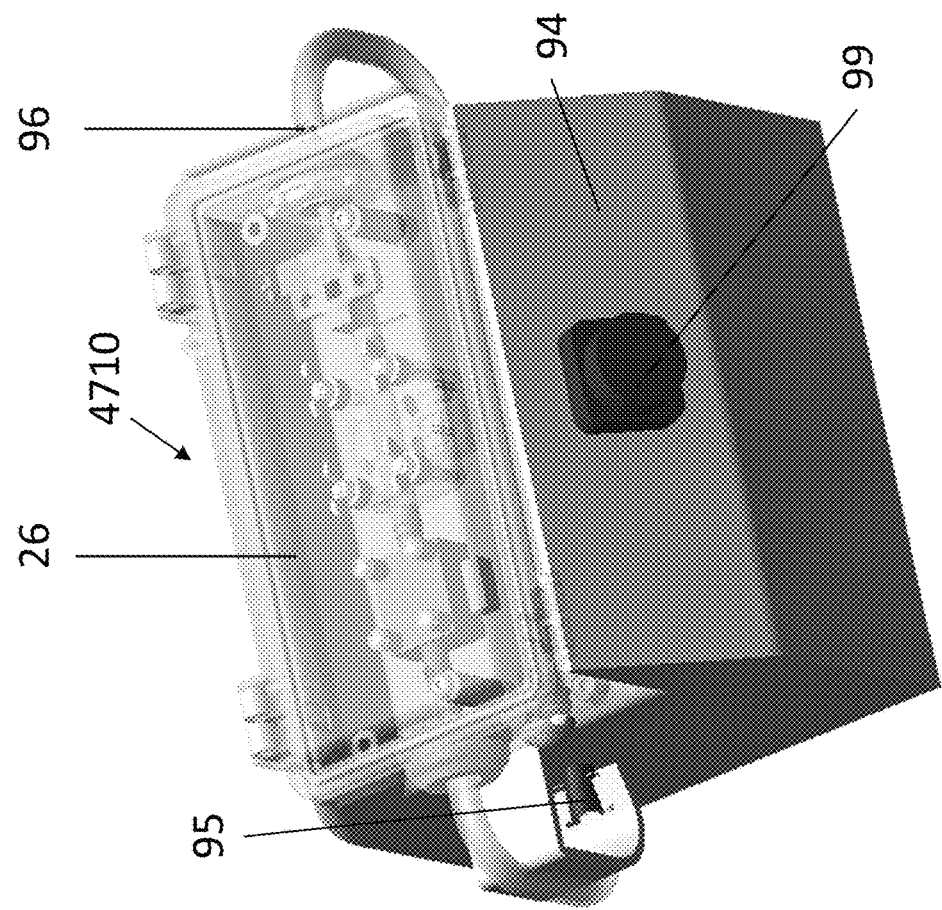
FIG. 47B illustrates a perspective view of an exemplary variation of a patient monitoring device coupled to the docking station.
Figure 47A:
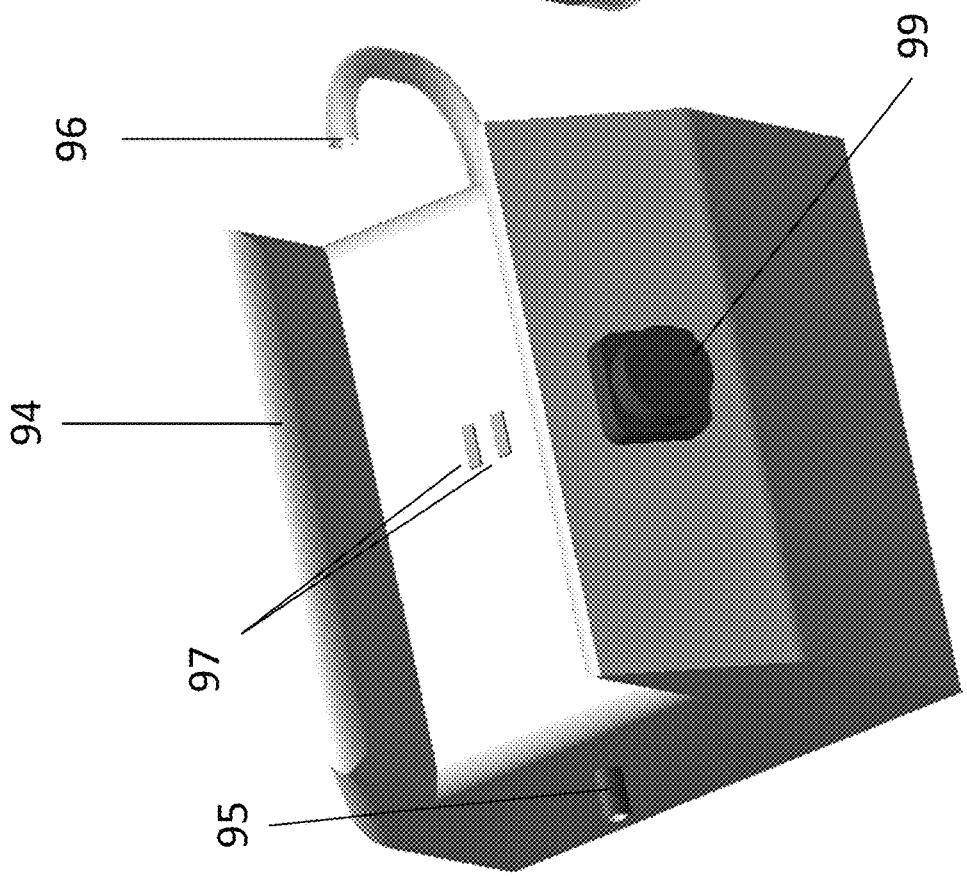
FIG. 47A illustrates a perspective view of an exemplary variation of a docking station.

In some variations, a docking system may be used in conjunction with the patient monitoring device. The docking system (e.g., dock station) may perform multiple functions including cleaning, calibrating, charging, data processing, and periodic data transmitting. The docking system itself may be plugged into an outlet power source (e.g., wall power outlet, power provided by a USB connection, etc.) and/or may have an internal battery that could be charged and used wirelessly. In some variations, the docking system may have a safety interlock feature, such that it is electronically functional only when connected to a valid power source (e.g., plugged into a working outlet power source, has a sufficiently charged battery, etc.). In one variation, the patient monitoring device is used in conjunction with a docking system to clean, charge, sterilize, and calibrate the device periodically. FIG. 47A depicts the dock station (94) and FIG. 47B depicts the dock station (94) assembled with a patient monitoring device (4710). The dock (94) may include, for example, two fluid port connectors (95, 96) that connect to the inlet and exit of the patient monitoring device's fluid conduit, respectively. Electrodes (97) on the dock (94) may be configured to mate with electrical connectors on the patient monitoring device (4710) for charging and/or data transmission. Cleaning and calibration fluid may fill a set of fluid chambers via a fluid port (99).

FIGS. 48A-48D illustrate another variation of a dock station (4800) comprising a set of fluid chambers (100, 101, 102) in fluid communication with a corresponding set of fill ports (103, 104, 105). In some variations, a fluid such as cleaning fluid may be stored in one or more of the fluid chambers (100, 101, 102). For example, a first cleaning fluid may be pumped from a first fluid chamber (101) and a second cleaning fluid may be pumped from a second fluid chamber (102) into the dock fluid conduit (98). Once a patient monitoring device is connected (such as shown in FIG. 47B), a first pump (106a) coupled to the first fluid chamber (100) may circulate the first fluid out of the first fluid chamber (100) and into the dock fluid conduit (98).

After circulating the first fluid through a patient monitoring device, a second pump (106b) coupled to the second fluid chamber (101) may circulate second fluid out of the second fluid chamber (101) and into the dock fluid conduit (98). Finally, a third pump (106c) coupled to the third fluid chamber (102) may circulate third fluid out of the third fluid chamber (102) and into the dock fluid conduit (98) after circulating the second fluid through a patient monitoring device.

In some variations, the circulating fluid may be pumped through the dock fluid conduit (98), the inlet port (95), the patient monitoring device, the outlet port (96) and into a separate compartment (e.g., waste chamber) (not shown) within the dock station to avoid mixing with the fresh fluid (e.g., cleaning fluid) stored in the fluid chambers. Additionally or alternatively, the circulating fluid may pass through a set of filters before returning to one or more of the fluid chambers (100, 101, 102). In some variations, the dock fluid conduit (98) may comprise one or more valves configured to divert circulating fluid between any of the fluid chambers and the waste chamber. In some variations, the fluid stored in the dock station may be a calibration fluid.

The calibration fluid may contain fluid of predetermined optical scatter/absorption, temperature, and conductivity characteristics. Furthermore, the calibration fluid may be pumped through a patient monitoring device at a predetermined flow rate. For example, an isotonic fluid, such as phosphate buffer solution may be warmed to about 37.0° C. in a calibration fluid chamber (102) and then pumped through a patient monitoring device at a constant 200 ml/min flow rate via the third pump (106c). A phosphate buffer solution is optically clear and has a known conductivity value of about 13,000 µS/cm. The patient monitoring device may calibrate its sensors based on the known characteristics of the calibration fluid. Thus, the patient monitoring device, in this example, may calibrate its set of optical scatter/absorption, temperature, conductivity, and flow rate sensors when docked to the dock station. In some variations, the calibration fluid, once pumped through the patient monitoring device, may be pumped back into a separate compartment (e.g., waste chamber) to avoid mixing with the fresh, unpumped calibration fluid. In another variation, the calibration fluid may be pumped through a filter and mixed with the rest of the calibration fluid in the calibration fluid chamber (102).

In some variations, the fluid for cleaning and calibration may recirculate in a closed loop system. In the docking system depicted in FIGS. 47A and 47B, inlet port (95) and outlet port (96) allow fluid to recirculate continuously for a predetermined amount of time. In some variations, fluid may be input and output from just one of the inlet port (95) and outlet port (96) in one or more cycles, thereby allowing a predetermined volume of fluid to wash a fluid conduit of a patient monitoring device in a back and forth manner for a predetermined amount of time. In some of these variations, the fluid may be recirculated fluid. In some variations, a cleaning cycle may include a predetermined soak time.

In some variations, a cleaning fluid may comprise chemicals configured to remove sources of fouling. For example, one or more of nitric acid and hydrochloric acid may be used as a cleaning fluid for protein removal. Additionally or alternatively, alkaline based cleaning solutions (e.g., Hellmanex® III, Mullheim Germany) may be used to effectively remove fats and proteins. Subsequent cleaning with alcohols (e.g., ethanol, isopropanol) or acetone may be used for removing oils and aqueous-based contaminants. Deionized water may also effectively remove aqueous-based contaminants. A valve may be configured to allow air to flush and dry the dock station when fluid circulation is completed.

In some variations, the docking system may further comprise a set of sensors configured to monitor fluid flow and confirm cleaning. For example, a set of optical sensors located in the fluid chambers (100, 101, 102) may measure an amount of fluid in the respective fluid chambers (100, 101, 102) and be used to indicate when the fluid needs to be replaced. A set of sensors of the dock station may also measure one or more of optical scatter/absorption, temperature, conductivity, and/or flow rate of fluid driven by a pump (106a, 106b, 106c).

For device calibration, a single program can perform a calibration of all of the sensors in the device or unique programs can be used for calibration of individual or sets of sensors. The calibration may be performed upon user selection, or remote selection by the healthcare provider or device manufacturer. The calibration can also be automatically performed every time the device is docked, based on a set frequency, or when performance tests dictate the need to calibrate. During the calibration, the device may be mechanically locked into the dock until the calibration process is complete. Calibration results may be sent to the healthcare provider or the device manufacturer for quality control and monitoring of device performance.

The interfaces between the device and dock may vary and can include a magnetic hold, using locks (e.g., axis lock, frame lock, liner lock, lock back, Luer lock), plugs, screw or nut holding the device into the dock. The release feature can involve pushing on a fixture on the device such as a button or the locking mechanism but may alternatively involve many other physical or electronic variations.

Cleaning the fluid channel can increase the longevity of the components by reducing or eliminating the presence of biofilms and other fouling mechanisms. Also, cleaning can be used to remove the residual fluid from samples that have been collected. The properties of the materials of the fluid-channel can dictate the cleaning mechanism of the dock. For example, materials with high hardness and solvent resistance such as quartz, borosilicate, or sapphire glass, can be used for abrasive and/or solvent cleaning. Other materials with high lubricity and solvent resistance, such as fluoropolymers (FEP, PTFE), can be used for cleaning via flushing with solvents and/or with mild abrasion. Alternatively, or in conjunction with other cleaning agents, a UV light could be used to sterilize the fluid channel of the device.

In some variations, a dock station may couple to a patient monitoring device without docking into the dock station. For example, an inlet port of the dock station may be flexibly extended to connect to a patient monitoring device without removing or detaching the patient monitoring device from its own connections (e.g., hooked onto a toilet seat). FIG. 48B illustrates the docking station (94) comprising a flexible tube (108) configured to transmit fluid and electrical current. FIG. 48C illustrates a detailed perspective view of an end of the flexible tube (108). The end of the flexible tube (108) may comprise a set of electrical connectors (109a, 109b) (e.g., electrical contact points) and a fluid lumen (110). FIG. 48C illustrates a detailed side view of a tubing set connector (407) of a patient monitoring device. The tubing set connector (407) may include a corresponding set of electrical connectors (408a, 408b). FIG. 48D illustrates a perspective view of the flexible tube (108) coupled with the tubing set connector (407) such that the electrical connectors are in contact and a fluidic seal is achieved. The set of electrical connectors may include additional electronic contact points. In some variations, the electrical connectors may be configured for charging and/or communication between the dock station and patient monitoring device. In the variation depicted in FIG. 48B, fluid pumped out of the docking system into the patient monitoring device may exit the patient monitoring device and into a drainage vessel such as a toilet. When the fluid cleaning step is complete, a valve in the docking station may be used to allow air to flush and dry the system.

To charge the patient monitoring device, the patient monitoring device can be placed on the dock, and the exposed electrodes on the dock mate with exposed connectors (45) on the patient monitoring device. Alternately, wireless charging may be used. Charging cycles, including a quick charge or full charge, may be implemented. In some variations, the docking station may comprise a battery charging port configured to charge a battery of the patient monitoring device. For example, a removable battery of the patient monitoring device may be docked to a battery charging port to charge the battery while another battery is used in the patient monitoring device.

The docking station may also transmit data from the patient monitoring device. The data transmission can be the singular method of data transmission for the system, or a redundant method of data transmission with the data transmission from the patient monitoring device in the case that communication failure occurs on one or the other systems. Thus, data transmission to the database can be performed by the sensor device and/or the dock. The sensor device may transmit the data via a wireless cellular LTE module, for example, but connectivity may be limited at times. Alternately, the dock may transmit the data from a wired Ethernet connection, or wireless through a modem, which can be used when the LTE signal is limited for the patient monitoring device.

The docking sensor may also store sensor data for each patient continuously. The data can be stored in addition to, or in lieu of data storage in the cloud. The data can be stored locally on an SD card or other memory device, for instance, and patients can transport the SD card to the provider during frequent visits to monitor the data. In some variations, the docking system may authenticate the patient monitoring device coupled thereto prior to performing one or more functions such as cleaning, calibration, data transfer, and the like.

Sample Collection

Figure 54B:
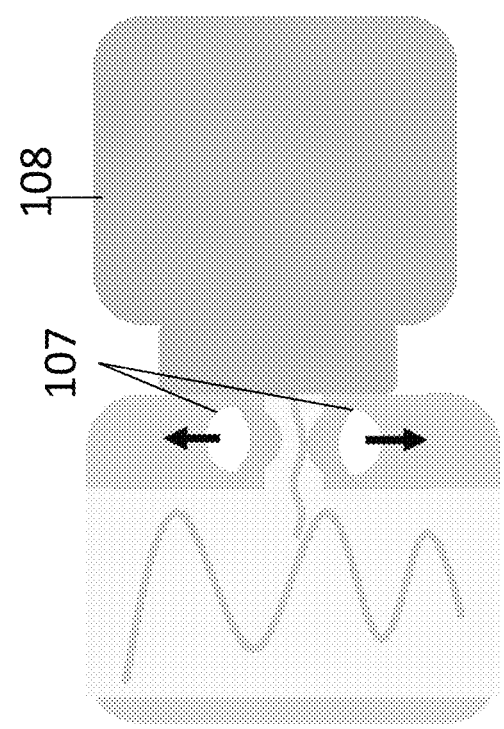
FIGS. 54A and 54B illustrate schematic cross-sectional views of an exemplary variation of a sample container coupled to a fluid conduit.
Figure 54A:
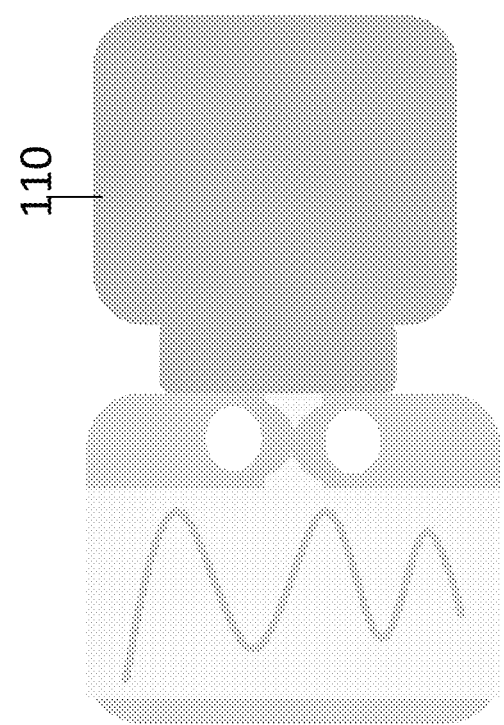

Additional actions may also be prompted by the system when certain threshold action limits are detected. In one example, there may be a sterile collection container loaded at all times in the device for fluid sample collection that can be sent to a laboratory for analysis. Upon detecting a potential complication, a sample of the fluid of the patient may be collected in the container. An example of the mechanism to collect the sample is having a sterile needle fluidically connected to the sample container poke through tubing in which the fluid is flowing to collect the sample. The needle may also be oriented the opposite way, such that the needle pokes through the lid of the collection container, permitting fluid to be collected while keeping a lid on the collection container. Alternatively, a pressure-based valve may apply positive or negative pressure to a fluid channel connected to the main tubing line and the collection container to open up the channel until enough sample fluid has been collected. In one variation, shown in FIG. 54, the channel to the sample collection container (110) remains closed due to the two walls of the channel being in contact with one another and preventing flow into the collection container. The walls can be made of a malleable material such as silicone that can have a negative pressure (e.g., suction) applied to it in vacuoles (107) beside the channel, which open up the channel for fluid (108) collection until the pressure stops being applied. As a last example, there may be a valve controlled manually or automatically that can divert flow to the sample collection container.

Figure 55C:
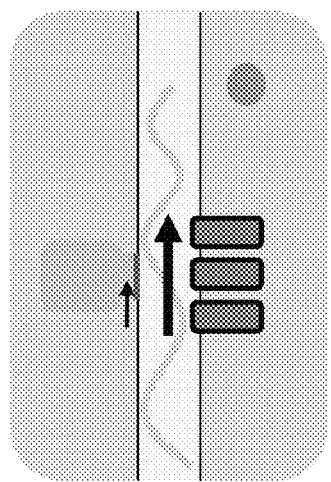
FIGS. 55A, 55B, and 55C illustrate schematic cross-sectional views of another exemplary variation of a sample container coupled to a fluid conduit.
Figure 55B:
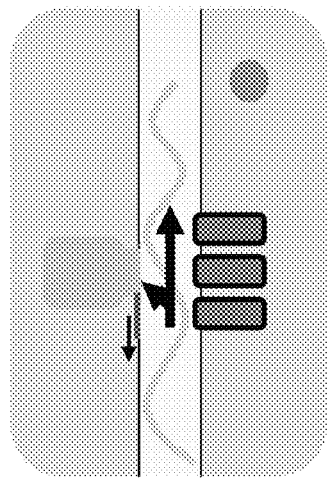
Figure 55A:
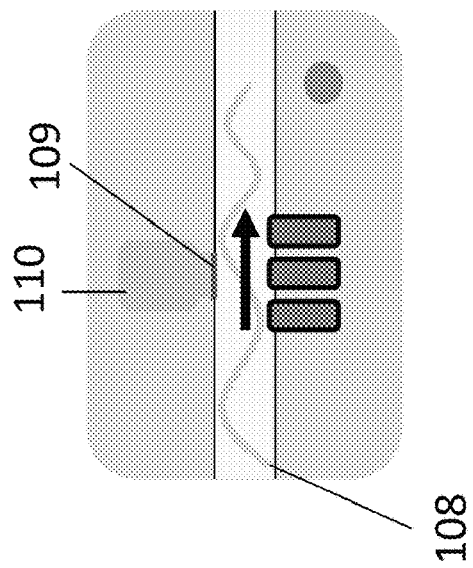

FIG. 55 illustrates one method of fluid sample collection. When the fluid (108) is detected by the sensors to have a complication and require a sample collection, a valve (109) in the fluid channel can open from a closed state, as in 55*a*, to an open state, as in 55*b*, that allows the fluid to flow into the sample collection container (110). When a sufficient amount of sample is collected, shown in 55*c*, the valve closes. When automatically collecting fluid, the system can determine when the sample collection container is full via weighing the container or using an optical device to determine when liquid has reached a threshold level in the container.

The container may be always sealed, as in the case when a needle perforates the lid of the container to collect the sample. Otherwise, the container may be sealed through methods including, but not limited to, a screw cap that is automatically screwed on after sample collection, a cap that snaps into a locking position, or a press fit of a cap onto the container. The container can additionally be sealed with a tamper-evident seal to ensure fidelity of the sample prior to further testing and labeled with a patient or sample identifier and timestamp. The container may also be labeled with a shipping label and ejected from the device or removed by the patient.

Therapeutic Agent

Figure 57C:
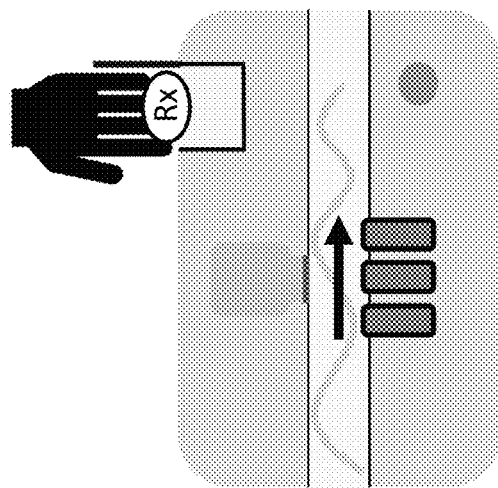
FIGS. 57A, 57B, 57C, 58A, 58B, and 58C illustrate exemplary methods for storing and accessing a therapeutic agent.
Figure 57B:
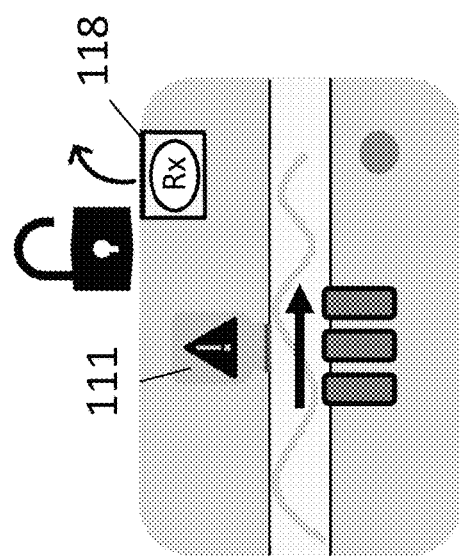
Figure 57A:
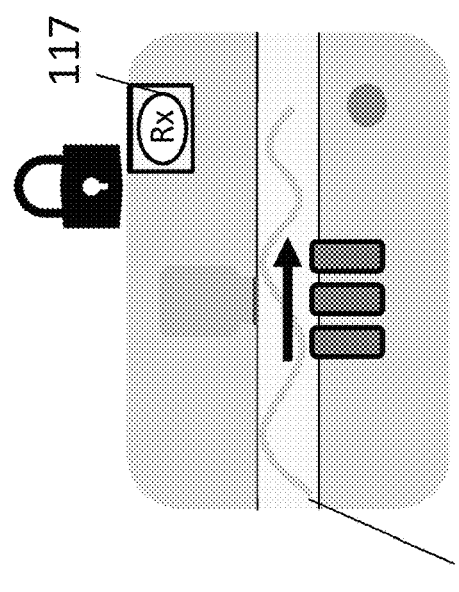

In another example, the device stores and administers therapeutic agents. When an action limit is detected for a potential complication such as infection or catheter blockage, the device infuses the appropriate therapeutic agent such as an antibiotic to treat the infection or a thrombolytic to resolve the catheter blockage. FIGS. 57A-57C illustrates an example setup of a therapeutic agent that is stored inside the device. Initially, shown in FIG. 57A, the therapeutic agent (117) is locked in the device. When the sensors indicate a complication requiring the therapeutic agent, a fluid sample is collected in a container for the laboratory test, and a notification (111) is made when the collection is finished, unlocking the compartment (118) holding the therapeutic agent, as shown in FIG. 57B. Next, FIG. 57C shows the patient being able to access the agent for immediate use upon detection of the corresponding complication.

Patient Infection Detection Methods

In one variation of the devices described above, the system may be used to monitor patient infection from drainage fluid exiting the catheter during each drainage cycle of therapy. The patient first assembles the disposable and reusable halves of the patient monitoring device, flushes the fluid conduit in the patient monitoring device with sterile saline solution, connects the patient monitoring device connector to the catheter, and applies the adhesive to the skin. The patient initiates the patient monitoring device by powering on the patient monitoring device, then powers on a tablet device, opens the user-interface application on the tablet device, verifies LTE connectivity, logs into the user-interface application on the tablet device to establish communication with the database server system, and establishes Bluetooth connection between the user-interface application on the tablet device and the patient monitoring device by inputting a unique identification code for the patient monitoring device into the user interface. The database server system authenticates the patient login credentials, and the patient monitoring device identification code, and sends authentication confirmation to the user interface system along with an encryption key for use in the communication requests. When powered on, the patient monitoring device microprocessor initializes the operating system and firmware, and cycles through readings of each of the sensors—the inline fluid thermistor, optical scatter/absorption sensor, flow sensor, pressure sensor, and pH sensor, skin surface color sensor, and PCB-mounted accelerometer/gyroscope position sensor. The patient monitoring device confirms sensor output signals and transmits confirmation of sensor operation through the user interface system to the database server. Once the system is initialized, the system enters a calibration mode and notifies the user calibration mode is starting via the user interface system.

During the calibration mode operation of the drainage infection detection system, the system first determines baseline readings for the flow sensor, pressure sensor, and skin surface color sensors. The patient monitoring device records readings from each of these sensors over a 30 second static duration at a 5-100 Hz sampling rate that is encrypted, temporarily stored on the patient monitoring device memory chip, and then transmitted through the user interface system to the database server system. Once the data is received, the database server system decrypts the data, sends communication for successful data transmission, averages the data from each sensor, and uses the average to establish a baseline voltage value associated for each sensor. In the next step of the calibration mode, the user interface system instructs the patient to cough, stand up, lay down, walk, sit down, and repeat the cycle. The accelerometer and gyroscope on the patient monitoring device, during this time, record data at a 20 Hz sampling rate that is encrypted, temporarily stored on the patient monitoring device memory chip, and then transmitted through the user interface system to the database server system. Once the data is received, the database server system decrypts the data, sends communication for successful data transmission, and performs correlation analysis between the accelerometer and gyroscope sensor data to each of the patient position states. Next, the user interface system instructs the patient to infuse 20 ml of sterile saline solution or other volume of fluid. The optical scatter/absorption sensor and pH sensor of the patient monitoring device record data at a 10 Hz or other sampling rate during this time that is encrypted, temporarily stored on the patient monitoring device memory chip, and then transmitted through the user interface system to the database server system. Once the data is received, the database server system decrypts the data, sends communication for successful data transmission, averages the optical scatter/absorption and pH sensor data, and uses the average to establish a baseline values associated with the reference solution. The user interface then indicates to the patient that the system setup is complete, and the system begins monitoring the patient. After initialization, the system maintains continuous Bluetooth connectivity between the patient monitoring device and tablet device user interface system. Text messages are sent to the patient mobile device, and push notifications are sent to the tablet device when the patient monitoring device battery or tablet device requires charging. Text messages may also be sent to the patient mobile device, and push notifications are sent to the tablet device during maintenance cycles, when the adhesive and disposable sections of the patient monitoring device are replaced on a bi-monthly cycle. On an annual cycle, the reusable sensor monitor may also be replaced, at which time, the full user initialization and calibration cycles are repeated. Similarly, if the patient monitoring device battery and backup battery are ever fully depleted, after the system is fully recharged again, the full initialization and calibration cycles are repeated.

During use of the monitoring system, users may utilize the dock station for charging, cleaning, sterilization, and calibration. At predetermined intervals, such as daily after completion of their peritoneal dialysis night cycling, a user (e.g., patient) may connect the patient monitoring device to the docking station. In some variations, the dock station may be placed in a fixed location, plugged into an electrical outlet and/or operate on battery power. A user may place the patient monitoring device into a cradle of the dock station, as shown in FIG. 47B. In some variations, the user may connect the two ends of the fluid conduit of the patient monitoring device to the corresponding input and output ports on the docking station. Once cradled, the dock station may detect electrical contact with the patient monitoring device and begin charging the patient monitoring device and cleaning of the fluid conduit using fluid stored within the dock station. In some variations, once a cleaning fluid is pumped through the patient monitoring device, the patient monitoring device may be recalibrated by the dock station. For example, calibration fluid may be pumped through the patient monitoring device.

The patient monitoring device may also communicate data to the dock station through, for example, the electrical contacts. In some variations, the docking system may be connected to an in-home wireless network to transfer data that the patient monitoring device is unable to transmit because of, for example, poor LTE wireless communication connectivity. A set of indicator lights disposed on an exterior surface of the docking system and/or device may indicate when the charging, cleaning, sterilization, calibration, and data cycles are complete.

During the monitoring operation of the drainage infection detection system, when there is no drainage of fluid through the fluid conduit, the flow sensor samples at a 1 Hz frequency on a continuous duty cycle, the gyroscope and accelerometer sample at a 5 Hz frequency on a continuous duty cycle, the pressure sensor samples at a 20 Hz frequency for a 30 second period once every four hours, the skin surface color sensor samples at a 5 Hz frequency for a 10 second period once every four hours, and the microprocessor operates in a lower-power mode, while no other sensors measure any data. During this low-power operation period, the data is temporarily stored on the patient monitoring device memory chip and not transmitted. The data is transmitted in full when the system enters active measurement mode.

During the monitoring operation of the drainage infection detection system, when the drainage of fluid begins, the flow sensors detect fluid flow and the microprocessor activates the system into active measurement mode. The microcontroller controls all sensors to record measurements during the active measurement mode, with varying duty cycles. The flow sensors measure the fluid flow at a continuous duty cycle and increases to a 10 Hz sampling rate. The thermistor measures the fluid temperature at a 5 Hz frequency for a 10 second period at the beginning of the drainage and for 2 seconds at the end of the drainage, when the fluid flow rate drops to zero. The optical scatter/absorption sensor measures the fluid optical scatter/absorption at a 5 Hz frequency for 30 seconds at the beginning of the drainage and for 10 seconds at the end of the drainage when the fluid flow rate drops to zero. The pH sensor measures the fluid pH level at a 5 Hz frequency for 5 seconds at the beginning of the drainage and for 30 seconds at the end of the drainage when the fluid flow rate drops to zero. During active measurement mode, at a frequency of once every 5 minutes, and also at the conclusion of the drainage cycle when fluid flow rate drops to zero, the data is encrypted, temporarily stored on the patient monitoring device memory chip, and then transmitted through the user interface system to the database server system. Once the data is received, the database server system decrypts the data, processes the data, stores the data, and sends communication for successful data transmission, and then the patient monitoring device deletes the sent data from the patient monitoring device memory chip.

In variations where test strips are used with the systems and devices described herein, actions may occur that are patient-initiated, automated, or a combination of the two. For example, the test strips may be positioned in a default inactive position (e.g., recessed in the test strip cartridge). However, upon drainage of the fluid of the patient, the patient may set the test strips into an active position in the fluid channel (e.g., by pushing a button to advance the test strips from their recessed, inactive state into their active state inside of the fluid conduit) to commence the measurement. In some of these variations, when test strips are used in conjunction with other sensors, one or more sensors (e.g., pressure sensor) may monitor one or more characteristics of the fluid in the fluid channel. Upon recognition of fluid in the channel, the test strips may be advanced automatically from an inactive position (e.g., recessed in the test strip cartridge) to an active position to measure the characteristics of the fluid. Upon the recognition of fluid, a notification may be sent to a mobile device of the patient that may ask the patient to confirm that fluid is flowing through the device before pushing the test strip into the fluid conduit, thus limiting the potential for false measurements such as when fluid has not reached a steady state or state desired for measurement.

During the monitoring operation of the drainage infection detection system the patient receives push notifications from the user interface system for additional data input. At the end of each day, the user interface requests the patient to input their overall feeling of wellness rated 1-5 (5=very well, 4=well, 3=average, 2=unwell, 1=very poor), and pain level around the catheter exit site rated 0-3 (0=no pain, 2=slight pain, 3=moderate pain, 4=severe pain). Once the data is input, the data is transmitted to the database server system, which processes the data to monitor patient infection by calculating the average patient ratings over time and identifying deviations to patient average values, or when any single rating for wellness is 1, or when any single rating for pain is 3 or 4.

During the monitoring operation of the drainage infection detection system, the pressure data is processed via the database server processor to monitor patient vital information (e.g., respiratory rate, heart rate). The accelerometer/gyroscope position sensor data are processed via the database server processor to monitor patient activity, to determine metrics for total steps the patient has taken on a daily basis, and total number of minutes per day the patient is lying down. The skin surface color sensor data, which is positioned next to the catheter exit site, is processed via the database server processor to monitor rash onset by the skin redness level differential from the baseline measurements. The fluid flow sensor data is processed via the database server processor to monitor patient fluid drain volumes on a daily or per cycle basis, by integrating the flow velocity vs. time plot and multiplying by the fluid conduit cross-sectional area in the fluid flow sensor section. The temperature sensor data is processed via the database server processor to monitor patient fever onset by calculating the temperature differential from the moving average values. The fluid optical scatter/absorption sensor data is processed via the database server processor to monitor infection onset by calculating the optical scatter/absorption differential from the baseline measurements. The fluid pH sensor data is processed via the database server processor to monitor infection onset by calculating the pH differential from the baseline measurements.

During the monitoring operation of the drainage infection detection system the provider inputs patient data into the user interface system. The provider inputs laboratory results from patient blood tests, urine tests, and vital system measurements taken during clinic visits. The provider additionally inputs observations notes from clinic visits, enters yes in a check-box when an infection is diagnosed along with pathogen name and date of diagnosis, and yes in a check-box for other complications along with complication name, and date of diagnosis. Once the data is input, the data is transmitted to the database server system. The laboratory test, vital test data, and observation notes are parsed and stored. When infection data or complication data is registered as a "yes", database server system performs regression analysis on all patient data 4 weeks prior to the date of diagnosis, and 1 week after diagnosis. The database server system additionally aggregates all patients' infection occurrence and 4 week patient data prior to the date of diagnosis, and 1 week after diagnosis. The system performs regression analysis on the aggregate data as a whole, and also individually for each specific infection pathogen. The database server system additionally aggregates all patients' complication occurrence and 4 week patient data prior to the date of diagnosis, and 1 week after diagnosis. The system performs regression analysis on the aggregate data as a whole, and also individually for each specific complication. The analysis determines if there are statistically significant correlations between the monitored data and complications or infections, and the database server system utilizes these results to update the algorithms for infection and complication detection.

During the monitoring operation of the drainage infection detection system, the processed data is presented on the user interface system for the patient and the provider. The user logs into the user interface system via login credentials or biometric input, which is communicated to the database server system. The database server system authenticates the patient login credentials or biometric input and sends authentication confirmation to the user interface system along with an encryption key for use in the communication requests. A graphical user interface presents the processed data in the form of graphs of data over time, highlighted data points deviating from average historical values (i.e. greater than two standard deviations from the average), highlighted data points deviating from accepted physiological norms (i.e. in the case of temperatures exceeding 99° F.), or the system diagnosis of infections or complications. For the provider, a summary view is provided of multiple patients, with specific patients highlighted only when those patients have data deviating from average historical values, data points deviating from accepted physiological norms, or the system diagnosis of infections or complications.

During the monitoring operation of the drainage infection detection system, the database server system generates infection alerts directly, or through third party services, to the patient and provider in the form of text messages, push notifications, and/or automated phone calls. The database server system determines alert levels based on several factors. For patient feeling of wellness and catheter exit site pain, the database system calculates a moving average and standard deviation and generates an alert when any single wellness rating drops two standard deviations from the average value, any single catheter exit site pain rating exceeds two standard deviation from the average value, or when any single rating for wellness is 1, or when any single rating for pain is 4. For temperature readings, the database system calculates a moving average and standard deviation, and generates alerts based on any temperature readings exceeding the average by one standard deviation. For patient activity level, the database system calculates a moving average and standard deviation, and generates alerts based on step counts or upright position time dropping below 2 standard deviations from the average for 2 days in a row. The patient activity level and pressure-sensor based patient vital data are also used to calculate a daily patient wellness score based on a scale of 1 or 2. When any patient activity level or pressure-sensor based patient vital data drop beyond one standard deviation of the patient average, a wellness score of 1 is assigned to the patient. Otherwise, the patient is given a score of 2. For fluid optical scatter/absorption, pH, and skin surface color redness differential values, the database server system calculates a moving average and standard deviation. When the patient wellness score is 1, alerts are generated when any fluid optical scatter/absorption values exceed one standard deviation of the average, or any pH values drop below one standard deviation of the average, or any skin surface color redness differential values, exceed one standard deviation of the average. When the patient wellness score is 2, alerts are generated when any fluid optical scatter/absorption values exceed two standard deviations of the average, or any pH values drop below two standard deviations of the average, or any skin surface color redness differential values, exceed two standard deviations of the average. The system additionally generates alerts based on diagnoses detected by the system through the algorithms based on outcome regression analysis.

In another variation, the system monitors infection in catheter systems in which fluid is only infused. In this case, the system monitors the patient with a skin-surface mounted thermistor, the skin surface color sensor, and the PCB-mounted accelerometer/gyroscope position sensor.

In another variation where a device is used to monitor peritoneal dialysis, the system monitors infection in peritoneal dialysis patients, where dialysate fluid is both infused and drained from the patient. In this case, the system comprises of the same sensors previously described for drainage catheters such as the inline fluid thermistor, optical scatter/absorption sensor, flow sensor, pressure sensor, and pH sensor, skin surface color sensor, and PCB-mounted accelerometer/gyroscope position sensor. However, instead of calibrating the optical scatter/absorption sensor and pH sensor, the system measures the optical scatter/absorption and pH of the fresh dialysate fluid during infusion cycles, in addition to the measurements taken on the waste dialysate solution in the drainage cycles. By measuring both the optical scatter/absorption and pH of both the fresh dialysate and waste dialysate, an optical scatter/absorption differential and pH differential can be calculated for every cycle. Use of differentials is desirable in conditions where sensor values drift over time due to performance degradation of the sensor mechanism or optical quality of the interface between the sensor and fluid medium. In addition, the system can use flow volume measurements to monitor patient compliance to prescribed therapy and monitor volume differentials calculated as a ratio of drained fluid flow volume divided by infused fluid flow volume for each cycle, which can be used to assess the efficacy of the dialysis.

Sensor Calibration Methods

Multiple sensor types require calibration. Optical-based sensors in particular, are sensitive to changes in optical quality of materials between the sensor and the test medium, including the optical sensor enclosure. Thus, it is important to have means to frequently calibrate the sensors for optimal accuracy. In the depicted variation from FIG. 13 in which fresh infused solution and drainage solution pass through the same fluid flow conduit and sensor network, there is an opportunity for the sensors to calibrate with each cycle of the fresh infused solution, assuming the fresh infused solution is optically constant.

Figure 49:
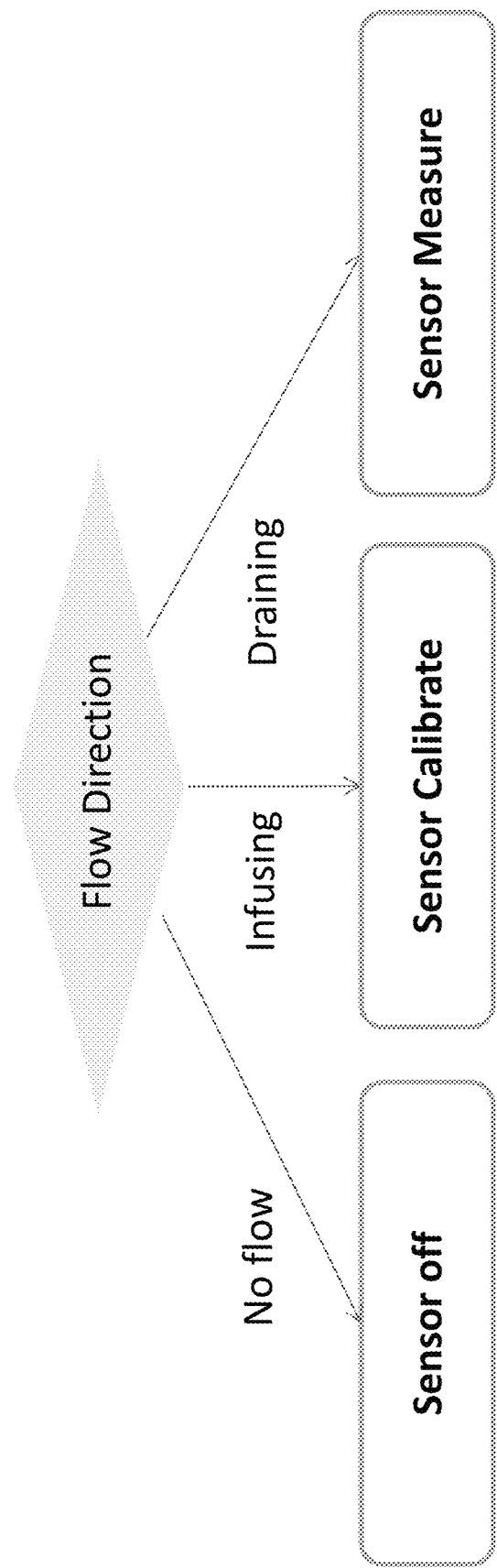
FIG. 49 illustrates an exemplary calibration process using flow monitoring.

FIG. 49 depicts a process for calibration of an optical sensor. The flow sensor first provides the reading on flow direction to the microprocessor, indicating whether fresh solution or drainage solution is passing through the sensor network. When fresh solution is infusing, the microprocessor enters calibration mode in which the sensor output is reset to a constant, known value of the infused solution. When the waste dialysate solution is draining, the microprocessor enters sensor measurement mode, and records the output reading. A similar process can be utilized for calibration of the pH sensor when the pH value of the fresh infused solution is known.

In some variations, calibration of an optical sensor may be performed at one or more predetermined intervals such as replacement of a fluid conduit, engagement of a fluid conduit with a durable component, upon device startup, detection of a clinical event, and the like. For example, the fluid conduit (6830) may be disposable and replaced frequently. Generally, disposable components may have variable tolerances dimensionally as well as variance in the material, surface cleanliness, and other manufacturing variances. Thus, re-calibration of a fluid conduit (6830) at one or more predetermined intervals may improve accuracy of optical sensor measurements. In some variations, a switch may be actuated when the fluid conduit (6830) is engaged to the housing (6802) to signal recalibration due to, for example, replacement of the fluid conduit (6830). Additionally or alternatively, the fluid conduit (6830) may comprise an identifier such as an RFID tag or unique ID chip used to identify the fluid conduit (6830) as a replacement disposable component. In some variations, after a new fluid conduit (6830) has been verified and/or authenticated, the patient monitoring device may perform one or more optical measurements to establish a baseline for optical sensor calibration.

In some variations, calibration may be performed for a patient monitoring device connected only to the fluid drainage conduit. The device, during maintenance periods (i.e. docking in a station for recharging, cleaning, and calibration), can have a calibration fluid having a predetermined (e.g., known) set of parameters passed through in which optical sensors, and/or pH sensors, and/or conductivity sensors may be calibrated.

In other variations, calibration may also be performed with active patient participation via the patient user interface. In one example, the accelerometer and gyroscope are calibrated once the hardware sensor system is attached to the patient. The user interface system of the application on the patient tablet device can then prompt the patient to lie down, sit up, and stand up. As the patient repositions to each state, the sensors calibrate accordingly.

Multiple sensor data can also be used concurrently in order to accurately determine monitoring metrics. For example, pH and conductivity measurements can be affected by temperature. By using a calibration function indicating the relationship of conductivity value and pH to temperature, the temperature input data can be used to convert the conductivity sensor and pH sensor values to an accurate output of the fluid conductivity and pH.

Sensor Measurement Methods

Sensors may measure in either absolute or relative terms. In the example of the temperature sensors, pressure sensors, and flow sensors, an absolute measurement may be desirable in order to accurately determine the patient temperature and flow volume infusing or draining out. Alternately, in the case the system is measuring the drainage fluid optical scatter/absorption, conductivity, or pH, values relative to the fresh infusing fluid may be sufficient.

The accuracy of sensors when measuring in absolute terms can be limited and design of such sensors can result in overly complex, large, and costly systems. Thus, it is desirable to have sensors that can measure in relative terms. In the described variation (depicted in FIG. 50) in which fresh solution and waste solution pass through the same conduit and sensor network, relative differences between the sensor values may be used. An optical scatter/absorption sensor, in one example utilizing infrared emitters that detect the light scattering by the detector, can compare light scattering from the fresh dialysate solution TUi to the waste dialysate solution TUw in order to determine an optical scatter/absorption ratio=TUw/TUi. The TUw/TUi values can then be monitored over time to establish baseline values and determine deviations to the baseline that may be indicative of patient infection.

In another example, the conductivity of the dialysate solution can be measured by a pair of spaced electrodes, passing a constant current between the electrodes and measuring an output voltage. The difference between the voltage of the fresh dialysate solution Vi and the waste dialysate solution Vw can be measured as Vw−Vi and monitored over time to establish baseline values and determine deviations to the baseline that may be indicative of patient infection.

Integrated Sensor Network

The sensors may individually accumulate data for the monitoring purposes indicated, and the sensors may also work in combination with other sensors. In the example depicted in FIG. 50, the firmware algorithms on the microcontroller determine the directional information provided from the flow sensor, which works in combination with any of the other sensors to provide contextual information about whether the test fluid is incoming fresh solution or drainage solution. Additionally, the flow rate information from the flow sensor may be used in combination with cell counter sensors to normalize the cell count data.

In another example, sensors can work together to limit power consumption. For example, the flow sensor can work in continuous operation to determine if there is any flow infusing into or out of the system. When flow has stopped, the process can keep some or all other sensors in off mode or powered down or a reduced power state. When flow initiates, sensors may be turned on, depending on the flow state.

Figure 50:
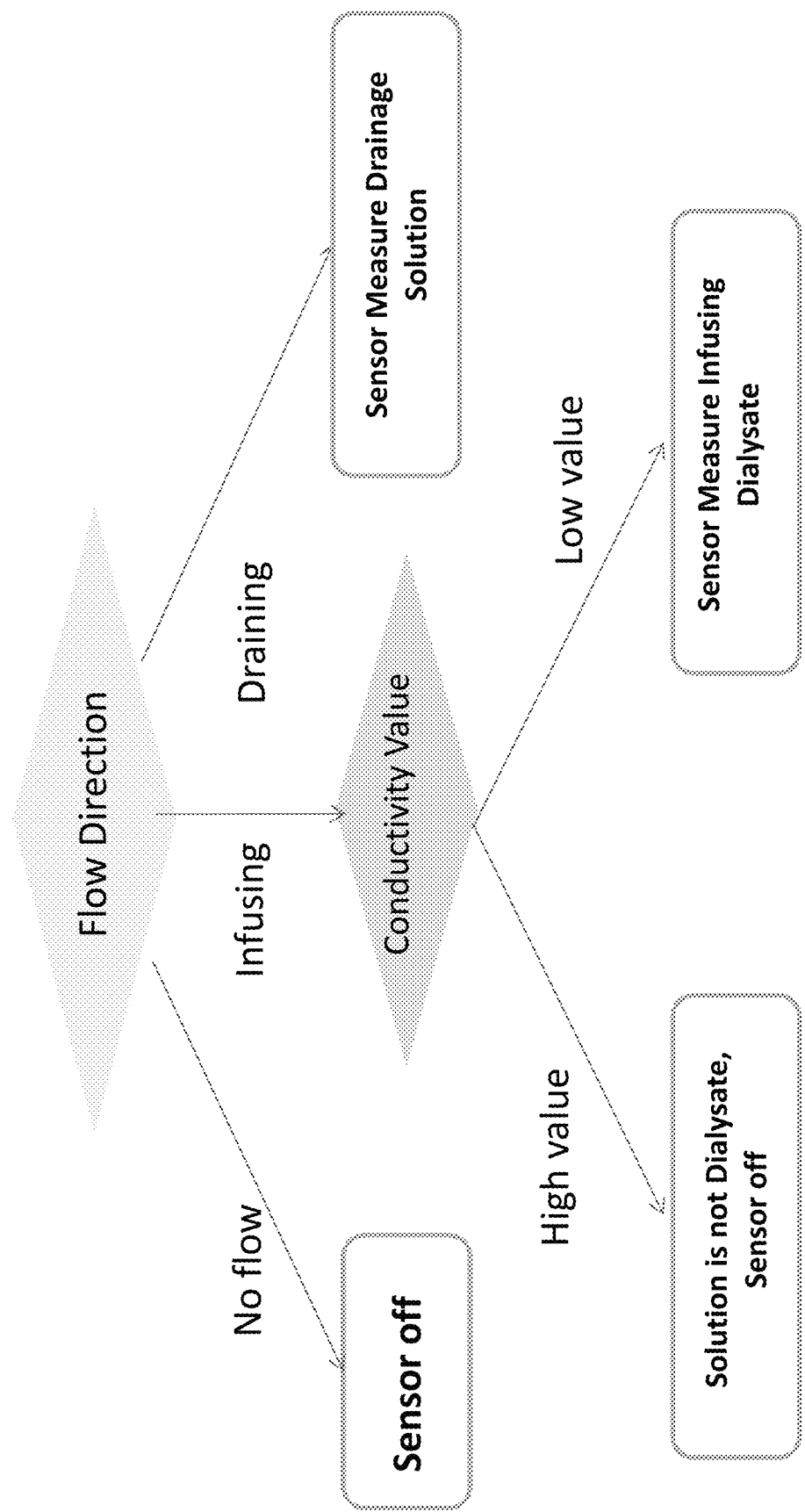
FIG. 50 illustrates an exemplary method for determining alternate solution flow states.

In another example, sensors can work in conjunction to determine alternate states. One procedure for catheter management includes flushing a small volume of heparin or other thrombolytic solution through the catheter in-between infusion cycles to avoid clogging of the catheter. Heparin injection through the sensor network can be interpreted as infused dialysis solution in absence of steps to detect such state. FIG. 50 depicts an exemplary process that utilizes of the flow sensor and conductivity sensor to detect this state.

Heparin has a high conductivity value that is typically higher than the fresh infusing solution. When the flow sensor detects that fluid is infusing, conductivity can then be measured. If conductivity values are higher than the infused therapeutic solution, a step of detecting an alternate solution being infused may be performed, and the flow volume measured may be excluded or flagged for exclusion from flow metrics. When the conductivity values match the infused therapeutic solution, the microprocessor may begin recording the flow volumes.

Different sensors may also have some redundancy and correlations. Urea content, for instance, which can be measured as part of ultrafiltration efficacy, is correlated to pH, which can be measured as part of infection complication detection. Due to the potential use of pH sensors to monitor infection, it is therefore important for the system to include redundant sensing mechanisms for ultrafiltration efficacy and infection detection, and steps to identify interactions. For example, in the case that the patient ultrafiltration efficacy changes, the urea sensor would include higher content of urea detected. The pH sensor, during this time, would show a decrease in pH levels, even if the patient does not have an infection. During this period, then, the firmware algorithm could exclude the pH data for infection monitoring. In another example, flow rate and pressure will have a high correlation in the case of a blocked catheter.

Sensor hardware may also be used for multiple purposes. For example, leads used for thermocouple temperature measurement may also be used in combination with a separate lead for conductivity or impedance measurements. When the system is measuring temperature, current only passes between the thermocouple leads. When the system is measuring conductivity, current passes between the thermocouple leads and separate conductivity electrode.

Similarly, optical sensors may utilize image analysis for detection of optical scatter/absorption and cell counts. In this example, optical scatter/absorption may be measured from an optical image, which is analyzed by the microprocessor on the patient monitoring device, or by a microprocessor in the database server system. The image can be analyzed for both overall optical scatter/absorption via color gradient, grayscale gradient, or alternate methods. The same image can also be analyzed for counting of individual cells.

Sensor data may also be used in conjunction to provide contextual data. For example, flow volume may be determined from measurements using the flow sensor. The flow sensor data and time stamp data may be used to determines an overall dwell time of the fluid exchanged for peritoneal dialysis patients. Both the flow volume and dwell time can be used to normalize the data generated by conductivity, urea, glucose and/or other sensors for analyte concentration. Similarly, flow volume and dwell time can be used to normalize the data generated by the fluid optical scatter/absorption sensor or cell counters.

Sensor Sampling Rate

Each sensor can operate at various sampling frequencies and duty cycles. In order to conserve the overall system power use, it is desirable for each sensor to operate only as necessary. A primary sensor like the flow sensor may work in continuous operation, but operate on a relatively low duty cycle during times when there is no fluid flow. The flow sensor would then operate on a relatively high duty cycle setting during times when there is fluid flow. The sampling rate would be optimized for sensor performance, as needed. When there is no flow, the sampling frequency of the flow sensor may operate at only 1 Hz, and increase to 10 Hz when the flow initiates again.

Secondary sensors like a conductivity or pH sensor may only measure the fluid for a few seconds during the beginning and end of dialysis infusion and drainage cycles, as the solutions generally have a homogenous pH and conductivity such that one portion of the volume of drainage or infused solution is representative of the overall volume of the fluid.

The sampling rate of the sensors may also be used to identify non-homogenous constituents. For example, with fluid optical scatter/absorption, a high sampling rate may be used to pick up non-homogenously mixed particles (e.g., fibrin) which have infrequent spikes in signal, when compared to homogenously mixed particles (i.e. white blood cells) which have a constant signal.

Data Processing and Alert Generation

All sensor-based data, patient input data, and provider input data will henceforth be categorized as "the patient data". The database server system receives, stores, and processes the patient data, and then allows the patient and provider software to retrieve the information via secure protocols. In one variation, the database server determines patient-specific historical baseline metrics over a specified period of time. As the patient data is continually retrieved, the database identifies data points deviating from the baseline metrics and signals alerts to the provider and/or patient.

In one example of such variation for patients on peritoneal dialysis therapy, the conductivity of the drainage dialysate solution is measured in voltage and represents the amount of solute diffused via ultrafiltration (UF). The conductivity is monitored during the patient's initial six week UF stabilization period and a baseline conductivity average and standard deviation values are established. In the following weeks, when the patient conductivity values rise above or fall below a predetermined number (e.g., two) of standard deviations from the baseline average, an alert is sent to the provider via the user interface software system GUI, email message, text message on a desktop or mobile device, push notification on a mobile device or other communication modalities. The alert may further be included in a provider's electronic medical record (EMR) for the patient via, for example, an application programming interface.

In another example, the database alerts the provider and/or patient when the patient data abruptly changes during a specific monitoring period. For patients on peritoneal dialysis therapy, the intraperitoneal pressure can be measured dining times when flow is stopped either during a dialysate dwell period, or in-between dialysis cycles. Temporal event changes to the pressure can be measured, for example, by calculating a moving average during the monitoring period, and any reading outside of three standard deviations (or other suitable predetermined threshold) may be detected and trigger an alert.

In another example, the database alerts the provider and/or patient when the patient data has fallen out of an absolute predetermined range. In an example of such variation, the skin surface temperature of patients with a PICC line is monitored. Any temperature values outside of the standard physiological range [97.7-99.5° F.] (or other suitable range) may trigger an alert to the provider and/or patient.

In another example, the prescribed patient therapy is input by the provider into the user interface software system and the data is transmitted and stored by the database server. The sensor network monitors the patient therapy starting infusing time, infusing volume, and, in some cases, the starting draining time. Alerts are sent to the provider and/or patient when the total number of daily infuse/drain cycles, infusing volume, infusion start times, dwell time, and other prescribed parameters are outside of the prescribed therapy.

One or more data inputs may be used to determine statistical alert limits for the purpose of monitoring a) patient compliance to prescribed therapy, b) therapy efficacy, c) complication detection, d) sensor calibration, e) device cleaning, and/or f) component replacement (e.g., cartridge replacement). In one example, for patients on peritoneal dialysis, the dialysate ultrafiltration efficacy is monitored by both the dialysate infusion to drainage flow volume ratio $V_i/V_w$, and dialysate drainage solution conductivity differential from fresh dialysate solution conductivity $C_i-C_w$. Alerts may be triggered when any one of the two parameters monitoring dialysate ultrafiltration efficacy has exceeded statistical alert limits, or when both parameters have exceeded statistical alert limits. When both parameters are used, each parameter may be weighted differently. For example, alert limits for flow volume ratio is based on one standard deviation of the baseline average value, while conductivity differential is based on three standard deviations of the baseline average value.

In addition to statistical limits of data values, alert sensitivity can be controlled by the number of instances in which the data values deviate from the statistical limits. For instance, a highly sensitive alert would require only a single data value deviating from statistical limits to trigger the alert. A low sensitivity system may require multiple data values deviating from the statistical limits to trigger the alert.

The alert sensitivity can be based off of predetermined values, or customized by the provider. For example, the provider can customize alert sensitivity based on the patient condition. In the case of a patient on dialysis with minimal renal function (flow differential is high) and poor overall health, the provider can set the statistical limit conservatively to one standard deviation and a single instance of the data deviating from the statistical limit to trigger the alert. In another case of a patient on dialysis with moderate renal disease (flow differential is low) and good overall health, the provider can set the statistical limit to three standard deviations, and four instances of the data deviating from the statistical limit to trigger the alert.

In an alternate variation, the database server system may analyze the patient information to determine the patient's overall health as a patient profile, and adapt alert sensitivity accordingly. The patient alert sensitivity may remain constant, or change over time. For example, the data for the patient's flow volume differential may be low and there are no recorded instances in a patient's profile of complications for the patient, so the database server adjusts the sensitivity level for alerts to the low settings. After some time, the data for the patient's flow volume differential increases to a high level, and the patient has two instances of infection recorded in their patient profile. The database server consequently adjusts the sensitivity level for alerts to be high.

Alert Types

When the alerts trigger, the alerts may present the data only, and/or a patient condition assessment. For example, temperature anomaly may be presented in an alert as "Temperature for patient X is 101.1° F." or alternately, "Patient X may have a fever".

Multiple data can be combined in an alert for the monitoring of a) patient compliance to prescribed therapy, b) dialysate ultrafiltration efficacy, and c) complication detection. For example, patient infection may be expressed by the patient with both an elevated core temperature as well as a drop in dialysate pH value. The alert, in this example may summarize the two inputs as "Patient has high risk of infection".

Alerts may also indicate the levels of severity through the use of different audio, vibratory, or visual cues such as pop-up windows with color markings in the software GUI. Severity is determined by the monitoring category as well as the magnitude of the statistical deviation. For instance, patient compliance deviations, such as when a patient performs his dialysis later than prescribed, would warrant a low severity alert. Successive missed dialysis sessions may warrant a higher severity alert. A high temperature exceeding 105° F. and a four standard deviation drop in pH value would warrant an extreme severity alert.

In another variation, the server and/or device processor may be configured to determine critical emergency scenarios of the patient's condition and triggers additional action. In one example for a patient with a urinary catheter, the temperature sensors measure the skin surface temperature at 110° F. and the accelerometers detect minimal patient movement over a 24 hour period. In addition to sending high-severity alerts to the provider, the system triggers a call to emergency personnel.

The alerts may be communicated within the user interface, or via phone call, text message, email, or separate alert hardware installed at the dialysis clinic. Depending on alert severity, one or more communication methods may be used. In addition, alert communication preferences may be customized by the provider and/or the patient.

In some variations, the functionality of the patient monitoring device may be limited by the database server if a user does not respond to a critical alert (e.g., critical alert to replace a cartridge/disposable component).

False Positive/Negative Alert Avoidance

Typically, certified nurse practitioners are the primary provider, and monitor about 15-20 peritoneal dialysis patients at any given point in time. Due to the high constraint on their time, it is desirable for the system to limit false positive alerts which waste both the patient's and the provider's time. One of the main false positive drivers are non-white blood cell particles that increase the turbidity of the effluent for a non-infection related reason. For example, red blood cells, proteins, triglycerides, and fibrin are common turbidity-related false positive drivers. However, as described herein, particle types may be differentiated based on optical measurements performed in different wavelength ranges and ratios calculated therefrom in order to improve white blood cell concentration measurement.

Figure 51:
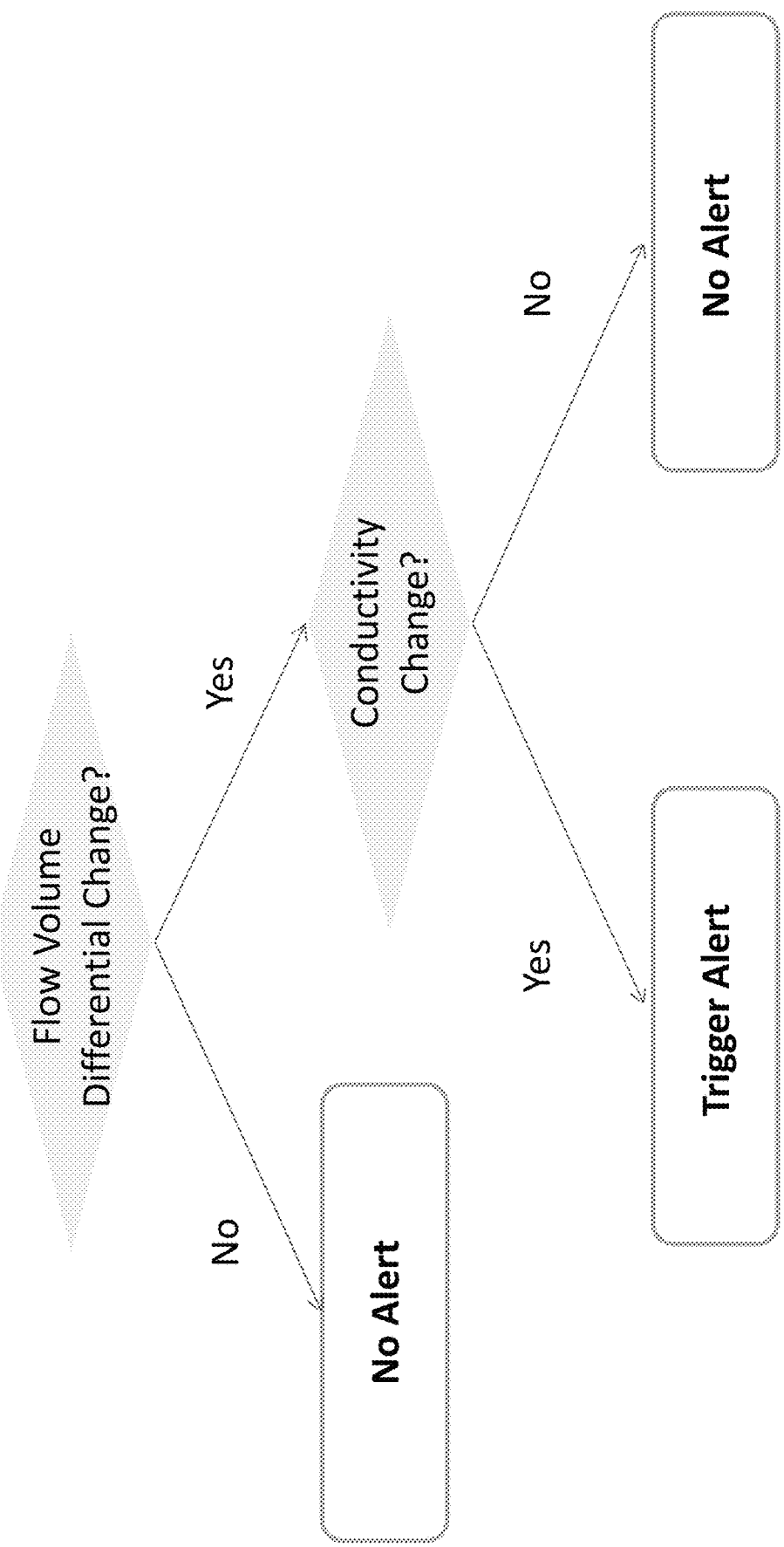
FIG. 51 illustrates an exemplary method for generating an alert for ultrafiltration efficacy change.

The frequency of false positive states can further be avoided or reduced with one or more redundant sensors. In the case of monitoring dialysate ultrafiltration efficacy, a conductivity sensor may be used in addition to a flow sensor which determines flow volume differentials. While flow volume differential primarily measures water diffusion during ultrafiltration, conductivity primarily measures salt diffusion during ultrafiltration. In cases where there is a change in ultrafiltration due to changes in the peritoneum permeability, both measured solutes—water and salt concentrations should be affected. Therefore, the process can take into account the change in both flow volume differential and conductivity before triggering an alert. FIG. 51 depicts the logic flow of utilizing flow volume differential and conductivity change, where both sensor systems need to demonstrate changes before an alert is triggered.

Figure 52:
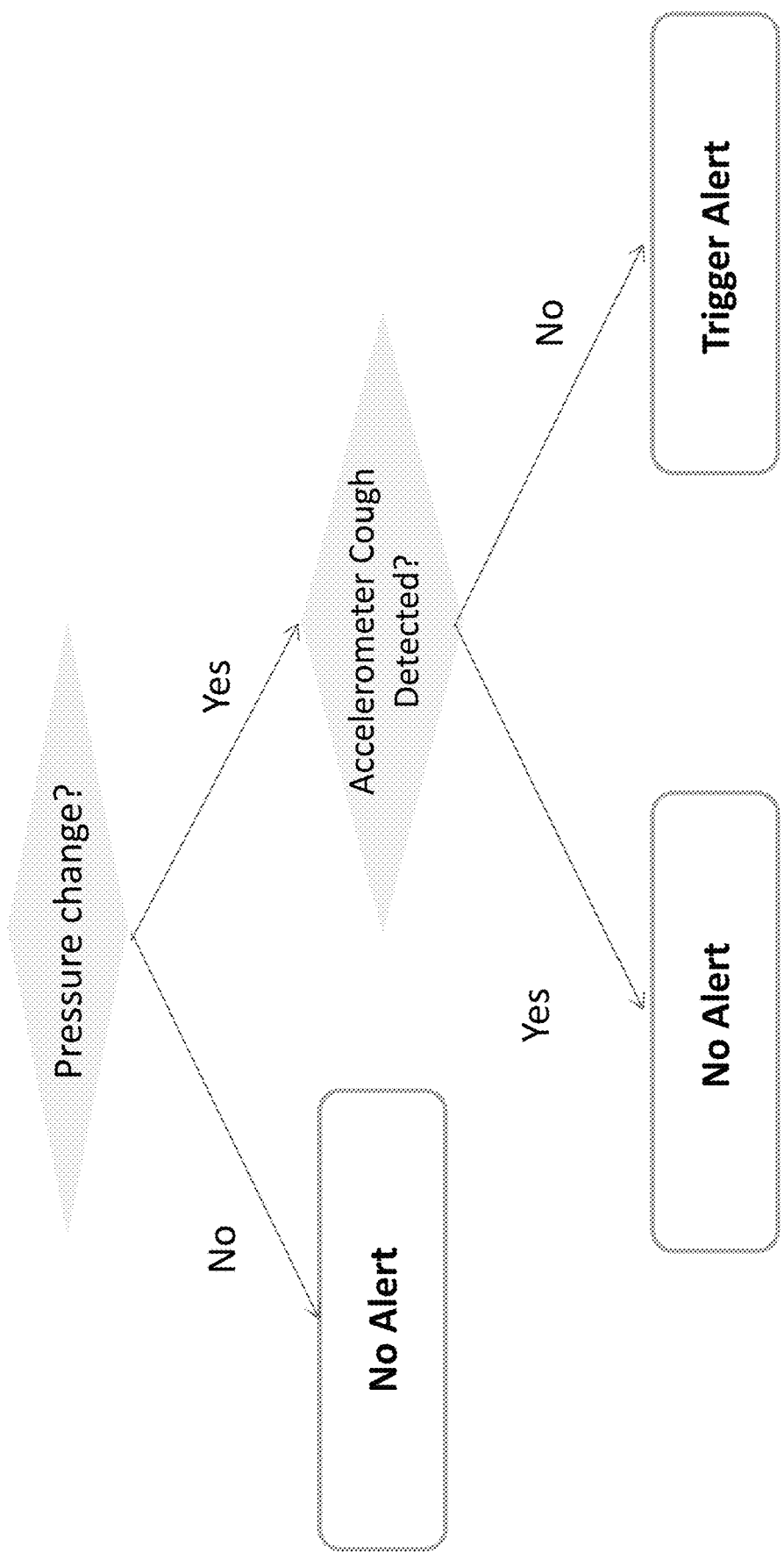
FIG. 52 illustrates an exemplary method for generating an alert based on pressure data.

False positives may also be avoided or reduced with unique sensors that monitor false-positive conditions. For example, pressure monitoring for patient hernia or catheter blockage complications can be supplemented by the use of an accelerometer. A patient hernia may result, for example in a rapid pressure change. However, coughing by the patient may similarly show rapid pressure changes. In this use case, an accelerometer integrated within the patient monitoring device can be used to detect coughs, which typically result in abrupt movement in the abdomen and diaphragm. Thus, the accelerometer can filter pressure sensor data to avoid false positives. FIG. 52 depicts the logic flow of pressure sensor data and accelerometer cough detection in order to filter the data or trigger alerts.

Another false-positive scenario can occur when a patient is exercising. During exercise, intraperitoneal pressure can rise and respiratory cycle frequency increases, and the pressure sensor data may indicate a patient complication. Accelerometers and/or gyroscopes can be used in combination with the pressure sensor to detect when patients are exercising due to the constant movement detected, and filter out the pressure data during the exercise period.

Figure 53:
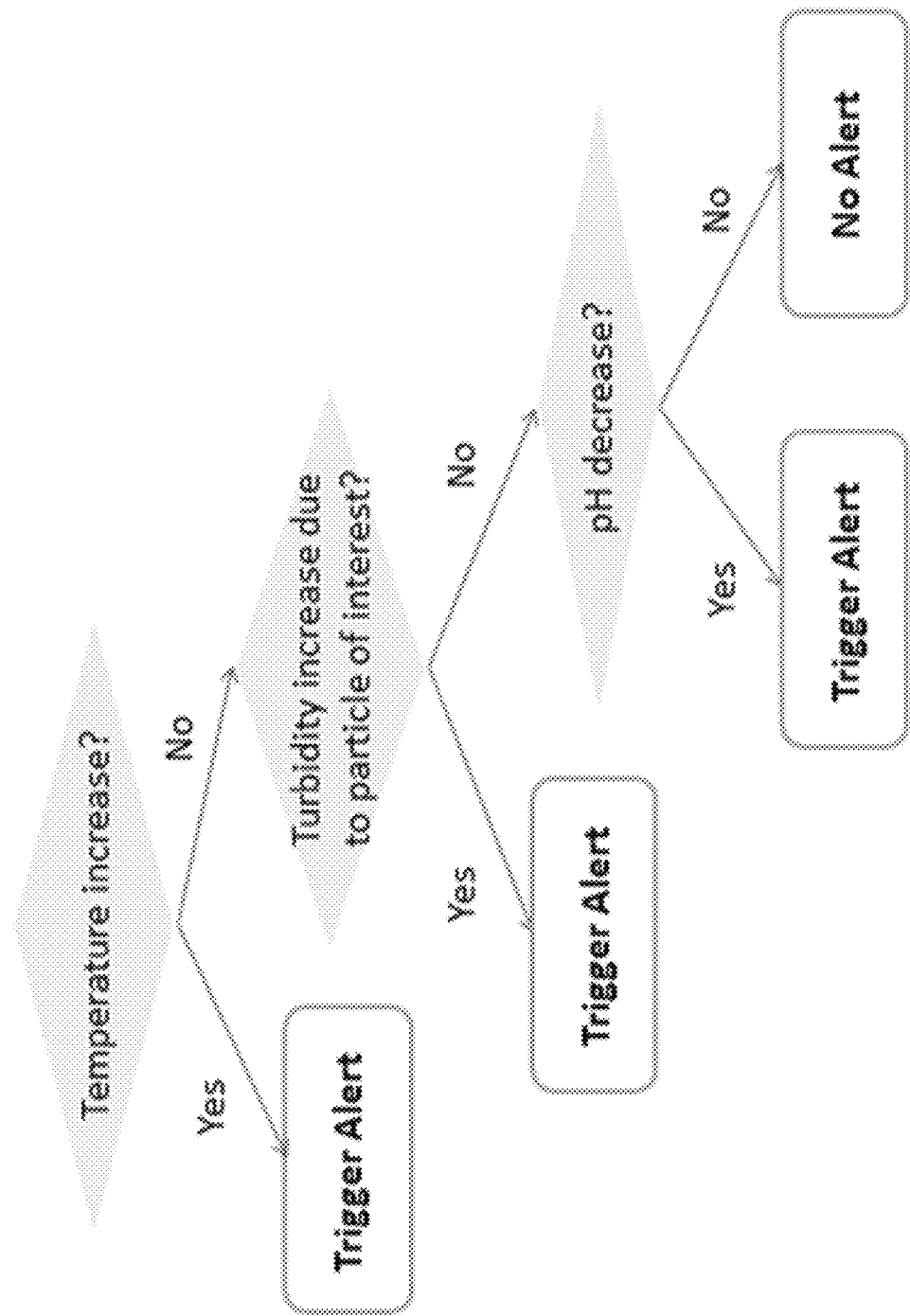
FIG. 53 illustrates an exemplary method for generating an alert for infection detection.
Figure 73:
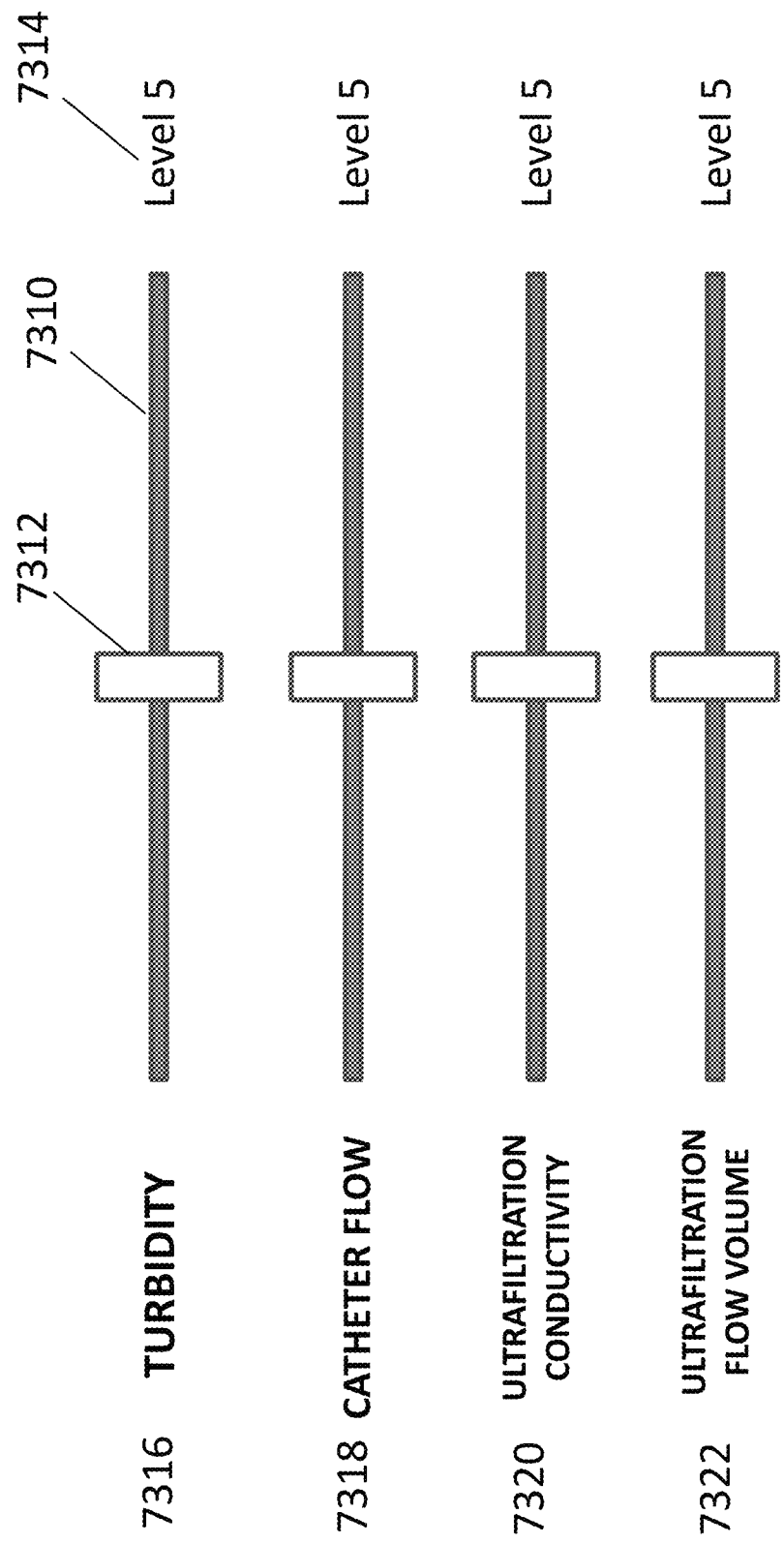

In addition, the system may be configured to increase the sensitivity for detecting certain states, to avoid or reduce the risk of missed patient infections, for example, can result in long hospital stays, or patient morbidity. False negatives states may also be avoided or reduced with redundant sensors. Systems designed to avoid false negatives are particularly useful in the case where detectability is low. Different pathogens, different types of infections, and different patient physiologies result in the expression of infection in different ways. Therefore, multiple sensors can be used for infection detection. In one example, pH sensors can be used in combination with optical scatter/absorption sensors and temperature sensors. During an infection, a patient may not express the infection via all three parameters, so a change in any of the sensors can trigger an alert. FIG. 53 depicts one exemplary process of optical scatter/absorption, temperature, and pH sensors, where any of the sensors can trigger an alert. FIG. 73 depicts one variation of a GUI configured to set a sensitivity of alert levels based on one or more parameters such as turbidity (7316), fluid flow (7318), ultrafiltration conductivity (7320), ultrafiltration flow volume (7322), and the like. For example, a provider may manipulate a slider 7312) along a predetermined scale (7310) to adjust a sensitivity level (7314) of an alert.

Additionally, upon detection of specific complications, the user (e.g., patient, health care provider) may be prompted to answer several questions through a graphical user interface to reduce false positive claims. For example, optical sensors may detect abnormal signals due to a nascent infection but also due to an unnatural dietary action of the patient. The patient may be asked through a user interface, or other communication medium if there were any abnormal behaviors (e.g., eating a large meal of meat when usually a vegetarian diet is followed) that may have caused the change in signal. The alert and subsequent answers by the patient may be recorded in the historical data, but potentially an alert is given to the provider only when there is no aberrant behavior as stated by the patient.

Furthermore, the data can be time-resolved to screen for false positives. For example, if an infection exists, this would lead to an elevated concentration of leukocytes that would likely be sustained or increased over time. For each patient, false positive alerts may arise after one reading of abnormal signals, but this metric may fall to a normal level upon the next reading. For each patient, time-resolved signal behavior for false positives could be learned. Increased ultrafiltration is also associated with peritonitis incidence. An increase in ionic conductivity paralleled with elevated optical scatter/absorption readings is an additional indicative parameter of infection origination.

Sample Collection Methods

Additional actions may also be prompted by the system when certain threshold action limits are detected. In one example, there may be a sterile collection container loaded at all times in the device for fluid sample collection that can be sent to a laboratory for analysis. Upon detecting a potential complication, a sample of the fluid of the patient may be collected in the container. The container may also be labeled with a shipping label and ejected from the device or removed by the patient. The samples may then be dropped directly into a mailbox for delivery to an analysis facility or automate a courier pick-up from the patient's home.

As a part of the sample collection, a separate sample may be collected to test in the device with test strips or another test modality for common pathogen identification. The results of the test may then be given to the healthcare provider or the analysis laboratory to expedite the analysis process by providing initial data about the identity of the pathogen causing the complication. Thus, the initial screen of the sample may be completed before arrival in the analysis facility. In some variations, an optical sensor may measure one or more optical characteristics (e.g., image, color) of a test indicator strip with the sensor signal automatically transmitted to one or more of memory, network, database, and service provider.

In another example, the alert may notify the device manufacturer, healthcare provider, analysis laboratory, courier service, or a third party service to collect a sample. Someone may be dispatched to go to the patient and directly collect a sample during the drainage process or from the previous drainage. Additionally or alternatively test strips may be stored in the device that the dispatched individual could use to test for common pathogens, or the results from automatically used test strips could be read.

After the sample collection, an alert generation cascade may be triggered. A notification (e.g., text, email, application notification) may be sent to the healthcare provider and analysis facility to alert them of the patient status and imminent sample arrival for testing. In one example, an alert may be sent to a courier service to pick up the sample, such that the patient would not need to put the sample in the mailbox. Alternatively, the patient may put the sample in the mailbox or another container outside for the courier to pick up the sample without the need for coordinating with the patient and decreasing the total transit time of the sample. Subsequent notifications may be triggered when the sample arrives at the testing facility, results are known, and key benchmarks are hit for the treatment of the complication in the patient.

The courier may have unique access to the sample container to ensure testing fidelity and patient security. The device may contain a locked compartment, which houses the sample and could be opened up by an authorized courier. The courier may then replace the sample with a new sample collection container into the device.

Figure 56:
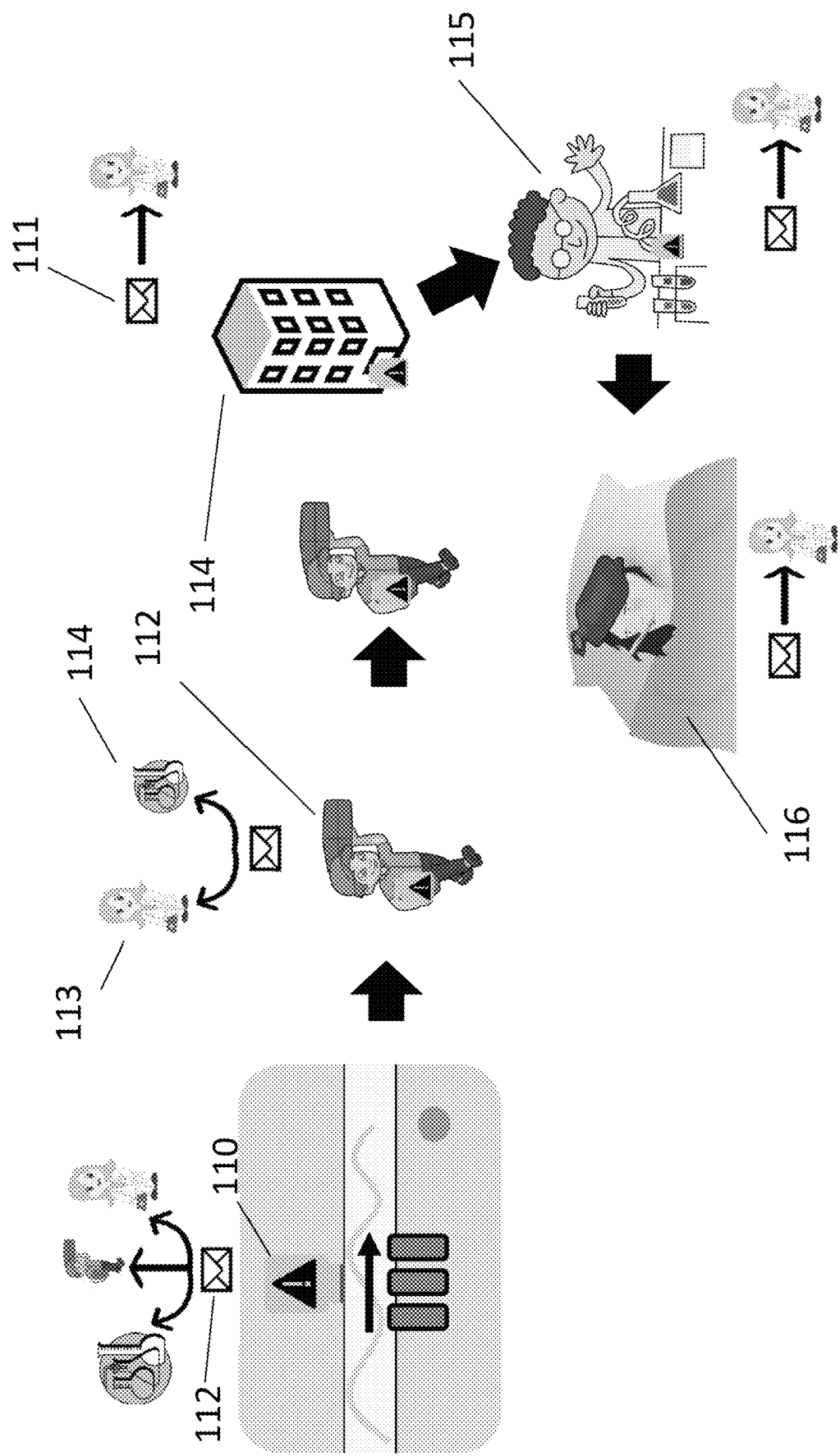
FIG. 56 illustrates an exemplary method for generating alerts to a set of stakeholders.

FIG. 56 illustrates one possible series of notifications. When the sample collection container (110) is filled and sealed for transport, a notification (111) is sent to the courier (112) to pick up the sample, the healthcare provider (113) to keep them informed, and the analysis laboratory (114) to inform them of the imminent testing. A further notification is sent to the healthcare provider and analysis facility when the courier picks up the sample. Then, the healthcare provider is notified when the courier drops off the sample at the analysis facility and when the test results (115) are known. As the treatment of the complication goes on, the healthcare provider is kept notified of benchmarks in the progression of the treatment of the patient (116).

As a part of the automatic response cascade, a treatment regimen could be started immediately after sample collection. For example, for an infection, this could be a broad-spectrum antibiotic, and for a catheter blockage, this could be a thrombolytic agent. In either case, the treatment could be delivered automatically into the infusing fluid line to the patient, or it could be in a locked receptacle accessible to the patient, that is remotely or automatically unlocked or through an access code sent to the patient. For treatments not directly injected into the incoming fluid (e.g., when there is only a drainage tube), the treatment can be administered orally, through the catheter, through a syringe, through a transdermal patch, etc. FIGS. 57A-C and 58A-C depict the treatment regimen beginning after sample collection but not as a part of the automatic response cascade.

In another example, when an action limit is detected for a potential complication such as infection or catheter blockage, the system may alert a pharmacy to deliver an antibiotic to treat the infection, or a thrombolytic to resolve the catheter blockage. The provider may be notified of the alert and be able to send a remote prescription to the patient through the device application or user interface for broad-spectrum antibiotics initially and more specific antibiotics later, either when they get results back from the sample analysis or observe low or no efficacy in the treatment. The remote prescriptions can work in conjunction with test strips or another testing modality in the device for common pathogens to increase information for the provider to use when prescribing a treatment.

Therapeutic Agent Methods

Figure 58C:
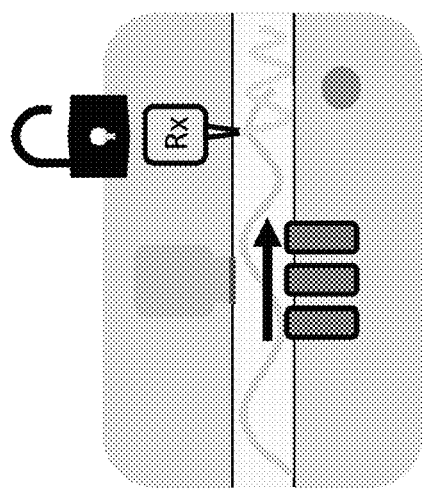
Figure 58B:
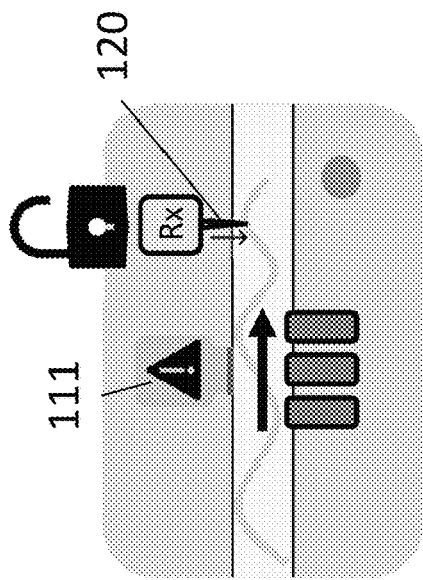
Figure 58A:
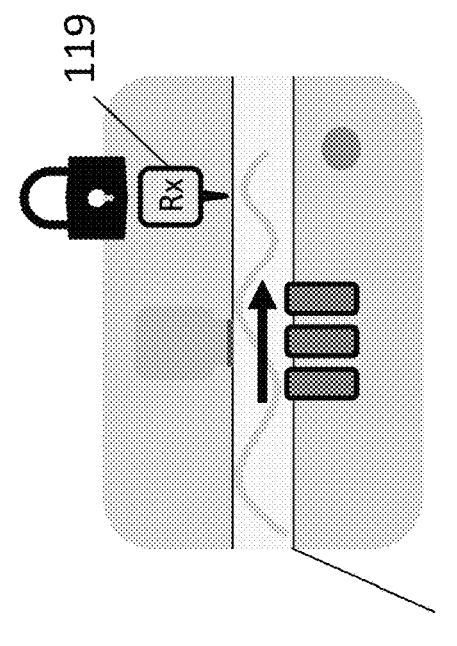

FIGS. 58A-58C depicts one variation of a method in which a therapeutic agent is injected directly into the fluid going into the patient. Similar to FIG. 57A, the injectable therapeutic agent (119) is protected from exposure to the patient initially, seen shown in FIG. 58A. After the sample is collected and the notification (111) has been made, a needle (120) is pushed forward and pierces the wall of the fluid channel, as shown in FIG. 58B. Next, FIG. 58C shows the injectable therapeutic agent being dispensed into the fluid in the channel of the device, which starts the treatment process immediately upon complication detection and sample collection.

Additional Data Inputs

In addition to the sensor data, metrics may be input by both the provider and patient via the software system. This data may be transmitted to the database server, which receives, processes, and stores the data. When processed, the data can be used independently to trigger alerts, or can be used in combination with other monitoring data.

In one example, the patient on peritoneal dialysis therapy manually inputs weight data from a separate scale before, during, and after a dialysis exchange cycle. The weight changes between each step in the dialysis cycle indicate fluid volume change. When the patient weight after the dialysis infusion cycle is input and the patient weight after dialysis drainage is input, the differential weight (Md) and calculated infused dialysis solution fluid weight (Ms) can be calculated (based on flow volume and density of the infused dialysate) into a mass differential ratio, Rm=Md/Ms. The ratio generally correlates directly to the ratio of waste fluid volume drained (Vw) and fluid volume infused (Vi), Rv=Vw/Vi. The mass data can be used as an alternate or supplement to flow sensor data in order to calculate volume differentials between infused and drained dialysate fluid. In the case the data is used to supplement the flow sensor data, false positives or false negatives may be avoided. In some variations, a weight scale may be configured to automatically transmit (e.g., wirelessly via Bluetooth or Wi-Fi) weight and time-stamp data for the patient.

In this example, the user interface software system can also prompt the patient for weight measurements during different periods in the dialysis cycle. Specific weighing points can be mandated by the software interface by only allowing readings taken at specific points to be transmitted to the database or not allowing for the next step of the exchange cycle to be initiated until patient weight is logged.

The weight data can also be used to help calculate the total body water volume. The total body water volume value "V" is an important component of the KT/V standard dialysis adequacy test, where K is the dialyzer clearance of urea, and T is the dialysis time.

Figure 59:
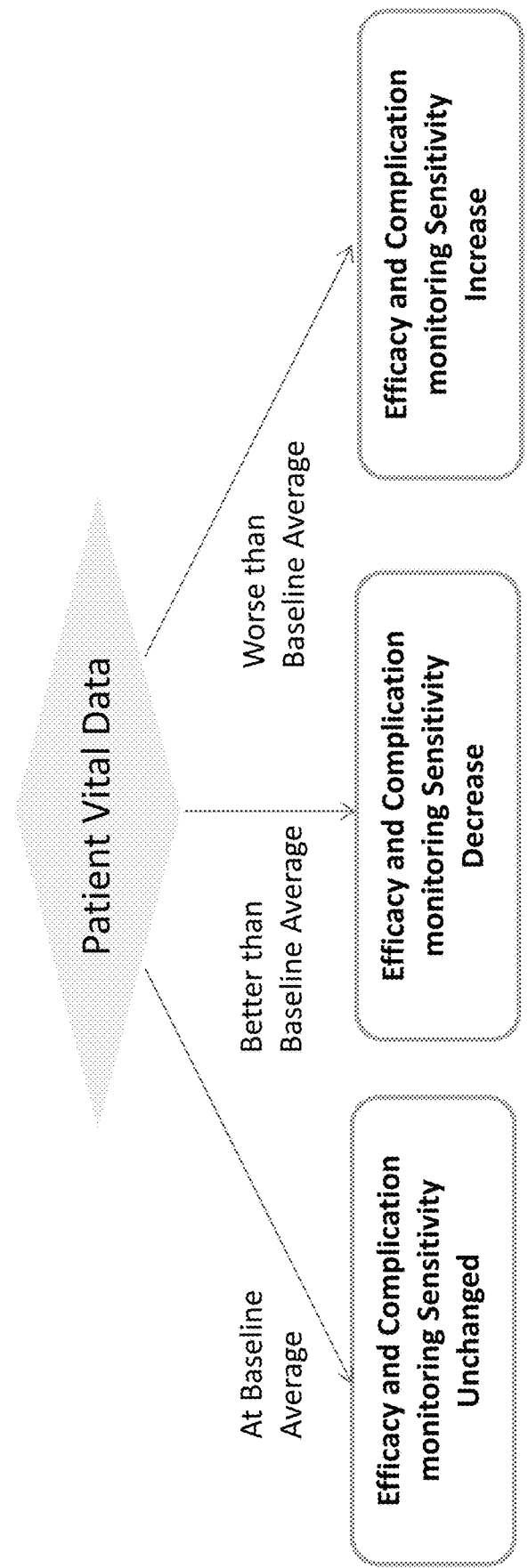
FIG. 59 illustrates an exemplary method for controlling an alert level sensitivity based on one or more patient vital measurements.

In another example, the patient blood pressure, heart rate, and/or oxygen level is input manually into the user interface software system by the patient or provider. The vital measurements and sensor data can be used together to determine the treatment efficacy and detect potential complications. FIG. 59 depicts one use of the vital data to change the sensitivity of the treatment efficacy and complication detection sensors. In one scenario, the patient blood pressure rises above one standard deviation from an average baseline value, so the sensitivity of the infection detection and treatment efficacy alert systems rise. The optical scatter/absorption, pH, and conductivity sensor data alert levels may drop from two standard deviations from the baseline average to one standard deviation from the baseline average.

In some variations, one or more diagnostic devices (e.g., blood pressure monitor, pulse oximetry device, vital sign monitoring device, heart rate monitor, temperature monitor) may be configured to automatically transmit (e.g., wirelessly via Bluetooth or Wi-Fi) diagnostic data and time-stamp data to one or more of memory, network, database, and service provider.

In another example, the patient physical activity may be monitored via an accelerometer, or similar means, in order to determine the level of patient physical activity. The level of patient activity can be correlated to dialysis treatment efficacy and complications. Poor dialysis treatment efficacy and infection can cause fatigue and lethargy, which translate to reduced patient activity. In one scenario, the patient accelerometer data indicates that the patient has reduced the total number of steps one standard deviation from the average baseline value and maintained a lying down position for total daily time duration greater than one standard deviation from the average baseline value. The sensitivity for the alert system for infection detection and dialysate efficacy may increase, and the alert threshold drops from two standard deviations to one standard deviation from the baseline average values of the sensors.

In another example, the patient provides daily inputs on several questions to determine their feeling of wellness and pain based on a numeric scale (i.e., 1-5) or graphical representation (smiley, sad faces) via the GUI of the user interface software system. The patient's feeling of wellness and pain can be correlated to dialysis efficacy and complications. Poor wellness ranging from loss of appetite, lethargy, and shortness of breath can correlate to poor dialysis efficacy. Abdominal pain can correlate to hernias or infection. In one use case, the patient inputs wellness data for energy, appetite, and pain based on a 1-5 scale (1=very bad, 2=poor, 3=average, 4=good, 5=excellent). The patient pain level drops two standard deviations from the baseline average value on successive days, and an alert is triggered for a potential patient complication. In another scenario, the value for the patient energy rating drops 2 standard deviations below the baseline average value on successive days. The threshold for the alert system for infection detection and dialysate efficacy then drop from two standard deviations to one standard deviation from the baseline average values of the sensors.

In addition, the user interface software system can allow for the dialysis providers to enter the data from monthly clinic-based tests to be input and continuously monitored similarly to the other aforementioned metrics, with alerts generated for long term changes that could indicate patient condition deterioration. Such tests include but not limited to blood work, urine sample analysis, and vital monitoring (e.g., blood pressure, weight, temperature). For peritoneal dialysis patients, additional data may include dialysate drainage analysis, and pro-card data from CCPD night cycling machines.

The user interface software system may have user-friendly data upload features that are integrated with existing lab data record systems and/or allow simple data transfers via uploading for csv files, txt files, or output files from the SD or other memory card directly from CCPD machines. The software system may be configured to allow the user to upload the data files, identify the file type, parse the data according to file type, and then transmit the data to the network database server system for storage. Alternatively, the data can be transmitted first to the database server system, which would perform the file type identification and data parsing.

In some variations, changes in the patient interface (such as color indicator) due to a possible complication (e.g., infection, catheter blockage) can be set to be resolved only when a health care provider (e.g., physician) or authorized user has reviewed and updated the patient's status. For example, a health care provider may be required to review patient data including culture results, lab generated cell counts, types of antibiotic administered, combinations thereof, and the like.

As opposed to patient or provider direct input into the user interface software system, external hardware may also communicate directly to the sensor hardware system, and/or the transmitter, and/or the user interface software system, and/or directly to the database. In one example, an internet-connected watch or other wearable, i.e., Fitbit, Apple Watch monitors physical activity through a proprietary application or via an existing health application, and data is sent wirelessly via LTE or other wireless connection directly to the database. In another example, a Bluetooth-enabled blood pressure cuff is connected to and communicates with the patient user software interface system via Bluetooth connection to the patient's tablet device. In another example, a pulse oximeter is plugged directly into the sensor hardware system. The I/O connector may be a unique port, or a standard port such as a micro-USB port.

Patient Events and Data Correlation Methods

In another variation, the server analyzes the data stored in the database to assess or determines a diagnosis or a clinical condition. The database may utilize regression analysis between clinical events (e.g., infection, catheter obstruction, and/or loss treatment efficacy) and sensor-based data or patient input data, to generate patient or population-based metrics or thresholds for generating alerts. This analysis may be retrospective statistical regression analysis from one or a multitude of patients' data. Regression analysis may be utilized to determine the relation of monitored parameters and patient clinical events. Once regressions are established, when a patient's monitored data indicates high probability of a clinical event, the server database may alert the provider of a specific diagnosis of the patient. In one example, the glucose levels in the drainage dialysate rise two standard deviations from the baseline levels in combination with conductivity of the drainage dialysate dropping 1 standard deviation from the baseline level. Based on prior data analysis, the database diagnoses with a high probability that there is a change in the peritoneum permeability, and that the prescribed dialysate solution has lost clinical efficacy.

The user interface software system for the patient provider additionally includes inputs on actual diagnosed patient events that are transmitted to the database server related to a) treatment efficacy, and b) treatment complications. This "output data" is analyzed in combination with the "input data" for the regression analysis in order to determine the algorithms for automated diagnosis of the events based on system inputs. In one example, the provider records the incidence of a patient hernia (output data point) at a specific time point in the GUI of the user interface software system. The patient hernia and time data are transmitted to the database server, which receives, and stores the output data point. The database server performs regression analysis of the pressure sensor data (input data point) before, during, and after the time of the hernia event. The regression analysis determines that the acute change in pressure dP exceeded, for example, 2.5 standard deviations $\sigma$ in the day immediately before the hernia event (or other suitable threshold). Thus, a predictive diagnosis algorithm for the patient hernia detection can be developed as $dP > 2.5\sigma$.

In another example, the provider diagnoses dialysis efficacy failure for patient on peritoneal dialysis, as the patient develops fatigue, nausea and vomiting. The provider records the efficacy failure (output data point) and time point of the event in the GUI of the user interface software system. The dialysis efficacy failure and time data are transmitted to the database server, which receives, and stores the output data point. The database server performs regression analysis of the volume differential data and conductivity data (input data points) before, during, and after the time of the dialysis efficacy failure event. The regression analysis demonstrates that the volume ratio data of the dialysate infused to dialysate waste, Vi/Vw had been decreasing over the prior 28 days, Vi/Vw=Vi/Vw(baseline average)−4/7 t. During the same period, the conductivity, C of the drainage solution had been decreasing, C=C(baseline average)−5/8 t. Thus, a predictive diagnosis algorithm for dialysate efficacy failure can be developed from conductivity, volume ratio, or a combination of the two.

In another example, the provider diagnoses an extraluminal infection. The provider records the extraluminal infection (output data point) and time point of the event in the GUI of the user interface software system. The extraluminal infection and time data are transmitted to the database server, which receives, and stores the output data point. The database server performs regression analysis of the drainage dialysate optical scatter/absorption, pH, and drainage dialysate temperature data (input data points) before, during, and after the time of the extraluminal infection event. The regression analysis demonstrates that there is no correlation between the patient's optical scatter/absorption and pH to the extraluminal infection event. However, there is a correlation with the patient's drainage dialysate temperature, T exceeding 38.4° C. Thus, a predictive diagnosis algorithm for extraluminal infection can be developed as T>38.4° C.

The predictive diagnosis algorithms can be further developed with additional data from the same patient and/or from multiple patients. In another variation, regression analysis and artificial intelligence can be implemented such that algorithms can be uniquely developed for each patient.

Data Transmission

In the patient monitoring device, the data is processed by the microcontroller, and the processed data is stored on a memory module locally. In one variation, the data is encrypted, then wirelessly sent via Bluetooth, Zigbee, NFC or other means to a local transmitter. The data may be transmitted as a continuous stream, or intermittently. In the case there is a failure of data transmission, the local memory module continues to store the data until the data transmission can be successfully completed. The transmitter may be a unique module dedicated to the monitoring system, a mobile device, smartphone device, phablet, tablet, PDA, personal computer, or similar form of hardware with data networking capabilities to send the data to the database system (29). The transmitter may also contain local memory storage, such that in the case there is a failure of data transmission to the database system, the local memory storage would retain all data until data transmission can be completed.

In another variation, all the processed data is stored on a removable storage card including but not limited to an SD card, then uploaded to a unique module dedicated to the monitoring system, a mobile device, smartphone device, phablet, tablet, PDA, personal computer, or similar form of hardware with data networking capabilities to send the data to the database system.

In another variation, the patient monitoring device contains a cellular data (e.g., 3G, 4G, LTE) transmission module, and sends the data directly to the database server via the cellular network.

Data Output

The user interface software system may be retrievable by any accessible computing device (e.g., Android, iOS), web browser accessing a secure website, and/or cloud computing solution. The patients and providers may register an account through the application and login to access the functionality. Via wired or wireless network communication, the user interface software system transmits the user login information, and requests data from the database server system. The database server system receives the requested data and login data, determines user access level from login information (e.g., administrator, patient, provider), authenticates the login data, and sends the requested data. The user interface software system receives the requested data from the database server system and parses the data for the user interface. The user interface software system may communicate with the database server system via an application program interface (API).

The patient and provider can use a graphical user interface (GUI) to review the patient data, and alerts. The GUI may include multiple page layouts, such as list view of multiple patients, and detail view of singular patient. The user can interact and navigate through the GUI via multiple input devices such as a computer mouse, keyboard, and/or a touchscreen. During the user interaction with the GUI, additional data requests may be sent, and communicated with the database server. The graphical user interface may be displayed in one or more customizable formats. Additionally or alternatively, data presentation, and/or alerts may include push-notifications, text messages, calls, and/or emails.

Figure 60:
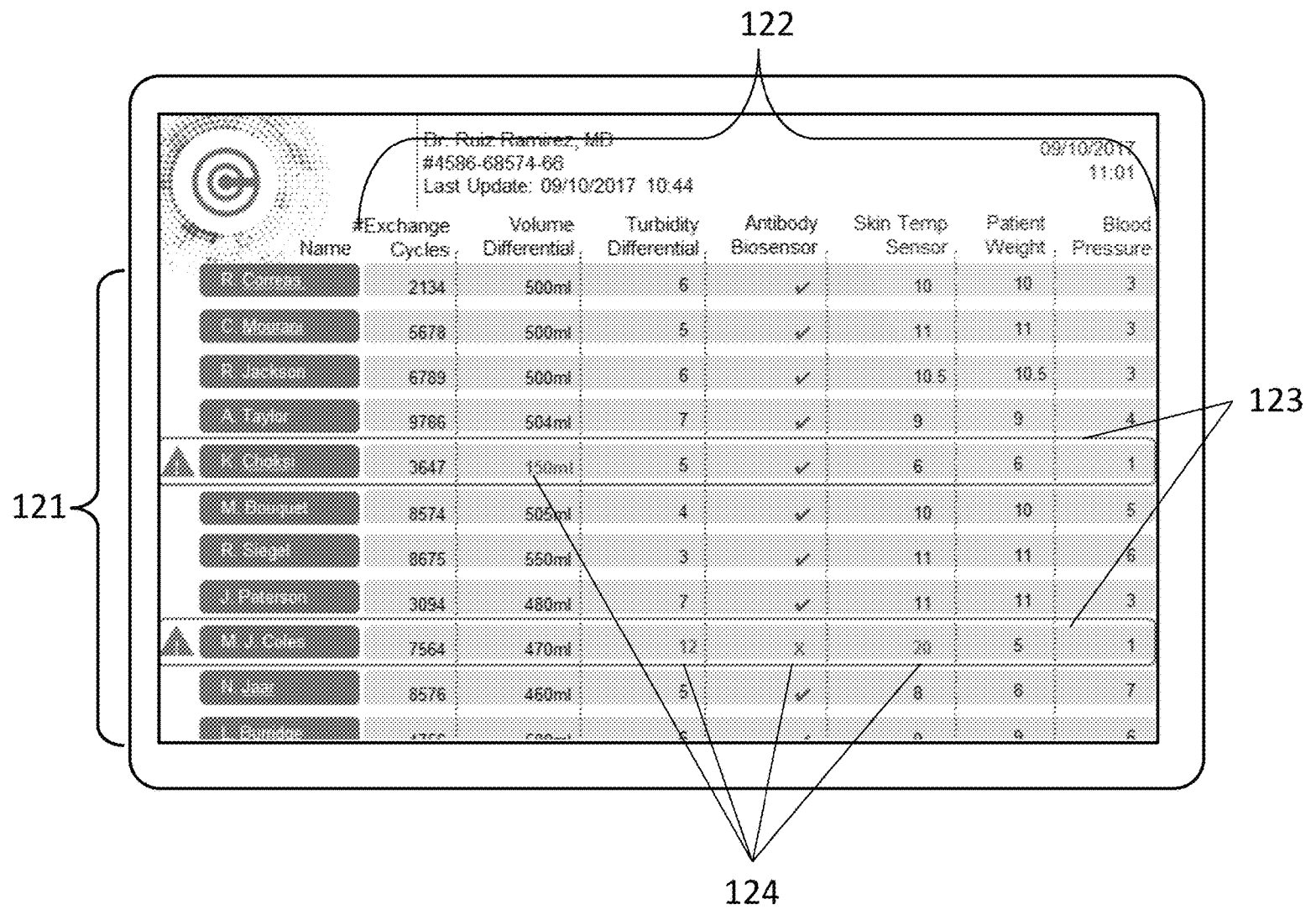
Figure 61:
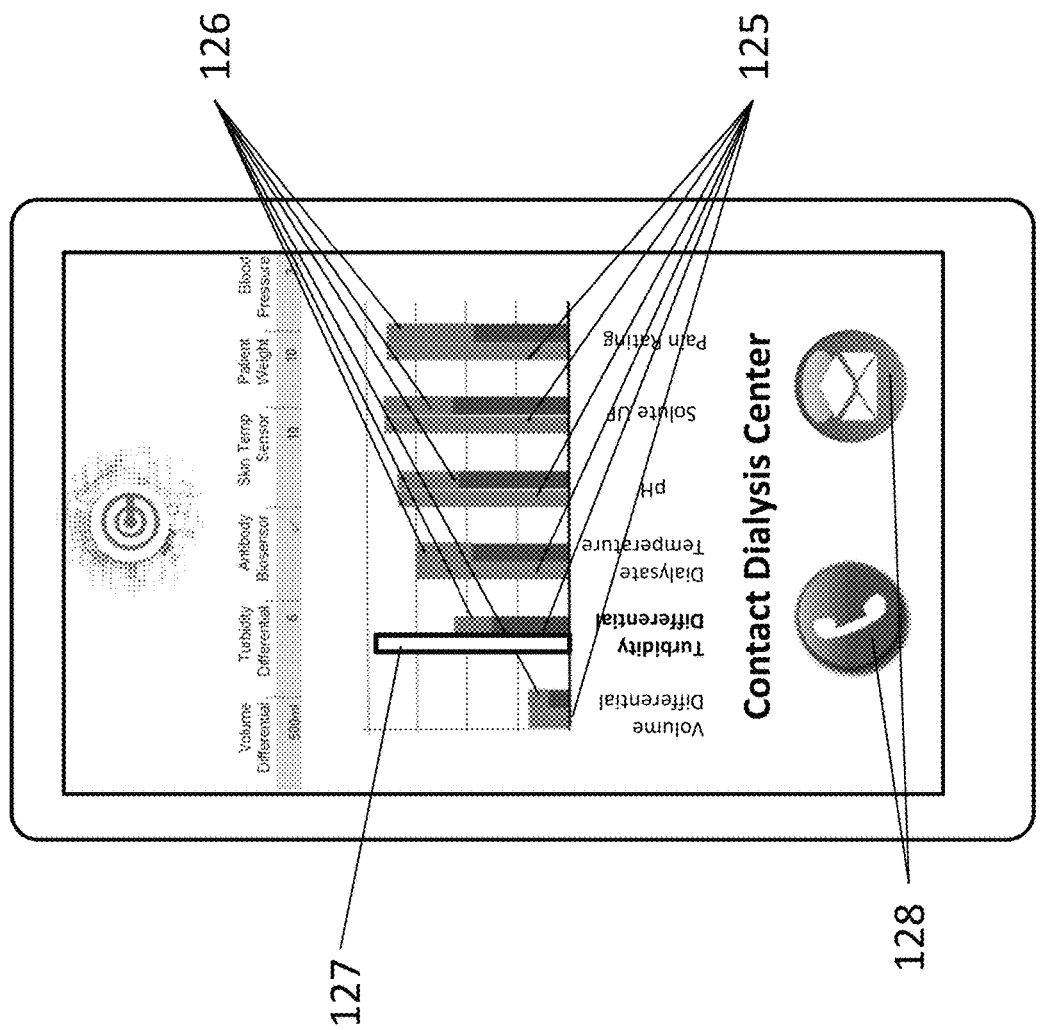
FIG. 61 illustrates an exemplary graphical user interface for patient monitoring by a patient.

In FIG. 60, the GUI for the provider displays multiple patients' information (121) and includes the display of multiple dialysis parameters (122) monitored. Alert boxes (123) highlight patients with parameters outside of standard ranges, and the specific out of range parameters (124) are highlighted. The user interface software system may include data from the server database system and from alternate sources, such as the lab database system In FIG. 61, the GUI for the patient includes a display of historical reference data (125), and the most recent data (126) for multiple dialysis parameters monitored. An example of an alert (127) for parameters out of baseline range is shown. In addition, contact buttons (128) facilitate communication to the provider.

Figure 72:
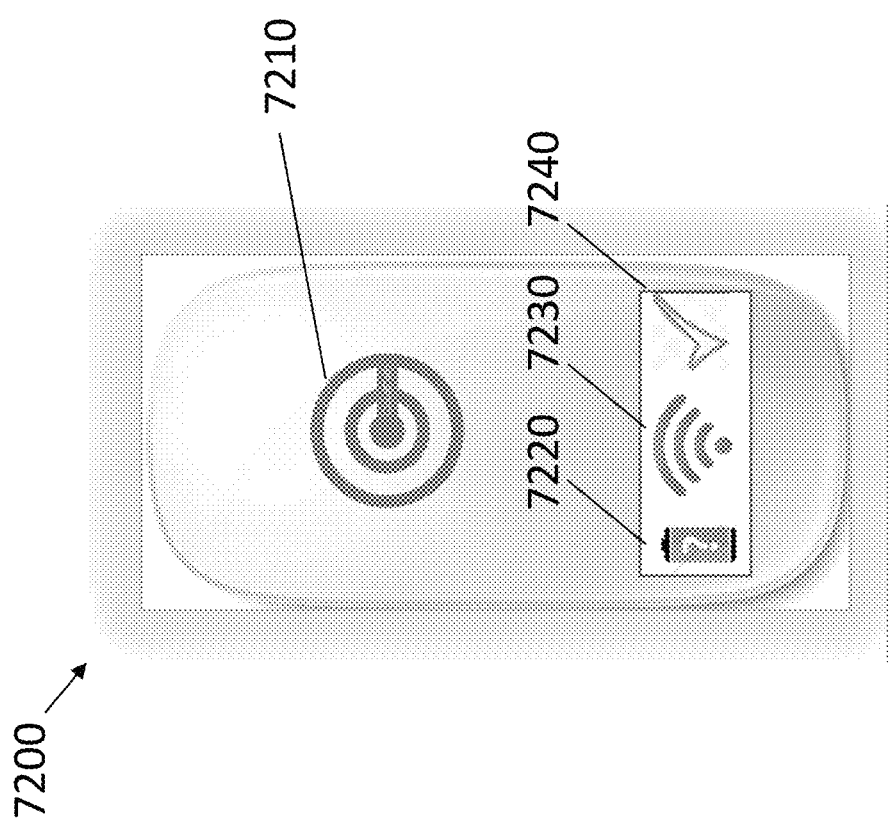
FIGS. 72 and 73 illustrate exemplary graphical user interfaces for patient monitoring by a patient.

In some variations, a GUI may be displayed by a patient monitoring device such as those depicted in FIGS. 64-71 or otherwise described herein. In some variations, the status of the patient monitoring device and/or patient may be communicated to the patient using one or more output methods. FIG. 72 is a GUI (7200) that may be displayed on an exterior of a durable component of the patient monitoring device. For example, a status of the system may be communicated to the operator using a set of light patterns emitted from one or more optical waveguides (e.g., light pipe). One or more optical waveguides may receive light from a light source (e.g., LED) using a predetermined combination of light output parameters (e.g., wavelength, frequency, intensity, pattern, duration) to provide a patient a predetermined visual indicator. The optical waveguides may be formed integral with the housing of a patient monitoring device to simplify manufacturing and allow for a compact design and minimal power usage.

An optical waveguide may refer to a physical structure that guides electromagnetic waves such as visible light spectrum waves to passively propagate and distribute received electromagnetic waves. Non-limiting examples of optical waveguides include optical fiber, rectangular waveguides, light tubes, light pipes, combinations thereof, or the like. For example, light pipes may comprise hollow structures with a reflective lining or transparent solids configured to propagate light through total internal reflection. The optical waveguides described herein may be made of any suitable material or combination of materials. For example, in some variations, the optical waveguide may be made from optical-grade polycarbonate. In some variations, the housings and frames as described herein may be co-injected molded to form the optical waveguides. In other variations, the optical waveguides may be formed separately and coupled to a respective housing or frame. In some variations, the optical waveguides described herein may comprise one or more portions configured to emit light. For example, at least one of the portions may comprise one or more shapes. For example, the optical waveguide may follow the edges of the housing and/or form a shape of a logo. In some variations, the optical waveguides described herein may comprise a surface contour including, for example, a multi-faceted surface configured to increase visibility from predetermined vantage points. Non-limiting examples of an illumination source (e.g., light source) include incandescent, electric discharge (e.g., excimer lamp, fluorescent lamp, electrical gas-discharge lamp, plasma lamp, etc.), electroluminescence (e.g., light-emitting diodes, organic light-emitting diodes, laser, etc.), induction lighting, and fiber optics.

In some variations, the patient monitoring device may emit one or more colors as a visual indicator of, for example, patient status. The GUI (7200) may be output by an LED or LCD and display one or more a patient monitoring device status, patient status, fluid monitoring status, disposable component status, communication status, combinations thereof, and the like. For example, GUI (7200) may display a battery life (7220), patient status (7210), communication status (7230), and disposable component status (7240) (e.g., attachment status, replacement status). The GUI (7200) may be configured to notify the patient to contact their doctor or health care professional due to a detected patient infection event. For example, an external portion of the patient monitoring device may glow green when an infection has not been detected and may glow orange when patient intervention is needed (e.g., contact service provider, health care professional).

The light patterns described herein may, for example, comprise one or more of flashing light, occulting light, isophase light, etc., and/or light of any suitable light/dark pattern. For example, flashing light may correspond to rhythmic light in which a total duration of the light in each period is shorter than the total duration of darkness and in which the flashes of light are of equal duration. Occulting light may correspond to rhythmic light in which the duration of light in each period is longer than the total duration of darkness. Isophase light may correspond to light which has dark and light periods of equal length. Light pulse patterns may include one or more colors (e.g., different color output per pulse), light intensities, and frequencies.

In some variations, one or more of visual, audible, and haptic output may be provided to a patient to communicate a device and/or patient status. For example, a device and/or patient status may additionally or alternatively be audibly communicated using an audio device. Variations of audio devices of the system may comprise, for example, one or more of a speaker, piezoelectric audio device, magnetostrictive speaker, and/or digital speaker.

The user interface software system for the patient may additionally be used to send patient reminders for dialysis therapy initiation, drainage, or other maintenance prescribed. Alerts may indicate when supplementary patient information (i.e. weight, blood pressure, pain condition) is missing. Reminders and alerts may also be sent to patients for the maintenance of the sensor system, such as battery replacement/charging and failure of data transmission that requires servicing of any equipment. Reminders for appointments with providers may also be sent through the user interface.

The user interface software system for the provider may additionally include reminders for patient appointments, patient data review times, or patient reports that require inputs.

The user interface software system may also contain communication channels such as video calls, private messaging, or phone calls between the patient, provider, and/or emergency personnel.

Alternate Applications for In-Dwelling Catheters

Alternate variations of continuous in-dwelling catheter monitoring include central venous lines, tunneled catheters, implanted access ports, insulin pumps for type one diabetics, long term feeding tubes, hydrocephalus drainage shunts, urinary tract catheters, percutaneous abscess drainage and ascites drainage catheters. Fever detection, for example, can be monitored through patient skin surface measurement and fluid temperature. Patient compliance to prescribed therapy can be applied via the combined use of flow sensors and time stamps. In addition, potential complications related to leakage or blockage of the catheter can be monitored via pressure sensors and/or flow sensors during drug infusion periods. Via the hydraulic connection of the sensor network to one of the catheter fluid ports, central venous pressure can be monitored in-between infusing periods, which provide additional patient monitoring data.

For all applications listed that do not include fluid drainage as a core component of treatment, sensing may be limited to fluid flow measurements, pressure sensing, skin surface sensing and/or exit wound site sensing technologies. The system may be configured to utilize data correlation capabilities to correlate the sensor data with various complication occurrence. The correlation data will support development of full diagnostic tools.

Urinary Tract Catheters

Urinary tract catheters can be used in hospitals, nursing homes, or in the homes of patients and can be used in a short-term or long-term context. In one variation used for urinary tract catheters, the patient monitoring device may be clamped onto the tubing of the catheter, as illustrated in FIGS. 10 and 11. The clamp-on device may punch holes into the tubing to enable direct contact with the fluid, or it may rely on sensors that take measurements without needing direct fluid contact. In another variation, the patient monitoring device may connect two tubing components in the catheter line.

Figure 62:
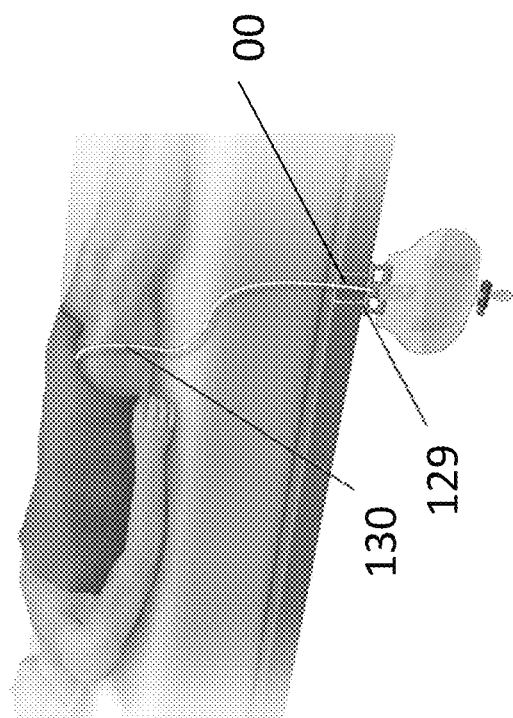
FIG. 62 illustrates an exemplary variation of a patient monitoring system including a patient monitoring device coupled to a urinary tract catheter.

FIG. 62 illustrates another variation of a patient monitoring device (00) used as a connector between the collection vessel (129) and tubing (130). The device may connect to the tubing and drainage vessel (129) through a Luer-lock interface, pressure fit, or other fluidically secure design. In another example, the device may be used only when emptying the drainage vessel. The patient monitoring device may be configured to monitor the patient and detect some of the complications that occur with the use of urinary tract catheters, including infection, blockage, and genitourinary trauma.

To detect infections and also monitor the progression of recovery once a treatment is implemented, the device can observe several parameters. The device can measure the flow rate of the fluid in the catheter, which may decrease in the case of an infection due to catheter obstruction stemming from the development of biofilm, blood clots, mineral content, or other sources in the lumen of the catheter. The presence of bacteria will cause an upward shift in the pH that the device can measure. Also, the temperature of the fluid and the body of the patient can be measured, which may be elevated in the case of an infection. An infection would lead to an increase in the leukocyte concentration, causing the solution to become turbid, which can be detected by the optical scatter/absorption sensor in the system. For urinary tract infections, 40 WBCs/μL has been shown to have a high sensitivity and specificity with positive culture for infections, which suggests using 40 WBCs/μL as a general threshold for this use case, instead of 100 WBCs/μL as for peritoneal dialysis. Lastly, more specific biomarkers for urinary tract catheter infections can be detected using the sensors of the device, such as the levels of nitrite, a known biomarker for urinary-tract infections, leukocyte esterase, a common marker of infections, heparin-binding protein, or interleukin-6 (IL-6). For detection of infections, aberrations from the baseline data or behavior of the individual patient or patient population with regard to the above noted parameters can be picked up early in the infection cycle with an alert sent to the healthcare provider or patient. Once an infected patient undergoes treatment, the regression of characteristics of infection (e.g., WBC concentration falling below about 40 WBCs/μL) can be monitored by the device to allow healthcare providers or the patients to view the efficacy of the treatment.

Trauma can also be detected by the device using optical sensors. Specifically, the device can detect hematuria by observing an elevated optical signal in areas active for hemoglobin. Optical signals at about 410 nm and about 550 nm are two examples of signals that could be monitored in an optical scatter/absorption system to catch the presence of blood in the urine that is suggestive of genitourinary trauma or non-catheter related trauma such as acute kidney injury (AKI). Non-catheter related injuries can also be detected with other biomarkers the device can detect, for example, serum creatinine concentration (sCR) in the case of AKI. An increase of the sCR of about 0.3 mg/dL within 48 hours or about a 50% increase in the patient baseline sCR within a week are typical indicators of AKI.

A reduction in the flow of the fluid in the urinary tract catheter can be observed through the flow sensor and pressure sensor. Notably, a reduction in flow, and increase in flow pressure, can be indicative of catheter blockage, in the case of an infection or the development of biofilm on the catheter unrelated to an infection, and the formation of a urethral stricture. A general low flow rate can be detected by the device and could indicate bad placement of the catheter or other medical conditions such as early signs of prostate enlargement.

Central Venous line Catheters

Central venous line catheterization is used in several therapeutic procedures, including but not limited to drug delivery. Examples include long-term intravenous antibiotics, long-term parenteral nutrition, especially in chronically ill persons, long-term pain medications, delivery of drugs that are prone to cause phlebitis in peripheral veins (caustic) such as calcium chloride, chemotherapy, hypertonic saline, potassium chloride (KCl) amiodarone, vasopressors (for example, epinephrine, dopamine) & plasmapheresis (peripheral blood stem cell collections).

For such applications in which fluid is infused into the patient, and no fluid is typically drained, the flow meters, skin surface temperature and luminal pressure sensing components of the system can be used in complication detection. Some of the common complications include, but are not limited to patient infection, which would result in a fever detectable by the temperature sensor. Complications also include catheter blockage, kinking and positional shifts from the expected placement position that cause variation in blood flow contact areas, which are detectable via the pressure sensor. The pressure sensor can also be used for patient vital system monitoring such as blood pressure, heart rate, and respiratory function. The vital system data can be used to detect cardiac complications that are relatively common which could progress to arrhythmia or cardiac arrest and pulmonary complications. Additionally, a pressure sensor could detect the backpressure exerted at the exit site that could be indicative of either a fibrin sheath formation in the line or bleeding near the site due to malposition of the line.

For the central venous line application, patients would use the device in a form factor attached to the skin via an adhesive similar to the depiction of FIGS. 1 and 13 or in a cylindrical shape that connects the in-dwelling component to the external fluid source similar to the depiction of FIG. 22. The housing would include skin surface temperature sensor, flow sensor, pressure sensor and an accelerometer for monitoring patient activity levels.

The patch would be placed next to the in-dwelling catheter at the point of installation. Patients would seamlessly administer their treatment in outpatient settings as they normally would, and the invention would collect the necessary data and transmit it to the cloud-based database viewable by the provider for remote monitoring.

With each dose administration, the flow sensors would indicate the exact volume inserted and time of injection, providing complete compliance assurance data to providers. A skin surface temperature sensor would take a reading of the exposed skin by the catheter exit wound site, decreasing variability in reading due to clothing insulation effects. The temperature sensor would take readings with each dose administration to spot temperature differential and identify fever for early infection detection. The pressure sensor would take a reading of the luminal pressure and compare it with the recorded base value for each patient. Any deviation in pressure values can indicate catheter kinking, blockage or misplacement from the ideal positioning. The pressure sensor would also record basic vital data, like blood pressure, heart beats per minute and respiration patterns.

Hemodialysis

Hemodialysis, with particular emphasis on home hemodialysis, is another central venous line application that can be monitored via the system. As hemodialysis administration includes the full circulation of the bloodstream into and out of the human body, the full range of the aforementioned sensing technology for peritoneal dialysis monitoring is applicable to remote monitoring of hemodialysis patients. The device for hemodialysis could take either a wearable form similar to FIG. 13 or coupled to a drain line, as in FIGS. 23 and 24.

Furthermore, common complications can be detected through sensors targeting specific small molecules or electrolytes. For example, electrolytes including potassium, sodium, and calcium could be detected by sensors specific to the electrolytes or by monitoring the conductivity or pH of the blood. These electrolytes are known to undergo abrupt changes during a hemodialysis session and can cause problematic alterations in osmolarity of intra- and extracellular concentrations. The resulting problems include hyponatremia (blood sodium levels of less than about 135 milliequivalents/L), which could lead to muscle cramps and a decrease in dialysis efficacy, reduced blood pressure, hyperkalemia (blood potassium levels of greater than about 5.5 milliequivalents/L), which can lead to cardiac abnormalities, and bone diseases, which can be seen through a decreased amount of vitamin D (normal concentration is greater than about 20 ng/dL) or increased amount of calcium (normal range is about 8.5-10.5 mg/dL).

Other complications could be detected through the sensors mentioned above. Notably, the blood pressure, which can be hyper or hypotensive in hemodialysis patients, can be tracked during a session to observe the initial value, final value, and shifts over the course of the session using the pressure sensor. Anemia, a low concentration of red blood cells in the blood, can be observed through optical sensors that can quantify the optical signal of hemoglobin, which has a unique optical signature and signal peaks around about 410 nm and about 550 nm. With the use of optical sensors, blood oxygenation can also be monitored. Lastly, pericarditis or other infections can be detected by looking at the count of leukocytes or proxies for leukocytes (e.g., leukocyte esterase).

Blood Drainage

In the case of a patient who just needs one single blood drain, the measurements would be compared to the standard population. In certain cases, previous blood draws could be used as a reference point if they are close enough to the time of the blood drain. For patients with multiple or chronic use of blood drainage techniques, a baseline could be established for the complication metrics.

Complications detected include but are not limited to detecting infections through an increased concentration of leukocytes through quantifying the cells or a proxy such as leukocyte esterase, hyper or hypotension through measurements of blood pressure, abnormal solute levels (e.g., hyperkalemia that can result in cardiac abnormalities and dysfunction), anemia, and problems with coagulation. These complications and others could be detected by the device and alert the healthcare providers, so they can start treatment immediately for complications for such issues as an infection or modify the blood drain in the case of hypotension due to excessive blood drain, for example.

Additionally, the total volume drained and speed of the drain could be monitored to ensure appropriate patient handling by the individual overseeing the blood drain. Alerts could be generated when blood is drawn too rapidly or too much blood is drawn, based on expected rates for the entire population or the specific patient's size and weight.

Hydrocephalus

Hydrocephalus is a condition in which excess fluid exists in the ventricles of the brain. Common treatment is to insert a subcutaneous shunt from the brain to another part of the body, such as the abdomen, to remove the excess fluid from the brain area. Given the sensitive nature of the brain, detecting and resolving complications as quickly as possible is critical for hydrocephalus patients.

A subcutaneous device embodying the full range of features detailed prior could be used to monitor patients remotely. FIGS. 63A-63C illustrate a variation of a subcutaneous patient monitoring device (132). The device may comprise a biocompatible sheath (131) around a circumference of the device (132) that allows it to remain subcutaneous. The sheath (131) can be cylindrical and wrap completely around the device, as shown in FIGS. 63A and 63B. The sheath (131) can interface with the shunt (133) through a pressure fit that can be applied during manufacturing. The subcutaneous patient monitoring device (132) may comprise one or more of the sensors described herein. Infections could be detected specifically through the data gathered from the optical scatter/absorption sensor, conductivity sensor, and temperature sensor. In some variations, the sheath (131) may function as a shield for the device (132) from the body of the patient, thus allowing the device (132) to have the same set of functionality as it does outside of the body. In one variation, the sheath-encapsulated device (132) may be surgically placed in the thoracic cavity beside the diaphragm and secured to the ribcage using any known attachment means. An elevated temperature, abnormal conductivity, or the increased presence of leukocytes, as determined by an optical scatter/absorption or other optical sensor, could all signal the onset of infection. Hardware malfunctions such as a shunt malfunction could be detected by flow or pressure sensors in the device that detect a deviation in normal flow or pressure of the fluid in the shunt. Characteristics of the drainage, such as the daily flux or biochemical composition, could be measured and recorded for historical patient documentation for the healthcare provider or patient.

In the case of an infection, the shunt often may be removed from the patient, and the excess fluid of the patient may be drained externally during treatment of the infection. In this scenario, an external device can be used to monitor the patient during treatment of the infection. For example, the fluid temperature (indicating fever) and white blood cell concentration could be used as indicators of the severity of an infection. Thus, a return to baseline for both values would indicate the treatment is effective and the patient has or is almost recovered from their infection. The external device can connect two tubing components, analogous to FIG. 10, or can exist at the end of the drainage line for the external shunt, with an interface such as in FIGS. 23 and 24.

Insulin Pumps

Insulin pumps remain continuously on individuals with type 1 diabetes. Complications may occur due to the presence of the insulin at the site of the tube running into the body and delivering the insulin. A wearable patient monitoring device, such as that shown in FIG. 13, could be used to detect common complications including infection at the exit site, lipohypertrophy, and pump cellulitis. Several different sensors could be used to detect an infection such as pump cellulitis or a general infection, including a temperature sensor to measure the temperature of the skin around the exit site or skin color sensor that could detect skin discoloration due to pus or other physical manifestations of infections. Lipohypotrophy can result in discoloration from the development of granulation tissue, and a skin color sensor could be used to detect this aberrant discoloration. Lipohypertrophy can produce an accumulation of fat tissue, creating a bulge in the skin. Thus, a light-based sensor can be used to detect abnormal contours of the skin that would suggest a liphypertrophy-induced bump.

Ascites Drainage

Ascites drainage involves either a permanently affixed apparatus (e.g., a peritoneal port or catheter or central venous catheter) or temporarily invasive hospital procedures, such as large volume paracentesis. For a permanently affixed apparatus, the patient monitoring device may be a wearable patient monitoring device adhered to the skin at the exit site of the patient (e.g., peritoneal port) or non-wearable and fixed to the tubing. The non-wearable device can connect two pieces of tubing, having fluidic contact between the two sets of tubing, as in FIG. 10. Alternately, patient monitoring device may be a clamped to a connector tube (with or without fluid contact), as in FIGS. 20 and 21, or attached to a drain vessel, as in FIGS. 23 and 24. Catheter leakage or obstruction can be detected by the flow rate or pressure of the drainage compared to a baseline. For patients with frequent ascites drainage (e.g., more than once a week), a patient-specific baseline could be developed over about 3 months or after about 25 drainage sessions are measured. For patients with less frequent drainage, such as on a monthly basis, then comparing the characteristics of the drainage of the patient against a population baseline may be more practical. For less frequently drained individuals, data could still be collected to establish an individualized baseline. However, until a sufficient amount of data points are collected (e.g., 25 sessions), a set of alerts may be derived from a population baseline. An infection can be detected by measuring the temperature of the patient skin surface. When the patient monitoring device is attached to the drainage fluid, an infection can be monitored via measurement of the drainage fluid temperature, conductivity, or optical markers of an infection (e.g., optical scatter/absorption caused by an elevated white blood cell count) and comparing this to the baseline values of the individual patient or patient population.

Feeding Tubes

Gastroenteric tube feeding plays a major role in the management of patients with poor voluntary intake, chronic neurological or mechanical dysphagia or gut dysfunction, and patients who are critically ill. This catheter is utilized to pass nutrients/food to a patient who cannot ingest food normally. In principle, tube systems for gastric or jejunal nutrition can be placed by nasal insertion (nasoenteral tubes; NETs), guided percutaneous application, or surgically. Metrics of functionality can be tracked using the system technology. Several complications may occur with feeding tubes.

Peristomal wound infections are the most common complication associated with the PEG procedure, with an incidence ranging from about 4% to about 30%. About three quarters of these are minor and resolve when treated with antibiotics. Being able to catch infection early would prevent further infection complications, hospitalization etc. Research has identified methicillin-resistant *Staphylococcus aureus* (MRSA) has emerged as an important cause of PEG-related wound infection. The system's temperature, pressure and PH sensing components can provide early infection detection.

Clogged feeding tubes are another potential complication. Since pH values below 4 have been described to promote protein coagulation, repeated gastric residual aspiration should be avoided or minimized. Tubes should also be flushed with 40-50 mL water before and after delivering medications or bulking agents (i.e., psyllium, resins). The flow sensing, conductivity, temperature and pressure sensors can be utilized in differentiating inserted fluids and treatment best practices compliance assurance, capturing infections at the earliest points of origination.

Peristomal leakage is another known issue. Several factors contributing to the risk of peristomal leakage have been identified, including excessive cleansing with hydroperoxide, infections, gastric hypersecretion and excessive side torsion along the PEG tube, as well as patient-specific factors that inhibit wound healing (malnutrition, immunodeficiency, diabetes)

Buried Bumper syndrome. Buried bumper syndrome (BBS) is a rare, mainly long-term complication of PEG, in which the internal bolster migrates from the gastric lumen and lodges in the gastric wall. Common symptoms include immobilization of the PEG tube, feeding difficulties or the need for more pressure when giving feeds, peritubular leakage, complete occlusion of the tube, and the occurrence of abdominal pain. Being able to track the pressure needed to feed a patient can help detect this complication early on in the disease state. It is normally not found for months, but with the system's monitoring capabilities, detection can be reduced to a matter of days. Leakage can also be identified utilizing the same sensor, the pressure or piezoelectric sensor, in the system, to find gradients in fluid motion, or location of high pressure, meaning there is an occlusion.

Percutaneous Abscess Drainage & Other Drainage Modalities

The system is applicable for all treatment modalities not specifically mentioned above incorporating fluid drainage from the body as a core step in the treatment administration. The drained fluids are available in the drainage path for a full spectrum analysis utilizing the system's full technology, similar to peritoneal dialysis treatment. Flow, temperature, optical scatter/absorption, pressure, conductivity, pH, lactate, glucose, urea and cell counters are all usable to detect patient compliance, complication origination and remote treatment efficacy/general wellness monitoring.

Server/Cloud Storage

The database server system includes network connectivity and communication, data processing via a computing processor and random access memory, and storage capabilities via hard drives or similar hardware. The database server system may include an application program interface (API) to define the communication procedures and protocols for interfacing to the hardware patient monitoring device, transmitter module, and/or the user interface software system. In addition, the database server system may have an API for communication with external systems for the purpose of storing additional data metrics for monitoring trends, alert generation, diagnosis or alternate purposes. For example, the dialysis center data system includes input of lab results such as blood test, urine test, and provider appointment notes. This data system can upload data directly to the database server system of the system. Alternately, the database server system of the system may upload data to the dialysis center data system. With multiple data sources used to monitor, diagnose, and treat dialysis patients, it is desirable to consolidate data within one system.

The database server system may be comprised of cloud-based storage and/or local servers. Network-based storage may be referred to as remote data storage or cloud data storage. EMG signal data stored in cloud data storage (e.g., database) may be accessible to respective users via a network, such as the Internet. Data stored on a cloud database may be accessible from any account and/or device that is granted access to that data. In some variations, a patient's computing device may connect to another service/platform containing patient data (e.g., valve data, sensor data, dialysis data) to receive that data.

In one variation, the database server system communicates to the patient monitoring device (directly or through a separate transmitter device) of the patient throughout the duration of the monitoring period via wireless or wired network communication channels (e.g., LTE, 4G cellular, wired internet or wireless internet). The database server system may send the patient monitoring device encryption keys, receive patient monitoring device data in raw, partially processed, or fully processed format, and send the patient monitoring device confirmation when data is successfully received. The database server system may decrypt the patient monitoring device data, process the patient monitoring device data by performing a series of mathematical calculations on the received data with or without historical received data, perform a series of image analysis algorithms, and store the data in memory drives. The database server additionally communicates with user interface systems via wireless or wired network communication channels (e.g., LTE, 4G cellular, wired internet or wireless interact). The database server system may receive login requests with user and password information from the user interface system, send the user interface system login confirmation with temporary access key or login access denial, receive data requests from the user interface system along with access key, send the user interface system requested data, receive additional user-input data in an encrypted format from the user interface system, decrypt and process the additional user-input data, and store the additional user-input data. The database server additionally communicates a system of alerts to the user interface system (e.g., push notifications, messages, alerts), directly to cellular phones (e.g., calls, text messages), via email (e.g., email messages), or to emergency personnel communication systems (e.g., 911 calls).

Processor

The processor may be any suitable processing device configured to run and/or execute a set of instructions or code and may include one or more data processors, image processors, graphics processing units, physics processing units, digital signal processors, and/or central processing units. The processor may be, for example, a general purpose processor, Field Programmable Gate Array (FPGA), an Application Specific Integrated Circuit (ASIC), and/or the like. The processor may be configured to run and/or execute application processes and/or other modules, processes and/or functions associated with the system and/or a network associated therewith. The underlying device technologies may be provided in a variety of component types, including but not limited to metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures mixed analog and digital, and the like.

Memory

In some variations, the memory may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, and the like. As used herein, database refers to a data storage resource. The memory may store instructions to cause the processor (to execute modules, processes and/or functions associated with the computing device, such as valve control, signal data processing, data analysis, sensor control, communication, and/or user settings. In some variations, storage may be network-based and accessible for one or more authorized users. Network-based storage may be referred to as remote data storage or cloud data storage. EMG signal data stored in cloud data storage (e.g., database) may be accessible to respective users via a network, such as the Internet. In some variations, the database server may be a cloud-based FPGA.

General

The systems, devices, and/or methods described herein may be performed by software (executed on hardware), hardware, or a combination thereof. Modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C++, Java®, Python, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

We claim:

1. A method of detecting infection of a patient, comprising:
   receiving patient fluid through a fluid conduit;
   measuring an optical characteristic of the patient fluid at two or more wavelength ranges;
   estimating a leukocyte concentration based at least in part on the optical characteristic measurement at the two or more wavelength ranges; and
   detecting an infection state of the patient based at least in part on the estimated leukocyte concentration.

2. The method of claim 1, wherein the optical characteristic comprises one or more of optical scatter and absorption.

3. The method of claim 1, wherein measuring the optical characteristic at a first wavelength range corresponds to a total particle concentration of the patient fluid and measuring the optical characteristic at a second wavelength range corresponds to a leukocyte concentration of the patient fluid, wherein the first wavelength range is different from the second wavelength range.

4. The method of claim 1, wherein the first wavelength range is between about 700 nm and about 1 mm and the second wavelength range is between about 260 nm and about 550 nm.

5. The method of claim 1, wherein measuring the optical characteristic at a first wavelength range corresponds to a total particle concentration of the patient fluid and measuring the optical characteristic at a second wavelength range corresponds to a non-leukocyte particle concentration of the patient fluid, wherein the first wavelength range is different from the second wavelength range.

6. The method of claim 1, further comprising:
receiving dialysate fluid through the fluid conduit; and
measuring the optical characteristic of the dialysate fluid, wherein the dialysate fluid is to be infused in the patient and the patient fluid is drained from the patient, and the estimated leukocyte concentration is based at least in part on the optical characteristic measurement of the dialysate fluid.

7. The method of claim 6, further comprising:
estimating an optical characteristic differential between the patient fluid and the dialysate fluid; and
updating the infection state of the patient based at least in part on the optical characteristic differential.

8. The method of claim 1, further comprising:
measuring one or more of a flow rate and total flow volume of the patient fluid using a flow sensor coupled to the fluid conduit; and
normalizing the optical characteristic measurement based on one or more of the flow rate and total flow volume measurement.

9. The method of claim 8, further comprising:
detecting one or more of an obstruction and flow direction based at least in part on the flow rate measurement.

10. The method of claim 8, further comprising:
estimating one or more of an infusion volume, drainage volume, infusion time, drainage time, and dwell time based at least in part on the flow rate measurement; and
estimating one or more of a dialysis efficiency and dialysis adequacy based at least in part on the estimated infusion volume, drainage volume, and dwell time.

11. A method of detecting infection of a patient, comprising:
receiving patient fluid through a fluid conduit;
measuring an optical characteristic of the patient fluid at two or more wavelength ranges;
measuring homogeneity of the patient fluid; and
estimating a leukocyte concentration based at least in part on the optical characteristic measurement at the two or more wavelength ranges and the measured homogeneity, wherein
a set of the optical characteristic measurements are excluded from the leukocyte concentration estimation based at least in part on the measured homogeneity.

12. A patient monitoring device, comprising:
an optical sensor arrangement comprising at least one emitter and at least one detector, the emitter configured to transmit light at one or more wavelength ranges through a patient fluid flowing through a fluid conduit, and the at least one detector configured to receive the light transmitted through the patient fluid and generate signal data based on the received light; and
a controller configured to estimate total particle concentration and leukocyte concentration using the signal data.

13. The patient monitoring device of claim 12, further comprising:
a housing enclosing the optical sensor arrangement, wherein the fluid conduit is configured to releasably engage to the housing.

14. The patient monitoring device of claim 13, wherein the housing is configured to transition between an open configuration with an exposed interior cavity and a closed configuration with an enclosed interior cavity.

15. The patient monitoring device of claim 12, wherein the fluid conduit comprises at least one transparent portion that is substantially transparent to at least one of ultraviolet light, visible light, and infrared radiation.

16. The patient monitoring device of claim 12, wherein the fluid path comprises an inlet configured to couple to at least one of an in-dwelling catheter and a drain line for peritoneal dialysis, and an outlet configured to open towards a drainage vessel.

* * * * *